(12) United States Patent
Zabeau et al.

(10) Patent No.: US 7,593,818 B2
(45) Date of Patent: Sep. 22, 2009

(54) GENETIC DIAGNOSIS USING MULTIPLE SEQUENCE VARIANT ANALYSIS

(75) Inventors: Marc Zabeau, Ghent (BE); Patrick Stanssens, Nazareth (BE); Yannick Gansemans, Ichtegem (BE)

(73) Assignee: Methexis Genomics N.V., Zwijnaarde, Ghent (BE)

( * ) Notice: Subject to any disclaimer, the term of this patent is extended or adjusted under 35 U.S.C. 154(b) by 442 days.

(21) Appl. No.: 11/077,564

(22) Filed: Mar. 9, 2005

(65) Prior Publication Data

US 2005/0277135 A1 Dec. 15, 2005

Related U.S. Application Data

(63) Continuation-in-part of application No. 10/788,260, filed on Feb. 26, 2004, and a continuation-in-part of application No. 10/788,043, filed on Feb. 26, 2004, now abandoned.

(30) Foreign Application Priority Data

Feb. 27, 2003 (EP) .................... 03447042

(51) Int. Cl.
*G01N 33/48* (2006.01)
(52) U.S. Cl. ...................................... 702/19
(58) Field of Classification Search .................. 702/19
See application file for complete search history.

(56) References Cited

U.S. PATENT DOCUMENTS

2005/0277135 A1 12/2005 Zabeau et al.

FOREIGN PATENT DOCUMENTS

WO WO-03/064600 A2 8/2003
WO PCT/BE2004/000027 2/2004

OTHER PUBLICATIONS

Aguade, Mol. Biol. Evol., 18(1):1-9 (2001).
Akhunov et al., Proc. Natl. Acad. Sci. USA, 100(19)10836-10841 (2003).
Alonso et al., Proc. Natl. Acad. Sci. USA, 98(3):864-869 (2001).
Anderson et al., Am. J. Hum. Genet., 74:40-49 (2004).
Andersson et al., Nat. Rev. Genet., 5:202-212 (2004).
Andolfatto et al., Genetics, 153:1297-1311 (1999).
Andolfatto et al., Genetics, 154:1681-1691 (2000).
Andolfatto et al., Genetics, 158:657-665 (2001).
Antunes et al., Mol. Biol. Evol., 19(8):1272-1287 (2002).
Anzai et al., Proc. Natl. Acad. Sci. USA, 100(13):7708-7713 (2003).
Ardlie et al., Am. J. Hum. Genet., 69:000-000 (2001).
Awadalla et al., Science, 286:2524-2525 (1999).
Ayala et al., Gene, 300:19-29 (2002).
Ayala et al., Mol. Biol. Evol., 13(10)1363-1367 (1996).
Ayala et al., Proc. Natl. Acad. Sci. USA, 97(13):6941-6944 (2000).
Baines et al., Mol. Biol. Evol., 19(7):989-998 (2002).
Balakirev et al., Gene, 288:167-177 (2002).
Balakirev et al., Genetics, 144:1511-1518 (1996).
Balakirev et al., Genetics, 153:1357-1369(1999).
Balakirev et al., Genetics, 164:533-544 (2003).
Barrier et al., Genetics, 163:723-733 (2003).
Barrier et al., Proc. Natl. Acad. Sci. USA, 98(18):10208-10213 (2001).
Barrio et al., Mol. Phylo. Evol., 7(1):79-93 (1997).
Batley et al., Plant Physiol., 132:84-91 (2003).
Baudry et al., Genetics, 158:1725-1735 (2001).
Begun et al., Genetics, 140:1019-1032 (1995).
Begun et al., Genetics, 162:1725-1735 (2002).
Beltran et al., Mol. Biol. Evol., 19(12):2176-2190 (2002).
Bennetzen et al., Proc. Natl. Acad. Sci. USA, 99(14):9093-9095 (2002).
Besansky et al., Proc. Natl. Acad. Sci. USA, 100(19):10818-10823 (2003).
Bishop et al., Proc. Natl. Acad. Sci. USA, 97(10):5322-5327 (2000).
Borevitz et al., Plant Pysiol., 132:718-725 (2003).
Broughton et al., Genetics, 163:1389-1401 (2003).
Buckler et al., Mol. Biol. Evol., 13(4):612-622 (1996).
Bustamante et al., Nature, 416:531-534 (2002).
Caicedo et al., Proc. Natl. Acad. Sci. USA, 96:302-306 (1999).
Carlson et al., Am. J. Hum. Genet., 74:106-120 (2004).
Carlson et al., Nat. Genet., 33:518-521 (2003).
Chakravarti et al., Nature, 421:412-414 (2003).
Charlesworth et al., Genetics, 164:1519-1535 (2003).
Charlesworth et al., Mol. Biol. Evol., 15(5):552-559 (1998).
Chung et al., Bioinformatics, 19(6):780-781 (2003).
Clark et al., Am. J. Hum. Genet., 63:595-612 (1998).
Clark et al., Proc. Natl. Acad. Sci. USA, 101(3):700-707 (2004).
Clauss et al., Mol. Ecol., 11:591-601 (2002).
Clauss et al., Mol. Ecol., 12:1287-1299 (2003).
Clement et al., Mol. Ecol., 9:1657-1659 (2000).
Collins et al., Plant Pysiol., 125:1236-1247 (2001).
Comeron et al., Genetics, 161:389-410 (2002).
Cong et al., Proc. Natl. Acad. Sci. USA, 99(21):13606-13611 (2002).
Couzin, 304(5671):671-673 (2004).
Crawford et al., Am. J. Hum. Genet., 74:610-622 (2004).

(Continued)

*Primary Examiner*—Jerry Lin
(74) *Attorney, Agent, or Firm*—McAndrews, Held & Malloy Ltd.

(57) ABSTRACT

The present invention is in the field of nucleic acid-based genetic analysis. More particularly, it discloses novel insights into the overall structure of genetic variation in all living species. The structure can be revealed with the use of any data set of genetic variants from a particular locus. The invention is useful to define the subset of variations that are most suited as genetic markers to search for correlations with certain phenotypic traits. Additionally, the insights are useful for the development of algorithms and computer programs that convert genotype data into the constituent haplotypes that are laborious and costly to derive in an experimental way. The invention is useful in areas such as (i) genome-wide association studies, (ii) clinical in vitro diagnosis, (iii) plant and animal breeding, (iv) the identification of micro-organisms.

10 Claims, 79 Drawing Sheets
(68 of 79 Drawing Sheet(s) Filed in Color)

OTHER PUBLICATIONS

Cronn et al., Am. J. Botany, 89(4):707-725 (2002).
Cronn et al., Proc. Natl. Acad. Sci. USA, 96(25):14406-14411 (1999).
della Torre et al., Science, 298:115-117 (2002).
Dennis, Nature, 425(6960):758-759 (2003).
Dermitzakis et al., Mol. Biol. Evol., 20(5):703-714 (2003).
Dingle et al., J. Clinic. Microbiol., 39(1):14-23 (2001).
Dingle et al., J. Clinic. Microbiol., 39(9):3346-3349 (2001).
Drysdale et al., Proc. Natl. Acad. Sci. USA, 97(19):10483-10488 (2000).
Dvornyk et al., Mol. Biol. Evol., 19(2):179-188 (2002).
Evans et al., Genetics, 164:621-627 (2003).
Eyre-Walker et al., Proc. Natl. Acad. Sci. USA, 95:4441-4446 (1998).
Farnir et al., Genome Res., 10:220-227 (2000).
Ferguson et al., Proc. Natl. Acad. Sci. USA, 98(7):3915-3919 (2001).
Feuillet et al., Ann. Botany, 89:3-10 (2002).
Feuillet et al., Plant Physiol., 125:1304-1313 (2001).
Feuillet et al., Proc. Natl. Acad. Sci. USA, 96:8265-8270 (1999).
Filatov et al., Genetics, 153:1423-1434 (1999).
Frary et al., Science, 289:85-88 (2000).
Freudenberg-Hua et al., Genome Res., 13:2271-2276 (2003).
Fu et al., Proc. Natl. Acad. Sci. USA, 99(14):9573-9578 (2002).
Garris et al., Genetics, 165:759-769 (2003).
Gaut et al., Plant Cell, 15(7):1502-1506 (2003).
Gaut et al., Proc. Natl. Acad. Sci. USA, 90:5095-5099 (1993).
Gaut et al., Proc. Natl. Acad. Sci. USA, 97(13):7008-7015 (2000).
Gazzani et al., Plant Physiol., 132:1107-1114 (2003).
Ge et al., Proc. Natl. Acad. Sci. USA, 96(25):14400-14405 (1999).
Gentile et al., Genetics, 161:1561-1578 (2002).
Glazier at al., Science, 298:2345-2349 (2002).
Gleason et al., Mol. Biol. Evol., 14(7):741-753 (1997).
Graustein et al., Genetics, 161:99-107 (2002).
Griffith et al., J. Mol. Evol., 45:232-237 (1997).
Grisart et al., Genome Res., 12:222-231 (2001).
Grisart et al., Proc. Natl. Acad. Sci. USA, 101(8):2398-2403 (2004).
Guo et al., Plant Cell, 15:1143-1158 (2003).
Hagenblad et al., Genetics, 161:289-298 (2002).
Hamblin at al., Genetics, 153:305-317 (1999).
Hammer et al., Mol. Biol. Evol., 18(7):1189-1203 (2001).
Hanson et al., Genetics, 143:1395-1407 (1996).
Haubold et al., Genetics, 161:1269-1278 (2002).
Hauser et al., Mol. Biol. Evol., 18(9):1754-1763 (2001).
Hayes et al., Genome Res., 13:635-643 (2003).
Hellmann et al., Genome Res., 13:831-837 (2003).
Hilton at al., Genetics, 150:863-872 (1998).
Hong et al., Plant Cell, 15:1296-1309 (2003).
Ingman at al., Nature, 408:708-713 (2000).
Innan et al., Genetics, 143:1761-1770 (1996).
Innan et al., Genetics, 147:1431-1444 (1997).
Innan et al., Genetics, 165:437-444 (2003).
Innan et al., Genome Res., 13:1158-1168(2003).
Jaenicke-Despres at al., Science, 302:1206-1208 (2003).
Jarvinen et al., Mol. Ecol., 12:369-384 (2003).
Jeffreys et al., Nat. Genet., 29:217-222 (2001).
Jensen at al., Genetics, 160:493-507 (2002).
Johanson et al., Science, 290:344-347 (2000).
Johnson et al., Nat. Genet., 29:233-237 (2001).
Kado et al., Genetics, 164:1547-1559 (2003).
Kamiya et al., Genet. Res., 80:89-98 (2002).
Kawabe et al., Genes Genet. Syst., 77:159-165(2002).
Kawabe et al., Genetics, 153:1445-1453(1999).
Kawabe et al., Genetics, 156:1339-1347 (2000).
Ke et al., Bioinformatics, 19(2):287-288 (2003).
Kelly, Genetics, 146:1197-1206 (1997).
Kennedy at al., Nat. Biotechnol., 21(10):1233-1237 (2003).
Kirby et al., Genetics, 144:635-645 (1996).
Kliman et al., Genetics, 156:1913-1931 (2000).
Koch et al., Genome Res., 10:1690-1696 (2000).
Koch et al., Mol. Biol. Evol., 17(10):1483-1498 (2000).
Koch et al., Mol. Biol. Evol., 18(10):1882-1891 (2001).
Koch et al., Mol. Biol. Evol., 20(3):338-350 (2003).
Kroymann at al., Proc. Natl. Acad. Sci. USA, 100 Suppl 2:14587-14592 (2003).
Kuitinen et al., Genetics, 155:863-872 (2000).
Kuittinen et al., Mol. Biol. Evol., 19(11):2030-2034 (2002).
Kumar et al., Proc. Natl. Acad. Sci. USA, 99(2):803-808 (2002).
Kwiatowski et al., J. Mol. Evol., 44:9-22 (1997).
Lagercrantz et al., Mol. Biol. Evol., 19(9):1474-1482 (2002).
Langley et al., Genetics, 156:1837-1852 (2000).
Lawton-Rauh et al., Mol. Ecol., 12:1301-1313(2003).
Le Corre et al., Mol. Biol. Evol., 19(8):1261-1271 (2002).
Lee et al., Proc. Natl. Acad. Sci. USA, 99(26):16835-16840 (2002).
Lewontin, Genetics, 140:377-388 (1995).
Lin et al., Genetics, 162:2007-2015 (2002).
Liu et al., Genetics, 151:343-357 (1999).
Lonjou et al., Proc. Natl. Acad. Sci. USA, 100(10):6069-6074 (2003).
Lowman et al., J. Hered., 90:514-520 (1999).
Lu et al., Genome Res., 13:2112-2117 (2003).
Machado et al., Mol. Biol. Evol., 19(4):472-488 (2002).
Maniatis et al., Proc. Natl. Acad. Sci. USA, 99(4):2228-2233 (2002).
Matsuoka et al., Proc. Natl. Acad. Sci. USA, 99(9):6080-6084 (2002).
Matsuoka et al., Theor. Appl. Genet., 104:436-450 (2002).
Mauricio et al., Genetics, 163:735-746 (2003).
McAllister et al., Genetics, 153:221-233 (1999).
Melton, Nature, 422:917, 919, 921,923 (2003).
Mishmar et al., Proc. Natl. Acad. Sci. USA, 100(1):171-176 (2003).
Miyashita et al., Mol. Biol. Evol., 13(2):433-436 (1996).
Miyashita et al., Mol. Biol. Evol., 15(11):1420-1429 (1998).
Miyashita et al., Mol. Biol. Evol., 18(2)164-171 (2001).
Morrell et al., Proc. Natl. Acad. Sci. USA, 100(19)10812-10817 (2003).
Morris et al., Proc. Natl. Acad. Sci. USA, 100(23):13442-13446 (2003).
Morton et al., Proc. Natl. Acad. Sci. USA, 98(9):5217-5221 (2001).
Munte et al., Mol. Biol. Evol., 17(12):1942-1955 (2000).
Nachman et al., Genetics, 156:297-304 (2000).
Nagamine et al., Genetics, 164:629-635(2003).
The International HapMap Consortium, Nature, 426:789-796 (2003).
Navarro et al., Science, 300:321-324 (2003).
Nesbitt et al., Genetics, 162:365-379 (2002).
Nickerson et al., Nature Genet., 19:233-240 (1998).
Nordborg et al., Nature Genet., 30:190-193 (2002).
Nordborg et al., TRENDS Genet., 18(2):83-90 (2002).
Ohta, Proc. Natl. Acad. Sci. USA, 99(25):16134-16137 (2002).
Olsen et al., Genetics, 160:1641-1650 (2002).
Olsen et al., Genetics, 162:941-950 (2002).
Olsen et al., Genetics, 167:1361-1369 92004).
Paabo et al., Nature, 421:409-412 (2003).
Palaisa et al., The Plant Cell, 15:1795-1806 (2003).
Park et al., Clin. Exp. Pharmacol. Physiol., 27:690-693 (2000).
Phillips et al., Nature Genet., 33:382-387 (2003).
Pielberg et al., Genome Res., 13:2171-2177 (2003).
Pritchard et al., Am. J. Hum. Genet., 69:1-14 (2001).
Purugganan et al., Genetics, 151:839-848 (1999).
Purugganan et al., Genetics, 155:855-862 (2000).
Purugganan et al., Proc. Natl. Acad. Sci. USA, 95:8130-8134 (1998).
Quesada et al., Genetics, 165:895-900 (2003).
Ramakrishna et al., Genetics, 162:1389-1400 (2002).
Remington et al., Mol. Biol. Evol., 19(9):1563-1574 (2002).
Remington et al., Proc. Natl. Acad. Sci. USA, 98(20)11479-11484 (2001).
Rioux et al., Nature Genet., 29:223-228 (2001).
Rodriguez-Trelles et al., J. Mol. Evol., 50:1-10 (2000).
Rodriguez-Trelles et al., J. Mol. Evol., 53:485-495 (2001).
Romero-Severson et al., Theor. Appl. Genet., 103:567-574 (2001).
Rosenberg et al., Nat. Rev. Genet., 3(5):380-390 (2002).
Rozas et al., Genetics, 158:1147-1155 (2001).
Sabatti et al., Genetics, 160:1707-1719 (2002).
Sabeti et al., Nature, 419:832-837 (2002).
Saez et al., Proc. Natl. Acad. Sci. USA, 100(4)1793-1798 (2003).

Salisbury et al., Mutat. Res., 526:53-61 (2003).
Sandhu et al., Plant Physiol., 128:803-811(2002).
Savolainen et al., Mol. Biol. Evol., 17(4):645-655 (2000).
Schaal et al., Proc. Natl. Acad. Sci. USA, 97(13):7024-7029 (2000).
Schaeffer et al., Genetics, 132:471-480 (1992).
Schaeffer et al., Genetics, 135:541-552 (1993).
Schaeffer et al., Proc. Natl. Acad. Sci. USA, 88:6097-6101 (1991).
Schaeffer et al., Proc. Natl. Acad. Sci. USA, 100(14):8319-8324 (2003).
Scherrer et al., Funct. Integr. Genomics, 2:40-50 (2002).
Schlenke et al., Genetics, 164:1471-1480 (2003).
Schmid et al., Genome Res., 13:1250-1257 (2003).
Schwartz et al., J. Comput. Biol., 10(1):13-19 (2003).
Sebastiani et al., Proc. Natl. Acad. Sci. USA, 100(17):9900-9905 (2003).
Senchina et al., Mol. Biol. Evol., 20(4):633-643 (2003).
Sharbel et al., Mol. Ecol., 9:2109-2118 (2000).
Shepard et al., Genetics, 163:1083-1095 (2003).
Shi et al., Proc. Natl. Acad. Sci. USA, 100(14):8331-8336 (2003).
Silva et al., TRENDS Genet., 18(11):544-547 (2002).
Sivasundar et al., Genetics, 163:147-157 (2003).
Small et al., Am. J. Bot., 85(9):1301-1315 (1998).
Small et al., Genetics, 155:1913-1926 (2000).
Small et al., Mol. Biol. Evol., 16(4):491-501 (1999).
Small et al., Mol. Biol. Evol., 19(5):597-607 (2002).
Small et al., Mol. Phylogenet. Evol., 16(1):73-84 (2000).
Smith et al., Genome Res., 12:1350-1356(2002).
Smith et al., TRENDS Genet., 18(6):281-283 (2002).
Song et al., Proc. Natl. Acad. Sci. USA, 100(15):9055-9060 (2003).
Sorrells et al., Genome Res., 13:1818-1827 (2003).
Stacey et al., Plant Physiol., 135:59-70 (2004).
Stahl et al., Nature, 400:667-671 (1999).
Stead et al., Genome Res., 13:2101-2111 (2003).
Stengard et al., Am. J. Hum. Genet., 71:501-517(2002).
Stephens, Mol. Biol. Evol., 2(6):539-556 (1985).
Stephens et al., Science, 293:489-493 (2001).
Stewart et al., Genome Res., 14:1176-1187 (2004).
Stumpf, TRENDS Genet., 18(5):226-228 (2002).
Tang et al., Genetics, 161:447-459 (2002).
Tapper et al., Ann. Hum. Genet., 67:487-494 (2003).
Tarrio et al., Proc. Natl. Acad. Sci. USA, 95:1658-1662 (1998).
Tatarenkov et al., Mol. Phylogenet. Evol., 20(2):321-325 (2001).
Tatarenkov et al., Mol. Phylogenet. Evol., 21(2):327-331 (2001).
Templeton et al., Genetics, 132:619-633 (1992).
Templeton et al., Genetics, 156:1259-1275 (2000).
Tenaillon et al., Genetics, 162:1401-1413 (2002).
Tenaillon et al., Proc. Natl. Acad. Sci. USA, 98(16):9161-9166 (2001).
Tian et al., Proc. Natl. Acad. Sci. USA, 99(17):11525-11530 (2002).
Tiffin et al., Genetics, 158:401-412 (2001).
Tiffin et al., Mol. Biol. Evol., 18(11):2092-2101 (2001).
Torjek et al., Plant J., 36:122-140 (2003).
Twells et al., Genome Res., 13:845-855 (2003).
Verheyen et al., Science, 300:325-329 (2003).
Vigouroux et al., Proc. Natl. Acad. Sci. USA, 99(15):9650-9655 (2002).
Wall et al., Am. J. Hum. Genet., 73:502-515 (2003).
Wall et al., Nat. Rev. Genet., 4(8):587-597 (2003).
Walsh et al., Am. J. Hum. Genet., 73:580-590 (2003).
Wang et al., Genetics, 147:1091-1106 (1997).
White et al., Genetics, 153:1455-1462 (1999).
Whitt et al., Proc. Natl. Acad. Sci. USA, 99(20):12959-12962 (2002).
Wicker et al., The Plant Cell, 15:1186-1197 (2003).
Whiltshire et al., Proc. Natl. Acad. Sci. USA, 100(6):3380-3385 (2003).
Winzeler et al., Genetics, 163:79-89 (2003).
Wright et al., Mol. Biol. Evol., 19(9):1407-1420 (2002).
Wright et al., Mol. Ecol., 12:1247-1263 (2003).
Xiong et al., Front. Biosci., 8:A85-A93 (2003).
Yalcin et al., Proc. Natl. Acad. Sci. USA, 101(26):9734-9739 (2004).
Yang et al., J. Mol. Evol., 48:597-604 (1999).
Yi et al., Genetics, 164:1369-1381 (2003).
Yoshida et al., Genes Genet. Syst., 78:11-21 (2003).
Yu et al., Genetics, 164:1511-1518 (2003).
Zhang et al., Am. J. Hum. Genet., 71:1386-1394 (2002).
Zhang et al., Am. J. Hum. Genet., 73:000-000 (2003).
Zhang et al., Genetics, 162:851-860 (2002).
Zhang et al., Genome Res., 14:908-916 (2004).
Zhang et al., Proc. Natl. Acad. Sci. USA, 99(11):7335-7339 (2002).
Zhang et al., Proc. Natl. Acad. Sci. USA, 99(26):17004-17007 (2002).
Zhu et al., Genetics, 163:1123-1134 (2003).
Zurovcova et al., Genetics, 162:177-188 (2002).
Fallin et al., Am. J. Hum. Genet., 67:947-959 (2000).
Li et al., Genomics, 26:199-206 (1995).
Nickerson et al., Genomics, 12:377-387 (1992).
Article: XP-002411880; Minimal haplotype tagging; Authors: Paola Sebastiani et al.; Dated: Aug. 19, 2003; Vo. 100 No. 17; pp. 990-9905.
Article: XP-002411881; SNP Subset Selection For Genetic Association Studies; Authors: M. C. Byng et al.; University College of London 2003; Annals of Human Genetics (2003); pp. 67,543-556.
Article: XP-002411882; Genetic Variation at the Chromosome 16 Chemokine Gene Cluster: Development of Strategy for Association Studies in Complex Disease; Authors: S. A. Fisher et al.; University College London 2003; Annals of Human Genetics (2003); pp. 67,377-390.
Kruglyak, Leonid, "Prospects for Whole-Genome Linkage Disequilibrium Mapping of Common Disease Genes," *Nature Genetics* 22:139-144 (1999).
Merriam-Webster Online Dictionary "article", http://mw1.merriam-webster.com/dictionary/article (last visited May 17, 2007).

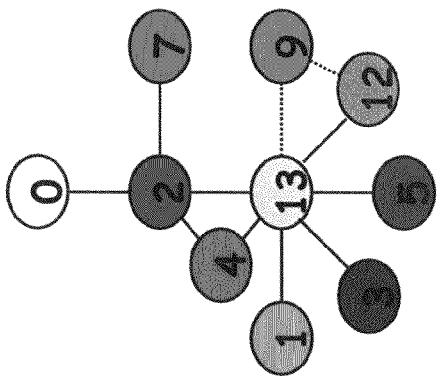

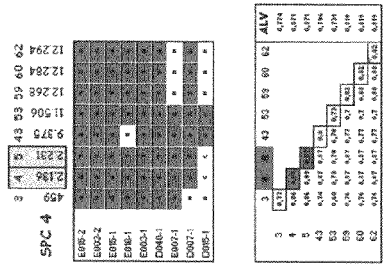
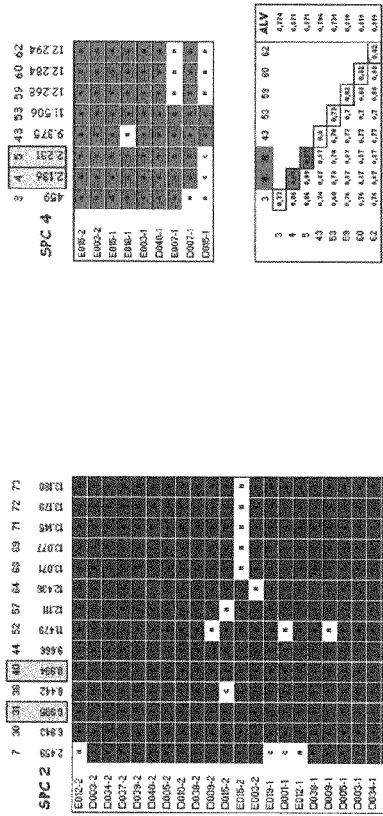
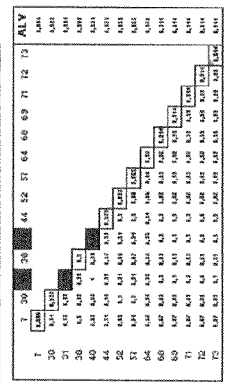
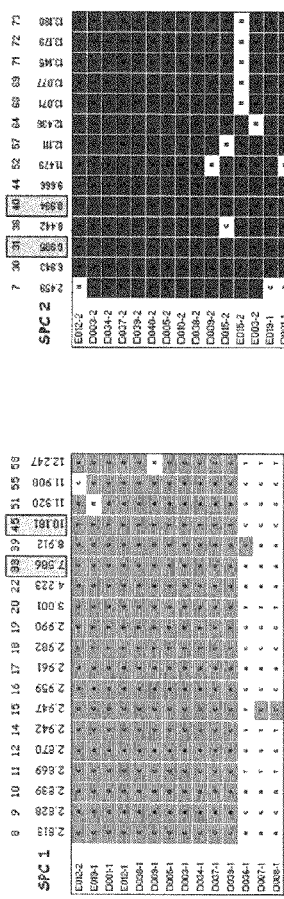
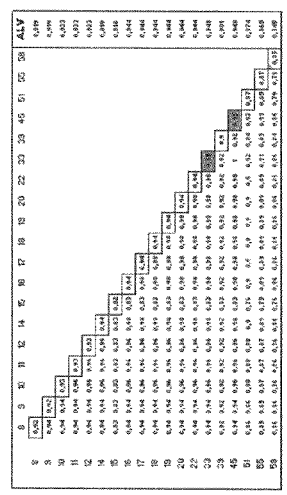
Figure 15E  Figure 15F  Figure 15G

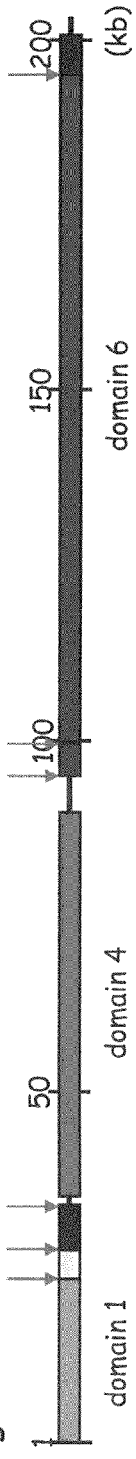
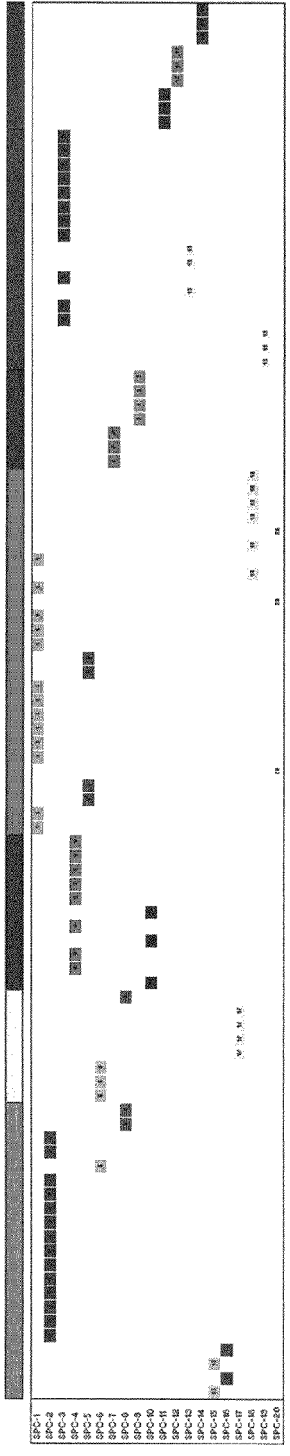
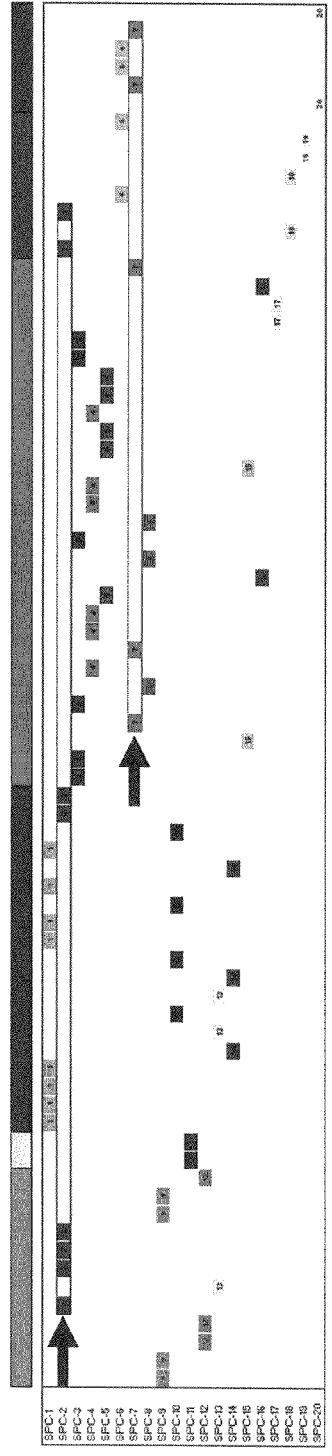
Figure 16A
Figure 16B
Figure 16C

SEQUENCE LISTING

```
<160> NUMBER OF SEQ ID NOS: 167

<210> SEQ ID NO 1
<211> LENGTH: 40
<212> TYPE: DNA
<213> ORGANISM: Artificial sequence
<220> FEATURE:
<223> OTHER INFORMATION: Synthetic

<400> SEQUENCE: 1
tctagagatg tttaccactg taatcccgtc aagttatgag                     40

<210> SEQ ID NO 2
<211> LENGTH: 40
<212> TYPE: DNA
<213> ORGANISM: Artificial sequence
<220> FEATURE:
<223> OTHER INFORMATION: Synthetic

<400> SEQUENCE: 2
cctggagatg gctatcactg gaatcccgcc aggttgtgcg                     40

<210> SEQ ID NO 3
<211> LENGTH: 40
<212> TYPE: DNA
<213> ORGANISM: Artificial sequence
<220> FEATURE:
<223> OTHER INFORMATION: Synthetic

<400> SEQUENCE: 3
tccaaatgag ttccccgcct taactgcatc tagtcaagcg                     40

<210> SEQ ID NO 4
<211> LENGTH: 40
<212> TYPE: DNA
```

```
<213> ORGANISM: Artificial sequence
<220> FEATURE:
<223> OTHER INFORMATION: Synthetic

<400> SEQUENCE: 4
tctaagtaaa tttcccgtcg tagttgcgtc tagccatgct                              40

<210> SEQ ID NO 5
<211> LENGTH: 40
<212> TYPE: DNA
<213> ORGANISM: Artificial sequence
<220> FEATURE:
<223> OTHER INFORMATION: Synthetic

<400> SEQUENCE: 5
tctaagtaaa tttcccgtcg tagttgcgtc taaccatgct                              40

<210> SEQ ID NO 6
<211> LENGTH: 40
<212> TYPE: DNA
<213> ORGANISM: Artificial sequence
<220> FEATURE:
<223> OTHER INFORMATION: Synthetic

<400> SEQUENCE: 6
tttaaataag tttccagccg tcattgtgta tagtcatgcg                              40

<210> SEQ ID NO 7
<211> LENGTH: 40
<212> TYPE: DNA
<213> ORGANISM: Artificial sequence
<220> FEATURE:
<223> OTHER INFORMATION: Synthetic

<400> SEQUENCE: 7
tctaaataag tttcccgccg taattgcgtc tagtcatgcg                              40

<210> SEQ ID NO 8
<211> LENGTH: 40
<212> TYPE: DNA
<213> ORGANISM: Artificial sequence
<220> FEATURE:
<223> OTHER INFORMATION: Synthetic

<400> SEQUENCE: 8
tttaaataag tttccagccg tcattgtgta tagtcatacg                              40

<210> SEQ ID NO 9
<211> LENGTH: 40
<212> TYPE: DNA
<213> ORGANISM: Artificial sequence
<220> FEATURE:
<223> OTHER INFORMATION: Synthetic

<400> SEQUENCE: 9
ttggaatggt tacgattgtg cactaaaagt taatctagtg                              40

<210> SEQ ID NO 10
<211> LENGTH: 40
<212> TYPE: DNA
<213> ORGANISM: Artificial sequence
<220> FEATURE:
<223> OTHER INFORMATION: Synthetic

<400> SEQUENCE: 10
ttgtgatgat tacaattgtg cgctgaaagc taatttagtt                              40
```

```
<210> SEQ ID NO 11
<211> LENGTH: 40
<212> TYPE: DNA
<213> ORGANISM: Artificial sequence
<220> FEATURE:
<223> OTHER INFORMATION: Synthetic

<400> SEQUENCE: 11
ctgtgataac tataatcgtg cgcggaaggc tgatttagct                          40

<210> SEQ ID NO 12
<211> LENGTH: 40
<212> TYPE: DNA
<213> ORGANISM: Artificial sequence
<220> FEATURE:
<223> OTHER INFORMATION: Synthetic

<400> SEQUENCE: 12
ctgtgatgac tataatcgtg cgcggaaggc tgatttagct                          40

<210> SEQ ID NO 13
<211> LENGTH: 40
<212> TYPE: DNA
<213> ORGANISM: Artificial sequence
<220> FEATURE:
<223> OTHER INFORMATION: Synthetic

<400> SEQUENCE: 13
ctgtggtgac cataaccgtt cgacggaggc tgattaaact                          40

<210> SEQ ID NO 14
<211> LENGTH: 40
<212> TYPE: DNA
<213> ORGANISM: Artificial sequence
<220> FEATURE:
<223> OTHER INFORMATION: Synthetic

<400> SEQUENCE: 14
ctgtggtgac cataaccgtt cgacggaggc tgattaagct                          40

<210> SEQ ID NO 15
<211> LENGTH: 40
<212> TYPE: DNA
<213> ORGANISM: Artificial sequence
<220> FEATURE:
<223> OTHER INFORMATION: Synthetic

<400> SEQUENCE: 15
ttagaaaggt tccggttacg gactggtagt cagcctcgtg                          40

<210> SEQ ID NO 16
<211> LENGTH: 40
<212> TYPE: DNA
<213> ORGANISM: Artificial sequence
<220> FEATURE:
<223> OTHER INFORMATION: Synthetic

<400> SEQUENCE: 16
ttagaaaggt tccggttacg gactggtagt cagtctcgtg                          40

<210> SEQ ID NO 17
<211> LENGTH: 40
<212> TYPE: DNA
<213> ORGANISM: Artificial sequence
<220> FEATURE:
```

<223> OTHER INFORMATION: Synthetic

<400> SEQUENCE: 17
ttagaaaggt tccggttacg gactggtaat cagtctcgtg    40

<210> SEQ ID NO 18
<211> LENGTH: 40
<212> TYPE: DNA
<213> ORGANISM: Artificial sequence
<220> FEATURE:
<223> OTHER INFORMATION: Synthetic

<400> SEQUENCE: 18
tcagaaaggt tccggttacg gactggtagt cagtctcgtg    40

<210> SEQ ID NO 19
<211> LENGTH: 40
<212> TYPE: DNA
<213> ORGANISM: Artificial sequence
<220> FEATURE:
<223> OTHER INFORMATION: Synthetic

<400> SEQUENCE: 19
tcaagtgttc ccacgaatcc catctaaaag tcaattgccc    40

<210> SEQ ID NO 20
<211> LENGTH: 40
<212> TYPE: DNA
<213> ORGANISM: Artificial sequence
<220> FEATURE:
<223> OTHER INFORMATION: Synthetic

<400> SEQUENCE: 20
tcaattgttc caacggctcc tgtctaaaag tcaattgccc    40

<210> SEQ ID NO 21
<211> LENGTH: 40
<212> TYPE: DNA
<213> ORGANISM: Artificial sequence
<220> FEATURE:
<223> OTHER INFORMATION: Synthetic primer

<400> SEQUENCE: 21
tcaattgtta caacggcttc tgtctaaaag ttaattgcac    40

<210> SEQ ID NO 22
<211> LENGTH: 40
<212> TYPE: DNA
<213> ORGANISM: Artificial sequence
<220> FEATURE:
<223> OTHER INFORMATION: Synthetic

<400> SEQUENCE: 22
ttagtagttc tcgcggatcg cgtataatag tcaacagcct    40

<210> SEQ ID NO 23
<211> LENGTH: 40
<212> TYPE: DNA
<213> ORGANISM: Artificial sequence
<220> FEATURE:
<223> OTHER INFORMATION: Synthetic

<400> SEQUENCE: 23
ttagtagttc tcgcggatcg cgtataatag ccaacagtct    40

```
<210> SEQ ID NO 24
<211> LENGTH: 40
<212> TYPE: DNA
<213> ORGANISM: Artificial sequence
<220> FEATURE:
<223> OTHER INFORMATION: Synthetic

<400> SEQUENCE: 24
ttagtaattc tcgcggatcg cgtatgatag tcaacagcct                              40

<210> SEQ ID NO 25
<211> LENGTH: 40
<212> TYPE: DNA
<213> ORGANISM: Artificial sequence
<220> FEATURE:
<223> OTHER INFORMATION: Synthetic

<400> SEQUENCE: 25
ctaatagctc ccgcggaccg cgccgaatag tcagctgccc                              40

<210> SEQ ID NO 26
<211> LENGTH: 40
<212> TYPE: DNA
<213> ORGANISM: Artificial sequence
<220> FEATURE:
<223> OTHER INFORMATION: Synthetic

<400> SEQUENCE: 26
ttgatagctc ccgttgaccg cgtcgaatga tcagctaccc                              40

<210> SEQ ID NO 27
<211> LENGTH: 40
<212> TYPE: DNA
<213> ORGANISM: Artificial sequence
<220> FEATURE:
<223> OTHER INFORMATION: Synthetic primer

<400> SEQUENCE: 27
ttgatagccc ccgctgaccg cgtcgagtgg tcggctgccc                              40

<210> SEQ ID NO 28
<211> LENGTH: 40
<212> TYPE: DNA
<213> ORGANISM: Artificial sequence
<220> FEATURE:
<223> OTHER INFORMATION: Synthetic

<400> SEQUENCE: 28
ttaatagttc ccgcggatcg cgtctaatag tcaactgccc                              40

<210> SEQ ID NO 29
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (24)..(24)
<223> OTHER INFORMATION: n is a, c, g, or t

<400> SEQUENCE: 29
tctagagatg tttaccactg taanccccgtc aagttatgag                             40

<210> SEQ ID NO 30
<211> LENGTH: 40
<212> TYPE: DNA
```

<213> ORGANISM: Artificial sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 30
tntagagatg tttaccactg taancccgtc aagttatgag          40

<210> SEQ ID NO 31
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 31
tctagagatg ttnaccactg taancccgtc tagttatgag          40

<210> SEQ ID NO 32
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 32
tcnagagatn tttaccactg taancccgtc aagttatgag          40

<210> SEQ ID NO 33
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

```
<220> FEATURE:
<221> NAME/KEY: misc_feature
<222> LOCATION: (19)..(19)
<223> OTHER INFORMATION: n is a, c, g, or t

<400> SEQUENCE: 33
tctaganang tttacnacng taatcccgtc aagttatgag                              40

<210> SEQ ID NO 34
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t

<400> SEQUENCE: 34
cctgaataag gctctcgccg gaattgcgcc tggtcntgng                              40

<210> SEQ ID NO 35
<211> LENGTH: 40
<212> TYPE: DNA
<213> ORGANISM: Artificial sequence
<220> FEATURE:
<223> OTHER INFORMATION: Synthetic

<400> SEQUENCE: 35
cctgaataag gctctcgccg gaattgcgcc tggtcgtgcg                              40

<210> SEQ ID NO 36
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t

<400> SEQUENCE: 36
cctgnataag gctctcgccg gaattncgcc tggtcgtgcg                              40

<210> SEQ ID NO 37
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (30)..(30)
<223> OTHER INFORMATION: n is a, c, g, or t

<400> SEQUENCE: 37
cctgaataag gctctcgccg gaattgcgcn tggtcgtgcg                              40

<210> SEQ ID NO 38
```

```
<211> LENGTH: 40
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t

<400> SEQUENCE: 38
cctgaataag gntctcgccg naattgcgcc tggncgtgcg            40

<210> SEQ ID NO 39
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (40)..(40)
<223> OTHER INFORMATION: n is a, c, g, or t

<400> SEQUENCE: 39
tccaaatgag ttccccgcct taactgcatc tagtcaagcn            40

<210> SEQ ID NO 40
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 40
nctaagtaaa tttcncgtcg tagttgcgtc tagccatgct            40

<210> SEQ ID NO 41
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t

<400> SEQUENCE: 41
```
tctaagnaaa tttcccgtcg tagttgcgtn taacnatgct    40

<210> SEQ ID NO 42
<211> LENGTH: 40
<212> TYPE: DNA
<213> ORGANISM: Artificial Sequence
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t

<400> SEQUENCE: 42
tctaagtaaa tttcccgtng tngttgcgtc tagccatgnt    40

<210> SEQ ID NO 43
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: n is a, c, g, or t

<400> SEQUENCE: 43
tctaagtaan tttcccgtcg tagttgcgtc tagccatgct    40

<210> SEQ ID NO 44
<211> LENGTH: 40
<212> TYPE: DNA
<213> ORGANISM: Artificial sequence
<220> FEATURE:
<223> OTHER INFORMATION: Synthetic

<400> SEQUENCE: 44
tctaagtaaa tttcccgtcg tagttgcgtc tagccatgct    40

<210> SEQ ID NO 45
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: n is a, c, g, or t

<400> SEQUENCE: 45
tctaagtaaa tttnccgtcg tagttgcgtc tagccatgct    40

<210> SEQ ID NO 46
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (5)..(5)

```
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 46
tctangtnaa tttcccgtcg taattgcgtc tagccatgct                              40

<210> SEQ ID NO 47
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t

<400> SEQUENCE: 47
nctaagtaaa tttcccntcg nagttgcgtc naaccatgct                              40

<210> SEQ ID NO 48
<211> LENGTH: 40
<212> TYPE: DNA
<213> ORGANISM: Artificial sequence
<220> FEATURE:
<223> OTHER INFORMATION: Synthetic

<400> SEQUENCE: 48
tctaagtaaa tttcccgtcg tagttgcgtc tagccatgct                              40

<210> SEQ ID NO 49
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (34)..(34)
<223> OTHER INFORMATION: n is a, c, g, or t

<400> SEQUENCE: 49
tctaagtaaa tttcccgtcg tagttgcgtc tagncatgct                              40

<210> SEQ ID NO 50
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
```

<222> LOCATION: (4)..(4)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 50
tntnagtaaa tttccngncg tagttgcntc tagccatgct                                40

<210> SEQ ID NO 51
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t

<400> SEQUENCE: 51
tttaaataag nttccagccg tcattgtgta tagtcatgcn                                40

<210> SEQ ID NO 52
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t

<400> SEQUENCE: 52
tttaaataag tttccngccg tcattgtgta tagtcatncg                                40

<210> SEQ ID NO 53
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (37)..(37)
<223> OTHER INFORMATION: n is a, c, g, or t

<400> SEQUENCE: 53
tttaaataag tttccagccg tcattgtgta tagtcangcg                                40

<210> SEQ ID NO 54
<211> LENGTH: 40
<212> TYPE: DNA

<213> ORGANISM: Artificial sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: n is a, c, g, or t

<400> SEQUENCE: 54
tctaaatang tttcccgccg taattgcgtc tagtcatgcg                40

<210> SEQ ID NO 55
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t

<400> SEQUENCE: 55
tctaagtaaa tttcccgccg tnattgcgtc tagncatgcg                40

<210> SEQ ID NO 56
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t

<400> SEQUENCE: 56
tctaantaag tttnccgccg taattgcgcc tngtactacg                40

<210> SEQ ID NO 57
<211> LENGTH: 40
<212> TYPE: DNA
<213> ORGANISM: Artificial sequence
<220> FEATURE:
<223> OTHER INFORMATION: Synthetic

<400> SEQUENCE: 57
tctaaataag tttcccgccg taattgcgtc tagtcatacg                40

<210> SEQ ID NO 58
<211> LENGTH: 40
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (32)..(32)
<223> OTHER INFORMATION: n is a, c, g, or t -continued

```
<220> FEATURE:
<221> NAME/KEY: misc_feature
<222> LOCATION: (39)..(39)
<223> OTHER INFORMATION: n is a, c, g, or t

<400> SEQUENCE: 58
tctaaataag tmtcccgccg taattgcgtc tngtcatgng                                40

<210> SEQ ID NO 59
<211> LENGTH: 11
<212> TYPE: DNA
<213> ORGANISM: Artificial sequence
<220> FEATURE:
<223> OTHER INFORMATION: Synthetic

<400> SEQUENCE: 59
ggtaatccat a                                                              11

<210> SEQ ID NO 60
<211> LENGTH: 11
<212> TYPE: DNA
<213> ORGANISM: Artificial sequence
<220> FEATURE:
<223> OTHER INFORMATION: Synthetic

<400> SEQUENCE: 60
ggtaatcctt a                                                              11

<210> SEQ ID NO 61
<211> LENGTH: 11
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 61
gnnaanccat a                                                              11

<210> SEQ ID NO 62
<211> LENGTH: 11
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: n is a, c, g, or t

<400> SEQUENCE: 62
atacgctgtc n                                                              11

<210> SEQ ID NO 63
<211> LENGTH: 11
<212> TYPE: DNA
<213> ORGANISM: Artificial sequence
<220> FEATURE:
<223> OTHER INFORMATION: Synthetic

<400> SEQUENCE: 63
```
atacgctgtc c                                                                                           11

<210> SEQ ID NO 64
<211> LENGTH: 11
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 64
ntacgctntc c                                                                                           11

<210> SEQ ID NO 65
<211> LENGTH: 11
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 65
anacgctctn c                                                                                           11

<210> SEQ ID NO 66
<211> LENGTH: 11
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 66
atacgntctc n                                                                                           11

<210> SEQ ID NO 67
<211> LENGTH: 11
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: n is a, c, g, or t

<400> SEQUENCE: 67
atangctgtc c                                                                                           11

```
<210> SEQ ID NO 68
<211> LENGTH: 11
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, g, or t

<400> SEQUENCE: 68
ntacgctgtc c                                                                11

<210> SEQ ID NO 69
<211> LENGTH: 11
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 69
atacnctgnc c                                                                11

<210> SEQ ID NO 70
<211> LENGTH: 11
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: n is a, c, g, or t

<400> SEQUENCE: 70
atncgctgtc c                                                                11

<210> SEQ ID NO 71
<211> LENGTH: 11
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 71
atacgctgnc n                                                                11

<210> SEQ ID NO 72
<211> LENGTH: 40
<212> TYPE: DNA
<213> ORGANISM: Artificial sequence
<220> FEATURE:
<223> OTHER INFORMATION: Synthetic
```

```
<400> SEQUENCE: 72
cctgaataag gctctcgccg gaattgcgcc tgttcgtccg                              40

<210> SEQ ID NO 73
<211> LENGTH: 40
<212> TYPE: DNA
<213> ORGANISM: Artificial sequence
<220> FEATURE:
<223> OTHER INFORMATION: Synthetic

<400> SEQUENCE: 73
tccaaatgag ttccccgcct taactgcatc tattcaatcg                              40

<210> SEQ ID NO 74
<211> LENGTH: 40
<212> TYPE: DNA
<213> ORGANISM: Artificial sequence
<220> FEATURE:
<223> OTHER INFORMATION: Synthetic

<400> SEQUENCE: 74
tataagtaaa tttcccgtcg tagttgcgtc tatccattct                              40

<210> SEQ ID NO 75
<211> LENGTH: 40
<212> TYPE: DNA
<213> ORGANISM: Artificial sequence
<220> FEATURE:
<223> OTHER INFORMATION: Synthetic

<400> SEQUENCE: 75
tttaaataag tttccagccg tcattgtgta tattcattcg                              40

<210> SEQ ID NO 76
<211> LENGTH: 40
<212> TYPE: DNA
<213> ORGANISM: Artificial sequence
<220> FEATURE:
<223> OTHER INFORMATION: Synthetic

<400> SEQUENCE: 76
tctagagatg tttaccactg taatcccgtc tattcattcg                              40

<210> SEQ ID NO 77
<211> LENGTH: 40
<212> TYPE: DNA
<213> ORGANISM: Artificial sequence
<220> FEATURE:
<223> OTHER INFORMATION: Synthetic

<400> SEQUENCE: 77
tctagagatg tttaccactg taatcccgtc aacttattag                              40

<210> SEQ ID NO 78
<211> LENGTH: 40
<212> TYPE: DNA
<213> ORGANISM: Artificial sequence
<220> FEATURE:
<223> OTHER INFORMATION: Synthetic

<400> SEQUENCE: 78
tctaaataag tttcccgccg taattgcgtc tattcattcg                              40

<210> SEQ ID NO 79
<211> LENGTH: 40
```

```
<212> TYPE: DNA
<213> ORGANISM: Artificial sequence
<220> FEATURE:
<223> OTHER INFORMATION: Synthetic

<400> SEQUENCE: 79
tctaaataag tttaccactg taatcccgtc aacttattag                          40

<210> SEQ ID NO 80
<211> LENGTH: 40
<212> TYPE: DNA
<213> ORGANISM: Artificial sequence
<220> FEATURE:
<223> OTHER INFORMATION: Synthetic

<400> SEQUENCE: 80
tctagagatg tttaccactg taatggcgtc tagccatgct                          40

<210> SEQ ID NO 81
<211> LENGTH: 40
<212> TYPE: DNA
<213> ORGANISM: Artificial sequence
<220> FEATURE:
<223> OTHER INFORMATION: Synthetic

<400> SEQUENCE: 81
tctagagatg tttaccactg taatcccgtc tagtcatacg                          40

<210> SEQ ID NO 82
<211> LENGTH: 40
<212> TYPE: DNA
<213> ORGANISM: Artificial sequence
<220> FEATURE:
<223> OTHER INFORMATION: Synthetic

<400> SEQUENCE: 82
tctagagatg tttaccactg taatcccgtc tagtcatgcg                          40

<210> SEQ ID NO 83
<211> LENGTH: 40
<212> TYPE: DNA
<213> ORGANISM: Artificial sequence
<220> FEATURE:
<223> OTHER INFORMATION: Synthetic

<400> SEQUENCE: 83
cctgaataag gctctcgccg gaattgcgcc aacttatgag                          40

<210> SEQ ID NO 84
<211> LENGTH: 40
<212> TYPE: DNA
<213> ORGANISM: Artificial sequence
<220> FEATURE:
<223> OTHER INFORMATION: Synthetic

<400> SEQUENCE: 84
cctgaataag gctctcgccg gaattgcgcc tagccatgct                          40

<210> SEQ ID NO 85
<211> LENGTH: 40
<212> TYPE: DNA
<213> ORGANISM: Artificial sequence
<220> FEATURE:
<223> OTHER INFORMATION: Synthetic

<400> SEQUENCE: 85
```

-continued tccaaatgag ttccccgcct taactgcatc tagccatgct          40

<210> SEQ ID NO 86
<211> LENGTH: 40
<212> TYPE: DNA
<213> ORGANISM: Artificial sequence
<220> FEATURE:
<223> OTHER INFORMATION: Synthetic

<400> SEQUENCE: 86
tttaaataag tttccagccg tcattgtgta tggtcgtgcg          40

<210> SEQ ID NO 87
<211> LENGTH: 40
<212> TYPE: DNA
<213> ORGANISM: Artificial sequence
<220> FEATURE:
<223> OTHER INFORMATION: Synthetic

<400> SEQUENCE: 87
tttaaataag tttccagccg tcattgtgta tagccatgct          40

<210> SEQ ID NO 88
<211> LENGTH: 40
<212> TYPE: DNA
<213> ORGANISM: Artificial sequence
<220> FEATURE:
<223> OTHER INFORMATION: Synthetic

<400> SEQUENCE: 88
tttaaataag tttccagccg tcattgtgta tagtcatgcg          40

<210> SEQ ID NO 89
<211> LENGTH: 40
<212> TYPE: DNA
<213> ORGANISM: Artificial sequence
<220> FEATURE:
<223> OTHER INFORMATION: Synthetic

<400> SEQUENCE: 89
tctaagtaaa tttcccgtcg tagttgcgtc aagttatgag          40

<210> SEQ ID NO 90
<211> LENGTH: 40
<212> TYPE: DNA
<213> ORGANISM: Artificial sequence
<220> FEATURE:
<223> OTHER INFORMATION: Synthetic

<400> SEQUENCE: 90
tctaagtaaa tttcccgtcg tagttgcgtc tggtcgtgcg          40

<210> SEQ ID NO 91
<211> LENGTH: 40
<212> TYPE: DNA
<213> ORGANISM: Artificial sequence
<220> FEATURE:
<223> OTHER INFORMATION: Synthetic

<400> SEQUENCE: 91
tctaagtaaa tttcccgtcg tagttgcgtc taaccatgct          40

<210> SEQ ID NO 92
<211> LENGTH: 40
<212> TYPE: DNA
<213> ORGANISM: Artificial sequence

```
<220> FEATURE:
<223> OTHER INFORMATION: Synthetic

<400> SEQUENCE: 92
tctaagtaaa tttcccgtcg tagttgcgtc tagtcatgcg                              40

<210> SEQ ID NO 93
<211> LENGTH: 40
<212> TYPE: DNA
<213> ORGANISM: Artificial sequence
<220> FEATURE:
<223> OTHER INFORMATION: Synthetic

<400> SEQUENCE: 93
tctaagtaaa tttcccgtcg tagttgcgtc tagtcaagcg                              40

<210> SEQ ID NO 94
<211> LENGTH: 40
<212> TYPE: DNA
<213> ORGANISM: Artificial sequence
<220> FEATURE:
<223> OTHER INFORMATION: Synthetic

<400> SEQUENCE: 94
tctaaataag tttcccgccg taattgcgtc tggtcgtgcg                              40

<210> SEQ ID NO 95
<211> LENGTH: 40
<212> TYPE: DNA
<213> ORGANISM: Artificial sequence
<220> FEATURE:
<223> OTHER INFORMATION: Synthetic

<400> SEQUENCE: 95
tctaaataag tttcccgccg taattgcgtc tggccatgct                              40

<210> SEQ ID NO 96
<211> LENGTH: 40
<212> TYPE: DNA
<213> ORGANISM: Artificial sequence
<220> FEATURE:
<223> OTHER INFORMATION: Synthetic

<400> SEQUENCE: 96
tctaaataag tttcccgccg taattgcgtc tagtcatacg                              40

<210> SEQ ID NO 97
<211> LENGTH: 30
<212> TYPE: DNA
<213> ORGANISM: Artificial sequence
<220> FEATURE:
<223> OTHER INFORMATION: Synthetic

<400> SEQUENCE: 97
tctagagatg tttaccactg taatcccgtc                                         30

<210> SEQ ID NO 98
<211> LENGTH: 30
<212> TYPE: DNA
<213> ORGANISM: Artificial sequence
<220> FEATURE:
<223> OTHER INFORMATION: Synthetic

<400> SEQUENCE: 98
cctgaataag gctctcgccg gaattgcgcc                                         30
```

<210> SEQ ID NO 99
<211> LENGTH: 30
<212> TYPE: DNA
<213> ORGANISM: Artificial sequence
<220> FEATURE:
<223> OTHER INFORMATION: Synthetic

<400> SEQUENCE: 99
tccaaatgag ttccccgcct taactgcatc                                    30

<210> SEQ ID NO 100
<211> LENGTH: 30
<212> TYPE: DNA
<213> ORGANISM: Artificial sequence
<220> FEATURE:
<223> OTHER INFORMATION: Synthetic

<400> SEQUENCE: 100
tttaaataag tttccagccg tcattgtgta                                    30

<210> SEQ ID NO 101
<211> LENGTH: 30
<212> TYPE: DNA
<213> ORGANISM: Artificial sequence
<220> FEATURE:
<223> OTHER INFORMATION: Synthetic

<400> SEQUENCE: 101
tctaagtaaa tttcccgtcg tagttgcgtc                                    30

<210> SEQ ID NO 102
<211> LENGTH: 30
<212> TYPE: DNA
<213> ORGANISM: Artificial sequence
<220> FEATURE:
<223> OTHER INFORMATION: Synthetic

<400> SEQUENCE: 102
tctaaataag tttcccgccg taattgcgtc                                    30

<210> SEQ ID NO 103
<211> LENGTH: 10
<212> TYPE: DNA
<213> ORGANISM: Artificial sequence
<220> FEATURE:
<223> OTHER INFORMATION: Synthetic

<400> SEQUENCE: 103
aagttatgag                                                          10

<210> SEQ ID NO 104
<211> LENGTH: 10
<212> TYPE: DNA
<213> ORGANISM: Artificial sequence
<220> FEATURE:
<223> OTHER INFORMATION: Synthetic

<400> SEQUENCE: 104
tagccatgct                                                          10

<210> SEQ ID NO 105
<211> LENGTH: 10
<212> TYPE: DNA
<213> ORGANISM: Artificial sequence
<220> FEATURE:
<223> OTHER INFORMATION: Synthetic

```
<400> SEQUENCE: 105
tggtcgtgcg                                                                  10

<210> SEQ ID NO 106
<211> LENGTH: 10
<212> TYPE: DNA
<213> ORGANISM: Artificial sequence
<220> FEATURE:
<223> OTHER INFORMATION: Synthetic

<400> SEQUENCE: 106
tagtcatgcg                                                                  10

<210> SEQ ID NO 107
<211> LENGTH: 40
<212> TYPE: DNA
<213> ORGANISM: Artificial sequence
<220> FEATURE:
<223> OTHER INFORMATION: Synthetic

<400> SEQUENCE: 107
hcthahtaah hhtchcghcg hahttgcghc thghchtgch                                 40

<210> SEQ ID NO 108
<211> LENGTH: 40
<212> TYPE: DNA
<213> ORGANISM: Artificial sequence
<220> FEATURE:
<223> OTHER INFORMATION: Artificial

<400> SEQUENCE: 108
tctagagatg tttaccactg taatcccgtc aagttatgag                                 40

<210> SEQ ID NO 109
<211> LENGTH: 40
<212> TYPE: DNA
<213> ORGANISM: Artificial sequence
<220> FEATURE:
<223> OTHER INFORMATION: Synthetic

<400> SEQUENCE: 109
hcthhahahg hhthhchchg haathhcghc hhgthhtghg                                 40

<210> SEQ ID NO 110
<211> LENGTH: 40
<212> TYPE: DNA
<213> ORGANISM: Artificial sequence
<220> FEATURE:
<223> OTHER INFORMATION: Synthetic

<400> SEQUENCE: 110
tctahhhahh ttthcchhhg tahthhcgtc haghhatghh                                 40

<210> SEQ ID NO 111
<211> LENGTH: 40
<212> TYPE: DNA
<213> ORGANISM: Artificial sequence
<220> FEATURE:
<223> OTHER INFORMATION: Synthetic

<400> SEQUENCE: 111
cctgaataag gctctcgccg gaattgcgcc tggtcgtgcg                                 40

<210> SEQ ID NO 112
```

-continued

```
<211> LENGTH: 40
<212> TYPE: DNA
<213> ORGANISM: Artificial sequence
<220> FEATURE:
<223> OTHER INFORMATION: Synthetic

<400> SEQUENCE: 112
tctahahahg ttthcchchg taathhcgtc hagthatghg                               40

<210> SEQ ID NO 113
<211> LENGTH: 40
<212> TYPE: DNA
<213> ORGANISM: Artificial sequence
<220> FEATURE:
<223> OTHER INFORMATION: Synthetic

<400> SEQUENCE: 113
thhaaathag tthcchgcch thahtghhth tagtcahgcg                               40

<210> SEQ ID NO 114
<211> LENGTH: 40
<212> TYPE: DNA
<213> ORGANISM: Artificial sequence
<220> FEATURE:
<223> OTHER INFORMATION: Synthetic

<400> SEQUENCE: 114
tctaahtaah tttcccghcg tahttgcgtc taghcatgch                               40

<210> SEQ ID NO 115
<211> LENGTH: 40
<212> TYPE: DNA
<213> ORGANISM: Artificial sequence
<220> FEATURE:
<223> OTHER INFORMATION: Synthetic

<400> SEQUENCE: 115
hcthaataag hhtchcgccg haattgcghc thgtchthcg                               40

<210> SEQ ID NO 116
<211> LENGTH: 40
<212> TYPE: DNA
<213> ORGANISM: Artificial sequence
<220> FEATURE:
<223> OTHER INFORMATION: Synthetic

<400> SEQUENCE: 116
hcthaataag hhtchcgccg haattgcghc thgtchtgcg                               40

<210> SEQ ID NO 117
<211> LENGTH: 40
<212> TYPE: DNA
<213> ORGANISM: Artificial sequence
<220> FEATURE:
<223> OTHER INFORMATION: Synthetic

<400> SEQUENCE: 117
thtaahtaah tttcchghcg thhttghgth tahhcatgch                               40

<210> SEQ ID NO 118
<211> LENGTH: 40
<212> TYPE: DNA
<213> ORGANISM: Artificial sequence
<220> FEATURE:
<223> OTHER INFORMATION: Synthetic

<400> SEQUENCE: 118
```
tchaahthah tthcccghch tahhthchtc taghcahgch            40

<210> SEQ ID NO 119
<211> LENGTH: 40
<212> TYPE: DNA
<213> ORGANISM: Artificial sequence
<220> FEATURE:
<223> OTHER INFORMATION: Synthetic

<400> SEQUENCE: 119
tctaaataag tttcccgccg taattgcgtc tagtcathcg            40

<210> SEQ ID NO 120
<211> LENGTH: 40
<212> TYPE: DNA
<213> ORGANISM: Artificial sequence
<220> FEATURE:
<223> OTHER INFORMATION: Synthetic

<400> SEQUENCE: 120
tttaaataag tttccagccg tcattgtgta tagtcatgcg            40

<210> SEQ ID NO 121
<211> LENGTH: 40
<212> TYPE: DNA
<213> ORGANISM: Artificial sequence
<220> FEATURE:
<223> OTHER INFORMATION: Synthetic

<400> SEQUENCE: 121
thtaahtaah tttcchghcg thhttghgth taghcatgch            40

<210> SEQ ID NO 122
<211> LENGTH: 40
<212> TYPE: DNA
<213> ORGANISM: Artificial sequence
<220> FEATURE:
<223> OTHER INFORMATION: Synthetic

<400> SEQUENCE: 122
tctaagtaaa tttcccgtcg tagttgcgtc tahccatgct            40

<210> SEQ ID NO 123
<211> LENGTH: 40
<212> TYPE: DNA
<213> ORGANISM: Artificial sequence
<220> FEATURE:
<223> OTHER INFORMATION: Synthetic

<400> SEQUENCE: 123
tctaagtaaa tttcccgtcg tagttgcgtc taaccatgct            40

<210> SEQ ID NO 124
<211> LENGTH: 40
<212> TYPE: DNA
<213> ORGANISM: Artificial sequence
<220> FEATURE:
<223> OTHER INFORMATION: Synthetic

<400> SEQUENCE: 124
tctaahtaah tttcccghcg tahttgcgtc taghcathch            40

<210> SEQ ID NO 125
<211> LENGTH: 40
<212> TYPE: DNA

<213> ORGANISM: Artificial sequence
<220> FEATURE:
<223> OTHER INFORMATION: Synthetic

<400> SEQUENCE: 125
cctggagatg gctatcactg gaatcccgcc aggttgtgag         40

<210> SEQ ID NO 126
<211> LENGTH: 40
<212> TYPE: DNA
<213> ORGANISM: Artificial sequence
<220> FEATURE:
<223> OTHER INFORMATION: Synthetic

<400> SEQUENCE: 126
tctagggata tttaccattg tagtcccgtc aagctatgat         40

<210> SEQ ID NO 127
<211> LENGTH: 40
<212> TYPE: DNA
<213> ORGANISM: Artificial sequence
<220> FEATURE:
<223> OTHER INFORMATION: Synthetic

<400> SEQUENCE: 127
cctgagtaaa gctctcgtcg gagttgcgcc tggccgtgct         40

<210> SEQ ID NO 128
<211> LENGTH: 40
<212> TYPE: DNA
<213> ORGANISM: Artificial sequence
<220> FEATURE:
<223> OTHER INFORMATION: Synthetic

<400> SEQUENCE: 128
cctgaataag gctctcgccg gaattgcgcc tggtcgtacg         40

<210> SEQ ID NO 129
<211> LENGTH: 40
<212> TYPE: DNA
<213> ORGANISM: Artificial sequence
<220> FEATURE:
<223> OTHER INFORMATION: Synthetic

<400> SEQUENCE: 129
tccaagtgaa ttccccgtct tagctgcatc tagccaagct         40

<210> SEQ ID NO 130
<211> LENGTH: 40
<212> TYPE: DNA
<213> ORGANISM: Artificial sequence
<220> FEATURE:
<223> OTHER INFORMATION: Synthetic

<400> SEQUENCE: 130
ttcaaatgag ttcccagcct tcactgtata tagtcaagcg         40

<210> SEQ ID NO 131
<211> LENGTH: 40
<212> TYPE: DNA
<213> ORGANISM: Artificial sequence
<220> FEATURE:
<223> OTHER INFORMATION: Synthetic

<400> SEQUENCE: 131
tttaagtaaa tttccagtcg tcgttgtgta taaccatgct         40

<210> SEQ ID NO 132
<211> LENGTH: 40
<212> TYPE: DNA
<213> ORGANISM: Artificial sequence
<220> FEATURE:
<223> OTHER INFORMATION: Synthetic

<400> SEQUENCE: 132
tttaagtaaa tttccagtcg tcgttgtgta tagccatgct                    40

<210> SEQ ID NO 133
<211> LENGTH: 40
<212> TYPE: DNA
<213> ORGANISM: Artificial sequence
<220> FEATURE:
<223> OTHER INFORMATION: Synthetic

<400> SEQUENCE: 133
tctaagtaaa tttcccgtcg tagttgcgtc tagccatact                    40

<210> SEQ ID NO 134
<211> LENGTH: 40
<212> TYPE: DNA
<213> ORGANISM: Artificial sequence
<220> FEATURE:
<223> OTHER INFORMATION: Synthetic

<400> SEQUENCE: 134
atctcgaatt gtcagcagcg caacctagaa attattgcag                    40

<210> SEQ ID NO 135
<211> LENGTH: 40
<212> TYPE: DNA
<213> ORGANISM: Artificial sequence
<220> FEATURE:
<223> OTHER INFORMATION: Synthetic

<400> SEQUENCE: 135
hccttgghta htccgcghtg aahghthgta htcachgcgg                    40

<210> SEQ ID NO 136
<211> LENGTH: 40
<212> TYPE: DNA
<213> ORGANISM: Artificial sequence
<220> FEATURE:
<223> OTHER INFORMATION: Synthetic

<400> SEQUENCE: 136
ahctcgaaht gtchhcagch haacctahaa athatthcag                    40

<210> SEQ ID NO 137
<211> LENGTH: 40
<212> TYPE: DNA
<213> ORGANISM: Artificial sequence
<220> FEATURE:
<223> OTHER INFORMATION: Synthetic

<400> SEQUENCE: 137
hhhthghhth gtchghhghg hahhhtagha hhhahghhg                     40

<210> SEQ ID NO 138
<211> LENGTH: 40
<212> TYPE: DNA
<213> ORGANISM: Artificial sequence
<220> FEATURE:

<223> OTHER INFORMATION: Synthetic

<400> SEQUENCE: 138
accttggata gtccgcggtg aaagctagta atcactgcgg                                40

<210> SEQ ID NO 139
<211> LENGTH: 40
<212> TYPE: DNA
<213> ORGANISM: Artificial sequence
<220> FEATURE:
<223> OTHER INFORMATION: Synthetic

<400> SEQUENCE: 139
acchhhhahh ghhchchghh ahahchahhh atchhthchh                                40

<210> SEQ ID NO 140
<211> LENGTH: 40
<212> TYPE: DNA
<213> ORGANISM: Artificial sequence
<220> FEATURE:
<223> OTHER INFORMATION: Synthetic

<400> SEQUENCE: 140
cchttgggta htccghghtg aaggathgta ghcacaghgg                                40

<210> SEQ ID NO 141
<211> LENGTH: 40
<212> TYPE: DNA
<213> ORGANISM: Artificial sequence
<220> FEATURE:
<223> OTHER INFORMATION: Synthetic

<400> SEQUENCE: 141
hchthghhhh gtcchhhghh aahhhtahha hhcahhhhg                                 40

<210> SEQ ID NO 142
<211> LENGTH: 40
<212> TYPE: DNA
<213> ORGANISM: Artificial sequence
<220> FEATURE:
<223> OTHER INFORMATION: Synthetic

<400> SEQUENCE: 142
cccttgggta atccgcgatg aaggatggta gtcacagcgg                                40

<210> SEQ ID NO 143
<211> LENGTH: 40
<212> TYPE: DNA
<213> ORGANISM: Artificial sequence
<220> FEATURE:
<223> OTHER INFORMATION: Synthetic

<400> SEQUENCE: 143
acchthgata ghhcgcggtg ahagchagth atchctgcgh                                40

<210> SEQ ID NO 144
<211> LENGTH: 40
<212> TYPE: DNA
<213> ORGANISM: Artificial sequence
<220> FEATURE:
<223> OTHER INFORMATION: Synthetic

<400> SEQUENCE: 144
hchttgghta gtccghggtg aahghtagta hhcachghgg                                40

```
<210> SEQ ID NO 145
<211> LENGTH: 40
<212> TYPE: DNA
<213> ORGANISM: Artificial sequence
<220> FEATURE:
<223> OTHER INFORMATION: Synthetic

<400> SEQUENCE: 145
hahhthghta ghhcghggtg ahhghhagth hhchchghgh                              40

<210> SEQ ID NO 146
<211> LENGTH: 40
<212> TYPE: DNA
<213> ORGANISM: Artificial sequence
<220> FEATURE:
<223> OTHER INFORMATION: Synthetic

<400> SEQUENCE: 146
cctttgggta gtccgtggtg aaggatagta gccacagtgg                              40

<210> SEQ ID NO 147
<211> LENGTH: 40
<212> TYPE: DNA
<213> ORGANISM: Artificial sequence
<220> FEATURE:
<223> OTHER INFORMATION: Synthetic

<400> SEQUENCE: 147
hhcthghhth htchgchhhg hahhhthgha hthahhgchg                              40

<210> SEQ ID NO 148
<211> LENGTH: 40
<212> TYPE: DNA
<213> ORGANISM: Artificial sequence
<220> FEATURE:
<223> OTHER INFORMATION: Synthetic

<400> SEQUENCE: 148
hcchthghta hhhcgcghtg ahhghhhgth htghchgcgh                              40

<210> SEQ ID NO 149
<211> LENGTH: 40
<212> TYPE: DNA
<213> ORGANISM: Artificial sequence
<220> FEATURE:
<223> OTHER INFORMATION: Synthetic

<400> SEQUENCE: 149
ahcthghath gtchgchghg haahctagha athahtgchg                              40

<210> SEQ ID NO 150
<211> LENGTH: 40
<212> TYPE: DNA
<213> ORGANISM: Artificial sequence
<220> FEATURE:
<223> OTHER INFORMATION: Synthetic

<400> SEQUENCE: 150
atctcgaatt gtcagcagcg caacctagaa attattgcag                              40

<210> SEQ ID NO 151
<211> LENGTH: 40
<212> TYPE: DNA
<213> ORGANISM: Artificial sequence
<220> FEATURE:
<223> OTHER INFORMATION: Synthetic
```

```
<400> SEQUENCE: 151
acctcgaatt gtccgcagcg aaacctagaa atcattgcag                              40

<210> SEQ ID NO 152
<211> LENGTH: 40
<212> TYPE: DNA
<213> ORGANISM: Artificial sequence
<220> FEATURE:
<223> OTHER INFORMATION: Synthetic

<400> SEQUENCE: 152
cctttgggta gtccgtggtg aaggatagta gccacagtgg                              40

<210> SEQ ID NO 153
<211> LENGTH: 40
<212> TYPE: DNA
<213> ORGANISM: Artificial sequence
<220> FEATURE:
<223> OTHER INFORMATION: Synthetic

<400> SEQUENCE: 153
cccttgggta atccgcgatg aaggatggta gtcacagcgg                              40

<210> SEQ ID NO 154
<211> LENGTH: 40
<212> TYPE: DNA
<213> ORGANISM: Artificial sequence
<220> FEATURE:
<223> OTHER INFORMATION: Synthetic

<400> SEQUENCE: 154
cccttgggta gtccgcggtg aaggatagta gtcacagcgg                              40

<210> SEQ ID NO 155
<211> LENGTH: 40
<212> TYPE: DNA
<213> ORGANISM: Artificial sequence
<220> FEATURE:
<223> OTHER INFORMATION: Synthetic

<400> SEQUENCE: 155
cctgttggta gctcgtggtg agggagagtg gccgcagtgt                              40

<210> SEQ ID NO 156
<211> LENGTH: 40
<212> TYPE: DNA
<213> ORGANISM: Artificial sequence
<220> FEATURE:
<223> OTHER INFORMATION: Synthetic

<400> SEQUENCE: 156
cccgttggta actcgcgatg agggagggtg gtcgcagcgt                              40

<210> SEQ ID NO 157
<211> LENGTH: 40
<212> TYPE: DNA
<213> ORGANISM: Artificial sequence
<220> FEATURE:
<223> OTHER INFORMATION: Synthetic

<400> SEQUENCE: 157
accgttgata gctcgcggtg agagcgagtg atcgctgcgt                              40

<210> SEQ ID NO 158
<211> LENGTH: 40
```

```
<212> TYPE: DNA
<213> ORGANISM: Artificial sequence
<220> FEATURE:
<223> OTHER INFORMATION: Synthetic

<400> SEQUENCE: 158
accgctaagt gctcacagca agaccgaaag atcgttacat                              40

<210> SEQ ID NO 159
<211> LENGTH: 40
<212> TYPE: DNA
<213> ORGANISM: Artificial sequence
<220> FEATURE:
<223> OTHER INFORMATION: Synthetic

<400> SEQUENCE: 159
ccttcgaggt gtccatagca aagcstssss gccstsstsg                              40

<210> SEQ ID NO 160
<211> LENGTH: 40
<212> TYPE: DNA
<213> ORGANISM: Artificial sequence
<220> FEATURE:
<223> OTHER INFORMATION: Synthetic

<400> SEQUENCE: 160
ctctcgagtt agcagcaacg cagcatggaa gttatagcag                              40

<210> SEQ ID NO 161
<211> LENGTH: 40
<212> TYPE: DNA
<213> ORGANISM: Artificial sequence
<220> FEATURE:
<223> OTHER INFORMATION: Synthetic

<400> SEQUENCE: 161
ctttcgagtt gtcagtagcg cagcatagaa gctatagtag                              40

<210> SEQ ID NO 162
<211> LENGTH: 40
<212> TYPE: DNA
<213> ORGANISM: Artificial sequence
<220> FEATURE:
<223> OTHER INFORMATION: Synthetic

<400> SEQUENCE: 162
atctcgaagt gtcaacagca caacctaaaa attattacag                              40

<210> SEQ ID NO 163
<211> LENGTH: 40
<212> TYPE: DNA
<213> ORGANISM: Artificial sequence
<220> FEATURE:
<223> OTHER INFORMATION: Synthetic

<400> SEQUENCE: 163
atctcgaatt gtcagcagcg caacctagaa attattgcag                              40

<210> SEQ ID NO 164
<211> LENGTH: 40
<212> TYPE: DNA
<213> ORGANISM: Artificial sequence
<220> FEATURE:
<223> OTHER INFORMATION: Synthetic

<400> SEQUENCE: 164
```

-continued

```
<210> SEQ ID NO 165
<211> LENGTH: 40
<212> TYPE: DNA
<213> ORGANISM: Artificial sequence
<220> FEATURE:
<223> OTHER INFORMATION: Synthetic

<400> SEQUENCE: 165
cctttgggta gtccgtggtg aaggatagta gccacagtgg                           40

<210> SEQ ID NO 166
<211> LENGTH: 40
<212> TYPE: DNA
<213> ORGANISM: Artificial sequence
<220> FEATURE:
<223> OTHER INFORMATION: Synthetic

<400> SEQUENCE: 166
cccttgggta atccgcgatg aaggatggta gtcacagcgg                           40

<210> SEQ ID NO 167
<211> LENGTH: 40
<212> TYPE: DNA
<213> ORGANISM: Artificial sequence
<220> FEATURE:
<223> OTHER INFORMATION: Synthetic

<400> SEQUENCE: 167
acctcgaagt gtccacagca aaacctaaaa atcattacag                           40
```

GENETIC DIAGNOSIS USING MULTIPLE SEQUENCE VARIANT ANALYSIS

The present application is a continuation-in part of U.S. application Ser. Nos. 10/788,260 and 10/788,043, now abandoned which were filed on Feb. 26, 2004, and claims the benefit of priority of European Patent Application No. 03447042.7, which was filed Feb. 27, 2003. Each of the aforementioned applications is incorporated herein by reference in its entirety.

FIELD OF INVENTION

The present invention is in the field of nucleic acid-based genetic analysis. More particularly, it discloses novel insights into the overall structure of genetic variation in all living species.

BACKGROUND OF THE INVENTION

Variation in the human genome sequence is an important determinative factor in the etiology of many common medical conditions. Heterozygosity in the human population is attributable to common variants of a given genetic sequence, and those skilled in the art have sought to comprehensively identify common genetic variations and to link such variations to medical conditions [Lander, Science 274:536, 1996; Collins et al., Science 278:1580, 1997; Risch, Science 273:1516, 1996]. Recently, it has been estimated that 4 million [Sachidanandam et al., Nature 409:928 [2001]; Venter et al., Science 291: 1304, 2001] of the estimated 10 million [Kruglyak, Nature Genet 27:234, 2001] common single nucleotide polymorphisms (SNPs) are already known. These developments in the field of DNA sequence analysis therefore are providing a rapid accumulation of partially and completely sequenced genomes. The next challenge involves obtaining an inventory of sequence variations (genetic polymorphisms) found in population samples, and using that information to unravel the genetic basis of the phenotypic variation observed among the individuals of that population. Ideally, such analyses would directly reveal the causative genetic variants that biochemically determine the phenotype.

In practice, the identification of loci/polymorphisms that have important phenotypic effects involves searching through a large set of sequence variations to find surrogate markers that are statistically associated with the phenotypic differences through linkage disequilibrium (LD) with variation(s) (at other sites) that are directly causative. LD is the non-random association of alleles at adjacent polymorphisms. When a particular allele at one site, is found to be co-inherited with a specific allele at a second site—more often than expected if the sites were segregating independently in the population—the loci are in disequilibrium. LD has recently become the focus of intense study in the belief that it might offer a shortcut to the mapping of functionally important loci through whole-genome association studies.

Unfortunately, LD is not a simple function of distance and the patterns of genetic polymorphisms, shaped by the various genomic processes and demographic events, appear complex. Gene-mapping studies critically depend on knowledge of the extent and spatial structure of LD because the number of genetic markers should be kept as small as possible so that such studies can be applied in large cohorts at an affordable cost. Thus, an important analytical challenge is to identify the minimal set of SNPs with maximum total relevant information and to balance any reduction in the variation that is examined against the potential reduction in utility/efficiency of the genome-wide survey. Any SNP selection algorithm that is ultimately used should also account for the cost and difficulty of designing an assay for a given SNP on a given platform—a particular SNP may be the most informative in a region but it may also be difficult to measure.

Except for the human species, SNPs have thus far not been surveyed extensively in many other systems. One study [Tenaillon et al., Proc. Natl. Acad. Sci. USA 98: 9161-9166, 2001] investigated the sequence diversity in 21 loci distributed along chromosome 1 of maize (Zea mays ssp. mays L.). The sample consisted of 25 individuals representing 16 exotic landraces and nine U.S. inbred lines. The first and most apparent conclusion from this study is that maize is very diverse, containing on average one SNP every 28 bp in the sample. This is a level of diversity higher than that of either humans or Drosophila melanogaster. A second major conclusion from the study was that extended regions of high LD may be uncommon in maize and that genome-wide surveys for association analyses in maize require marker densities of one SNP every 100 to 200 bp.

Multi-SNP haplotypes have been proposed as more efficient and informative genetic markers than individual SNPs [Judson et al., Pharmacogenomics 1: 15-26, 2000; Judson et al;, Pharmacogenomics 3: 379-391, 2002; Stephens et al., Science 293: 489-493, 2001; Drysdale et al., Proc. Natl. Acad. Sci. USA 97: 10483-10488, 2000; Johnson et al., Nat. Genet. 29: 233-237, 2001]. Haplotypes capture the organization of variation in the genome and provide a record of a population's genetic history. Therefore, disequilibrium tests based on haplotypes have greater power than single markers to track an unobserved, but evolutionary linked, variable site.

Recent studies in human genetics [Daly et al., Nat. Genet. 29: 229-232, 2001; Daly et al., patent application US 2003/0170665 A1; Patil et al., Science 294: 1719-1723, 2001; Gabriel et al., Science 296: 2225-2229, 2002; Dawson et al., Nature 418: 544-548, 2002; Philips et al., Nat. Genet. 33: 382-387, 2003; reviewed by Wall & Pritchard, Nature Rev. Genet. 4: 587-597, 2003] have shown that at least part of the genome can be parsed into blocks: sizeable regions over which there is little evidence for recombination and within which only a few common haplotypes are observed, i.e. the sequence variants observed in a block often appear in the same allelic combinations in the majority of individuals. The major attraction of the 'haplotype block' model is that it may simplify the analysis of genetic variation across a genomic region—the idea is that a limited number of common haplotypes capture most of the genetic variation across sizeable regions and that these prevalent haplotypes (and the undiscovered variants contained in these haplotypes) can be diagnosed with the use of a small number of 'haplotype tag' SNPs (htSNPs). The 'haplotype block' concept has fuelled the International HapMap Project [http://www.hapmap.org; Dennis C., Nature 425: 758-759 (2003)]. So far, the haplotype block structure has only been investigated in humans.

Others have reported that a large proportion (75-85%) of the human and Drosophila melanogaster genomes are spanned by so-called "yin-yang haplotypes", i.e. a pair of high-frequency haplotypes that are completely opposed in that they differ at every SNP [Zhang et al., Am. J. Hum. Genet. 73: 1073-1081, 2003].

Most recently, Carlson and coworkers [Carlson et al., Am. J. Hum. Genet. 74: 106-120, 2004] developed an algorithm to select the maximally informative subset of SNPs (referred to as tagSNPs) for assay in association studies. The selection algorithm is based on the pattern of LD rather than the 'haplotype block' concept. It makes use of the $r^2$ LD statistic to group SNPs as a bin of associated sites. Within the bin any SNP that exceeds an adequately stringent $r^2$ threshold with all other sites in the bin may serve as a tagSNP, and only one tagSNP needs to be genotyped per bin. SNPs that do not exceed the threshold with any other SNP in the region under study are placed in singleton bins.

The determination of haplotypes from diploid unrelated individuals, heterozygous at multiple loci, is difficult. Conventional genotyping techniques do not permit determination of the phase of several different markers. For example, a genomic region with N bi-allelic SNPs can theoretically yield $2^N$ haplotypes in the case of complete equilibrium, whereas the actual number should be less than the number of SNPs in the absence of recombination events and recurrent mutations [Harding et al., Am. J. Hum. Genet. 60: 772-789, 1997; Fullerton et al., Am. J. Hum. Genet. 67: 881-900, 2000]. Large-scale studies [Stephens et al., Science 293: 489-493, 2001] indicate that the haplotype variation is slightly greater than the number of SNPs.

One approach for determining haplotypes is the use of molecular techniques to separate the two homologous genomic DNAs. DNA cloning, somatic cell hybrid construction [Douglas et al., Nat. Genet. 28: 361-364, 2001], allele-specific PCR [Ruano & Kidd, Nucl. Acids Res. 17: 8392, 1989], and single molecule PCR [Ruano et al., Proc. Natl. Acad. Sci. USA 87: 6296-6300, 1990; Ding & Cantor, Proc. Natl. Acad. Sci. USA 100: 7449-7453, 2003] have all been used. Alternatively, haplotypes may be resolved (partially) when the genotypes of first-degree relatives are available, e.g. father-mother-offspring trios [Wijsman E. M., Am. J. Hum. Genet. 41: 356-373, 1987; Daly et al., Nat. Genet. 29: 229-232, 2001].

To avoid the difficulties and cost in experimental and pedigree-based approaches, several computational algorithms have been developed to predict the phase from unrelated individuals or to estimate the population-haplotype frequencies. The approaches include Clark's parsimony method [Clark A. G., Mol. Biol. Evol. 7: 111-121, 1990], maximum likelihood methods such as the EM algorithm [Excoffier & Slatkin, Mol. Biol. Evol. 12: 921-927, 1995], methods based on Bayesian statistics such as PHASE [Stephens et al., Am. J. Hum. Genet. 68: 978-989, 2001] and HAPLOTYPER [Niu et al., Am. J. Hum. Genet. 52: 102-109, 2002], and perfect phylogeny-based methods [Bafna et al. J. Comput. Biol. 10: 323-340, 2003]. These probabilistic methods all have limitations in accuracy (dependent on the number of SNPs being handled and the size of the population being examined) and scalability.

A number of recent empirical studies [supra] have greatly augmented the knowledge of the overall structure of genetic variation. It should be noted, however, that for example the haplotype block concept remains to be validated, that not all regions of the human genome may fit the concept and/or that the concept may have limited value in other species. Irrespective of the outcome, the complexities of genetic variation data are such that the art would greatly benefit from novel breakthroughs that advance the understanding of the organization of a population's genetic variation, which would eventually lead to the identification/development of the most informative markers. Discoveries about the structure of genetic variations would be useful in different areas, including (i) genome-wide association studies, (ii) clinical diagnosis, (iii) plant and animal breeding, and (iv) the identification of micro-organisms.

SUMMARY OF THE INVENTION

The present invention discloses novel insights into the overall structure of genetic variation in all living species. The structure can be revealed with the use of any data set of genetic variants from a particular locus. The invention is useful to define the subset of variations that are most suited as genetic markers to search for correlations with certain phenotypic traits. Additionally, the insights are useful for the development of algorithms and computer programs that convert genotype data into the constituent haplotypes that are laborious and costly to derive in an experimental way. The invention is useful in areas such as (i) genome-wide association studies, (ii) clinical in vitro diagnosis, (iii) plant and animal breeding, (iv) the identification of micro-organisms.

The present invention is based on the recognition that patterns of genetic variation at a locus are formed by clusters of interspersed polymorphisms that exhibit strong linkage, e.g. the alleles at the polymorphic sites of each group are essentially found in only two combinations. These groups of polymorphisms are herein named Sequence Polymorphism Clusters (SPC). Certain SPCs are specific to one haplotype while others are common to several haplotypes, and thus can be used to define clades of related haplotypes. The relationship of SPCs can be represented by means of a hierarchical network. Some SPCs are found in an independent relationship with one another and occur on separate haplotypes. Other SPCs are dependent and can be ranked according to their level of inclusiveness: a dependent SPC co-occurs partially with one or more clade-specific SPCs. SPCs can be interrupted by recombination events. The number of polymorphisms in an SPC as well as its span is variable and, consequently, the set of SPCs in a genomic region of interest need not share the same boundaries.

A comprehensive catalogue of the SPCs can provide the foundation to systematically test the involvement of genetic variation in a variety of phenotypes and traits. The invention relates to methods (computer programs) of producing (building, making) an SPC map comprising a pattern of related SPCs. The SPC map can be used to identify cluster tag polymorphisms (e.g. ctSNP), which uniquely identify each SPC in an SPC map of the genomic region of interest for use in subsequent genotyping studies. An SPC map may depend on the population under study as well as on the size of the sample and should be used accordingly. All or a portion of these ctSNPs can then be used in methods to identify an association between a phenotype or trait and an SPC, to localize the position of a gene associated with the phenotype or trait, to in vitro diagnose samples for the presence of specific SPC allelic variations, and to determine the identity of samples. The SPC structure can also be used in methods (algorithms, programs) for the deconvolution of diploid genotypes into the component haplotypes and as a method for the identification of errors in a collection of genotype calls, which may require experimental verification.

Thus, in one aspect, the invention is directed to an SPC map of a region of interest of a genome or of an entire genome, comprising a pattern of related SPCs across the region of interest or of the entire genomic region. In another aspect, the invention is directed to a method of producing an SPC map of a region of interest of a genome, comprising determination of the pattern of SPCs across the region of interest. As discussed in further detail below, in one embodiment, the SPC map is produced starting from haplotypes (sequence or genotyping data). In another embodiment, the SPC map is produced starting from unphased diploid genotype data. In a still a further alternative embodiment, the SPC map is produced starting from uncharacterized allelic variation data. In a specific embodiment, the uncharacterized allelic variation data are obtained by hybridization of the region of interest or the entire genome to arrays of oligonucleotides.

Thus, the present invention is directed to a SPC map of a genomic region of interest comprising one or more sequence polymorphism clusters (SPCs), wherein each SPC comprises a subset of polymorphisms from the genomic region wherein the polymorphisms of the subset coincide with each other polymorphism of the subset. In specific embodiments, each polymorphism of the subset coincides with each other polymorphism of the subset according to a percentage coincidence of the minor alleles of the polymorphisms of between 75% and 100%. The coincidence of each polymorphism with each other polymorphism may be calculated by any convenient measure commonly used by those of skill in the art. In exemplary embodiments, such a calculation may be made according to a parameter selected from but, not limited to, the group consisting of a pairwise C value, a r2 linkage disequilibrium value, and a d linkage disequilibrium value. In particular exemplary embodiments, the parameter is a pairwise C value of from 0.75 to 1.

Also contemplated herein is a method of producing an SPC map of a genomic region of interest comprising the steps of obtaining the nucleic acid sequence of the genomic region of interest from a plurality of subjects; identifying a plurality of polymorphisms in the nucleic acid sequences; and identifying one or more SPCs, wherein each SPC comprises a subset of polymorphisms from the nucleic acid sequence wherein the polymorphisms of the subset coincide with each other polymorphism of the subset.

Another specific aspect of the invention contemplates a method of producing an SPC map of a genomic region of interest from unphased diploid genotypes comprising the steps of obtaining the unphased diploid genotypes of a genomic region of interest from a plurality of subjects; determining the major and minor metatypes found in the unphased diploid genotypes; and identifying one or more SPCs, wherein each SPC comprises a subset of polymorphisms from the metatypes wherein the polymorphisms of the subset coincide with each other polymorphism of the subset.

In the methods of producing the maps of the present invention, it is contemplated that the identification of the one or more SPCs comprises identifying each. polymorphism of the subset that coincides with each other polymorphism of the subset according to a percentage coincidence of the minor alleles of the polymorphisms of between 75% and 100%. In particular embodiments, it is contemplated that it may, but need not necessarily, be required to identify the one or more SPCs through multiple rounds of coincidence analysis. It may be that in such an iterative process, each successive round of coincidence analysis is performed at a decreasing percentage coincidence from 100% coincidence to 75% coincidence. Typically, in the methods the coincidence of each the polymorphism of the subset with each other polymorphism of the subset is calculated according to a parameter selected from the group consisting of a pairwise C value, a r2 linkage disequilibrium value, and a d linkage disequilibrium value. In specific embodiments, the parameter is a pairwise C value of from 0.75 to 1.

The polymorphisms identified for use in the producing the SPC maps of the invention may be identified using any method conventionally employed to identify polymorphisms and sequence variations. For example, the identification of a plurality of polymorphisms in the target nucleic acid sequences may be determined by an assay selected from, but not limited to, the group consisting of direct sequence analysis, differential nucleic acid analysis, sequence based genotyping DNA chip analysis, and PCR analysis.

A further aspect of the invention includes a method of selecting one or more polymorphisms from a genomic region of interest for use in genotyping, comprising the steps of obtaining an SPC map as described herein, selecting at least one cluster tag polymorphism which identifies a unique SPC in the SPC map; and selecting a sufficient number of cluster tag polymorphisms for use in a genotyping study of the genomic region of interest. In specific embodiments, the cluster tag polymorphism is selected from the group consisting of a single nucleotide polymorphism (SNP), a deletion polymorphism, an insertion polymorphism; and a short tandem repeat polymorphism (STR). In particularly preferred embodiments, the cluster tag polymorphism is a known SNP associated with the trait.

The present invention further provides a teaching of a method of identifying a marker for a trait or phenotype comprising obtaining a sufficient number of cluster tag polymorphisms as described above; and assessing the cluster tag polymorphisms to identify an association between a trait or phenotype and at least one cluster tag polymorphism, wherein identification of the association identifies the cluster tag polymorphism as a marker for the trait or phenotype. More particularly, it is preferred that the cluster tag polymorphism is correlated with a trait or phenotype selected from the group comprising a genetic disorder, a predisposition to a genetic disorder, susceptibility to a disease, an agronomic or livestock performance trait, a product quality trait. More specifically, the marker is preferably a marker of a genetic disorder and the SPC map is prepared by obtaining the nucleic acid sequence of the genomic region of interest from a plurality of subjects that each manifests the same genetic disorder; identifying a plurality of polymorphisms in the nucleic acid sequences; and identifying one or more SPCs, wherein each SPC comprises a subset of polymorphisms from the nucleic acid sequence wherein the polymorphisms of the subset coincide with each other polymorphism of the subset. Preferably in these methods the identification of a plurality of polymorphisms in the target nucleic acid sequences is determined by an assay selected from the group consisting of direct sequence analysis, differential nucleic acid analysis, sequence based genotyping, DNA chip analysis and polymerase chain reaction analysis.

Also provided herein is a method of identifying the location of a gene associated with a trait or phenotype comprising identifying a plurality of SPCs identified in a given genomic region associated with the phenotype, wherein each SPC comprises a subset of polymorphisms from the genomic region of interest wherein the polymorphisms of the subset are associated with each other polymorphism of the subset; identifying a set of cluster tag polymorphisms wherein each member of the set of cluster tag polymorphisms identifies a unique SPC in said plurality of SPCs; and assessing the set of cluster tag polymorphisms to identify an association between a trait or phenotype and at least one cluster tag polymorphism, wherein identification of the association between the cluster tag polymorphism and the trait or phenotype is indicative of the location of the gene. More specifically, the trait or phenotype is selected from the group comprising a genetic disorder, a predisposition to a genetic disorder, susceptibility to a disease, an agronomic or livestock performance trait, a product quality trait, or any other trait that may be determined in a genetic analysis.

The present application also contemplates a method for in vitro diagnosis of a trait or a phenotype in a subject comprising obtaining a marker for the trait or phenotype as outlined above; obtaining a target nucleic acid sample from the subject; and determining the presence of the marker for the trait or a phenotype in the target nucleic acid sample, wherein the presence of the marker in the target nucleic acid indicates that the subject has the trait or the phenotype.

Another aspect of the invention is directed to a method of determining the genetic identity of a subject comprising obtaining a reference SPC map of one or more genomic regions from a plurality of subjects; selecting a sufficient number of cluster tag polymorphisms for the genomic regions as described herein; obtaining a target nucleic acid of the genomic regions from a subject to be identified; determining the genotype of the cluster tag polymorphisms of the genomic regions of the subject to be identified; and comparing the genotype of the cluster tag polymorphism with the SPC to determine the genetic identity of the subject of interest.

Yet a further embodiment of the present application is directed to a method method of determining the SPC-haplotypes from unphased diploid genotype of a genomic region of interest of a subject, comprising obtaining an SPC map according the methods described herein; determining the SPC-haplotypes from said SPC map, wherein each SPC-haplotype comprises a subset of SPCs from a genomic region wherein said SPCs of said subset coincide; and identifying the SPC-haplotype of a test subject by comparing the SPCs of said subject with the SPC-haplotypes determined from said SPC map.

Yet a further embodiment of the present invention comprises a method of identifying an error in a genotype comprising obtaining genotype data from a subject of interest and comparing the genotype data with a reference SPC map prepared from a plurality of individuals, wherein a difference between the genotype of the subject and the SPC map indicates an error in the genotype of the subject.

In addition to the methods of the invention, the present invention further contemplates computer programs/algorithms for performing such methods. More particularly, the present application describes an article comprising a machine-accessible medium having stored thereon instructions that, when executed by a machine, cause the machine to obtain a nucleic acid sequence information of a genomic region of interest from a plurality of subjects; identify a plurality of polymorphisms in said nucleic acid sequence; identify one or more SPCs, wherein each SPC comprises a subset of polymorphisms from said nucleic acid sequence wherein said polymorphisms of said subset coincide with each other polymorphism of said subset. In addition, the article may have further instructions that, when executed by the machine, cause the machine to identify each polymorphism of said subset that coincides with each other polymorphism of said subset according to a percentage coincidence of the minor alleles of said polymorphisms of between 75% and 100%. The article also may further have instructions that, when executed by the machine, cause the machine to perform each successive round of coincidence analysis at a decreasing percentage coincidence from 100% coincidence to 75% coincidence. Additionally, the article may have further instructions that, when executed by the machine, cause the machine to calculate the coincidence of each said polymorphism of said subset with each other polymorphism of said subset according to a parameter selected from the group consisting of a pairwise C value, C* value, a $r^2$ linkage disequilibrium value, a $\Delta$ linkage disequilibrium value, a $\delta$ linkage disequilibrium value, and a d linkage disequilibrium value.

Also part of the instant disclosure is an article comprising a machine-accessible medium having stored thereon instructions that, when executed by a machine, cause the machine to: obtain a set of unphased diploid genotypes of a genomic region of interest from a plurality of subjects; determine the major and minor metatypes found in said set of unphased diploid genotypes; identify one or more SPCs, wherein each SPC comprises a subset of polymorphisms from said metatypes wherein said polymorphisms of said subset coincide with each other polymorphism of said subset. This article may further have instructions that, when executed by the machine, cause the machine to identify each polymorphism of said subset that coincides with each other polymorphism of said subset according to a percentage coincidence of the minor alleles of said polymorphisms of between 85% and 100%. In addition, the article may further have instructions that, when executed by the machine, cause the machine to identify each polymorphism of said subset that coincides with each other polymorphism of said subset according to a percentage coincidence of the minor alleles of said polymorphisms of between 75% and 100%. In addition, the article may have further instructions that, when executed by the machine, cause the machine to identify a plurality of polymorphisms in said target nucleic acid sequences based on an assay selected from the group consisting of direct sequence analysis, differential nucleic acid analysis, sequence based genotyping DNA chip analysis, and PCR analysis.

Additionally, the invention provides an article comprising a machine-accessible medium having stored thereon instructions that, when executed by a machine, cause the machine to: obtain an SPC map of a genomic region of interest; select at least one cluster tag polymorphism which identifies a unique SPC in the SPC map; and select a sufficient number of cluster tag polymorphisms for use in a genotyping study of the genomic region of interest. Preferably, the article further may have further instructions that, when executed by the machine, cause the machine to select the cluster tag polymorphism from the group consisting of a single nucleotide polymorphism (SNP), a deletion polymorphism, an insertion polymorphism; and a short tandem repeat polymorphism (STR).

Also provided is an article comprising a machine-accessible medium having stored thereon instructions that, when executed by a machine, cause the machine to: obtain a sufficient number of cluster tag polymorphisms from a genomic region of interest for use in genotyping; assess the cluster tag polymorphisms to identify an association between a trait or phenotype and at least one cluster tag polymorphism, wherein identification of the association identifies the cluster tag polymorphism as a marker for the trait or phenotype. Such an article may further have instructions that, when executed by the machine, cause the machine to correlate a cluster tag polymorphism with a trait or phenotype selected from the group consisting of a genetic disorder, a predisposition to a genetic disorder, susceptibility to a disease, an agronomic or livestock performance trait, a product quality trait. In addition, the article may further have instructions that, when executed by the machine, cause the machine to identify the plurality of polymorphisms in the target nucleic acid sequences based on an assay selected from the group consisting of direct sequence analysis, differential nucleic acid analysis, sequence based genotyping, DNA chip analysis and polymerase chain reaction analysis.

Also provided is an article comprising a machine-accessible medium having stored thereon instructions that, when executed by a machine, cause the machine to: identify a plurality of SPCs identified in a given genomic region associated with a trait or phenotype, wherein each SPC comprises a subset of polymorphisms from the genomic region wherein the polymorphisms of the subset are associated with each other polymorphism of the subset; identify a set of cluster tag polymorphisms wherein each member of the set of cluster tag polymorphisms identifies a unique SPC in the plurality of SPCs; and assess the set of cluster tag polymorphisms to identify an association between a trait or phenotype and at least one cluster tag polymorphism, wherein identification of the association between the cluster tag polymorphism and the trait or phenotype is indicative of the location of the gene. Such an article may have further instructions that, when executed by the machine, cause the machine to select the trait or phenotype from the group consisting of a genetic disorder, a predisposition to a genetic disorder, susceptibility to a disease, or an agronomic or livestock performance trait, a product quality trait.

Additionally, the invention teaches an article comprising a machine-accessible medium having stored thereon instructions that, when executed by a machine, cause the machine to: obtain a marker for a trait or phenotype in a subject; obtain a target nucleic acid sample from the subject; and determine the presence of the marker for the trait or a phenotype in the target nucleic acid sample, wherein the presence of the marker in the target nucleic acid indicates that the subject has the trait or the phenotype. The article may further have instructions that, when executed by the machine, cause the machine to select the trait or phenotype from the group consisting of a genetic disorder, a predisposition to a genetic disorder, susceptibility to a disease, an agronomic or livestock performance trait, or a product quality trait.

Also provided is an article comprising a machine-accessible medium having stored thereon instructions that, when executed by the machine, cause the machine to: obtain a reference SPC map of one or more genomic regions from a plurality of subjects; select a sufficient number of cluster tag polymorphisms for the genomic regions; obtain a target nucleic acid of the genomic regions from a subject to be identified; determine the genotype of the cluster tag polymorphisms of the genomic regions of the subject to be identified; and compare the genotype of the cluster tag polymorphisms with the reference SPC map to determine the genetic identity of the subject of interest. In addition, there is an article comprising a machine-accessible medium having stored thereon instructions that, when executed by a machine, cause the machine to: obtain an SPC map of a genomic region of interest; determine the SPC-haplotypes from the SPC map, wherein each SPC-haplotype comprises a subset of SPCs from a genomic region wherein the SPCs of the subset coincide; and identify the SPC-haplotype of a test subject by comparing the SPCs of the subject with the SPC-haplotypes determined from the SPC map.

Other SPC maps of the invention, include an SPC map of a genomic region of interest comprising one or more sequence polymorphism clusters (SPCs), wherein each SPC comprises a subset of polymorphisms from said genomic region wherein said polymorphisms of said subset coincide with each other polymorphism of said subset; and wherein said map further comprises non-clustering polymorphisms that are associated with the map, wherein said non-clustering polymorphisms are such that they do not cluster with any other polymorphism but are associated with at least one SPC.

Also contemplated is a method of producing an SPC map of a genomic region of interest comprising the steps of obtaining the nucleic acid sequence of said genomic region of interest from a plurality of subjects; identifying a plurality of polymorphisms in said nucleic acid sequences; identifying one or more SPCs, wherein each SPC comprises a subset of polymorphisms from said nucleic acid sequence wherein said polymorphisms of said subset coincide with each other polymorphism of said subset; and identifying polymporphisms that do not coincide with any other polymorphism but do cosegregate with at least one SPC.

Another embodiment contemplates a method of producing an SPC map of a genomic region of interest from unphased diploid genotypes comprising the steps of obtaining the unphased diploid genotypes of a genomic region of interest from a plurality of subjects; determining the major and minor metatypes found in said unphased diploid genotypes; identifying one or more SPCs, wherein each SPC comprises a subset of polymorphisms from said metatypes wherein said polymorphisms of said subset coincide with each other polymorphism of said subset; and identifying polymporphisms that do not coincide with any other polymorphism but do cosegregate with at least one SPC.

Another method contemplates producing an SPC map of a genomic region of interest from the genotypes of sample pools comprising the steps of obtaining the genotypes of a genomic region of interest from a plurality of sample pools; determining the major and minor metatypes found in said genotypes; identifying one or more SPCs, wherein each SPC comprises a subset of polymorphisms from said metatypes wherein said polymorphisms of said subset coincide with each other polymorphism of said subset.

Also part of the invention is a method of selecting one or more polymorphisms from a genomic region of interest for use in genotyping, comprising the steps of obtaining an SPC map; selecting at least one cluster tag polymorphism which identifies a specific SPC in said SPC map; and selecting a sufficient number of cluster tag polymorphisms for use in a genotyping study of the genomic region of interest.

Yet another method comprises identifying a marker for a trait or phenotype comprising obtaining a sufficient number of cluster tag polymorphisms; and assessing said cluster tag polymorphisms to identify an association between a trait or phenotype and at least one cluster tag polymorphism, wherein identification of said association identifies said cluster tag polymorphism as a marker for said trait or phenotype.

Also contemplated is a method of in vitro diagnosis of a trait or a phenotype in a subject comprising obtaining a marker for said trait or phenotype; obtaining a target nucleic acid sample from said subject; and determining the presence of said marker for said trait or a phenotype in said target nucleic acid sample, wherein the presence of said marker in said target nucleic acid indicates that said subject has the trait or the phenotype.

Another method contemplated is one for the in vitro diagnosis of the presence of a plurality of genetic variations known to be associated with a phenotype or trait in a genomic region of a subject, comprising the steps of obtaining an SPC map/network of said genomic region, and select there from a subset of SPCs, each of which coincides with a subset of the genetic variations; obtaining a target nucleic acid sample from said subject; and determining the presence of said subset of SPCs in said target nucleic acid sample, wherein the presence of an SPC identifies the presence of a subset of genetic variations associated with the phenotype or trait in said subject.

A method of determining the genetic identity of a subject is provided which comprises obtaining a reference SPC map of one or more genomic regions from a plurality of subjects; selecting a sufficient number of cluster tag polymorphisms for said genomic regions; obtaining a target nucleic acid of said genomic regions from a subject to be identified; and determining the genotype of said cluster tag polymorphisms of said genomic regions of said subject to be identified; and comparing said genotype of said cluster tag polymorphisms with said reference SPC map to determine the genetic identity of said subject of interest.

Other methods involve determining the SPC-haplotypes from unphased diploid genotype of a genomic region of interest of a subject, comprising obtaining an SPC map; determining the SPC-haplotypes from said SPC map, wherein each SPC-haplotype comprises a subset of SPCs from a genomic region wherein said SPCs of said subset coincide; and identifying the SPC-haplotype of a test subject by comparing the SPCs of said subject with the SPC-haplotypes determined from said SPC map.

Also contemplated is a method of identifying an error in a genotype comprising obtaining genotype data from a subject of interest and comparing said genotype data with a reference SPC map prepared from a plurality of individuals, wherein a difference between the genotype of said subject and the SPC map indicates an error in the genotype of said subject.

It is contemplated that any of the methods described herein may be used for the production of an article that comprises a machine-accessible medium having stored thereon instructions that, when executed by a machine, cause the machine to perform the steps of the methods described above.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

DESCRIPTION OF THE DRAWINGS

This patent or application file contains at least one drawing executed in color. Copies of this patent or patent application publication with color drawing(s) will be provided by the Office upon request and payment of the necessary fee. The following drawings form part of the present specification and are included to further illustrate aspects of the present invention. The invention may be better understood by reference to the drawings in combination with the detailed description of the specific embodiments presented herein.

The results shown in FIGS. 1 through 20 that are part of the present invention can best be represented and viewed on color printouts. The Figures are however also legible on black/white printouts where the different colors, referred to in the Figure legends, are represented/replaced by different shades of grey or by any other means of differentially representing or visualizing results. Additionally, the Figures may also incorporate alternative indications (for example a numbering of the originally coloured or shaded regions) to facilitate the readability of such black/white representations.

FIG. 1 illustrates an SPC structure that consists of a number of independent SPCs. An idealized imaginary genetic variation data set, essentially devoid of confounding data, was used. The various SPCs, more specifically the minor alleles of the SNPs that belong to these SPCs, are differentially highlighted. Different colors are used to indicate the various SPCs. The representations in FIGS. 1A and 1B correspond to the output of the algorithm. The first two rows in FIGS. 1A and 1B indicate respectively the SNPs and the SPCs to which the SNPs belong. FIG. 1A shows the genetic variation table (in which each column represents a polymorphic site and each row represents a sample) onto which the SPCs are visualized. The original table is sorted such that individuals that share the same SPC are grouped. Polymorphic sites that do not cluster are marked in grey (e.g. SNPs 33 and 38).

FIG. 2 illustrates an SPC structure that consists of a number of dependent SPCs. An idealized imaginary genetic variation data set, devoid of confounding data, was used. Different colors are used to indicate the various SPCs. The representations in FIGS. 2A and 2B correspond to the output of the algorithm. The first two rows in FIGS. 2A and 2B indicate respectively the SNPs and the SPCs to which the SNPs belong. FIG. 2A shows the genetic variation table (in which each column represents a polymorphic site and each row represents a sample) onto which the SPCs are depicted. The original table is organized such that individuals that share the same SPCs are grouped. Polymorphic sites that do not cluster are marked in grey (e.g. SNPs 2, 8, 29, 34 and 38). FIG. 2B shows the matrix of the pairwise C-values calculated from the data set of FIG. 2A. All clustering positions for which C=1 are differentially highlighted and all positions for which C=0 are left blank. The partial co-occurrence of SNPs belonging to dependent SPCs is reflected by pairwise values of C<1. FIGS. 2D and 2E show the SPCs identified in the genetic variation table and the corresponding networks using a threshold value for C of 0.9. It should be noted that in this case there is no longer a distinction between SPC-1 and SPC-1.1 of FIG. 2A.

FIG. 4 represents the SPC structure at various stringencies using a data set containing missing genotype calls. The data set is the same as that used for FIG. 1 wherein 4.5% of the allele calls were replaced by "N", symbolizing a missing data point, and 0.5% of the allele calls were replaced by the opposite allele, to mimic incorrect data. Different colors are used to indicate the various SPCs. Throughout the Figure, the same numbering is used to indicate the various SPCs. FIGS. 4A, 4B and 4C show the various SPCs identified at a gradually lower threshold level: C=1, C≧0.9 and C≧0.75 respectively. The first two rows in FIGS. 4A, 4B and 4C indicate respectively the SNPs and the SPCs to which the SNPs belong. The SNPs that are not clustered are marked in grey while the missing positions ("N") are left blank. FIG. 4E shows the network structure of the SPCs detected at C=1 and C≧0.9, while FIGS. 4G, 4H, and 4I illustrate the selection of ctSNPs that tag the SPCs 1, 3 and 4, respectively. For each SPC, a condensed genetic variation table lists the scores observed at the polymorphic sites that belong to that cluster. The accompanying matrix shows the pairwise C-values as well as a calculation of the average strength of association of each polymorphism with the other polymorphisms of the cluster. These average C-values are given along the diagonal as well as in the right margin. The most preferred ctSNP is highlighted.

FIG. 5 exemplifies the effect of a limited number of historical recombination events on the SPC structure. An imaginary genetic variation data set was used; non-clustering polymorphisms were omitted for the sake of simplicity. Different colors are used to indicate the various SPCs. Throughout the Figure, the same numbering is used to indicate the various SPCs. FIG. 5A shows the genetic variation table onto which the SPCs are visualized at a threshold value of C=1. The first two rows in FIG. 5A indicate respectively the SNPs and the SPCs to which the SNPs belong. The original table was sorted such that individuals that share the same SPC are grouped. Certain samples reveal recombination events between SPC-0 and SPC-1. As a result, adjacent sets of SNPs do not cluster perfectly (C=1) and form dependent SPC-1x and SPC-1y. FIGS. 5E and 5F show the various SPCs found at a threshold level of C≧0.9 and the corresponding network. FIGS. 5G and 5H show the various SPCs at threshold level C≧0.8 and the corresponding network.

FIG. 6 exemplifies the effect of a recombination hotspot on the SPC structure. An imaginary genetic variation data set was used. Different colors are used to indicate the various SPCs. The recombination hotspot demarcates two adjacent regions. A black bar indicates the junction and in the two regions the major alleles (i.e. SPC-0) are differentially highlighted. FIG. 6A shows the original genetic variation table onto which the SPCs are depicted. The first two rows in FIG. 6A indicate respectively the SNPs and the SPCs to which the SNPs belong. The genetic variation table is arranged such that individuals that share the same SPCs in the left region are grouped. Polymorphic sites that do not cluster are marked in grey (e.g. SNPs 33, 37 and 38). Note that all SPCs are in an independent relationship and that the SPCs that belong to the distinct regions occur in various combinations, as indicated in the left margin.

FIG. 7 illustrates the identification of SPCs that are in an independent configuration starting from diploid genotype data as well as the deconvolution of these genotype data. FIG. 7A is a visual representation of the diploid genotypes, with positions homozygous for the major allele having a pale taint, the minor allele having a dark taint and the heterozygous calls ("H") having a grey taint. The genotype data were generated by random pairwise combination of the SPC-haplotypes of FIG. 7E. Haplotypes are named according to the SPCs thereby neglecting the non-clustering SNPs. The haplotype combinations are shown for each genotype on the left side. In FIGS. 7B to 7F different colors are used to indicate the various SPCs. FIG. 7B shows the matrix of the pairwise C-values calculated from the data set of FIG. 7C. All clustering SNP positions for which C=1 are differentially highlighted in the same way as in FIGS. 7C/D/E/F and all positions for which C=0 are left blank. FIGS. 7C and 7D show the metatype table, onto which the SPCs are visualized, and which for the sake of representation is shown in two halves. In essence, this table was obtained by duplicating FIG. 7A wherein the "H" positions were replaced once by the minor allele (the resulting minor metatypes are indicated by the letter "a" after the haplotype combination and are shown in FIG. 7C) and once by the major allele (the resulting major metatype are indicated by the letter "b" after the haplotype combination and are shown in FIG. 7D). The two tables are sorted such that metatypes that share the same SPC are grouped as much as possible. Polymorphic sites that do not cluster (positions 33 and 38) are marked in grey. FIG. 7F shows the SPC relationship which can be deduced from the data in FIGS. 7C and 7D. This SPC structure permits the deconvolution of the diploid genotypes into the component SPC-haplotypes shown in FIG. 7E.

FIG. 8 illustrates the identification of a complex SPC structure starting from diploid genotype data as well as the deconvolution of these data. FIG. 8A is a visual representation of the diploid genotypes, with positions homozygous for the major allele having a pale taint, the minor allele having a dark taint and the heterozygous calls ("H") having a grey taint. The genotype data were generated by random pairwise combination of the SPC-haplotypes in FIG. 8E. In case the combined alleles were different, these were replaced by "H". The haplotype combinations are shown for each genotype on the left side. In FIGS. 8B to 8F different colors are used to indicate the various SPCs. FIG. 8B shows the matrix of the pairwise C-values calculated from the data set of FIG. 8C. All clustering SNP positions for which C=1 are differentially highlighted in the same way as in FIG. 8C/D/E/F and all positions for which C=0 are left blank. FIGS. 8C and 7D show the metatype table, onto which the SPCs are visualized, and which for the sake of representation is shown in two halves. In essence, this table was obtained by duplicating FIG. 8A wherein the "H" positions were replaced once by the minor allele (the resulting minor metatypes are indicated by the letter "a" after the haplotype combination and are shown in FIG. 8C) and once by the major allele (the resulting major metatype are indicated by the letter "b" after the haplotype combination and are shown in FIG. 8D). The two tables are sorted such that metatypes that share the same SPC are grouped as much as possible. FIG. 8F shows the SPC relationship which can be deduced from the data in FIG. 8C. This SPC structure permits the deconvolution of the diploid genotypes into the component SPC-haplotypes shown in FIG. 8E.

FIG. 9 shows the intraspecies SPC map of the sh2 locus of maize. Different colors are used to indicate the various SPCs.

FIG. 11 shows the intraspecies SPC map of the Y1 locus of maize. Different colors are used to indicate the various SPCs.

FIG. 13 shows the SPC map of the FRI locus of *Arabidopsis thaliana*. Different colors are used to indicate the various SPCs.

FIG. 15 shows the SPC structure of the human CYP4A11 gene. Different colors are used to indicate the various SPCs. FIG. 15B shows the different SPC combinations observed in the three classes of metatypes. Each rectangle of two rows shows the minor and the major metatype of a sample, the SPCs observed and the SPC combinations. The two SPC-haplotypes are obtained after deconvolution of the genotype. FIG. 15C presents the hierarchical relationship between the SPCs of the CYP4A11 gene. The putative source sequence that is devoid of an SPC is referred to as SPC-0. The full and dotted lines represent respectively confirmed and putative relationships. FIGS. 15E, F and G illustrate the selection of ctSNPs that tag the SPCs 1, 2 and 4, respectively. For each SPC, a condensed metatype table lists the scores observed at the polymorphic sites that belong to that cluster. The accompanying matrix shows the pairwise C-values as well as a calculation of the average strength of association of each polymorphism with the other polymorphisms of the cluster.

These average C-values are given along the diagonal as well as in the right margin. The most preferred ctSNPs are highlighted.

Figure 16D:
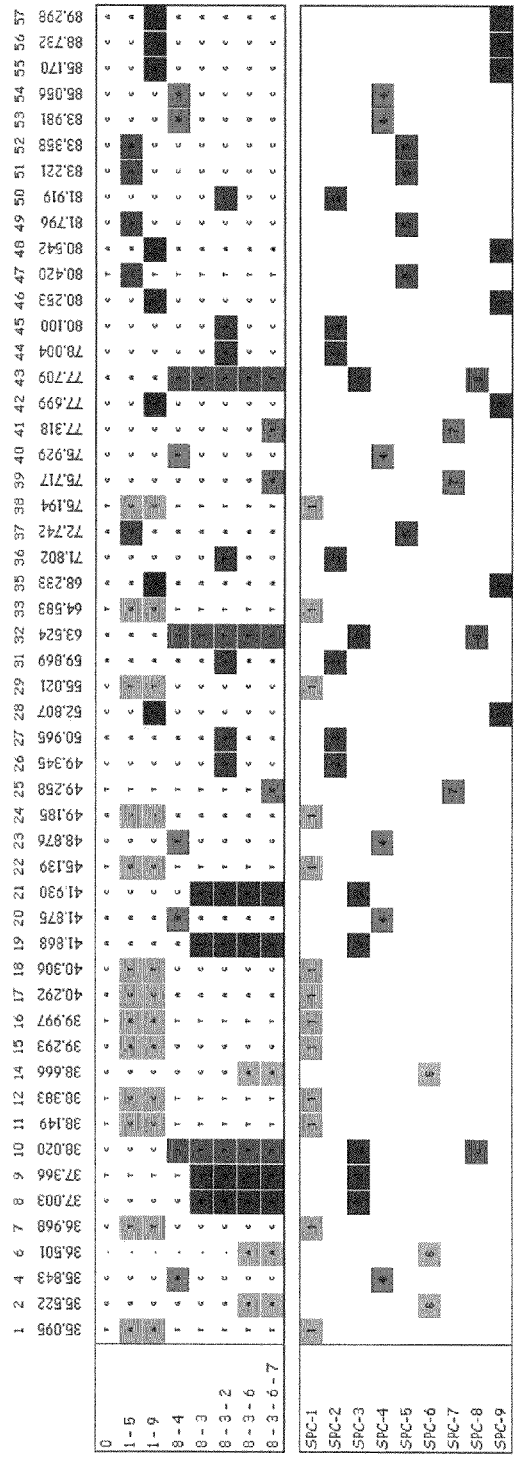
Figure 16E:
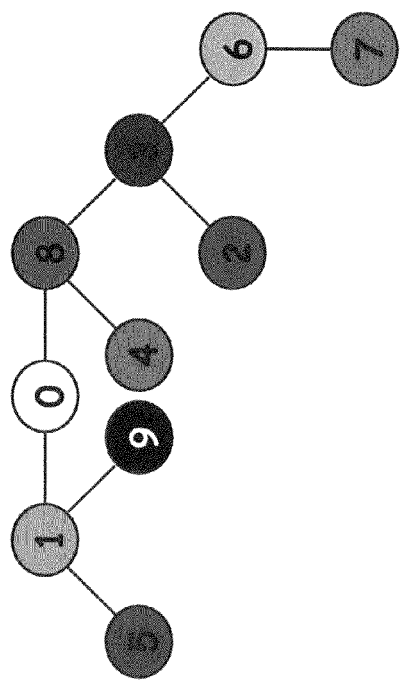

FIG. 16 shows the SPC structure of a segment of the human MHC locus. Different colors are used to indicate the various SPCs. FIG. 16A is a schematic representation of the physical map of the 200 kb Class II region of the MHC locus, in which the differentially highlighted rectangles symbolize the 7 domains from FIGS. 16B and C. The positions of the hotspots of recombination are indicated by the vertical arrows. FIGS. 16B and C show the SPC map of the region in which each SPC is represented on a different row and marked by a different color. The differentially highlighted rectangles represent the domains inferred from the SPC maps. FIG. 16B represents the SPC map of the subgroup of SNPs with high frequency minor alleles (frequency >16%) and FIG. 16C represents the SPC map of the subgroup the SNPs characterized by low frequency minor alleles ($\leq$–16%). SPCs that span different domains are outlined and marked by horizontal arrows. FIG. 16D shows an SPC map of domain 4 of FIG. 16A from position 35,095 to position 89,298. In the upper row the polymorphic sites are numbered consecutively and the physical map position of each polymorphic site is indicated above the columns. Polymorphic sites that do not cluster are omitted. The upper panel shows the inferred SPC-haplotypes onto which the SPCs are depicted. The lower panel shows the SPCs in which each SPC is represented on a different row and marked by a different color. FIG. 16E presents the hierarchical relationship between the SPCs of domain 4.

Figures 17A, 17B:
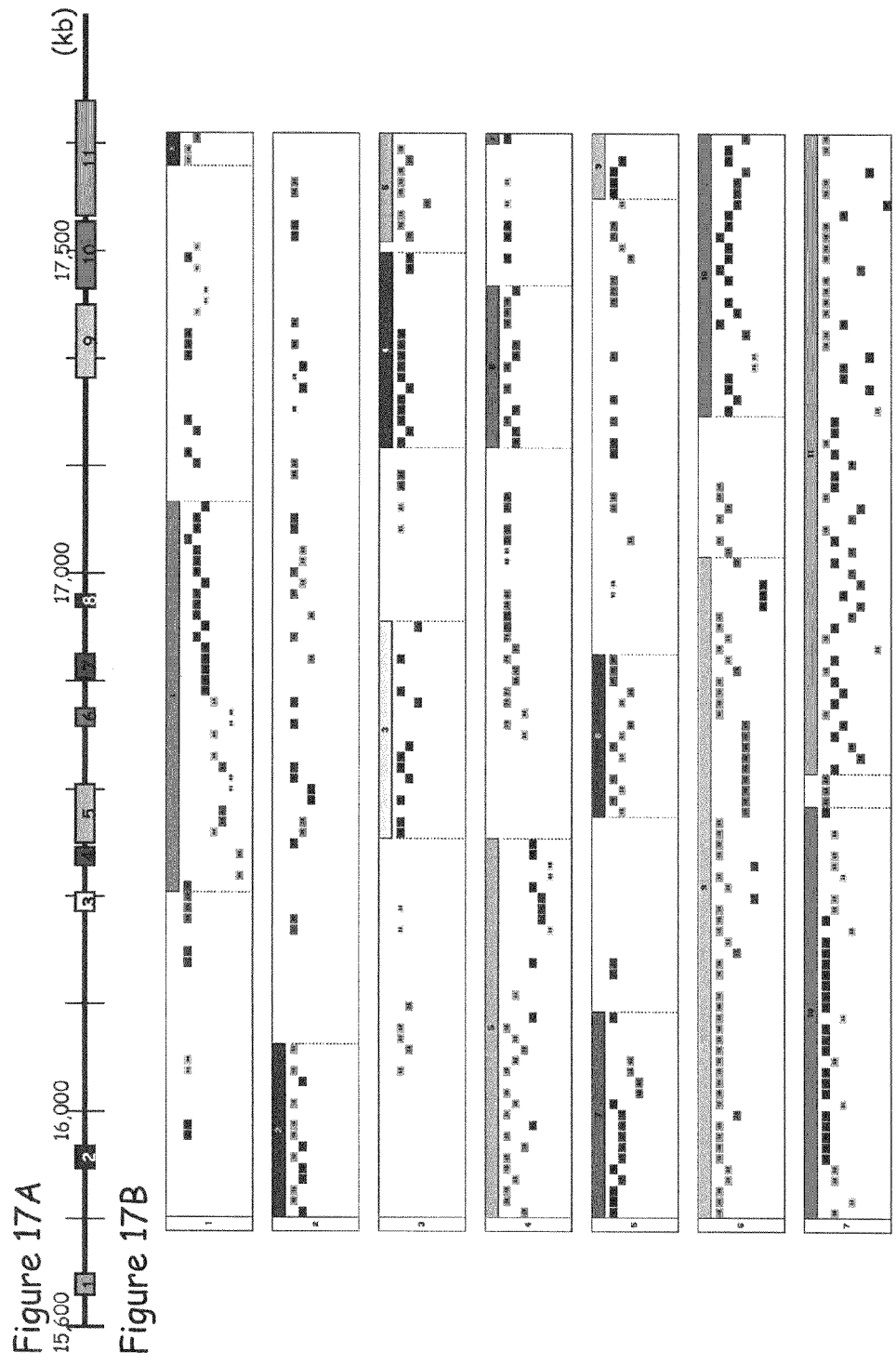
Figure 17C:
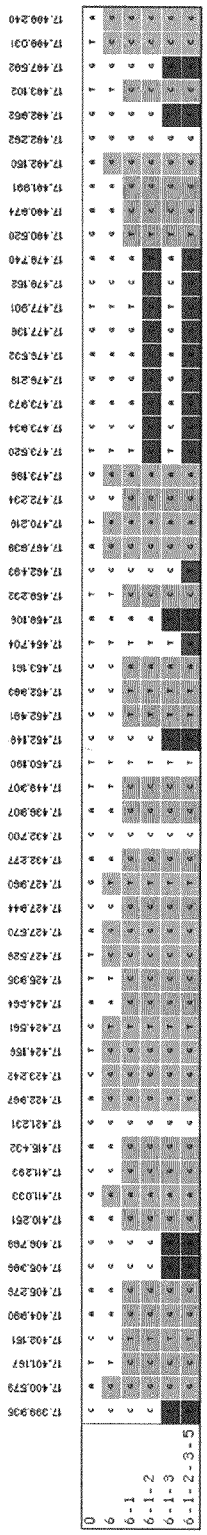
Figure 17D:
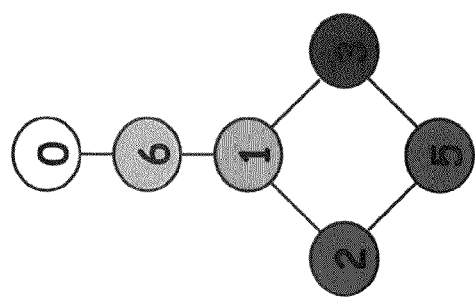

FIG. 17 shows the SPC map of the HapMap SNPs of human Chromosome 22. FIG. 17A is a schematic representation of the physical map of a segment of 2.27 Mb of chromosome 22 in which the differentially highlighted and numbered rectangles symbolize the 11 domains of FIG. 17B. The domains are drawn to scale. The map positions represent the positions on chromosome 22. FIG. 17B shows the SPC map of 700 SNPs of chromosome 22. The figure is composed of 7 panels, numbered 1 through 7, which represent 100 polymorphic sites each. The rectangles at the top of each panel represent the domains comprising 10 or more clustered SNPs. All non overlapping SPCs are shown on the first row of each panel, while overlapping SPCs are displayed in consecutive rows. Different colors are used to mark the different SPCs. Note that domains may be represented in consecutive panels, and that corresponding SPCs may be represented on different rows and marked by a different color. FIG. 17C shows the SPC map of domain 9 of FIG. 17B from position 17,399,935 to position 17,400,240. The chromosomal map position of each SNP is indicated above the columns. The figure shows the inferred SPC-haplotypes onto which the SPCs are depicted. Polymorphic sites that do not cluster are omitted. FIG. 17D presents the hierarchical relationship between the SPCs of domain 9. It can be seen that one of the haplotypes, 6-1-2-3-5, has a complex history. FIG. 17E corresponds to the output of the algorithm and shows the metatypes of three trios (parents and child) onto which the SPCs are depicted, with their corresponding SPC-haplotypes. The metatypes are shown in the order: parents (father and mother; marked P) and child (marked C). The alleles marked by a black frame and arrows represent the genotyping errors.

Figure 18:
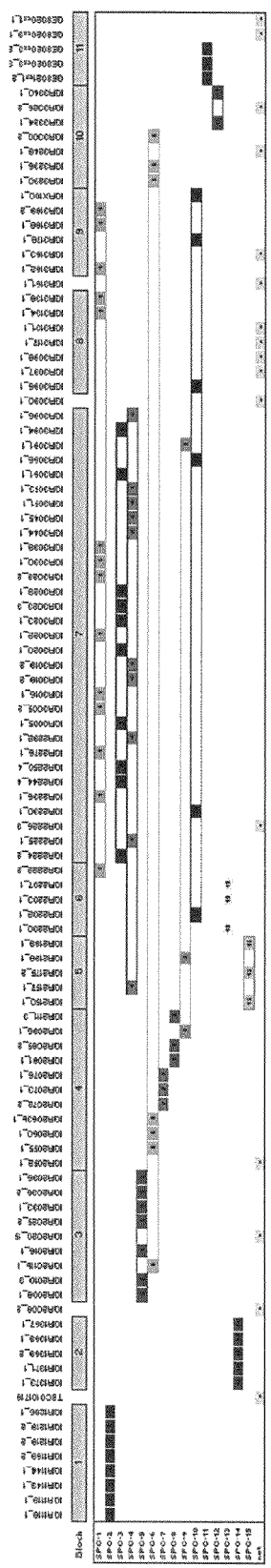

FIG. 18 shows the SPC map of 500 kilobases on chromosome 5q31. Different colors are used to indicate the various SPCs which are represented on different rows. SNPs that do not cluster are shown on the bottom row. The SNP names are indicated above the columns. The grey rectangles, numbered 1 through 11, represent the haplotype blocks identified by Daly et al. [Daly et al., Nat. Genet. 29: 229-232, 2001]. SPCs than span different haplotype blocks are framed in their respective colors.

Figure 19:
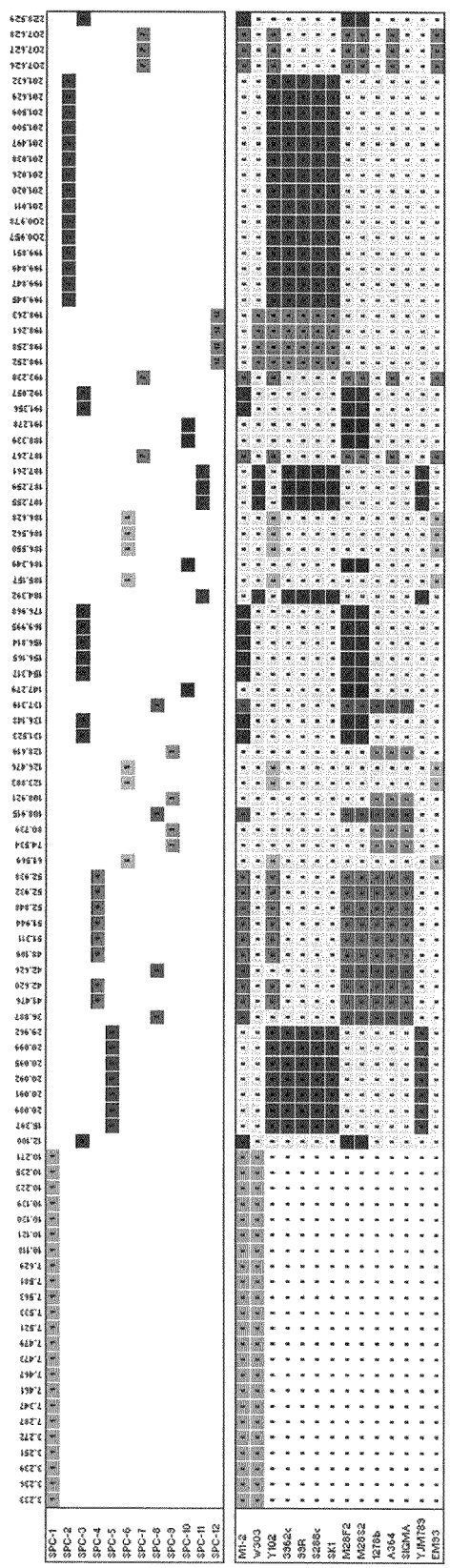

FIG. 19 shows the SPC map of single-feature polymorphisms (SFPs) in yeast. Different colors are used to indicate the various SPCs. The upper panel shows the SPCs in which each SPC is represented on a different row and marked by a different color. The lower panel corresponds to the output of the algorithm and shows the genetic variation table onto which the SPCs are depicted. Only those SFPs that belong to SPCs having 4 or more SFPs are shown. The yeast strains for each genotype are shown in the left most column. The position of each variation on the physical map of chromosome 1 is indicated above the columns.

Figure 20:
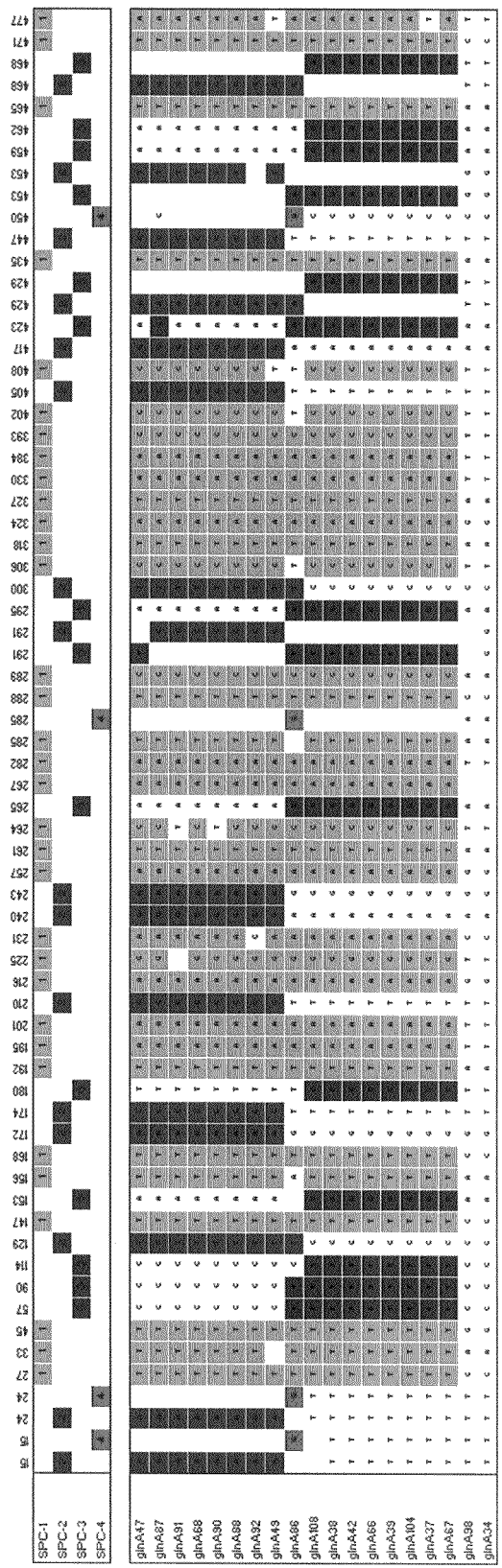

FIG. 20 shows the SPC map of the glnA locus of *Campylobacter jejuni*. Different colors are used to indicate the various SPCs. The upper panel shows the SPCs in which each SPC is represented on a different row and marked by a different color. The lower panel corresponds to the output of the algorithm and shows the genetic variation table onto which the SPCs are depicted. Only those polymorphisms that belong to SPCs having 3 or more polymorphisms are shown. The *Campylobacter jejuni* strains for each genotype are shown in the left most column. The position of each variation is indicated above the columns.

Figure 21:
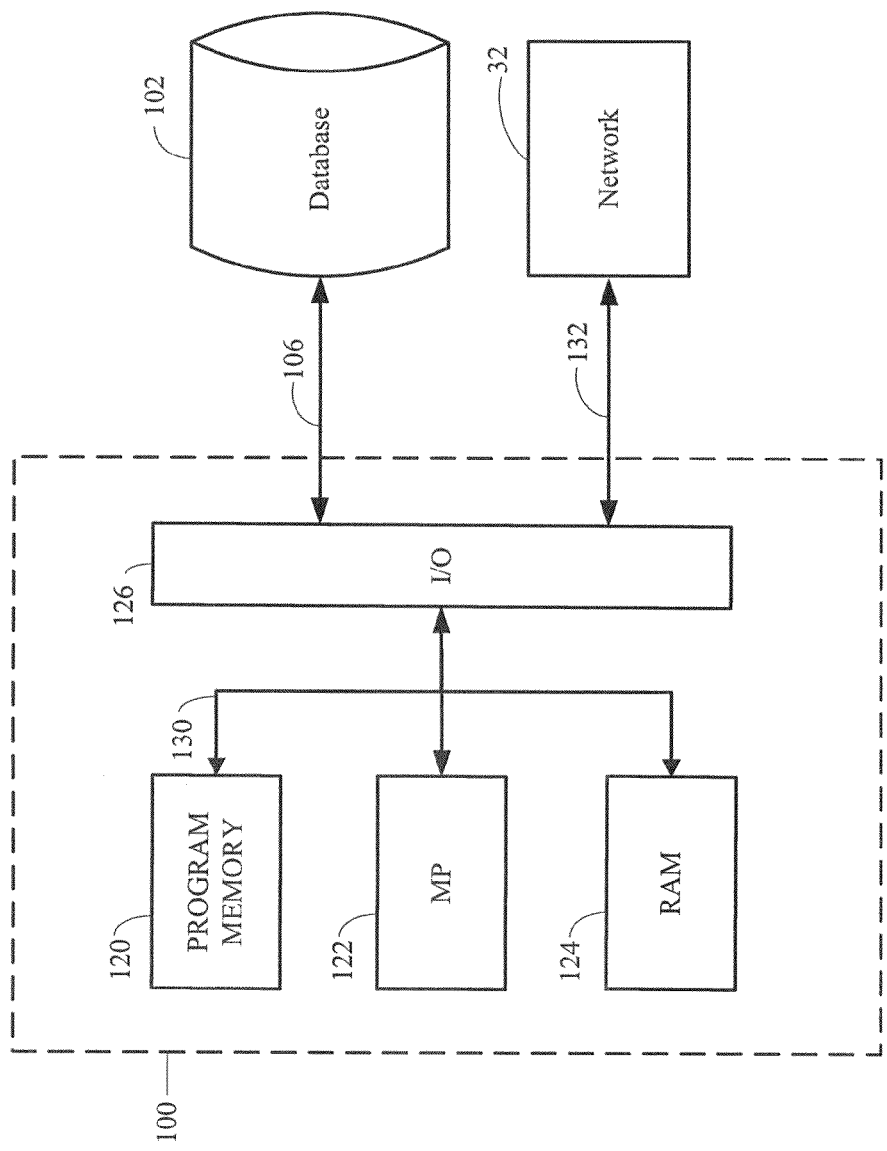

FIG. 21 is a schematic diagram of some of the components of a computer.

Figure 22:
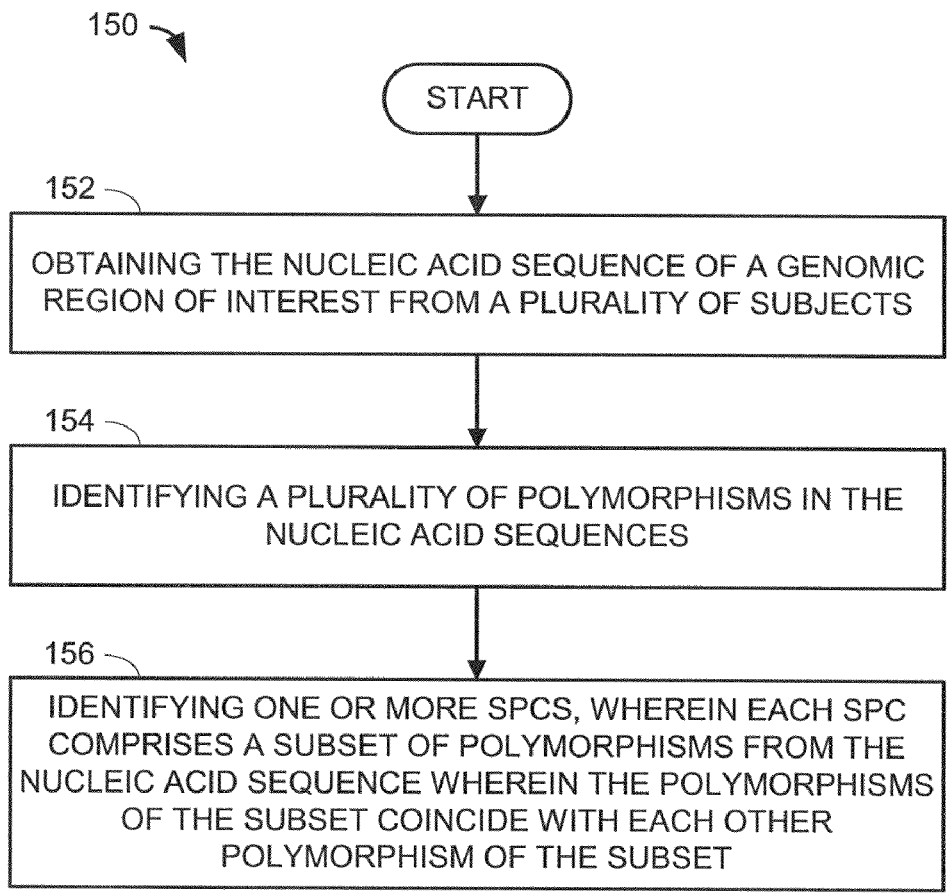

FIG. 22 is an exemplary flowchart showing some of the steps used to facilitate the production of an SPC map of a genomic region of interest.

Figure 23:
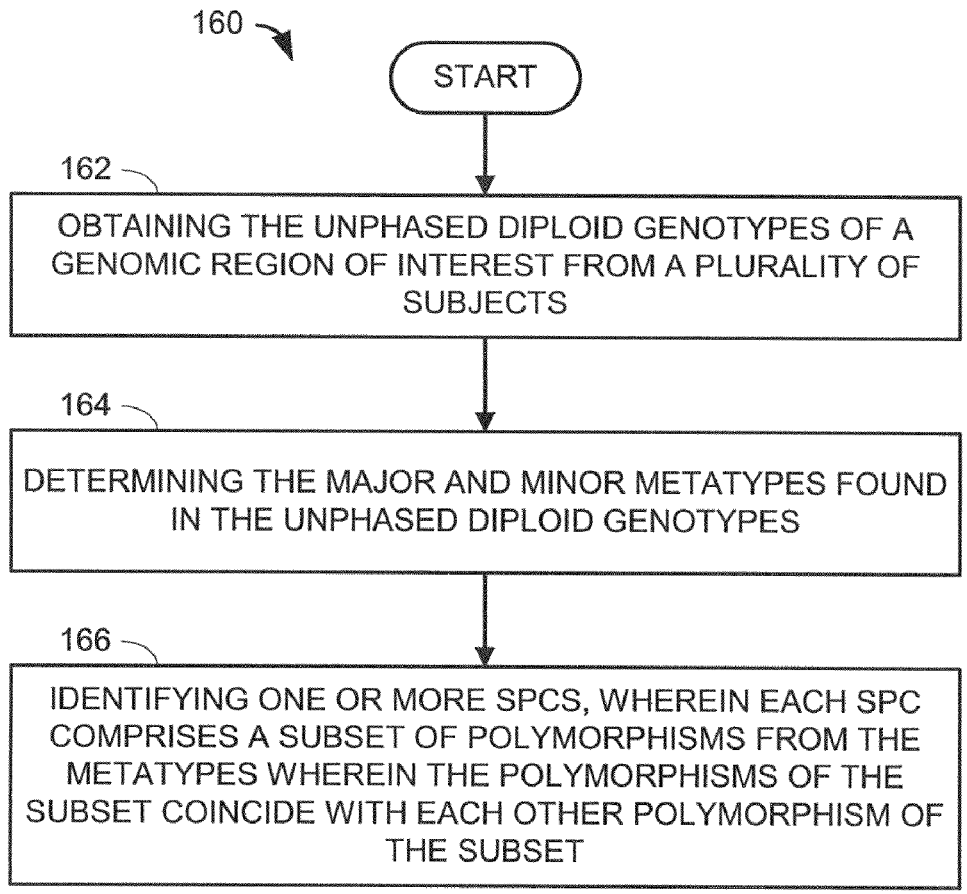

FIG. 23 is an exemplary flowchart showing some of the steps used in an alternative embodiment to the embodiment shown in FIG. 22.

Figure 24:
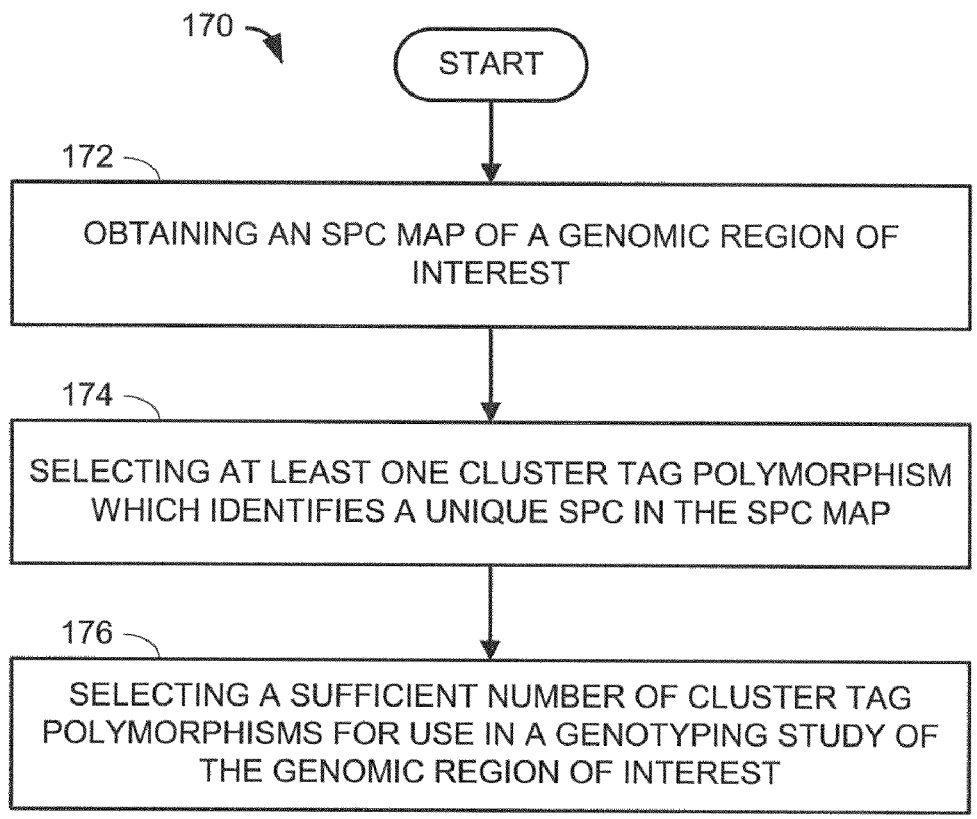

FIG. 24 is an exemplary flowchart showing some of the steps used in a method of selecting one or more polymorphisms from a genomic region of interest for use in genotyping.

Figure 25:
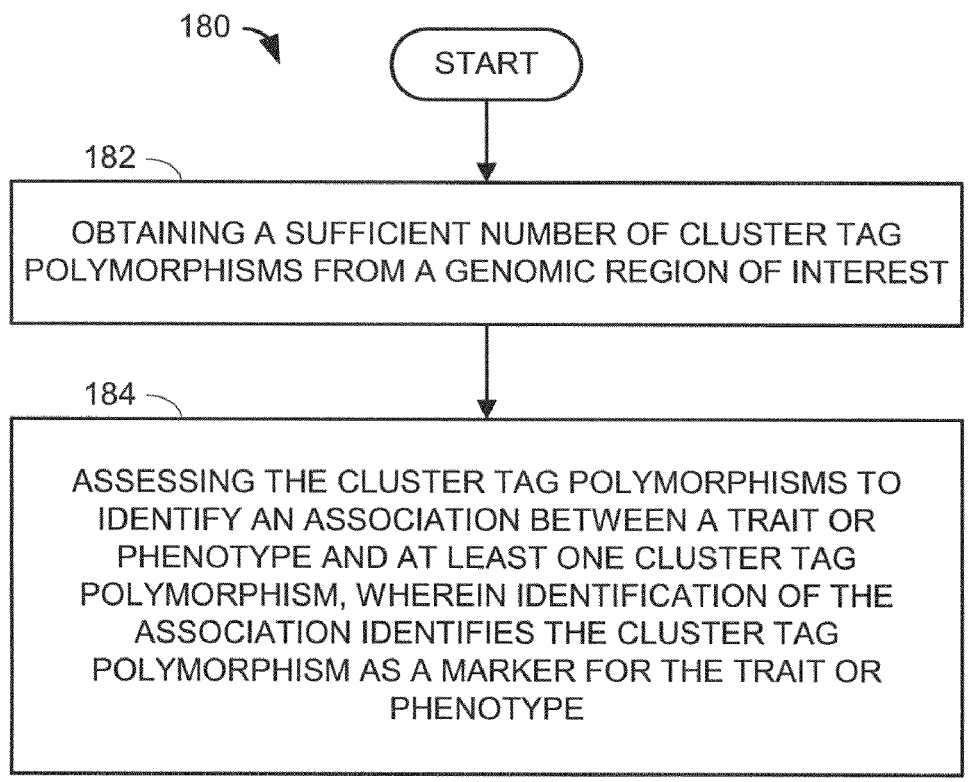

FIG. 25 is an exemplary flow chart describing some of the steps used to facilitate the identification of a marker trait or phenotype.

Figure 26:
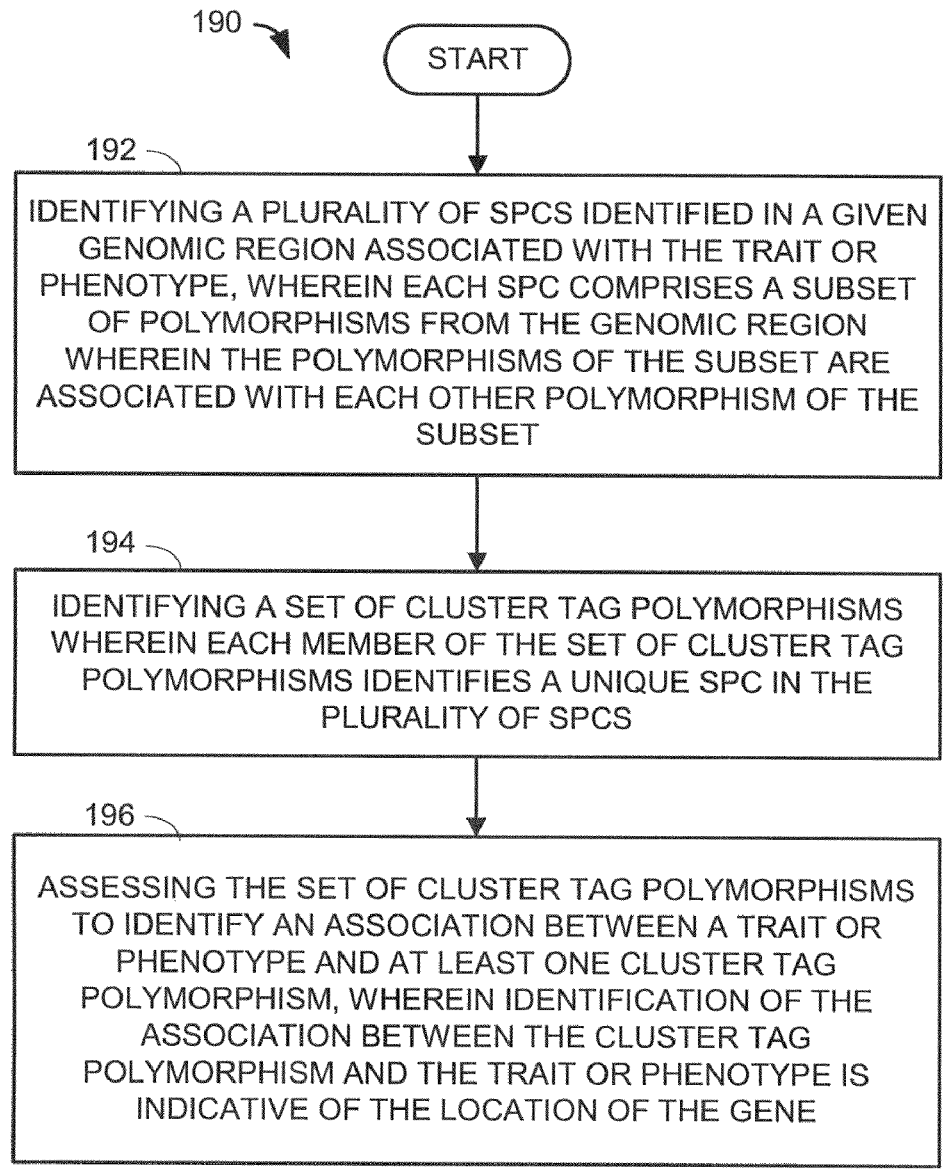

FIG. 26 is an exemplary flow chart describing some of the steps used to facilitate the identification of a location of a gene associated with a trait or phenotype.

Figure 27:
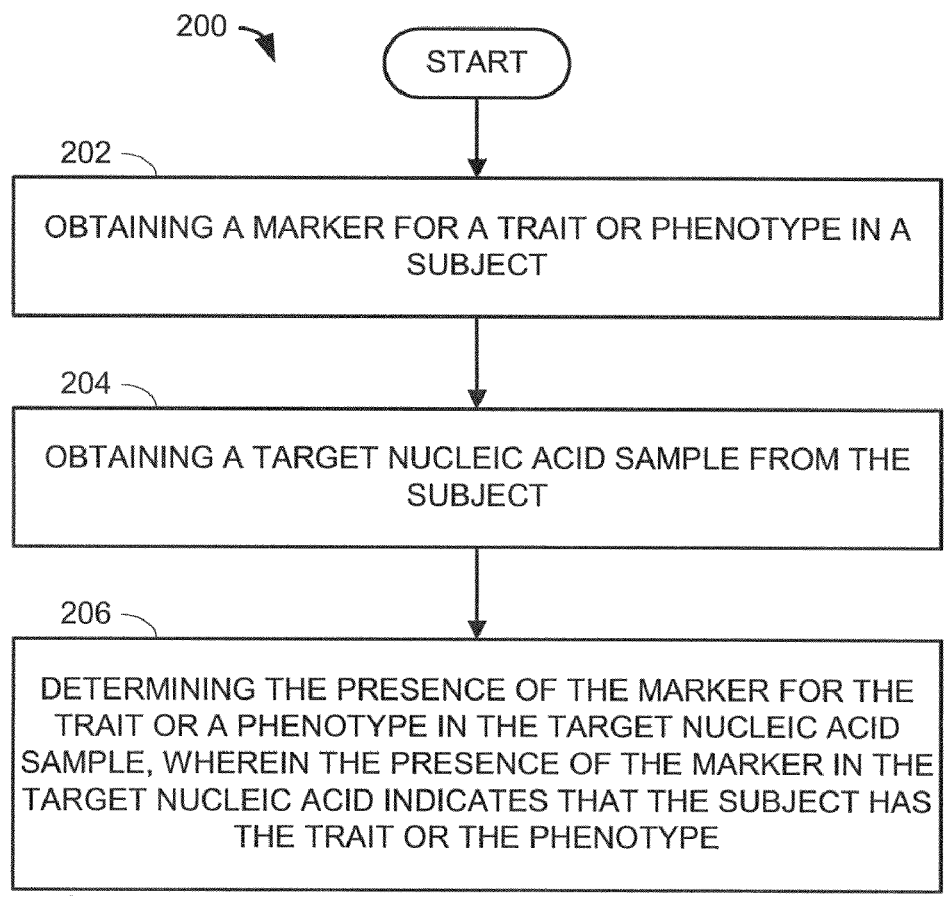

FIG. 27 is an exemplary flow chart describing some of the steps used in a method for in vitro diagnosis of a trait or phenotype.

Figure 28:
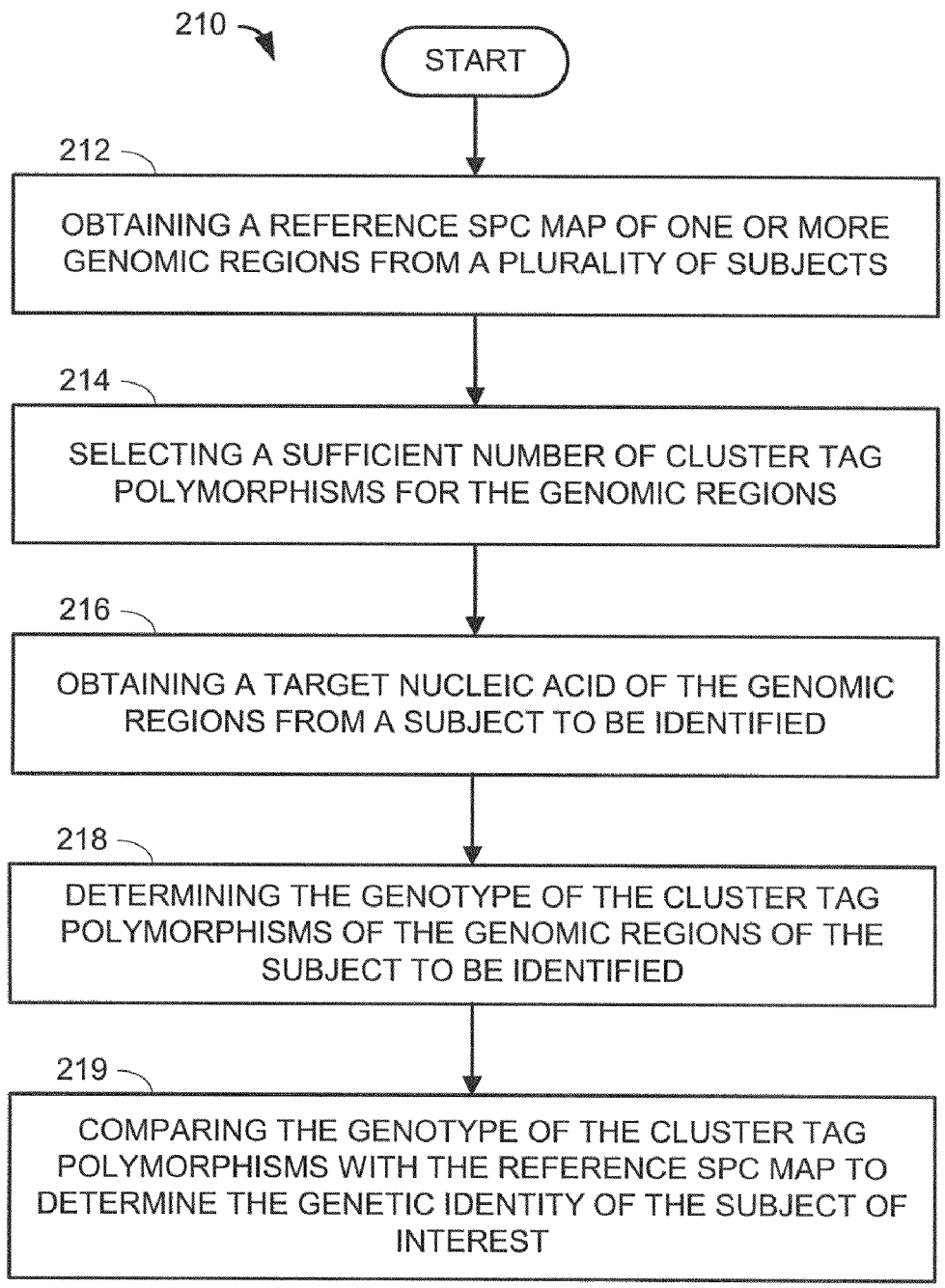

FIG. 28 is an exemplary flow chart describing some of the steps used in a method of determining the genetic identity of a subject.

Figure 29:
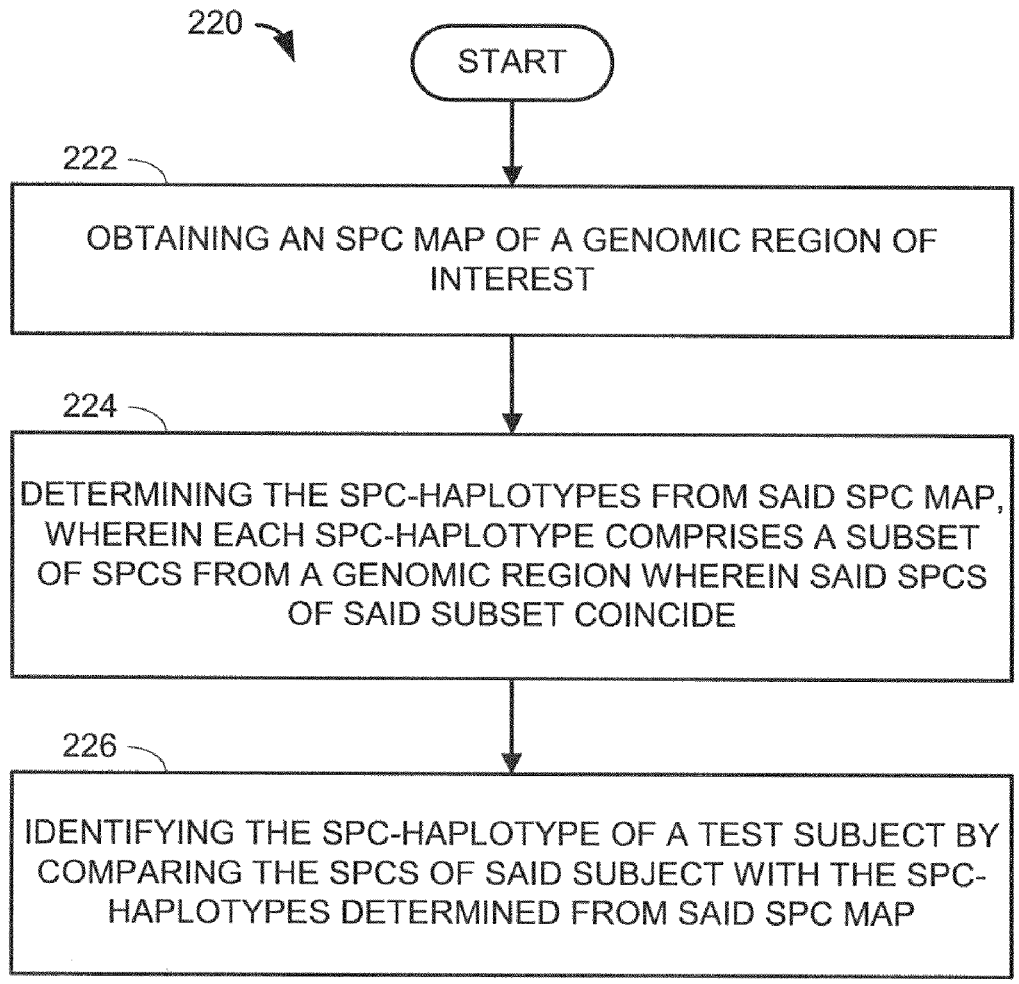
Figure 30A:
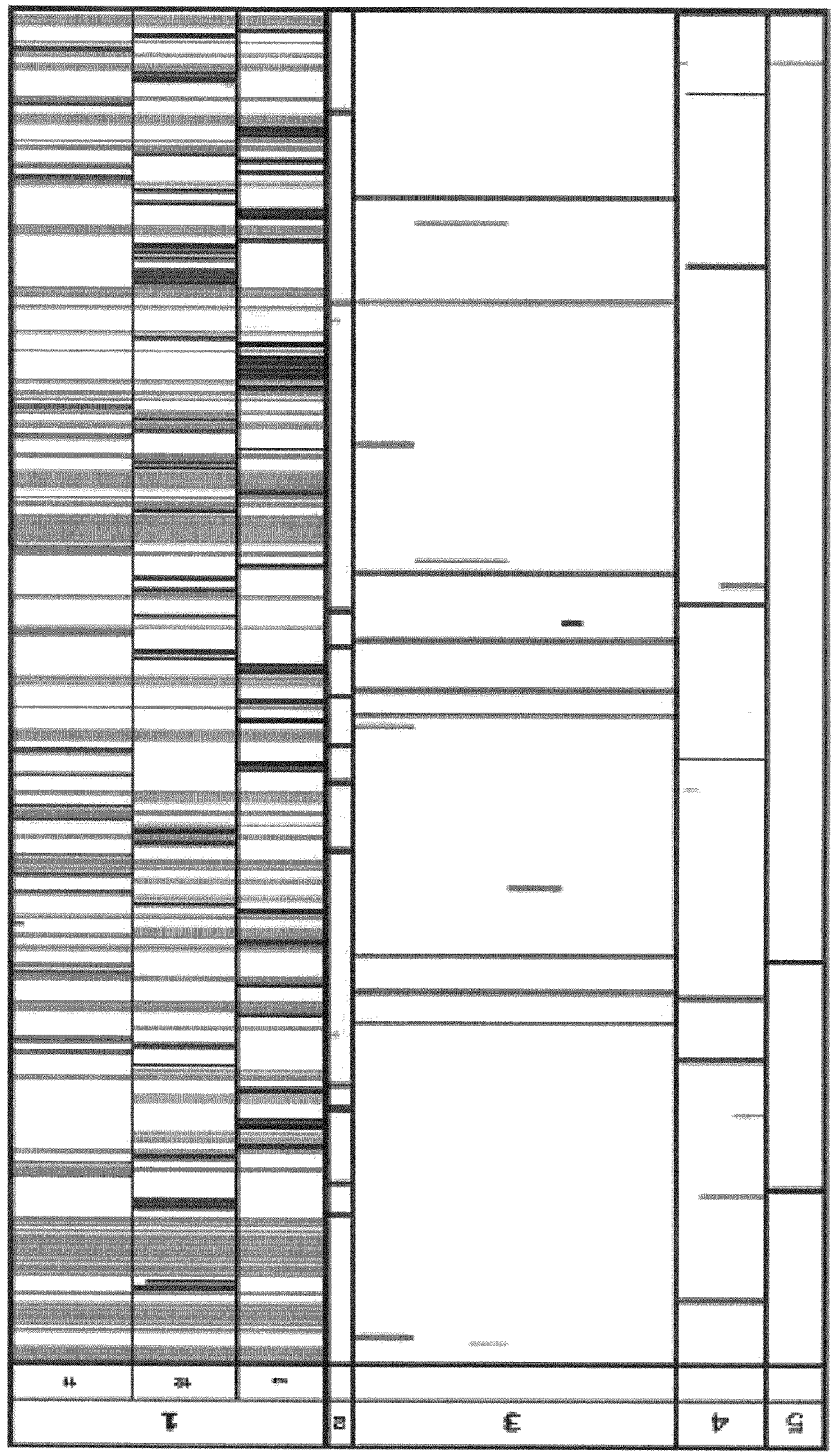
Figure 30B:
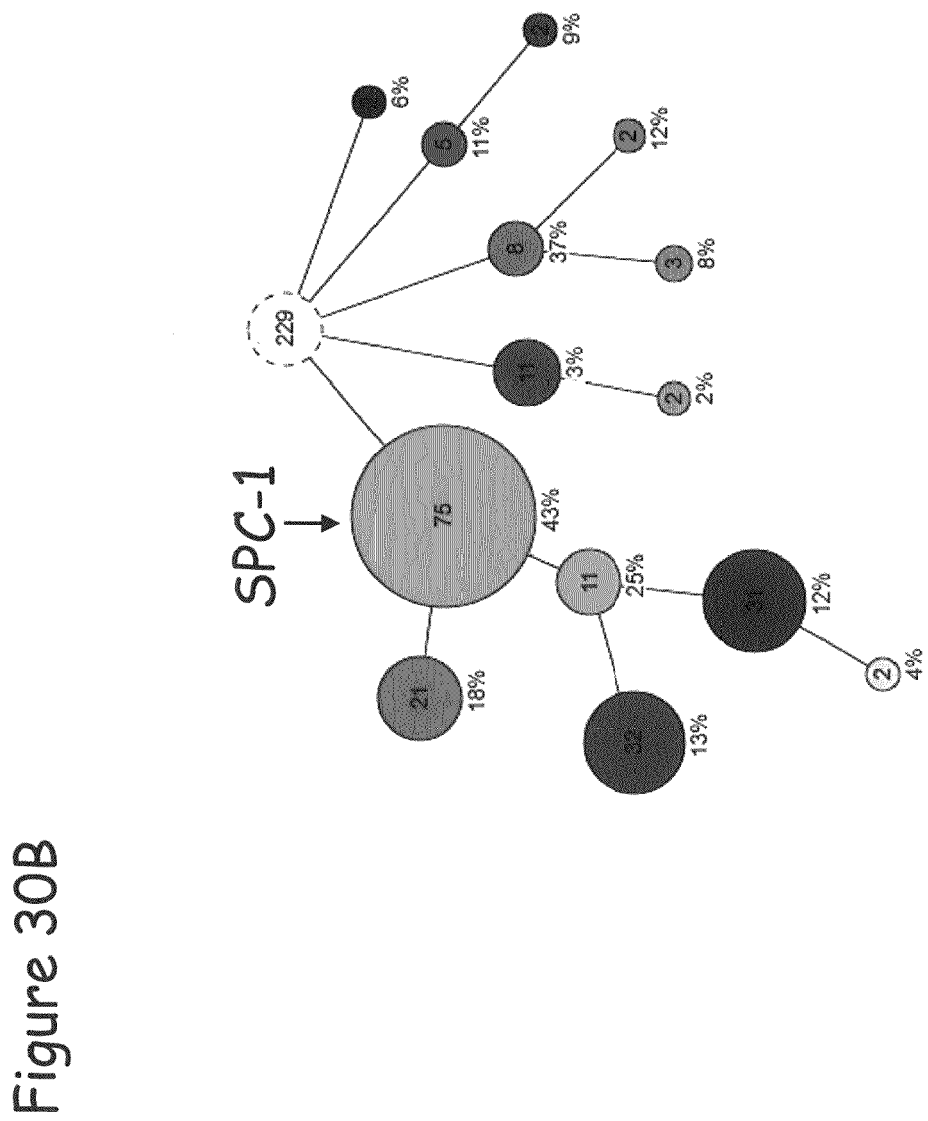
Figure 30C:
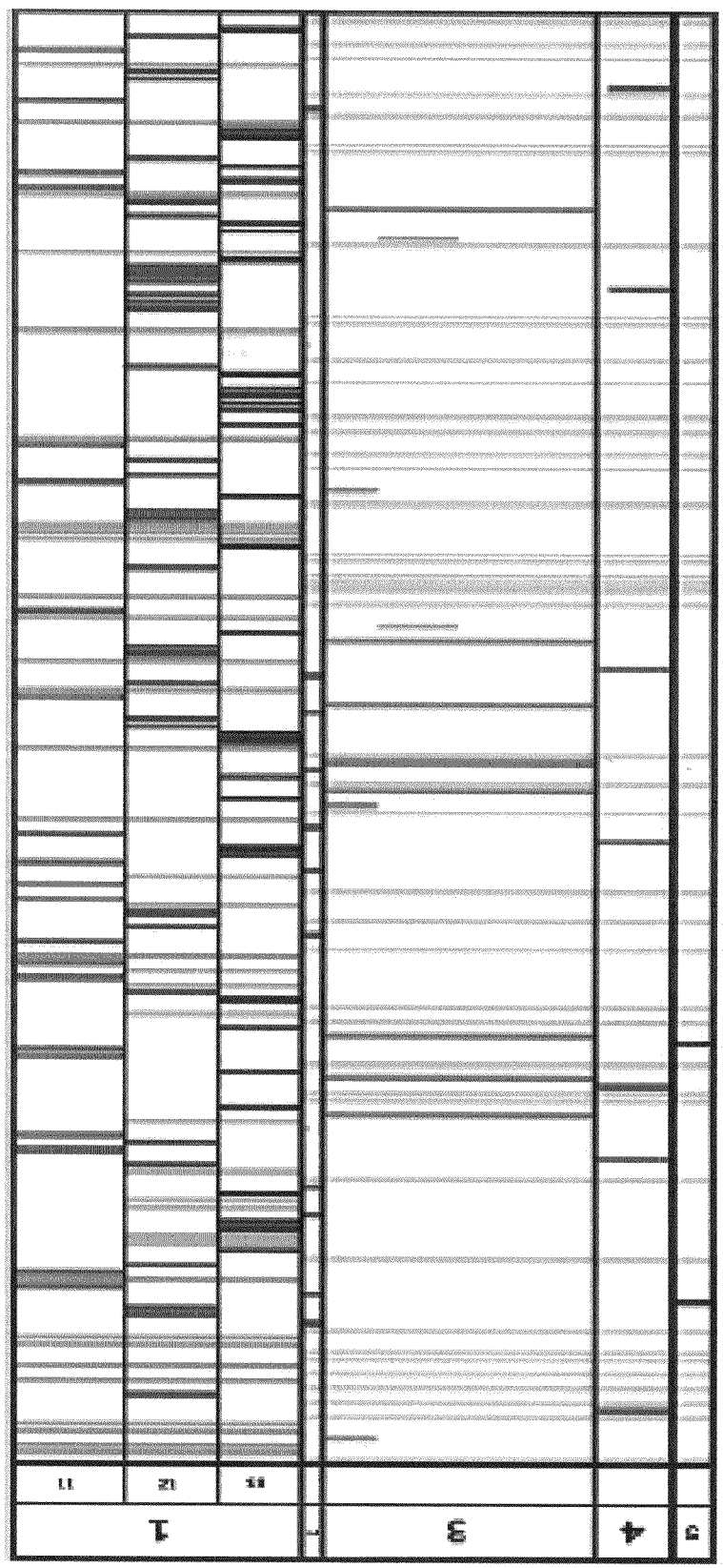
Figure 30D:
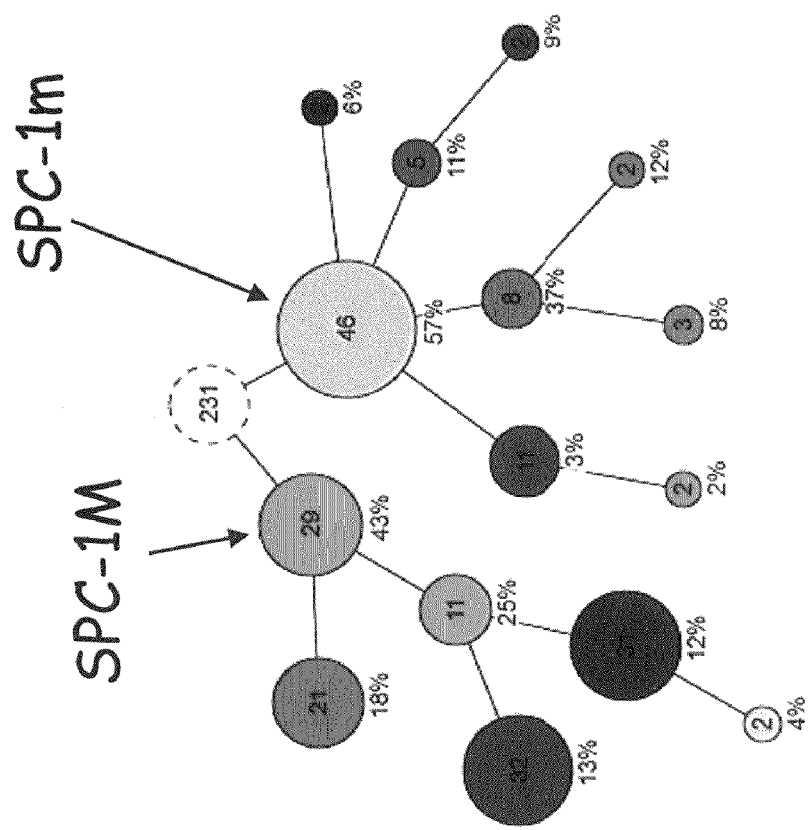

FIG. 29 is an exemplary flow chart describing some of the steps used in a method of determining the SPC-haplotypes from unphased diploid genotype of a genomic region of interest.

FIG. 30 illustrates the rooting of an SPC network by means of an outspecies sequence. The region under study runs from position 126,499,999 to 126,612,618 on human chromosome 7 (build 34). Panel A shows the genetic variation data set onto which the SPCs are depicted. Each row represents a sample and each column symbolizes an SNP. The allelic state is represented by colors: minor alleles are colored according to the SPC they belong to while the major allele is indicated by a light yellow color. The table is organized such that individuals that share the same SPCs are grouped. The horizontal lines and the numbering to the left indicate the SPCs and the major haplotypes. Panel B shows the SPC network. In contrast to the standard representations herein, the present network indicates, for each SPC, the number of SNPs (also reflected by the size of the nodes) as well as the occurrence frequency. Panel C shows the table of genetic variations relative to a bona fide ancestral sequence (compare with the table shown in panel A). Part of the SPC-1 minor SNP alleles turned out to be ancestral. As a consequence, the major allele is colored at these polymorphic sites. Panel D shows the rooted SPC network. SPC-1 (see panel B) is split into SPC-1M (polymorphic sites where the major allele corresponds to the chimpanzee sequence) and SPC-1m (sites where the minor allele is ancestral).

Figure 31A:
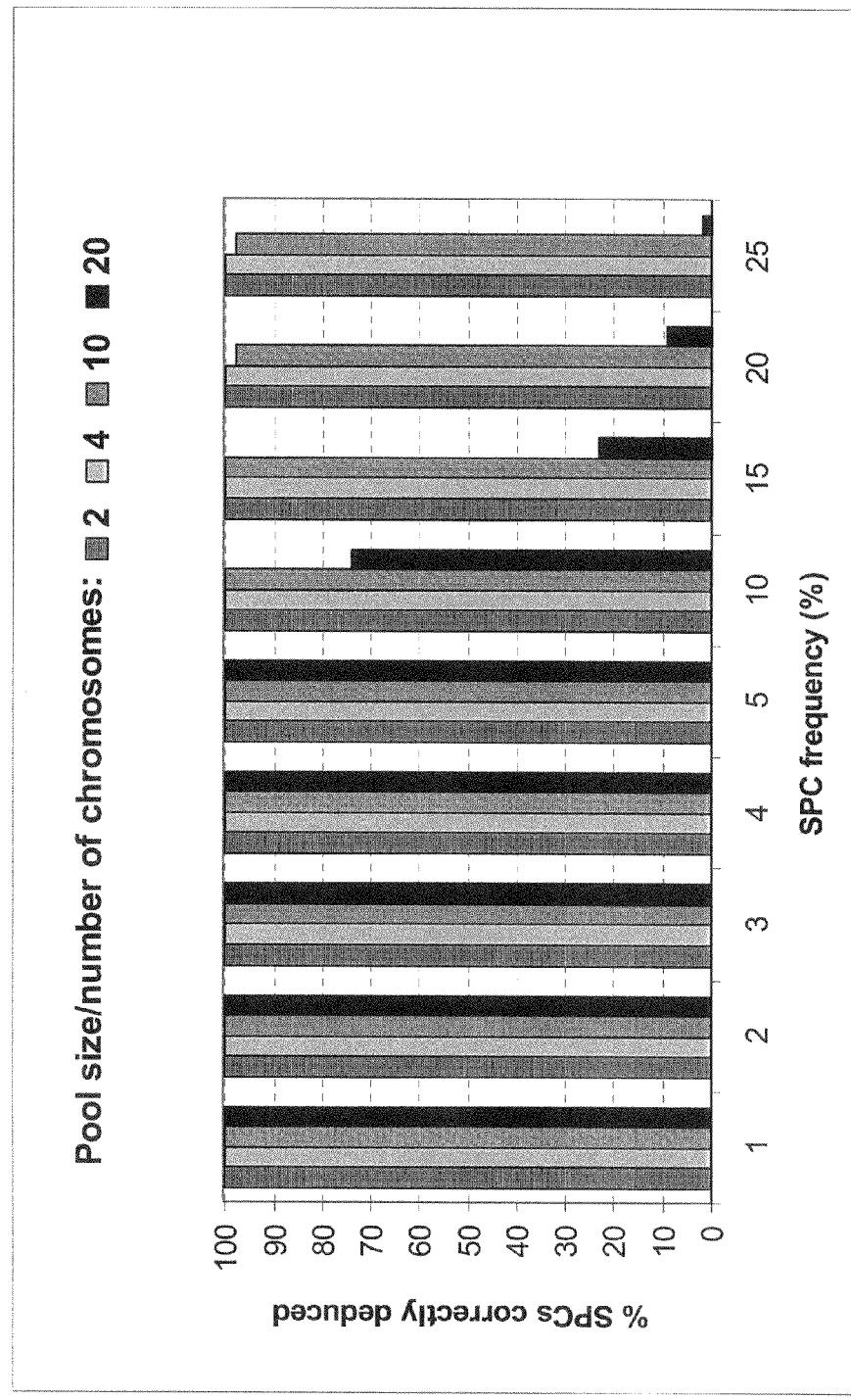
Figure 31B:
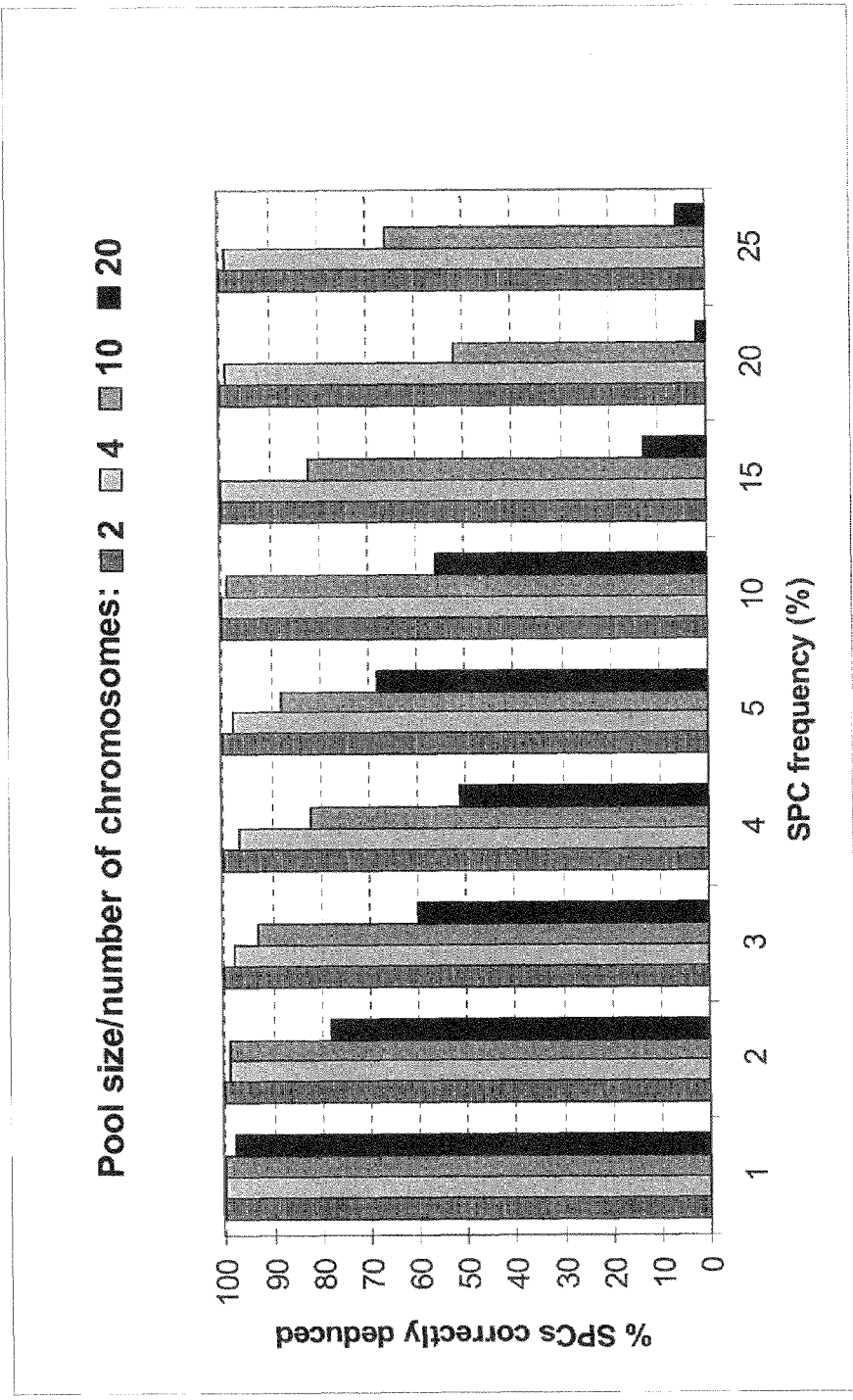

FIG. 31A illustrates the effect of SPC frequency and pool size on the success rate of identification of a series of independent SPCs using a pooling strategy. FIG. 31B illustrates the same for SPCs that are in a dependent relationship. The genotypes of sample pools were generated by random combination of known haplotypes and were subsequently analyzed by the SPC algorithm. The figure plots the success rate with which particular SPCs were identified in 100 repeat analyses using various pool sizes.

Figure 32A:
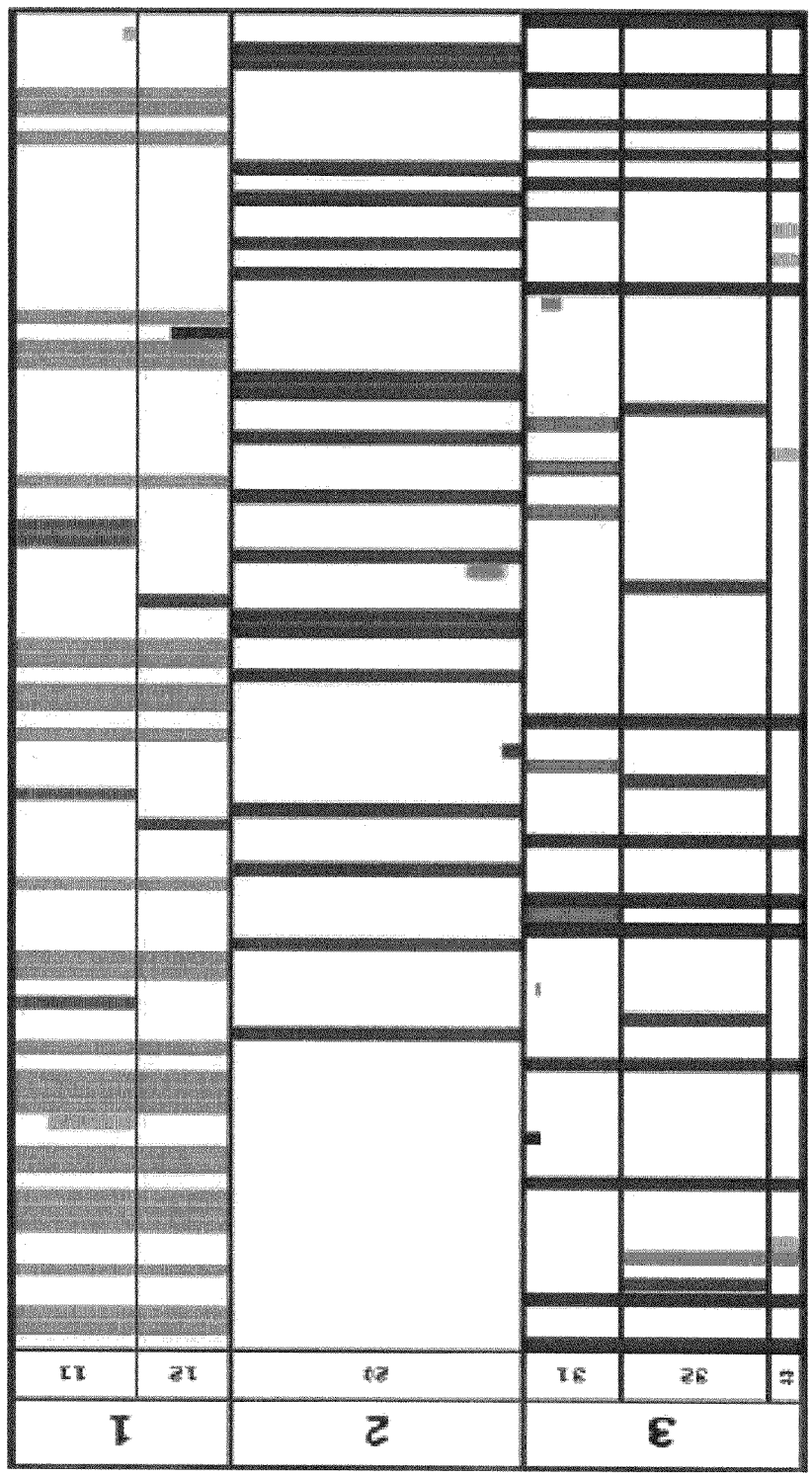
Figure 32B:
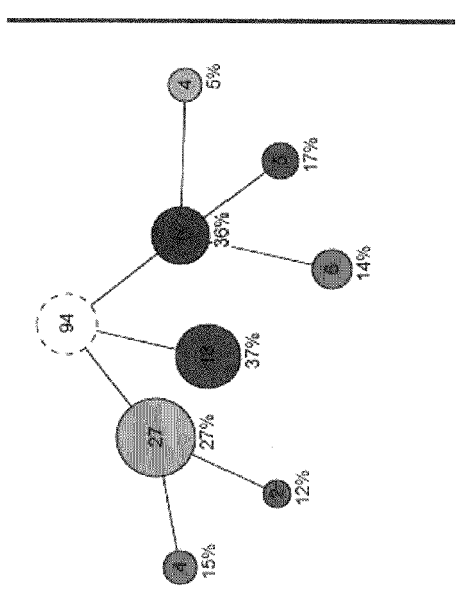
Figure 32C:
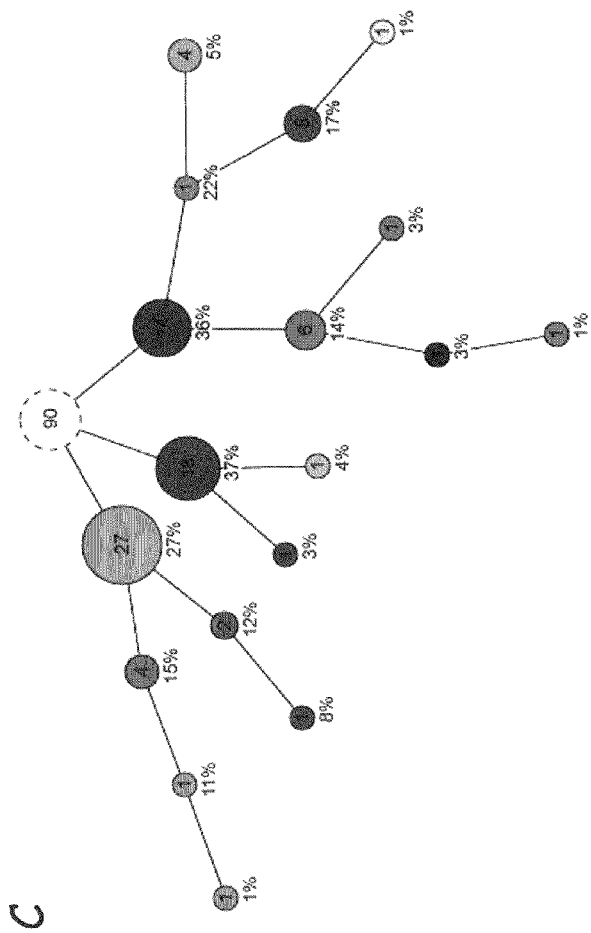
Figure 33A:
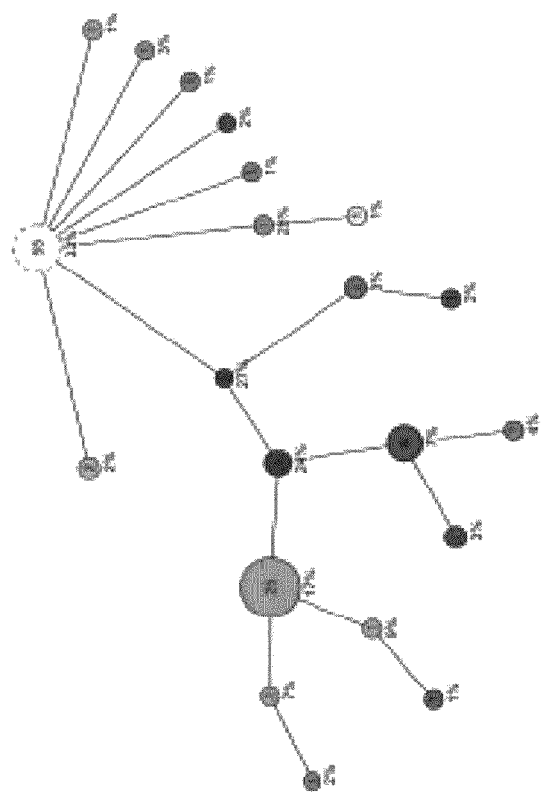
Figure 33A:
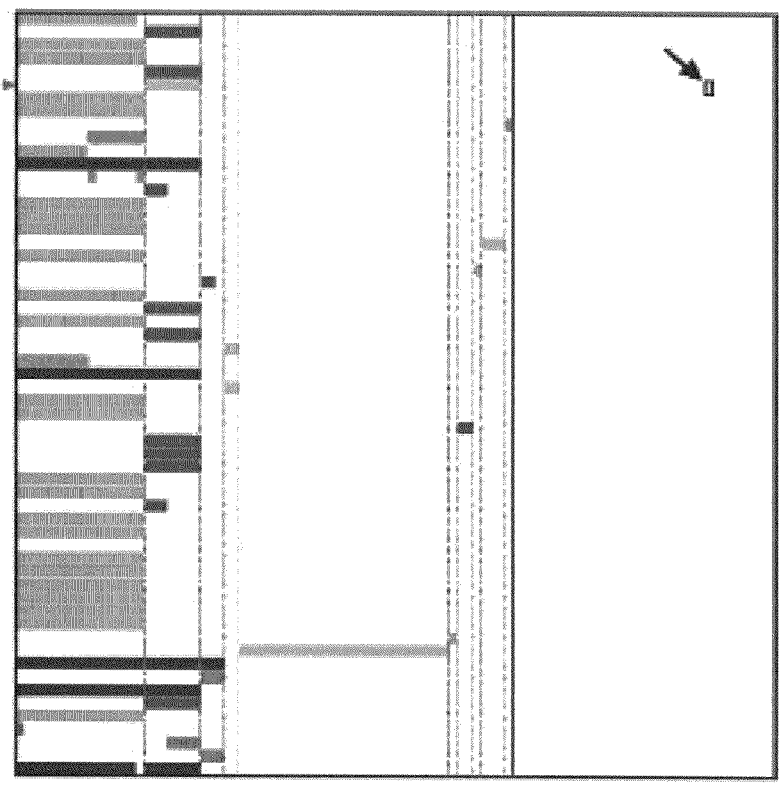
Figure 33B:
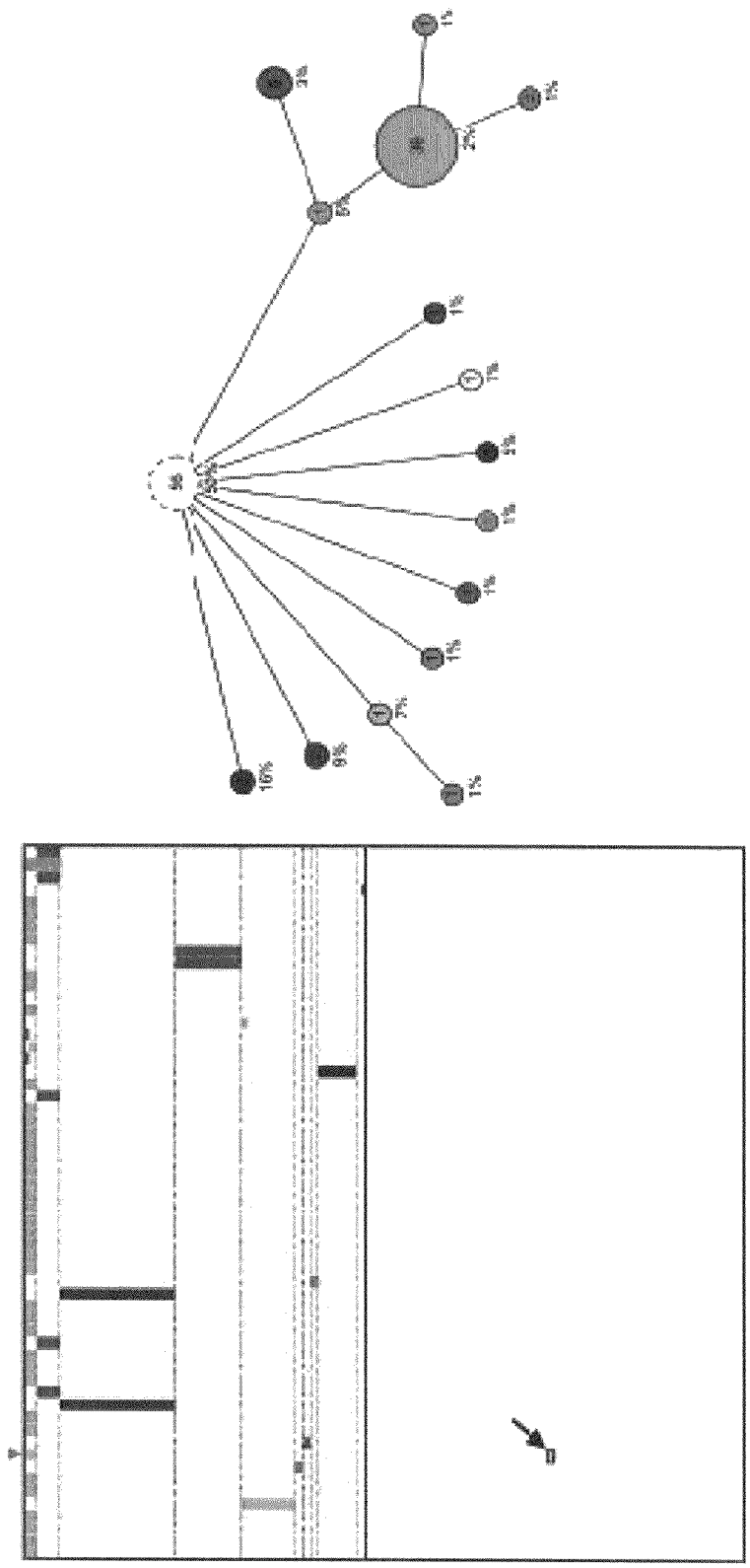
Figure 33C:
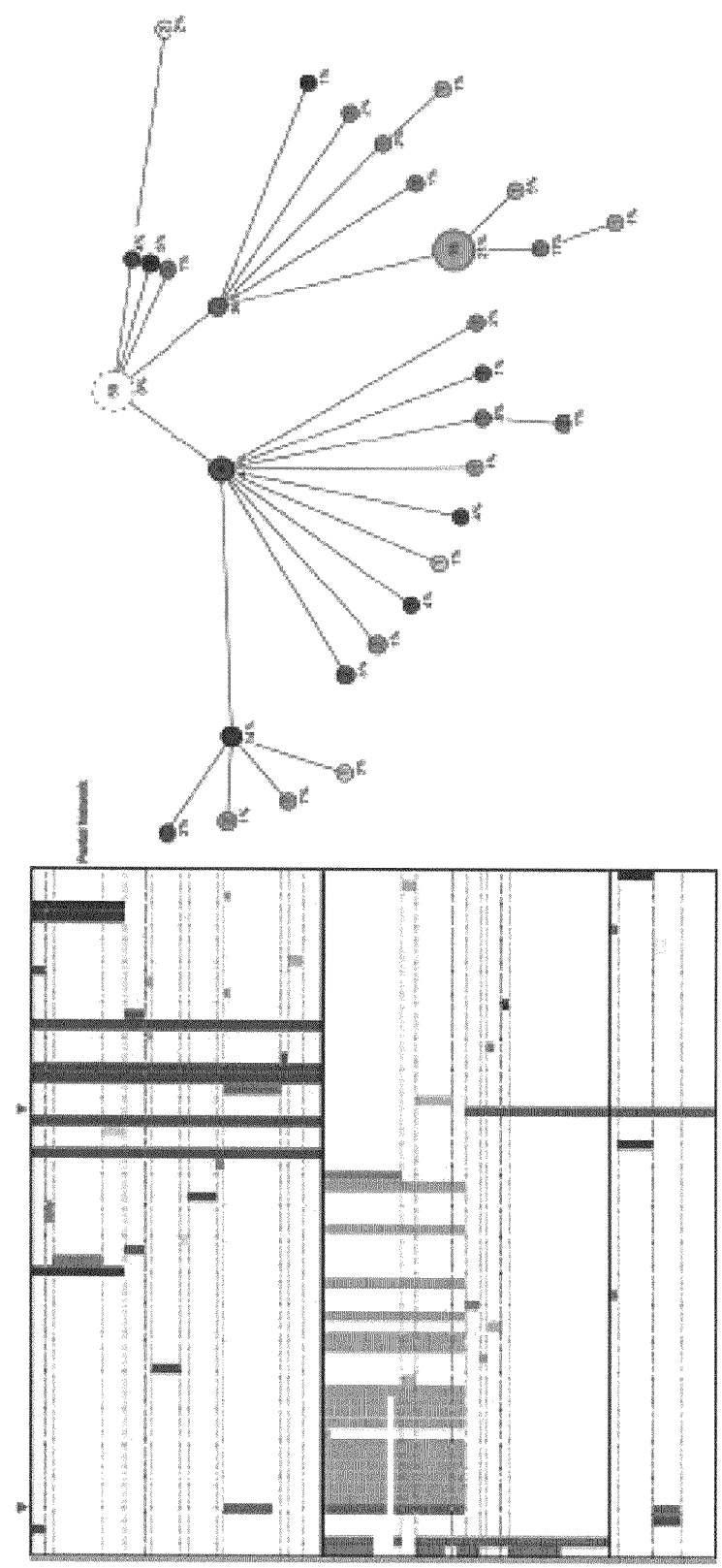
Figure 33D:
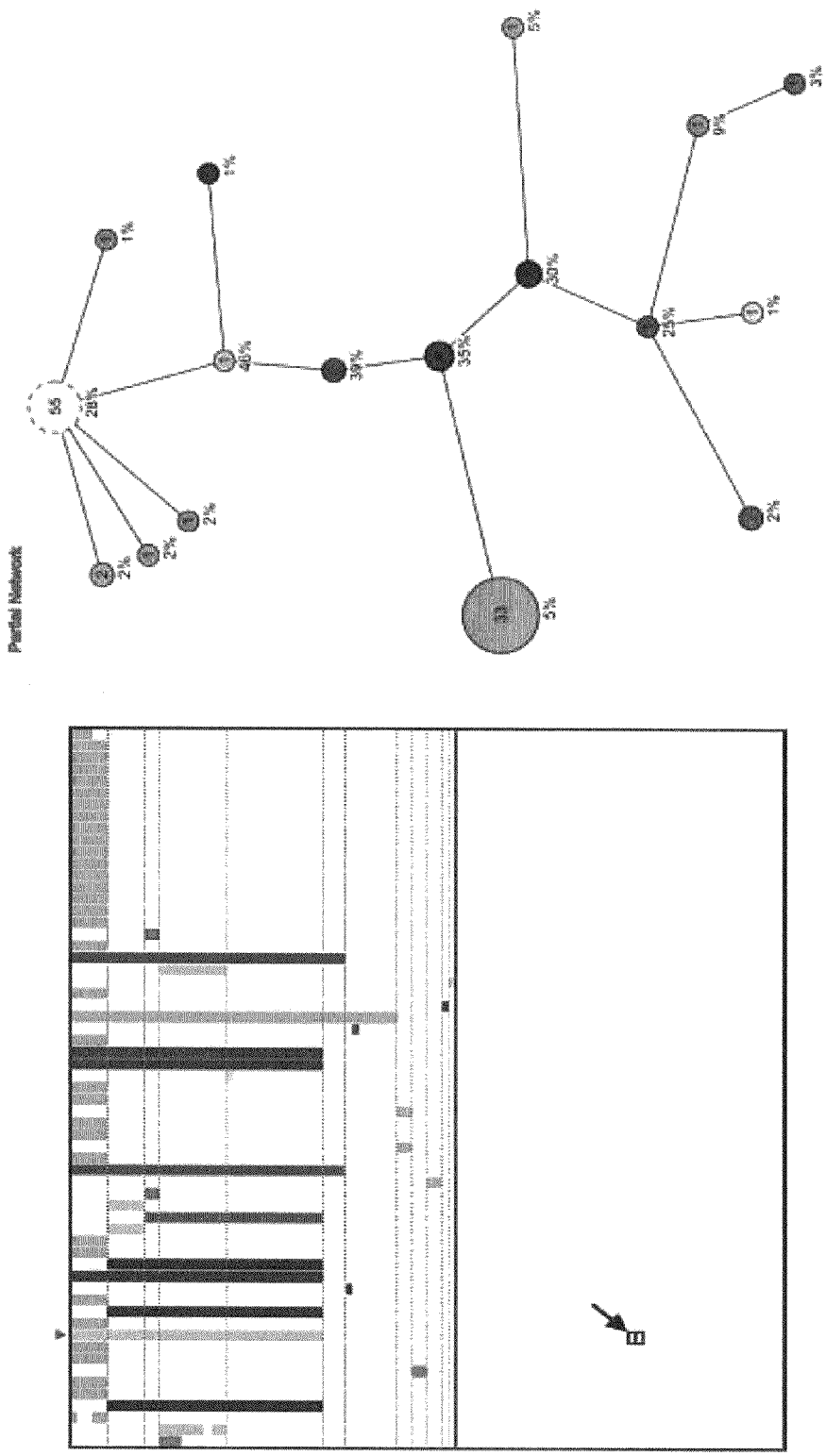
Figure 33E:
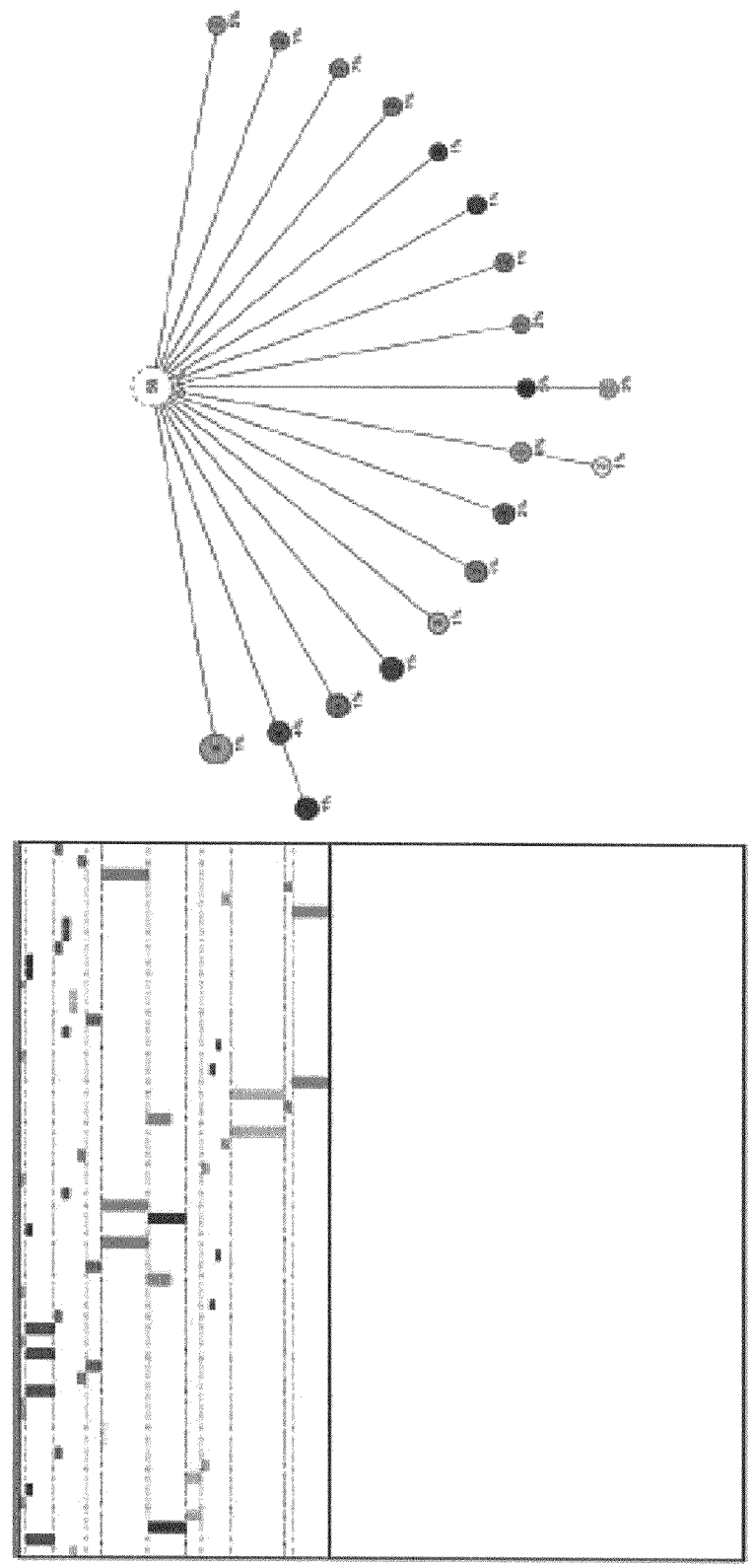
Figure 34:
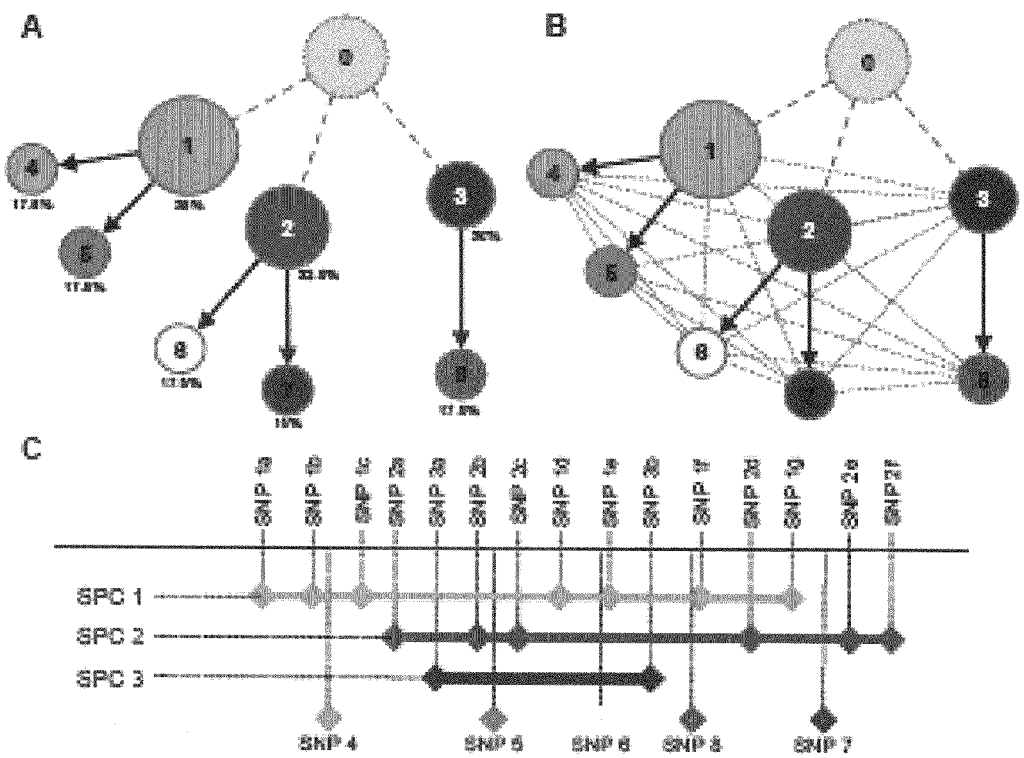
Figure 36:
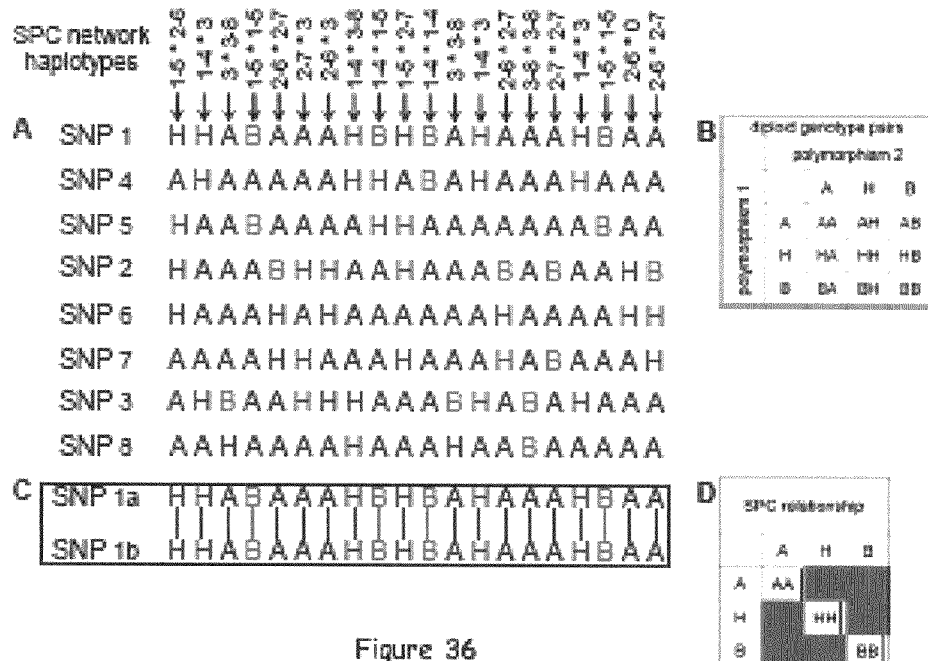
Figure 36:
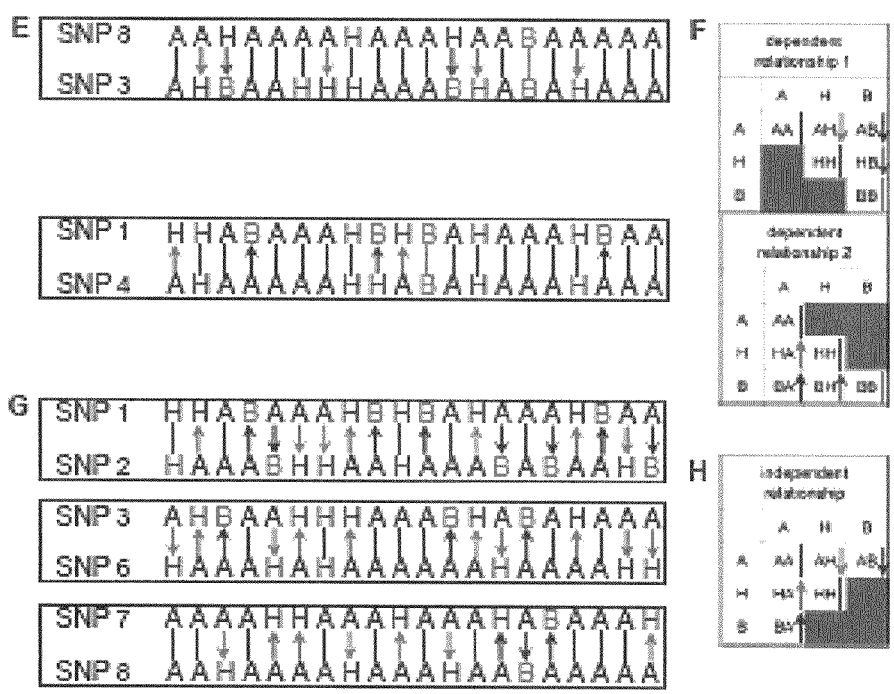
Figure 37:

FIG. 32 shows an SPC network that includes non-clustering polymorphisms. The region under study runs from position 126,135,436 to 126,178,670 on human chromosome 7 (build 34). Panel A shows the genetic variation data set onto which the SPCs as well as the non-clustering SNPs are depicted. Each row represents a sample and each column symbolizes an SNP. The allelic state is represented by colors: minor alleles are colored according to the SPC they belong to while the major allele is indicated by a light yellow color. The table is organized such that individuals that share the same SPCs/non-clustering SNP are grouped. The horizontal lines and the numbering to the left indicate the SPCs and the major haplotypes. Panel B shows the SPC network. For each SPC, the number of SNPs (also reflected by the size of the nodes) as well as the occurrence frequency is indicated. Panel C represents the SPC network to which the non-clustering SNPs were added (symbolized by the digit 1).

FIG. 33 illustrates the unambiguous placement of non-clustering polymorphisms in the SPC network of various *Arabidopsis* genomic regions. Each panel (A, B, C, D, and E) shows the SPC structure in one of five amplicons derived from *Arabidopsis* chromosome 1. All polymorphisms, including the singletons and those that do not cluster, were incorporated. The genetic variation tables contain the scores at the various polymorphic sites (columns) for a multitude of samples (rows). As explained in the text, tri-allelic SNPs and indels of two or more nucleotides are converted into two polymorphic scores. The allelic state is represented by colors: minor alleles are colored according to the SPC they belong to while the major allele is indicated by a light yellow color. The table is organized such that individuals that share the same SPCs are grouped. The horizontal lines separate the various SPCs/major haplotypes. The red arrowheads above the table indicate the polymorphic scores (colored in gray) that do not conform to the SPC network. In panel A, B and D, the arrows indicate the (presumably erroneous) allele calls that cause the nonconformity. In contrast to the standard representations herein, the present networks indicate, for each SPC, the number of SNPs (also reflected by the size of the nodes) as well as the occurrence frequency.

DETAILED DESCRIPTION OF THE INVENTION

The present invention is directed to methods, algorithms and computer programs for revealing the structure of genetic variation and to the selection of the most informative markers on the basis of the underlying structure. The methods can be applied on any data set of genetic variation from a particular locus. In one aspect, the analysis of the genetic variation is based on haplotype data. In a second aspect, the structure is uncovered using diploid genotype data, thereby avoiding the need to either experimentally or computationally infer the component haplotypes. In a third aspect, the present method can be applied onto uncharacterized allelic variation that results from the interrogation of a target nucleic acid with an experimental procedure that provides a record of the sequence variation present but does not actually provide the entire sequence or, in particular, the sequence at the variable positions. The underlying structure of genetic variation is also useful for the deduction of the constituent haplotypes from diploid genotype data.

The term "polymorphism", as used herein, refers to a condition in which two or more different nucleotide sequences can exist at a particular locus in DNA. Polymorphisms can serve as genetic markers. Polymorphisms include "single nucleotide polymorphism" (SNP) and indels. Such polymorphisms also are known as restriction fragment length polymorphisms (RFLP). A RFLP is a variation in DNA sequence that alters the length of a restriction fragment, as described in Botstein et al., Am. J. Hum. Genet. 32:314-331 (1980). The restriction fragment length polymorphism may create or delete a restriction site, thus changing the length of the restriction fragment. RFLPs have been widely used in human and animal genetic analyses (see WO 90/13668; WO90/11369; Donis-Keller, Cell 51:319-337 (1987); Lander et al., Genetics 121:85-99 (1989)). When a heritable trait can be linked to a particular RFLP, the presence of the RFLP in an individual can be used to predict the likelihood that the animal will also exhibit the trait.

Polymorphisms also exist as "short tandem repeats" (STRs) that include tandem di-, tri- and tetra-nucleotide repeated motifs. These tandem repeats are also referred to as variable number tandem repeat (VNTR) polymorphisms. VNTRs have been used in identity and paternity analysis (U.S. Pat. No. 5,075,217; Armour et al., FEBS Lett. 307:113-115 (1992); Horn et al., WO 91/14003; Jeffreys, EP 370,719), and in a large number of genetic mapping studies.

The term "allele(s)', as used herein, indicate mutually exclusive forms (sequences) of a single polymorphic site or of a combination of polymorphic sites.

The term "single nucleotide polymorphism" (SNP), as used herein, is used to indicate a polymorphism or genetic marker that involves a single nucleotide. Typically, SNPs are bi-allelic polymorphisms/markers.

The term "indel", as used herein, indicates an insertion/deletion polymorphism that involves two or more nucleotides.

The term "major allele", as used herein, refers to the most frequent of two or more alleles at a polymorphic locus.

The term "minor allele(s)", as used herein, refers to the less frequent allele(s) found at a polymorphic locus.

The term "diploid", as used herein, refers to the state of having each chromosome in two copies per nucleus or cell.

The term "haplotype", as used herein, denotes the combination of alleles found at multiple contiguous polymorphic loci (e.g. SNPs) on the same copy of a chromosome or haploid DNA molecule.

The term "genotype", as used herein, indicates the allele or pair of alleles present at one or more polymorphic loci. For diploid organisms, two haplotypes make up a genotype. For diploid inbred (plant or animal) species, which are principally homozygous, the genotype corresponds to the haplotype.

The term "metatype", as used herein, refers to an artificial haplotype. Metatypes originate from the replacement of the heterozygous calls in a genotype by either the minor or the major allele observed at the applicable positions.

The term "sequence polymorphism cluster (SPC)", as used herein, refers to a set of tightly linked (coinciding, co-occurring; co-segregating) sequence polymorphisms. More specifically, the term SPC indicates the set of coinciding minor alleles.

The term "cluster tag SNP(s)" (ctSNP), as used herein, refers to one or more SNPs that best represent the sequence polymorphism cluster to which the SNP(s) belong and that are preferred as markers for the detection of that sequence polymorphism cluster.

The term "cluster tag polymorphism(s)," as used herein, refers to one or more polymorphisms that best represent the sequence polymorphism cluster to which the polymorphisms belong and that can serve as markers for the detection of that sequence polymorphism cluster. "Cluster tag SNP(s)" (ctSNP) are preferred cluster tag polymorphisms.

The term "SPC-haplotype", as used herein, refers to the haplotype formed by those polymorphisms that belong to one or more SPCs.

The term "singleton", as used herein, means an instance of a category that has only one element or occurs only once; the context makes clear what is meant. A singleton SNP or SPC occurs only once in the sample under investigation.

The term "clade", as used herein, denotes a group of sequences or haplotypes that are related in that these haplotypes have one or more SPCs in common while also differing from one another in at least one SPC.

SPC-algorithm

In the present invention a novel computational approach has been developed for the identification of organizational features in sequence polymorphisms. The present approach is different from the conventional approach for identifying haplotype blocks in that it does not look for blocks of contiguous polymorphisms that are in linkage disequilibrium, but rather determines the presence of clusters of sequence polymorphisms that exhibit significant clustering statistics are searched. As such, clusters of the present invention can but need not be of contiguous sequences along a gene. The structures revealed by the method of the present invention are referred to as sequence polymorphism clusters (SPCs). These are groups of coinciding markers, i.e. sets of markers that are co-inherited or that co-segregate (the latter term being more common in the agricultural sector). The alleles at such marker sites have not been separated by recombination, gene conversion or recurrent mutation and have identical frequencies (a condition that can be described as perfect or absolute LD). In this case, only two out of the four possible two-site haplotypes are observed in the sample, i.e. observations at one marker provide complete information about the other marker. In essence, SPCs are identified by first quantifying the percentage coincidence between pairs of (bi-allelic) sites followed by the stepwise assembly of marker alleles that exhibit coincidence above a gradually less stringent threshold.

Coincident marker alleles can be identified with the use of certain measures for assessing the strength of LD. Many different LD statistics have been proposed [Lewontin R. C., Genetics 140: 377-388, 1995; Devlin & Risch, Genomics 29: 311-322, 1995]. One frequently used LD measure that is suitable with the present invention is $r^2$ (sometimes denoted $\Delta^2$). $r^2$ ranges from zero to one and represents the statistical correlation between two sites; it takes the value of 1 if only two out of the four possible two-site haplotypes are observed in the sample. The popular |D'| statistic and similar measures [e.g. Q; see Devlin & Risch, Genomics 29: 311-322, 1995] are not appropriate for the present algorithm as these measures return the maximum value irrespective of whether there are two or three haplotypes formed by the pair of markers.

Adopting the standard notation for two loci—with a major (A,B) and a minor (a,b) allele at each site—$r^2$ is determined by dividing the square of Lewontin's D value [Lewontin R. C., Genetics 49: 49-67, 1964] by the product of all four allele frequencies:

$$r^2 = (P_{ab}P_{AB} - P_{aB}P_{Ab})^2 / P_a P_b P_A P_B$$

The notation for observed haplotype and marker allele frequencies is given in the 2×2 association Table 1. It should be kept in mind that the P-values are only sample estimates of some underlying unknown parameters. By the convention of naming alleles: $P_A \geq P_a \geq P_b$.

TABLE 1

Notation for observed haplotype and marker allele frequencies

|  |  | Site 1 |  |  |
|---|---|---|---|---|
| Marker |  | major allele A | minor allele a |  |
| Site 2 | major allele B | $P_{AB}$ | $P_{aB}$ | $P_B$ |
|  | minor allele b | $P_{Ab}$ | $P_{ab}$ | $P_b$ |
|  |  | $P_A$ | $P_a$ | 1 |

The identification of clusters of coinciding markers can also be performed with the use of other LD-measures [refer to Devlin & Risch, Genomics 29: 311-322, 1995], including $\Delta$ (the square root of $\Delta^2$), $\delta$, and the difference in proportions d:

$$d = P_{ab}/P_a - P_{Ab}/P_A$$

Yet another expression that was found useful is:

$$C^* = P_{ab} - P_a P_b / P_a - P_a P_b$$

Similar to many other LD measures, the numerator of the above equation equals to Lewontin's D value [Lewontin R. C., Genetics 49: 49-67, 1964]. The denominator, which serves to standardize D is however such that, in contrast to the more commonly used |D'| measure, $C^* = 1$, if, and only if, two out of the four possible two-locus haplotypes are observed in the sample. Note that the value of $C^*$ can be positive (coupling) or negative (repulsion) and that in this case absolute values are taken into consideration. The formula consistently used herein simply measures the proportion (%) of the haplotype consisting of the minor alleles a and b ($P_{ab}$), relative to the frequency of the most common minor allele (i.e. $P_a$):

$$C = P_{ab}/P_a$$

This formula has obvious shortcomings as a measure for LD mainly because the observed haplotype frequency $P_{ab}$ is not offset against the expected frequency such as in $C^*$. For instance, $C=0$ whenever $P_{ab}=0$, a situation which does not necessarily imply there is linkage equilibrium. Conversely, C can be greater than 0 in case there is complete equilibrium, e.g. when all four haplotypes are equally frequent. Nevertheless, the formula is practical because of its transparency (i.e. the direct relation to the % coincidence) and is adequate when used in combination with appropriate threshold values.

The use of alternative formulas can yield different estimates of the strength of association. Moreover, it is important to realize that a typical genetic variation data set contains a significant number of missing allele calls and that, consequently, haplotype and marker allele frequencies may also be calculated in different ways which on itself may already have a marked effect on the returned value. In most cases the frequency was estimated by simply dividing the observed number of a particular allele or two-site haplotype by the total number of samples, thereby neglecting missing data. An alternative calculation consists of the ratio of the observed number of alleles/haplotypes over the total number of unambiguous calls. According to a third method, the missing data points were treated in a statistical way and were taken as both the minor and major allele in proportion to the observed allele ratio at that polymorphic position. Similarly, the two-site haplotypes may also occur as fractions. In such a case, the number of alleles or haplotypes was divided by the total number of samples. In yet another method only those samples that have an allele call at both polymorphic positions are considered to calculate the haplotype as well as the allele frequency. Note that, in this case, the allele frequencies at one particular polymorphic site are not fixed but depend on the site with which association is being calculated. The latter approach tends to overestimate the strength of association and may be utilized for the detection of SPCs in data sets with numerous missing allele calls. It will be understood that the different approaches are identical when the sample genotypes are devoid of missing data.

The following section provides a description of the elements of the SPC algorithm/program. The input consists of a genetic variation table containing the alleles present at a given number of polymorphic sites (columns) for a plurality of subjects (rows), i.e. basically a set of haplotypes (although it is shown herein that diploid genotype data may also be processed). The program can derive this table from a 'multiple sequence alignment file'. The first step in the algorithm consists of the generation of a matrix with all pairwise calculations of the strength of coincidence (e.g. values of C as defined above). Subsequently, a clustering operation is performed whereby one or more sequence polymorphism clusters (SPC) are formed and an SPC map is assembled. An SPC assembles sequence polymorphisms that coincide with each other to an extent that exceeds an empirically defined threshold level. The minimum number of polymorphisms that an SPC has to incorporate as well as its occurrence frequency in the sample in order for that SPC to be statistically meaningful varies from one data set to the other.

The clustering operation is an iterative process. First, sequence polymorphisms are grouped that exhibit absolute linkage, i.e. C=1 for all pairwise measurements. The clusters that are formed are allowed to expand and new clusters are to emerge by gradually decreasing (e.g. using steps of 0.1, 0.05 or 0.025) the threshold value down to a bottom value. SPCs can be defined at any threshold value, including 1, $\geq 0.95$, $\geq 0.90$, $\geq 0.85$, $\geq 0.80$, $\geq 0.75$, $\geq 0.70$, $\geq 0.65$, $\geq 0.60$, $\geq 0.55$, and $\geq 0.50$. Those of ordinary skill in the art will recognize that the adequacy of the threshold settings depends, among other things, on the measure that is used to calculate the strength of association of the marker alleles. When using the measure $C=P_{ab}/P_a$, the SPC maps are typically generated at multiple threshold values between C=1 and $C \geq 0.75$. The clustering operation may be performed according to several different criteria. In one approach, all pairwise coincidence values of the cluster polymorphisms must exceed the chosen threshold level. Alternatively, individual polymorphisms or entire clusters are merged when the average association value exceeds a certain practical threshold level. Yet another option requires that at least one polymorphism is in association with all other polymorphisms of the cluster above the threshold value. As used herein, a cluster may assemble not only the group of primary polymorphisms whose pairwise association surpasses the threshold but also secondary polymorphisms that are in association above the threshold with one of the primary polymorphisms.

It is important to realize that the C-measure only considers the haplotype consisting of the minor alleles a and b ($P_{ab}$). This renders the formula less suited in cases where the allele frequencies are close to 0.5. Also, mis-assignment of the minor allele can happen especially in small data sets, more specifically at polymorphic sites where the observed frequency of the two alleles is exactly 0.5 or when as a result of missing genotype data the apparent major allele is observed in less than half of the samples. In such cases both alleles need to be tested for coincidence with other marker alleles. The SPCs that the program has identified can be visualized in a number of different ways including a color-coded version of the above-mentioned matrix with coincidence values (C-values) and a color-coded version of the original input genetic variation table (sorted such that the individuals that share the same SPCs are grouped). Several examples of the output, adapted for readability in black/white illustration, are shown herein.

The SPC-program incorporates a module for the selection of cluster tag polymorphisms. This selection is based on the identification of the one or more polymorphisms that best represent the SPC they belong to. Typically, SNPs are chosen as cluster tag polymorphisms; cluster tag SNPs are herein also named ctSNPs. According to a preferred method, the average strength of association (herein also referred to as Average Linkage Value or ALV) of each polymorphism with all other polymorphisms of the cluster is calculated and used as the decisive criterion: the one or more polymorphisms/SNPs that exhibit the highest ALV are retained as markers for subsequent genotyping experiments.

In addition to most common bi-allelic SNPs, indels as well as multi-allelic polymorphisms were sometimes included in the analyses. While multi-allelism is a rather rare event in humans it was encountered occasionally in the data sets that derive from highly polymorphic organisms such as maize. When more than one minor allele was observed at an SNP site, the input genetic variation table containing the allele calls (genotypes) at all the polymorphic sites for each individual was adapted: the site was duplicated and modified so that each entry lists the major allele in combination with one of the minor alleles while all other allele calls were replaced by blanks. The procedure ensures that at each position in the table only two variants are observed. Unless otherwise specified, indels were identified by two dots at, respectively, the start and the end position of the deletion. In between these dots blank spaces may be present whenever polymorphic sites occur at intervening positions in the other samples. Blank spaces in the genetic variation table are ignored and frequencies are calculated by simply dividing the observed number of a particular allele or two-site haplotype by the total number of samples.

As disclosed herein, the algorithm can not only be applied to a data set of genetic variants from a particular locus but also, in a generic sense, to experimental data that capture all or part of that genetic variation. The genetic variation table can also consist of diploid genotype data. To process such a data set, the input table is adapted to contain each individual twice; all heterozygous scores are then replaced by the minor allele in one entry and by the major allele in the second entry. The resultant artificial haplotypes are herein named metatypes and the adapted genetic variation table is called a metatype table.

The present clustering method may presumably also be performed with the use of other measures for the strength of association between marker alleles than those mentioned herein. These measures can either be known or newly conceived. For instance, a statistic that measures the strength of association between multi-allelic rather than bi-allelic loci could be utilized [e.g. refer to Hedrick P. W., Genetics 117: 331-341, 1987 for a multi-allelic version of D']. In general, the use of alternative measures in combination with appropriate threshold levels will expose a set of SPCs. This, and other variations in the algorithm may be readily adapted by those skilled in the art. These variations may to a certain extent affect the output of the program (as is often the case with iterative clustering procedures) but are equally useful in exposing the fundamental SPC structure of genetic variation data—these variations are therefore also within the scope of the present invention.

The algorithms of the invention also may be described according to FIGS. 21-29. FIG. 21 is a schematic diagram of one possible embodiment of a computer (i.e., machine) 30. The computer 30 may be used to accumulate, analyze, and download data relating to defining the subset of variations that are most suited as genetic markers to search for correlations with certain phenotypic traits. The computer 30 may have a controller 100 that is operatively connected to a database 102 via a link 106. It should be noted that, while not shown, additional databases may be linked to the controller 100 in a known manner.

The controller 100 may include a program memory 120, a microcontroller or a microprocessor (MP) 122, a random-access memory (RAM) 124, and an input/output (I/O) circuit 126, all of which may be interconnected via an address/data bus 130. It should be appreciated that although only one microprocessor 122 is shown, the controller 100 may include multiple microprocessors 122. Similarly, the memory of the controller 100 may include multiple RAMs 124 and multiple program memories 120. Although the I/O circuit 126 is shown as a single block, it should be appreciated that the I/O circuit 126 may include a number of different types of I/O circuits. The RAM(s) 124 and programs memories 120 may be implemented as semiconductor memories, magnetically readable memories, and/or optically readable memories, for example. All of these memories or data repositories may be referred to as machine-accessible mediums. The controller 100 may also be operatively connected to a network 32 via a link 132.

For the purpose of this description and as briefly discussed above, a machine-accessible medium includes any mechanism that provides (i.e., stores and/or transmits) information in a form accessible by a machine (e.g., a computer, network device, personal digital assistant, manufacturing tool, any device with a set of one or more processors). For example, a machine-accessible medium includes recordable/non-recordable media (e.g., read only memory (ROM); random access memory (RAM); magnetic disk storage media; optical storage media; flash memory devices), as well as electrical, optical, acoustical or other form of propagated signals (e.g., carrier waves, infrared signals, digital signals); etc.

One manner in which an exemplary system may operate is described below in connection with a number of flow charts which represent a number of portions or routines of one or more computer programs. As those of ordinary skill in the art will appreciate, the majority of the software utilized to implement the routines is stored in one or more of the memories in the controller 100, and may be written at any high level language such as C, C++, or the like, or any low-level assembly or machine language. By storing the computer program portions therein, various portions of the memories are physically and/or structurally configured in accordance with the computer program instructions. Parts of the software, however, may be stored and run on one or more separate computers that are operatively coupled to the computer 30 via a network. As the precise location where the steps are executed can be varied without departing from the scope of the invention, the following figures do not address which machine is performing which functions.

FIG. 22 is a flow chart 150 describing some of the steps used to facilitate the production of a sequence polymorphism cluster (SPC) map of a genomic region of interest. The flowchart 150 begins with the step of obtaining the nucleic acid sequence of a genomic region of interest from a plurality of subjects (block 152). After obtaining the nucleic acid sequence, the flow chart 150 proceeds to identifying a plurality of polymorphisms in the nucleic acid sequences (block 154) and then to identifying one or more SPCS, wherein each SPC comprises a subset of polymorphisms from the nucleic acid sequence wherein the polymorphisms of the subset coincide with each other polymorphism of the subset (block 156). It should be noted that the identification of the one or more SPCs may include identifying each polymorphism of the subset that coincides with each other polymorphism of the subset according to a percentage coincidence of the minor alleles of the polymorphisms of between 75% and 100%. The identification of the one or more SPCs also may include multiple rounds of coincidence analysis, wherein each successive round of coincidence analysis is performed at a decreasing percentage coincidence from 100% coincidence to 75% coincidence. Alternatively, the coincidence of each of the polymorphism of the subset with each other polymorphism of the subset may be calculated according to a parameter, such as, for example, a pairwise C value, a r2 linkage disequilibrium value, and a d linkage disequilibrium value, wherein the pairwise C value ranges from 0.75 to 1. It should also be noted that the identification of a plurality of polymorphisms in the target nucleic acid sequences may be determined by an assay, such as, for example, direct sequence analysis, differential nucleic acid analysis, sequence based genotyping DNA chip analysis, and PCR analysis.

FIG. 23 is a flow chart 160 describing some of the steps used to facilitate the production of an SPC map of a genomic region of interest from unphased diploid genotypes. The flowchart 160 may begin with the step of obtaining the unphased diploid genotypes of a genomic region of interest from a plurality of subjects (block 162). After obtaining the unphased diploid genotypes, the flow proceeds to determining the major and minor metatypes found in the unphased diploid genotypes (block 164) and then to identifying one or more SPCs, wherein each SPC comprises a subset of polymorphisms from the metatypes wherein the polymorphisms of the subset coincide with each other polymorphism of the subset (block 166). It should be noted that the step of identifying the one or more SPCs may include identifying each polymorphism of the subset that coincides with each other polymorphism of the subset according to a percentage coincidence of the minor alleles of the polymorphisms of between 85% and 100%.

As with the exemplary method of producing the SPC map described with reference to FIG. 22, the exemplary method disclosed in FIG. 23 may include multiple rounds of coincidence analysis, wherein each successive round of coincidence analysis is performed at a decreasing percentage coincidence from 100% coincidence to 75% coincidence. Alternatively, the coincidence of each of the polymorphism of the subset with each other polymorphism of the subset may be calculated according to a parameter, such as, for example, a pairwise C value, a r2 linkage disequilibrium value, and a d linkage disequilibrium value, wherein the pairwise C value ranges from 0.75 to 1. It should also be noted that the identification of a plurality of polymorphisms in the target nucleic acid sequences may be determined by an assay, such as, for example, direct sequence analysis, differential nucleic acid analysis, sequence based genotyping DNA chip analysis, and PCR analysis.

FIG. 24 is an exemplary flow chart 170 describing some of the steps used in a method of selecting one or more polymorphisms from a genomic region of interest for use in genotyping. The flowchart 170 may begin with the step of obtaining an SPC map of a genomic region of interest (block 172). After obtaining the SPC map, the flow chart 170 may proceed to selecting at least one cluster tag polymorphism which identifies a unique SPC in the SPC map (block 174) and then to selecting a sufficient number of cluster tag polymorphisms for use in a genotyping study of the genomic region of interest (block 176). It should be noted that the cluster tag polymorphism may be, for example, a single nucleotide polymorphism (SNP), a deletion polymorphism, an insertion polymorphism; or a short tandem repeat polymorphism (STR). Also, the cluster tag polymorphism may be a known SNP associated with a genetic trait.

FIG. 25 is a flow chart 180 describing some of the steps used to facilitate the identification of a marker trait or phenotype. The flowchart 180 may begin with the step of obtaining a sufficient number of cluster tag polymorphisms from a genomic region of interest (block 182). After obtaining the sufficient number of cluster tag polymorphisms, the flow proceeds to assessing the cluster tag polymorphisms to identify an association between a trait or phenotype and at least one cluster tag polymorphism, wherein identification of the association identifies the cluster tag polymorphism as a marker for the trait or phenotype (block 184). The cluster tag polymorphism may be correlated with a variety of traits or phenotypes, such as, for example, a genetic disorder, a predisposition to a genetic disorder, susceptibility to a disease, an agronomic or livestock performance trait, a product quality trait. Also, the marker may be a marker of a genetic disorder and the SPC map may be prepared according to the method described in FIG. 22, and the plurality of subjects each manifests the same genetic disorder. It should also be noted that the identification of the plurality of polymorphisms in the target nucleic acid sequences may be determined by a number of assays, including, for example, direct sequence analysis, differential nucleic acid analysis, sequence based genotyping, DNA chip analysis and polymerase chain reaction analysis.

FIG. 26 is an exemplary flow chart 190 describing some of the steps used to facilitate the identification of a location of a gene associated with a trait or phenotype. The flowchart 190 may begin with the step of identifying a plurality of SPCs identified in a given genomic region associated with the trait or phenotype, wherein each SPC comprises a subset of polymorphisms from the genomic region wherein the polymorphisms of the subset are associated with each other polymorphism of the subset (block 192). After identifying the plurality of SPCs, the flow proceeds to identifying a set of cluster tag polymorphisms wherein each member of the set of cluster tag polymorphisms identifies a unique SPC in the plurality of SPCs (block 194). The flow may then continue with assessing the set of cluster tag polymorphisms to identify an association between a trait or phenotype and at least one cluster tag polymorphism, wherein identification of the association between the cluster tag polymorphism and the trait or phenotype is indicative of the location of the gene (block 196). It should be noted that the phenotype may be, for example, a genetic disorder, a predisposition to a genetic disorder, susceptibility to a disease, an agronomic or livestock performance trait, or a product quality trait.

FIG. 27 is an exemplary flow chart 200 describing some of the steps used in a method for in vitro diagnosis of a trait or phenotype. The flowchart 200 may begin with the step of obtaining a marker for a trait or phenotype in a subject (block 202). After obtaining the marker, the flow proceeds to obtaining a target nucleic acid sample from the subject (block 204) and determining the presence of the marker for the trait or a phenotype in the target nucleic acid sample, wherein the presence of the marker in the target nucleic acid indicates that the subject has the trait or the phenotype (block 206). The trait or phenotype may be, for example, a genetic disorder, a predisposition to a genetic disorder, susceptibility to a disease, an agronomic or livestock performance trait, or a product quality trait.

FIG. 28 is an exemplary flow chart 210 describing some of the steps used in a method of determining the genetic identity of a subject. The flowchart 210 may begin with the step of obtaining a reference SPC map of one or more genomic regions from a plurality of subjects (block 212). After obtaining the reference SPC map, the flow proceeds to selecting a sufficient number of cluster tag polymorphisms for the genomic regions (block 214) and obtaining a target nucleic acid of the genomic regions from a subject to be identified (block 216). The flow may continue with determining the genotype of the cluster tag polymorphisms of the genomic regions of the subject to be identified (block 218) and comparing the genotype of the cluster tag polymorphisms with the reference SPC map to determine the genetic identity of the subject of interest (block 219). In some embodiments, the reference SPC map may be prepared according to the methods described in connection with FIG. 22 or 23.

FIG. 29 is an exemplary flow chart 220 describing some of the steps used in a method of determining the SPC-haplotypes from unphased diploid genotype of a genomic region of interest. The flowchart 220 begins with the step of obtaining an SPC map of a genomic region of interest (block 222). After obtaining the reference SPC map, the flow proceeds to determining the SPC-haplotypes from the SPC map, wherein each SPC-haplotype includes a subset of SPCs from a genomic region wherein the SPCs of the subset coincide (block 224) and identifying the SPC-haplotype of a test subject by comparing the SPC of the subject with the SPC-haplotypes determined from the SPC map (block 226).

Genetic Polymorphisms are Often Organized in a Hierarchical SPC Structure

Using the computational approach described above, certain organizational features in sequence polymorphisms can be identified. When studies reporting a relatively high marker density over contiguous regions are examined, it can be noted that, in many of these genomic regions, a good number of the SNPs (as well as indels) present are organized into one or more sequence polymorphism clusters (SPC), i.e. sets of polymorphisms that are essentially in absolute linkage (i.e. pairwise C-value is 1 or close to 1). Several analyses indicate that, in general, the various SPCs can comprise between 60% and 95% of all the polymorphisms present in the sample under study. The inventors have found this to be true in all species for which sufficient data on genetic variation are available, including human, maize, *Arabidopsis, Drosophila*, and yeast. Typically, the polymorphisms in an SPC are non-contiguous and the polymorphisms that belong to different SPCs are intermingled. The present finding is different from the haplotype block concept in which areas of contiguous polymorphisms are identified that are essentially devoid of recombination (i.e. high values of Lewontin's D' measure) and/or that display limited haplotype diversity [refer to Wall & Pritchard, Nature Rev. Genet. 4: 587-597, 2003 for various definitions of haplotype blocks].

Figure 1A:
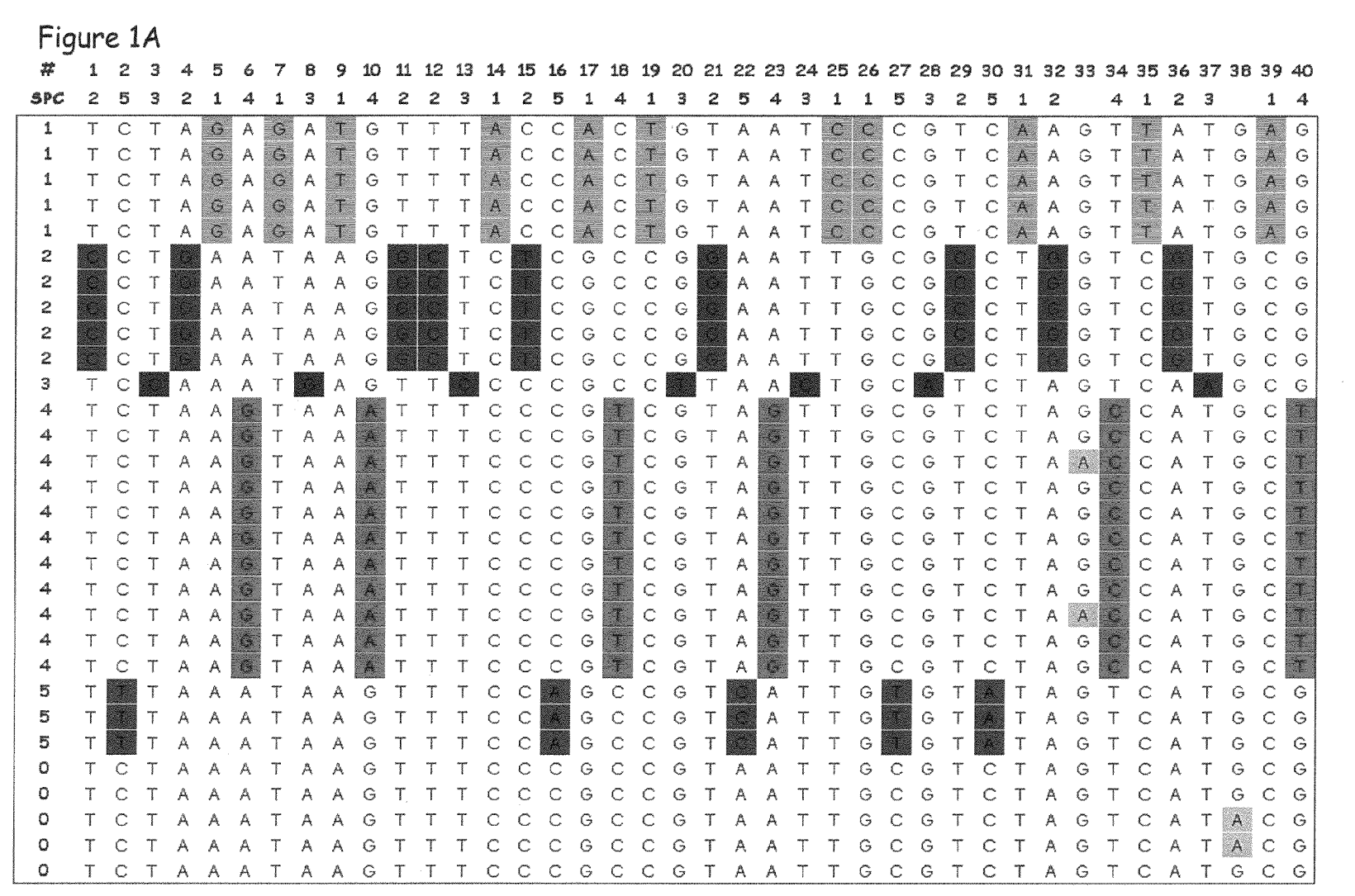
Figure 2A:
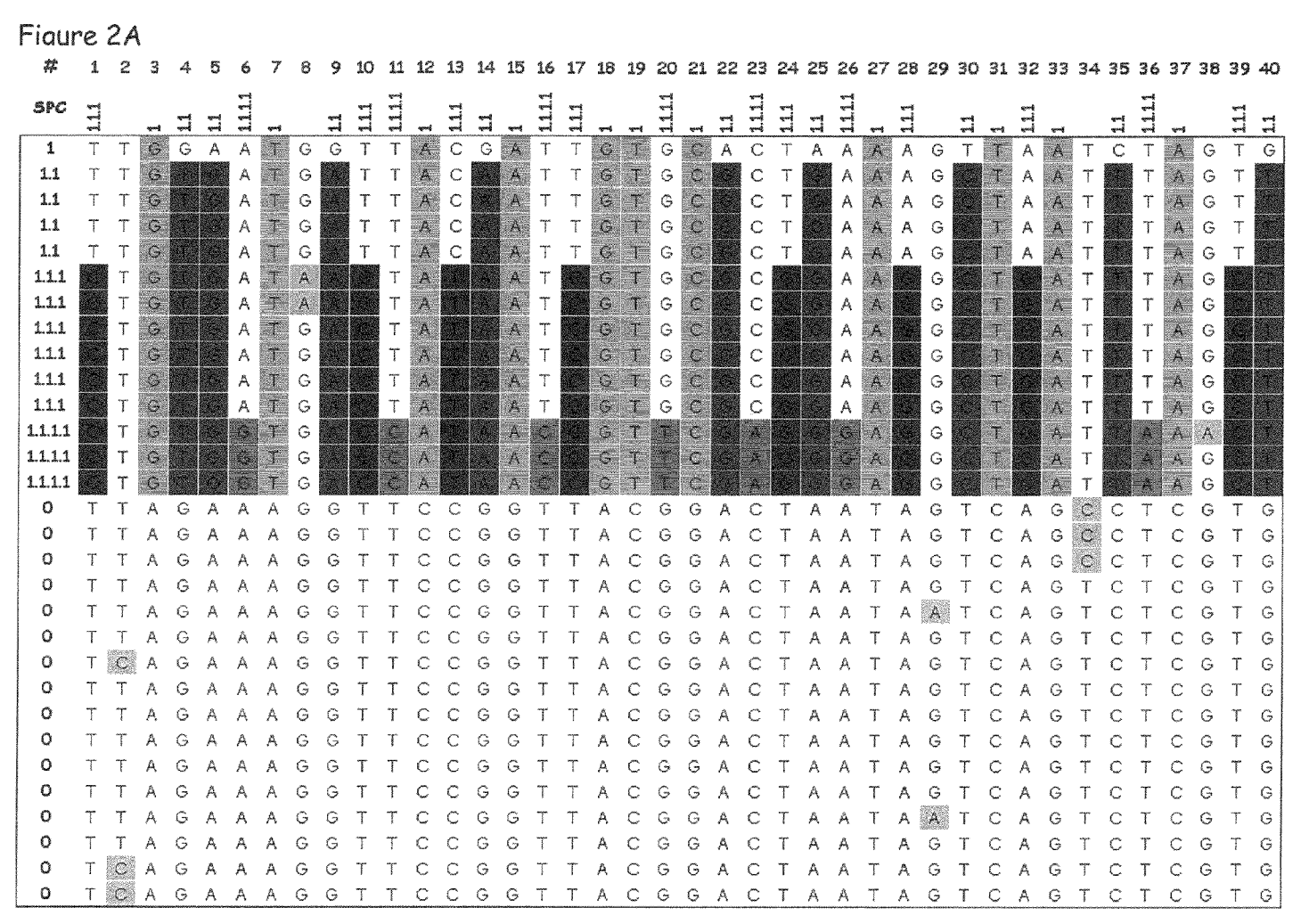
Figure 2B:
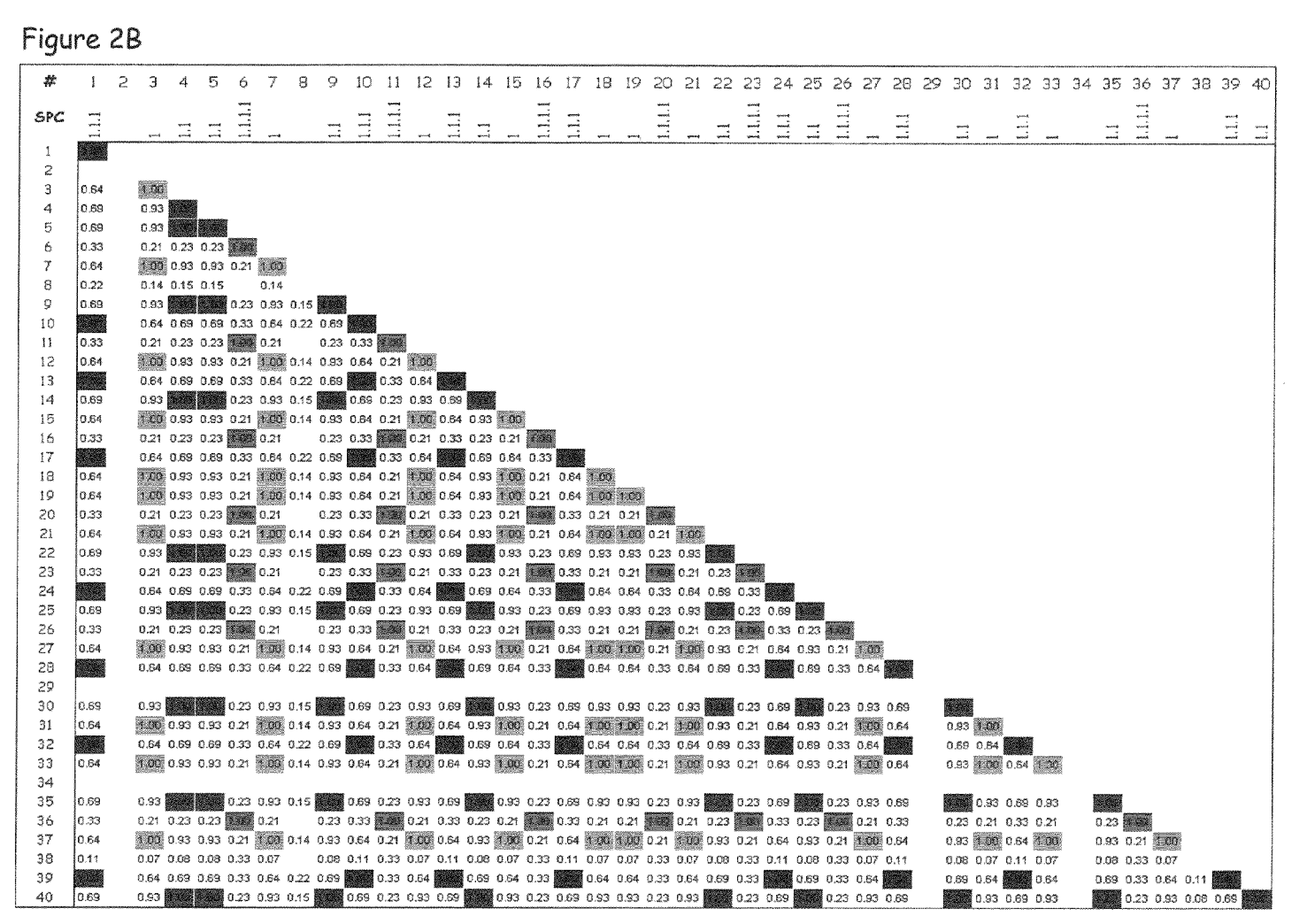
Figure 1B:
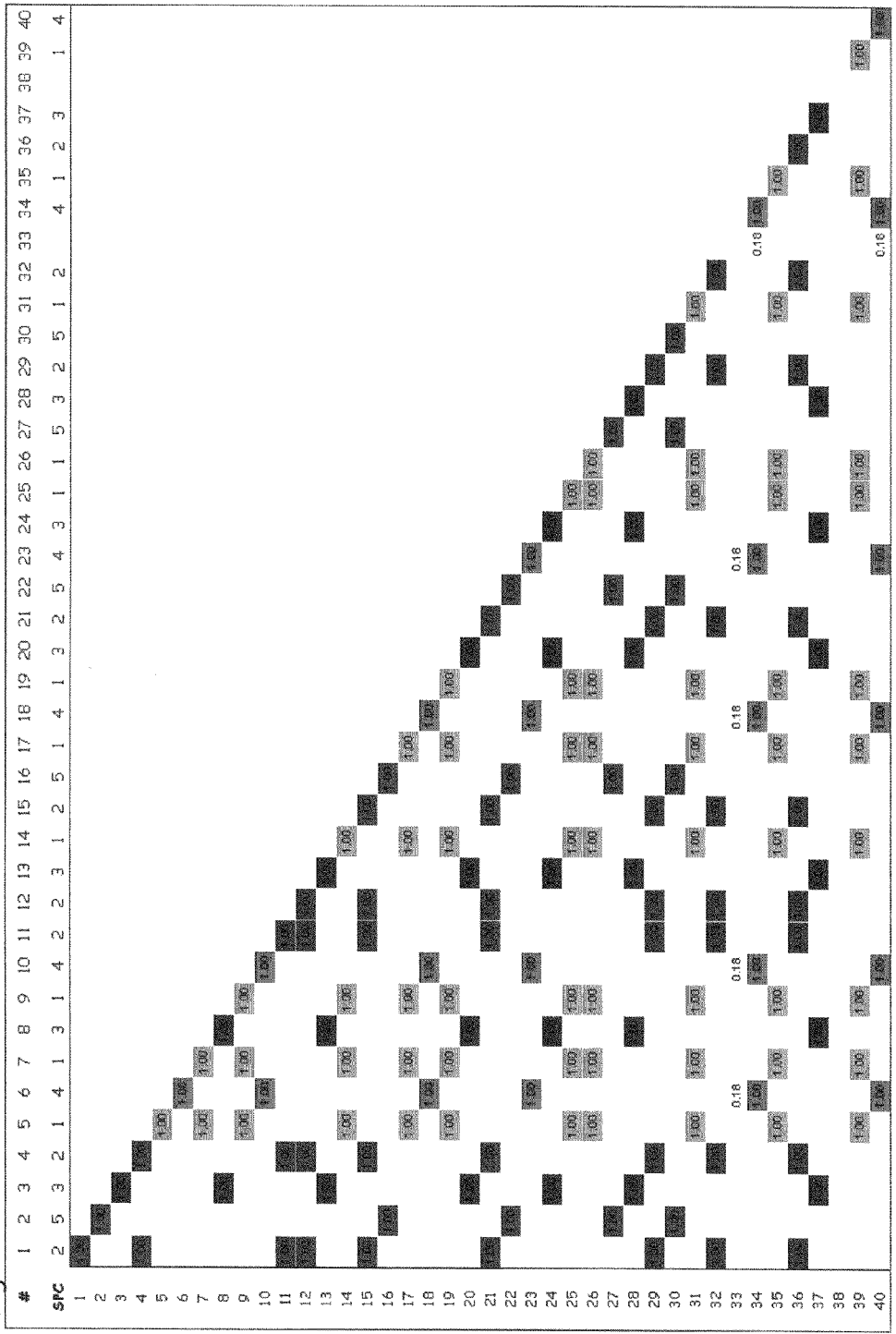
FIG. 1B shows the matrix of the pairwise C-values calculated from the data set of FIG. 1A. All the clustering positions for which C=1 are differentially highlighted and all positions for which C=0 are left blank. The few positions where C>0 relate to the limited co-occurrence of SNP-33 and SPC-4. The trivial values on the diagonal do not represent pairwise associations but are included in the color scheme to better visualize the pattern of associated SNPs in the matrix.
Figure 1C:
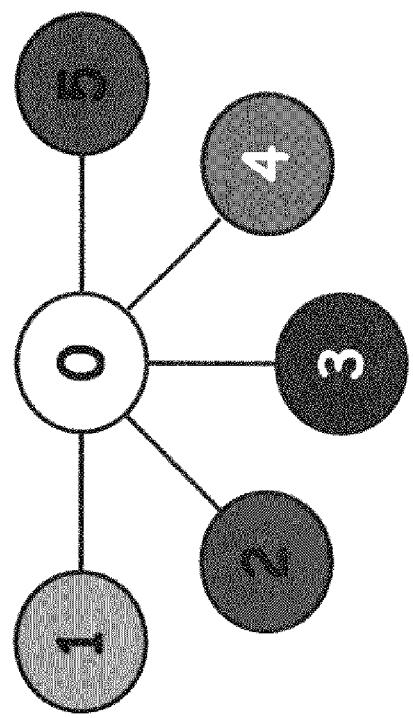
FIG. 1C shows the SPC network. SPCs are numbered as in FIG. 1A; the putative source sequence that is devoid of an SPC is referred to as SPC-0.
Figure 2E:
Figure 3A:
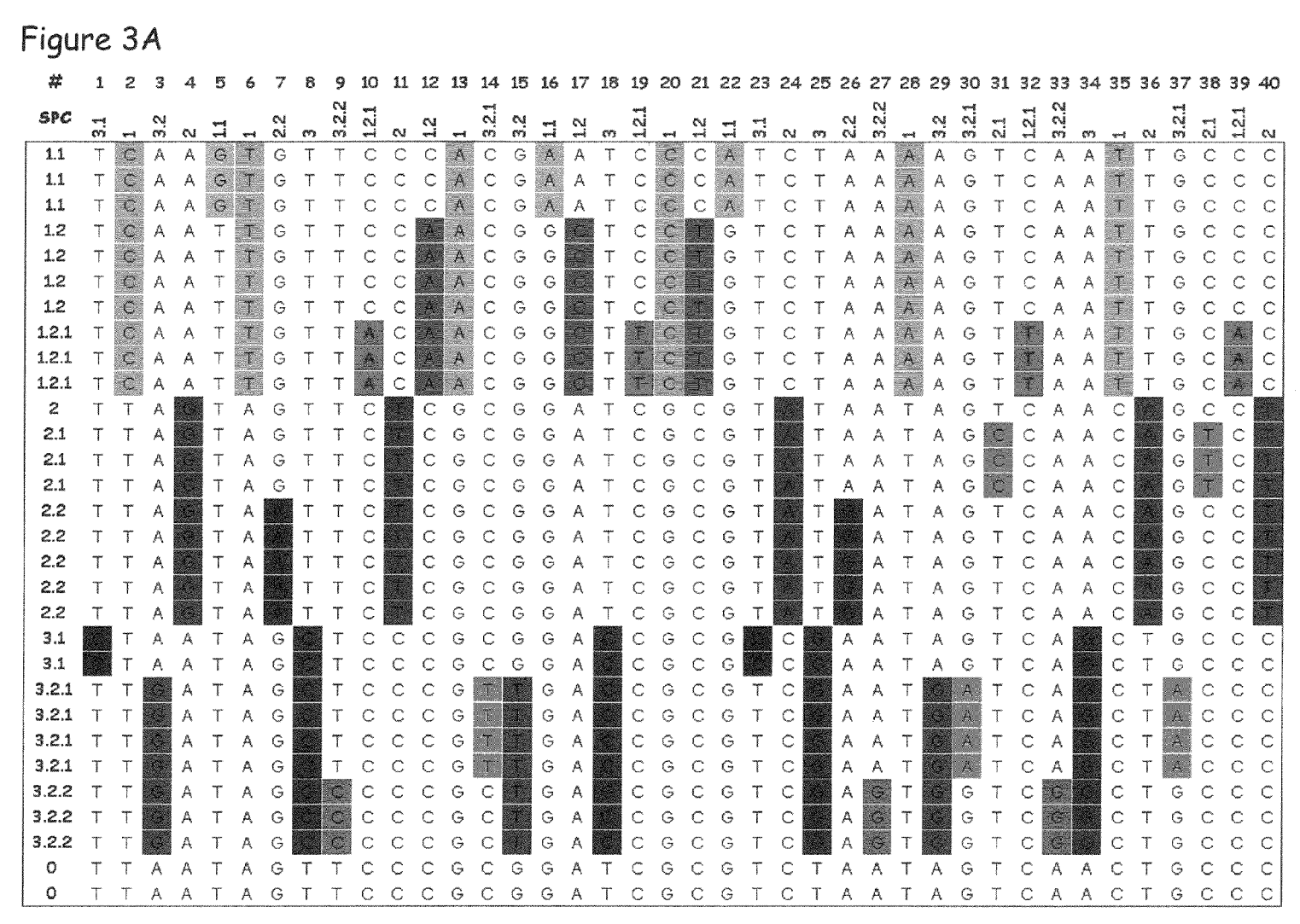

The structures revealed by the method of the present invention are referred to as sequence polymorphism clusters (SPCs). The most important recurrent characteristics of these SPC structures are exemplified in FIGS. 1 to 3. These Figures are based on idealized imaginary genetic variation data sets (containing the allele calls at all the polymorphic sites for a plurality of test subjects), which are devoid of confounding data. The SPC structures observed in publicly available authentic data sets, derived from various species, are discussed in the Examples provided below. FIGS. 1A and 2A typify frequently observed patterns of SPCs; in practice, mostly combinations of these two patterns are found (FIG. 3A). Groups of interspersed polymorphisms exhibit strong linkage, e.g. the alleles at the polymorphic sites are essentially found in only two combinations. Matrices with all pairwise C-values are shown in FIGS. 1B and 2B.

In the matrix of FIG. 1B, all SNPs belonging to the same SPC have pairwise values of C=1, while all SNPs belonging to the different SPCs have pairwise values of C=0. The few positions where C>0 reflect the limited association of SPC-4 with the non-clustering SNP at position 33. In FIG. 2B it can be seen that all SNPs belonging to the same SPC have pairwise values of C=1, while all SNPs belonging to the different SPCs have pairwise values of C<1. The SPCs differ in the occurrence frequency of the minor alleles in the population as well as the number of component SNPs. A fraction of the polymorphisms present do not exhibit the tendency to cluster. These non-clustering polymorphisms are mostly found in conjunction with only one type of SPC.

The SPCs display one of two different relationships. Some SPCs are unrelated/independent, i.e. the minor alleles occur on distinct haplotypes (FIG. 1A). Other SPCs are dependent and can be ranked according to their level of inclusiveness; the minor allele of a dependent SPC occurs on a subset of the haplotypes on which the minor alleles of one or more higher-level SPCs are found (FIG. 2A). As a rule, an SPC is not found both in conjunction with (dependent relationship), as well as separate from another SPC (independent configuration). In other words, the minor alleles of two SPCs are not both found on distinctive haplotypes as well as jointly on a third haplotype. The orderly SPC structure can be represented by means of a simple network wherein each branch corresponds to the appearance/disappearance of one particular SPC (see FIGS. 1C, 2C and 3B). When ignoring the non-clustering polymorphisms, the nodes of the network correspond to the various sequences/haplotypes, which may or may not be observed in the plurality of samples under study (see for example FIG. 3B).

Figure 2C:
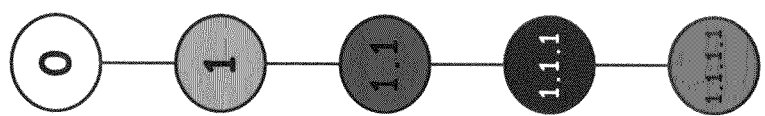
FIG. 2C shows a network representation of the SPC relationships. SPCs are numbered to reflect the hierarchy; the putative source sequence that is devoid of an SPC is referred to as SPC-0.
Figure 2D:
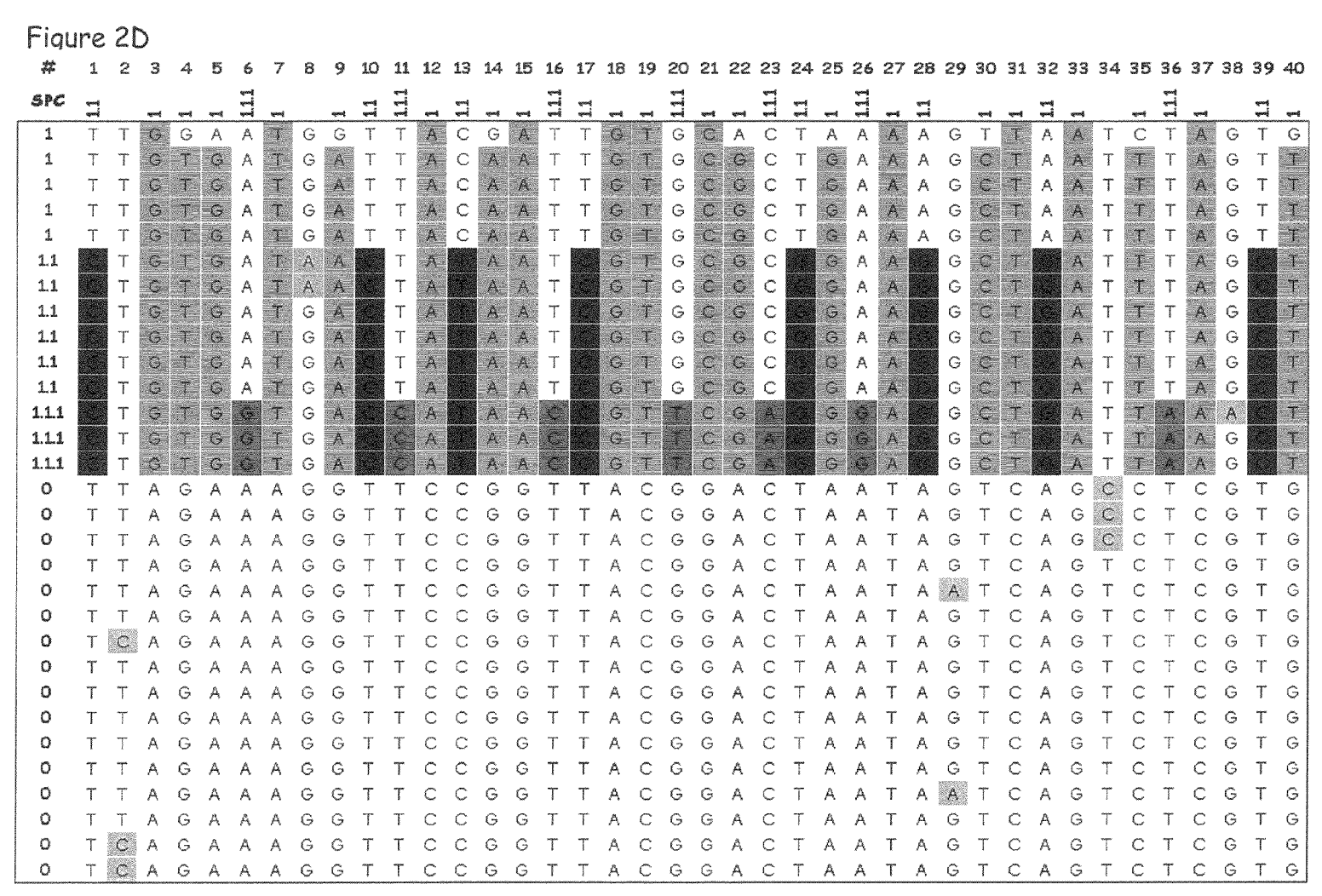

Haplotypes and their closest relatives that differ only by the presence of non-clustering polymorphisms are herein named after the SPCs they contain (see FIGS. 1A and 2A), and are herein referred to as SPC-haplotypes. The network clarifies the relationship between SPCs on the one hand and haplotypes on the other hand: the SPCs can be viewed as the elements with which the various haplotypes are built. Certain SPCs are specific to one haplotype while others are common to several haplotypes, thus defining a clade of related haplotypes. The SPC organization translates into one of two different hierarchical network structures. Unrelated SPCs branch off from a single central point (FIG. 1C); i.e. all of the 'sub-sequences' differ by one SPC from an apparent source sequence. In the case of dependent SPCs, certain sequences have moved away two or more SPCs from the point of reference (FIG. 2C). The SPC network establishes an apparent genealogical relationship between the main sequences, i.e. the sequences devoid of the non-clustering polymorphisms. It should be realized that the network is unrooted (due to the lack of an "outspecies" or sequence from an accepted common ancestor) and, consequently, that evolutionary relationships deduced from the network are ambiguous. In the network representations, shown herein, the branches do not reflect evolutionary distance or extent of sequence divergence while the size of the nodes does not relate to the occurrence frequency of the various sequences. Various alternative representations, that include a variable amount of evolutionary information, are known in the art, such as a dendrogram and a cladogram. Skilled persons will also recognize that the network structure depends on the (depth of) sampling as well as the population under study.

The method of the present invention is thus capable of revealing intrinsic structures of DNA sequence variation in any species. This structure stands out against and can explain the often complex patterns of LD between adjacent markers and the overall lack of correlation between the level of LD and physical distance. It was surprisingly discovered with the use of the present novel computational approach that the sequence variations, in for example maize, that previously had been described as displaying very little LD [Tenaillon et al., Proc. Natl. Acad. Sci. USA 98: 9161-9166, 2001; Remington et al., Proc. Natl. Acad. Sci. USA 98: 11479-11484, 2001; Gaut & Long, The Plant Cell 15: 1502-1505, 2003], are highly structured and that SPCs extend over greater distances.

The haplotype notion and the more recently developed haplotype block concept [Daly et al., patent application US 2003/0170665 A1] represent practical approaches to capture most of the common genetic variation with a small number of SNPs. However, until now, the essentially modular structure of haplotypes and the genealogical record it provides has not been recognized. As set forth hereinafter, the knowledge of the underlying SPC organization in a genomic region allows for the logical and most powerful design and interpretation of genetic analyses.

Construction of an SPC-map

The method of the present invention is directed to an SPC map of a genomic region of interest or an entire genome and to methods of constructing such an SPC map. An SPC map can be used to select an optimal set of markers, all or part of which can be assayed in subsequent genotyping studies, i.e. to establish an association between a genotype and a phenotype/trait or for in vitro diagnostic purposes. The SPC map can also reveal the full breadth of genetic diversity in a species as well as its close relatives, such as certain economically important crops and livestock, and thereby provide opportunities for marker-assisted (inter)breeding. The SPC map can be constructed with genetic variation data derived from any population sample. It is important however to realize that the SPC map depends to some extent on the population under study as well as the depth of investigation (i.e. the size of the sample) and that the map should be used accordingly. For example, it will be clear that especially in a clinical diagnostic context, the value of certain assays is directly correlated with the validity and comprehensiveness of the SPC map on which the assays are based and that, therefore, the map has to be built starting from a representative and sufficiently large sample of the population.

The construction of an SPC map comprises determining the pattern of SPCs across the genomic region of interest, their relationship as well as their boundaries. The pattern of SPCs is preferably analyzed at a variety of threshold levels rather than one single predetermined stringency. SPCs can be defined at any threshold value, including 1, $\geq 0.95$, $\geq 0.90$, $\geq 0.85$, $\geq 0.80$, $\geq 0.75$, $\geq 0.70$, $\geq 0.65$, $\geq 0.60$, $\geq 0.55$, and $\geq 0.50$. Those of ordinary skill in the art will recognize that the adequacy of the threshold settings depends, among other things, on the measure that is used to calculate the strength of association of the marker alleles. When measuring association as $C=P_{ab}/P_a$, the SPC maps are typically generated at multiple threshold values between $C=1$ and $C \geq 0.75$.

In real life the identification of SPCs is confounded by the quality of the experimental data (missing and erroneous data) while, additionally, significant departures from the model SPC structure can occur as a result of certain genomic processes (including recombination, gene conversion, recurrent mutation and back-mutation). These aspects make it difficult to construct the SPC structure of a region in its fullest extent at one given threshold. For instance, at $C=1$ not all SPCs may be revealed, at least not to their full extent. At lower threshold values, on the other hand, certain SPCs may be merged. This is the case with pairs of dependent SPCs that have only minor differences in occurrence frequency. In some cases, SPCs were observed that coincide on all except one single sample sequence (this is exemplified by the SPCs 1 and 1.1 in FIG. 2A). Such SPCs rapidly unite into one single SPC when the threshold C-value is set lower than 1. This is illustrated in FIG. 2D/E: the separate SPCs 1 and 1.1 observed at $C=1$ in FIG. 2A become one at $C \geq 0.90$. Thus, it is only through the assessment at multiple threshold values that the complete SPC map can be constructed. However in most preferred embodiments, the lower threshold is $C=0.75$.

Figure 4A:
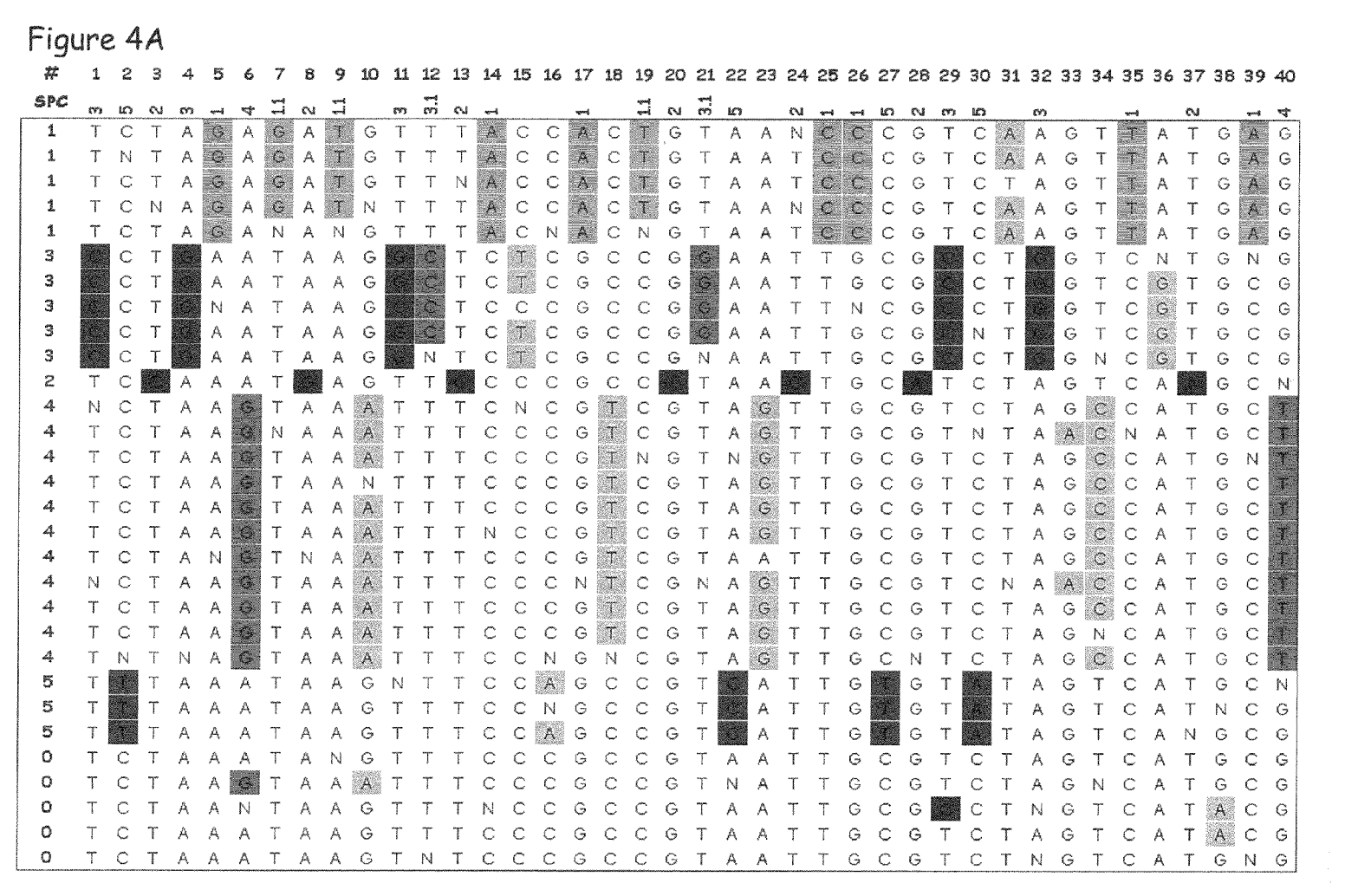
Figure 4B:
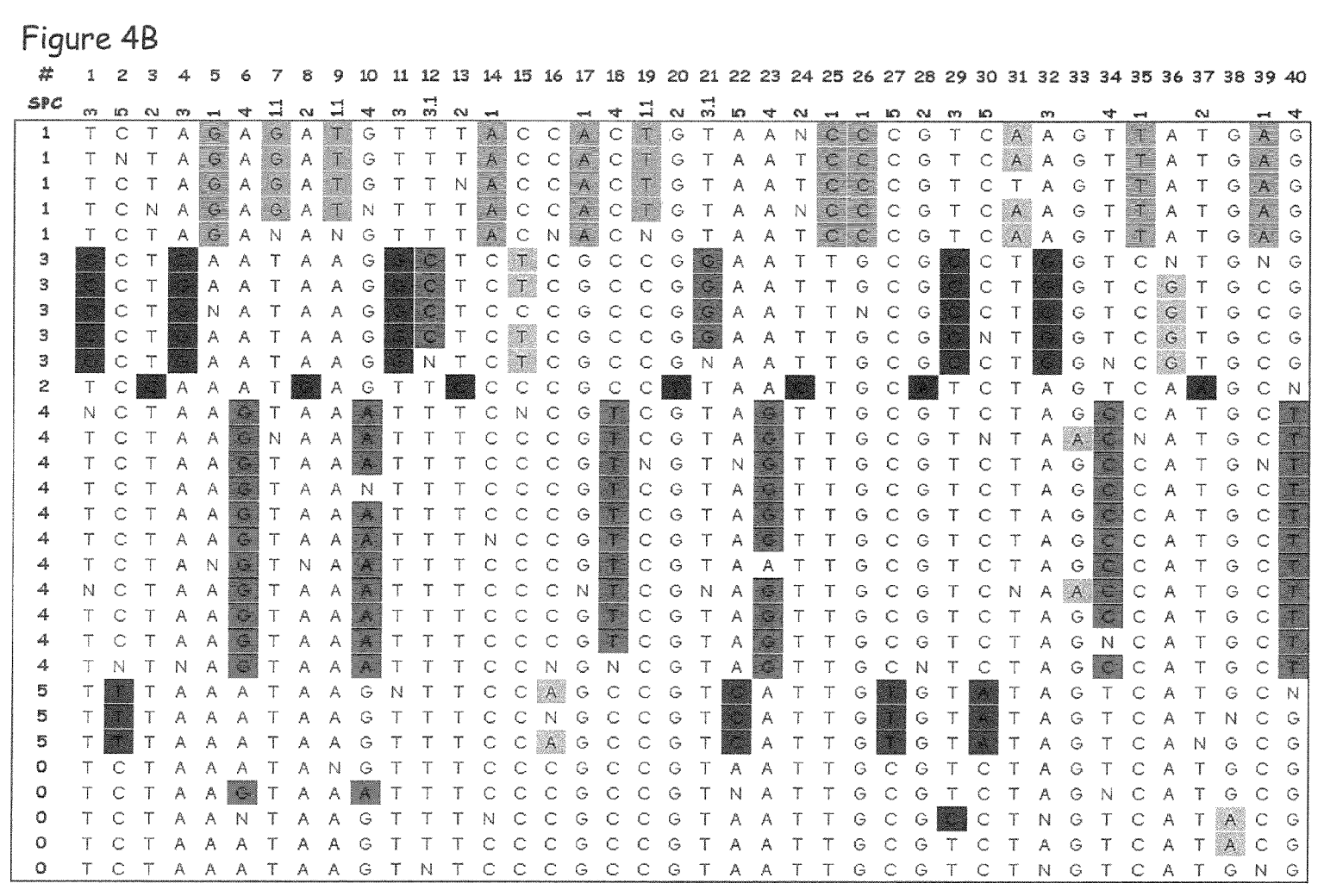
Figure 4C:
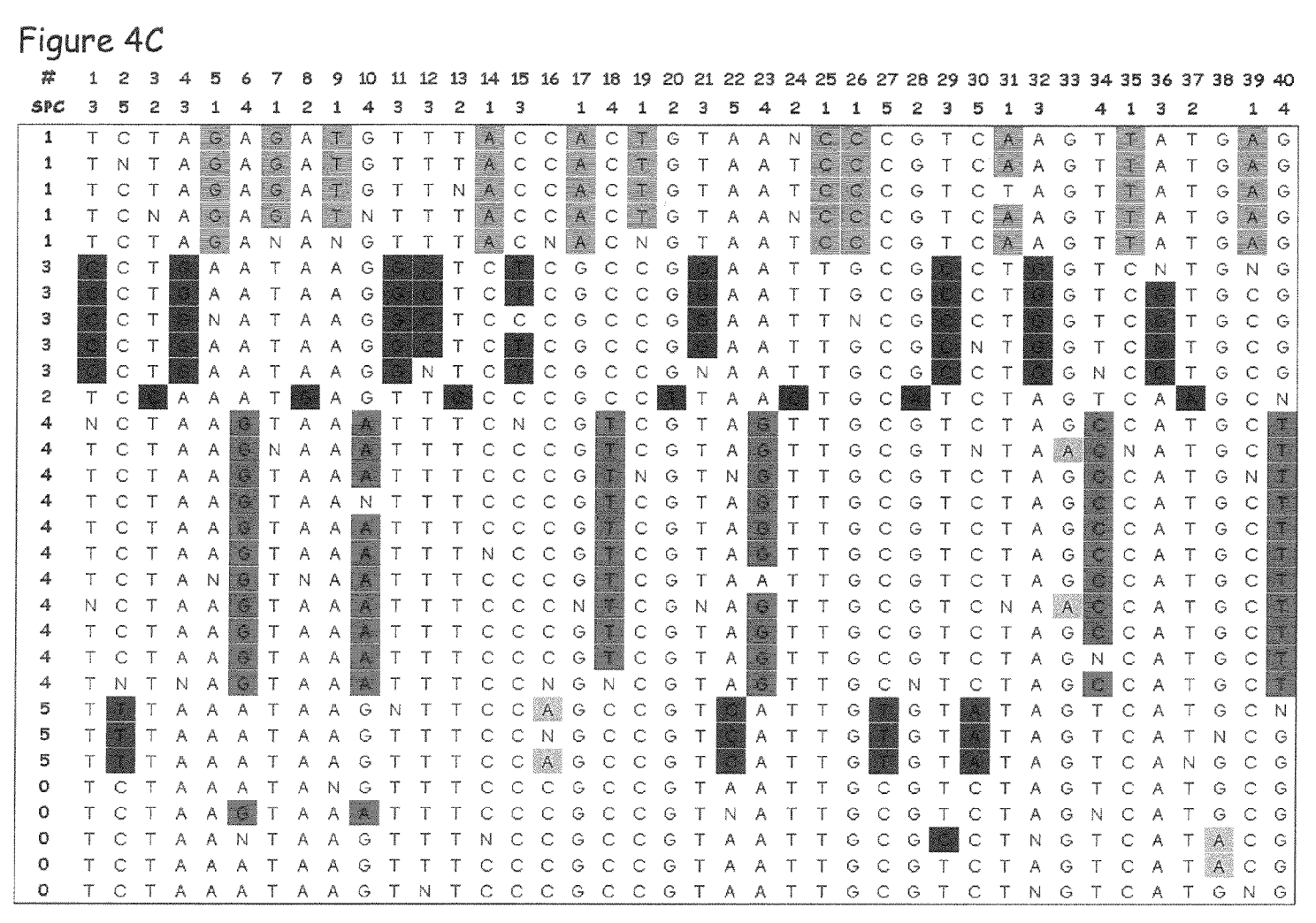

The effects of experimental deficiencies and the genomic processes on the SPC map at different threshold values are discussed in more detail. A primary factor that may confound the analysis is the quality of the genetic variation data. With state of the art genotyping technologies, especially under high-throughput conditions, a realistic error rate of about 0.5% may be achieved while the dropout rate in single pass experiments may be as high as 5-10%. It will be clear that missing or erroneous data points at a SNP position may eliminate that SNP from the cluster at a threshold value for C of 1 because the association will no longer be perfect. The method of the present invention foresees in gradually lowering the threshold level so as to fully expose the SPCs starting from the SPC-nuclei already recognized at $C=1$ and to recover certain polymorphisms that were excluded at $C=1$. This is illustrated in FIG. 4. The genetic variation data set used for this figure is the same as that for FIG. 1 except that 5% of the allele calls, chosen at random, were replaced by missing data (4.5%; symbolized by "N") or an incorrect result (0.5%; the accurate allele was substituted for the opposite allele observed at that position). The SPCs identified at $C=1$, $C \geq 0.9$ and $C \geq 0.75$ are shown in FIGS. 4A, 4B and 4C, respectively.

Figure 4D:
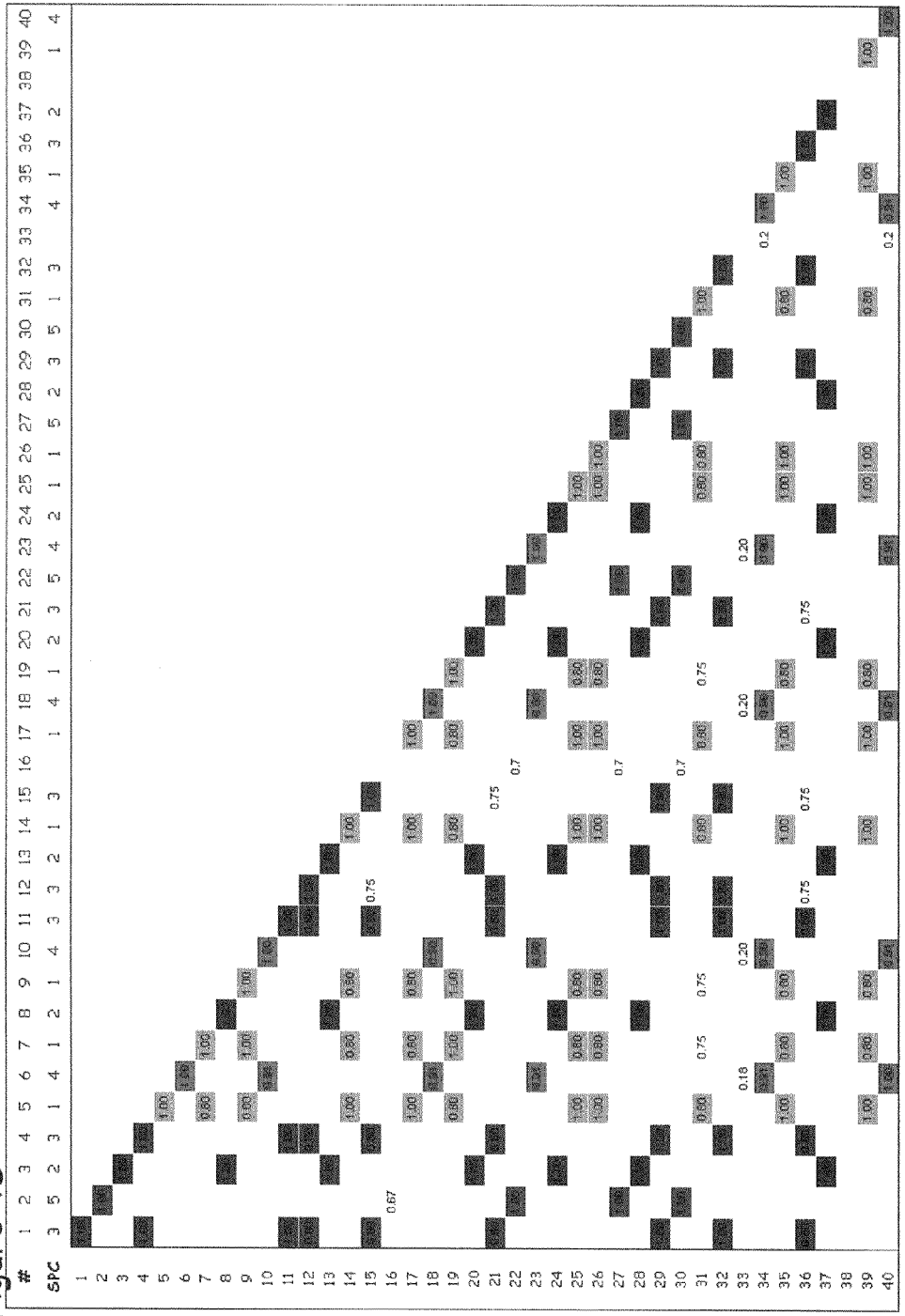
FIG. 4D shows the matrix of the pairwise C values. In this case all positions for which C≧0.75 are differentially highlighted and all positions for which C=0 are left blank.
Figure 4F:
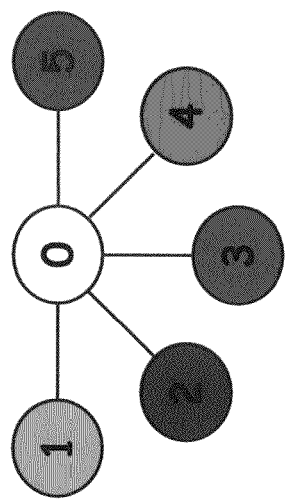
FIG. 4F shows the network for the SPCs found at C≧0.75.
Figure 4E:
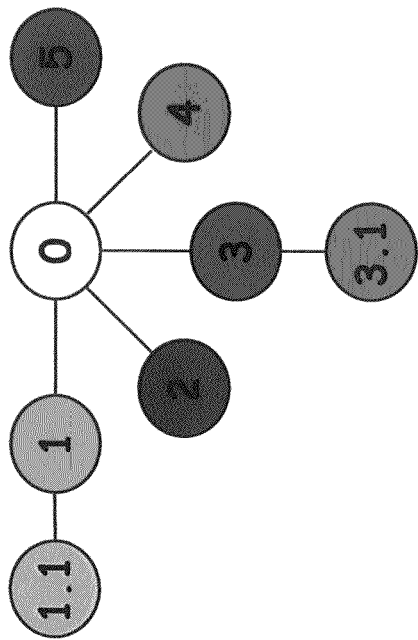

The matrix of pairwise C-values is shown in FIG. 4D. It can be seen that, by lowering the stringency, the largest part of the SNPs that do not cluster at $C=1$ can be recuperated. At $C \geq 0.75$ all but one of the SNPs of the five different SPCs are clustered (compare FIG. 4C with FIG. 1A). It is also of note that two dependent SPCs form at $C=1$, namely SPC-1.1 and SPC-2.1 (FIG. 4E). These clusters are also present at $C \geq 0.9$ but merge with SPC-1 and SPC-2 respectively at the $C \geq 0.75$ threshold (FIG. 4F). This observation substantiates the necessity to examine SPCs at multiple threshold levels.

In the present example distinct clusters are observed at $C=1$ that in fact belong to the same SPC which becomes apparent at lower threshold levels whereas in other cases, illustrated in FIG. 2, certain genuine SPCs detected at $C=1$ may be overlooked at too low a threshold level. Inspection of the genotype data as well as the clustering at various stringencies will generally reveal the most adequate threshold level for the data at hand. Finally, it is possible that with certain data sets no single threshold value captures all of the SPCs and that the SPC map has to be compiled from the analyses at various threshold values. The inconsistencies and imperfections of the SPC map of a region, such as shown in FIG. 4C, can in turn be used to identify in a genetic variation data set the most critical missing results as well as possible erroneous data points. Thus, the present invention also encompasses a method to emphasize those data points that need experimental determination or verification in a repeat analysis.

In addition to data quality, the analysis of the genetic variation may also be confused by various known genomic processes, including recombination, gene conversion, recurrent mutation and back-mutation. It should be noted that some of these events cannot be distinguished from experimental errors. For example, back-mutations or recurrent mutations may equally well be interpreted as errors. All of the processes have the effect of lowering the extent of association between certain marker alleles and may be dealt with by a careful analysis of the SPC structures that are generated at a gradually decreasing stringency as described above.

Figure 5A:
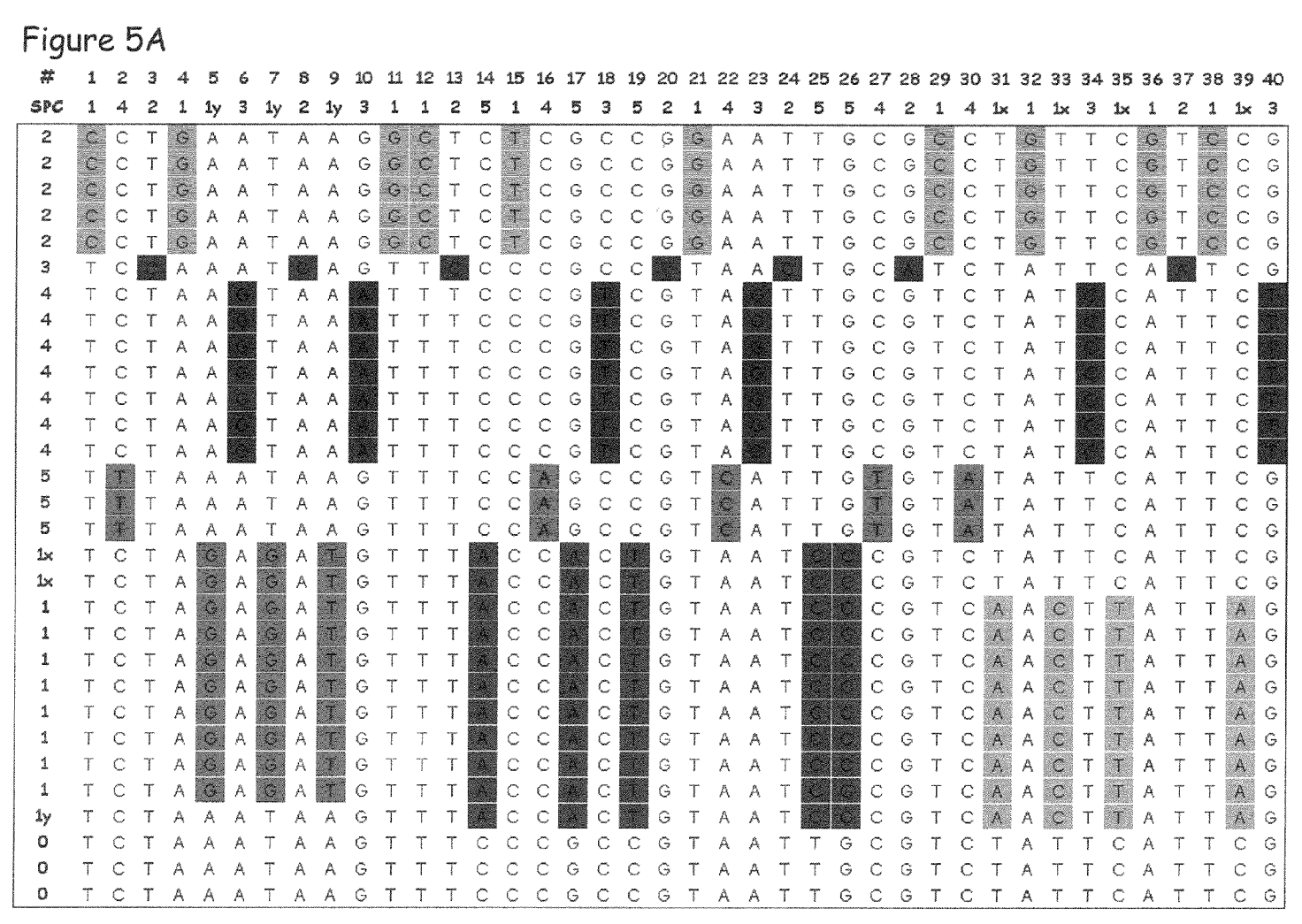
Figure 5B:
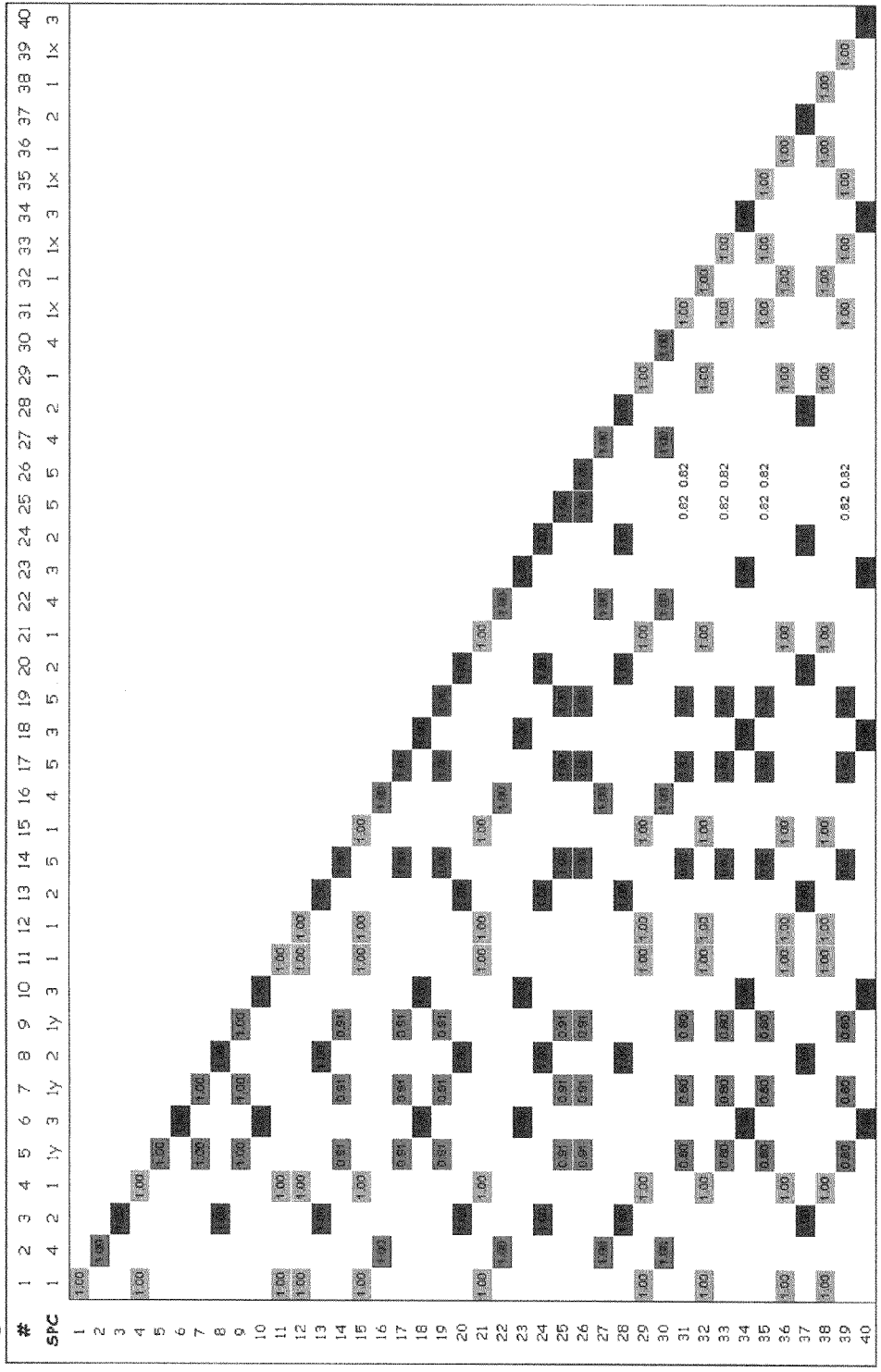
FIG. 5B shows the matrix of the pairwise C-values calculated from the data set of FIG. 5A. All positions for which C=1 are differentially highlighted and all positions for which C=0 are left blank.
Figures 5C, 5D:
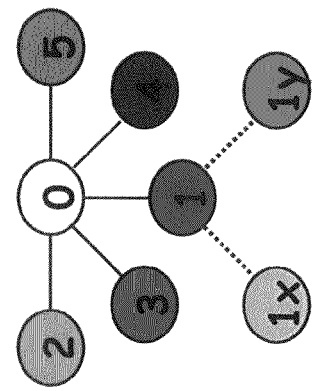
FIG. 5C shows an SPC map of the locus in question. While SPC-1 is interrupted on both sides, the other SPCs are continuous.
FIG. 5D is a network representation of the SPCs detected at C=1.
Figure 5E:
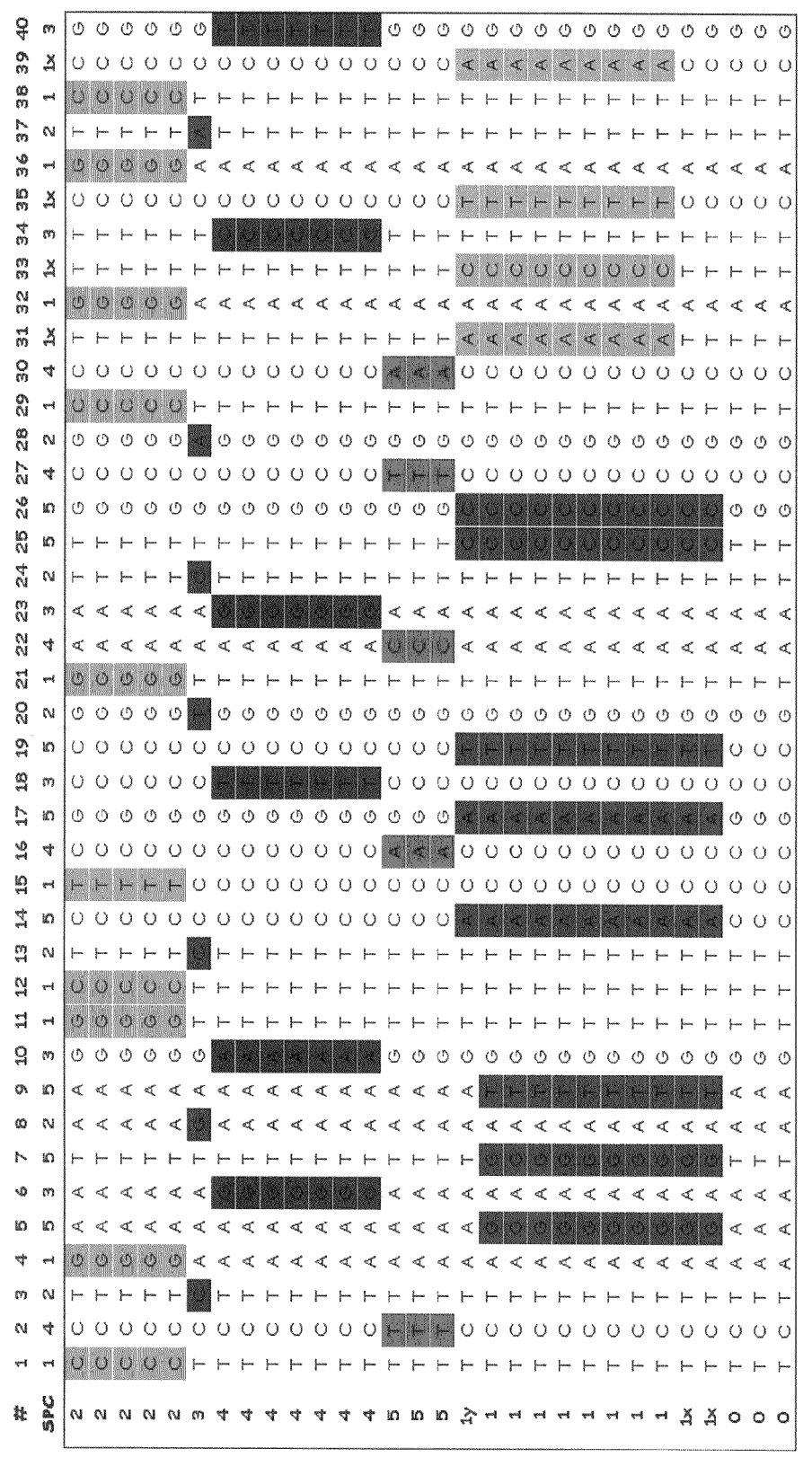
Figure 5H:
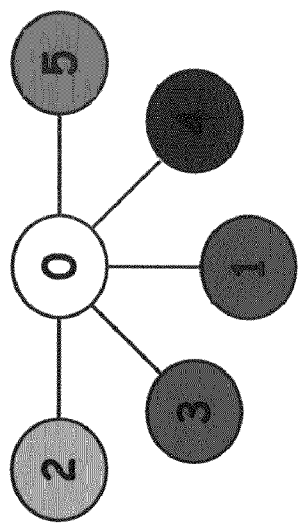
Figure 5F:
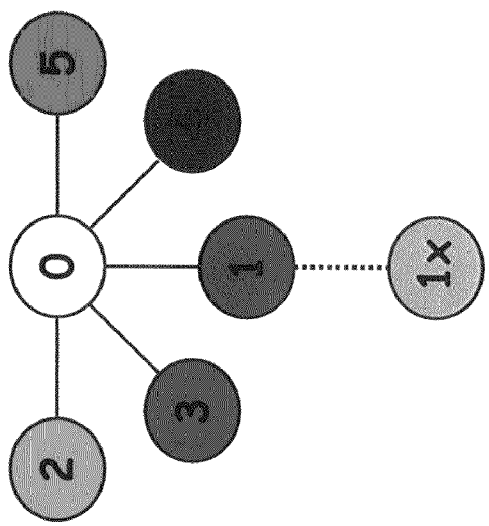
Figure 5G:
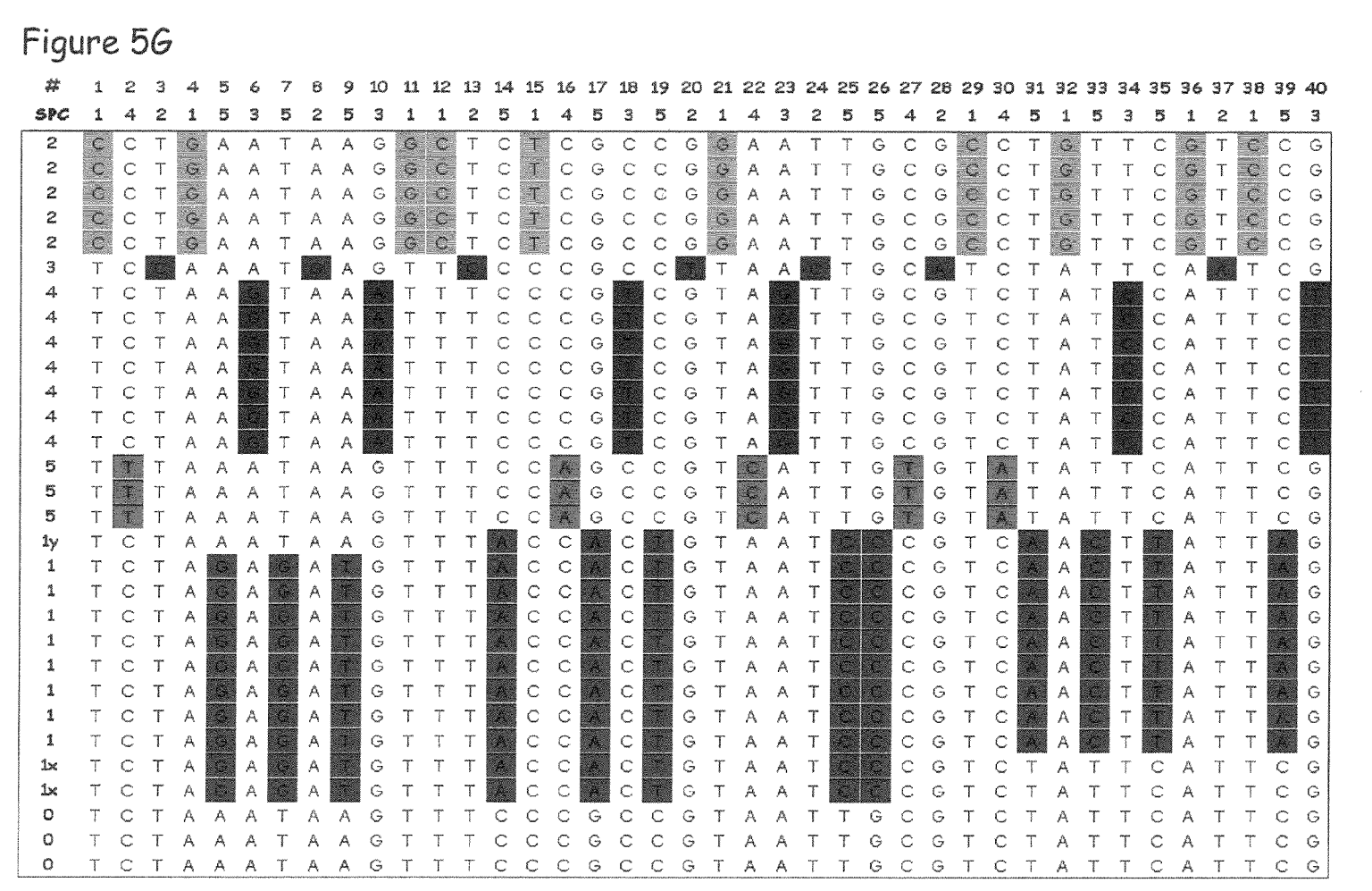

SPCs are primarily ended by recombination events. This is illustrated in FIG. 5 and FIG. 6. FIG. 5A/B exemplifies the effect of a few historical recombination events on the SPC structure. As a result of the recombination events, one particular SPC, namely SPC-1, is broken up in three different SPCs at a threshold value of $C=1$. The recombination events are recognized by the simple fact that the SNPs of the new SPCs (e.g. SPC-1x and SPC-1y) do not intermingle with those of SPC1, as is typically be the case for SPCs in non-recombinant regions, and instead produce adjacent SPCs. Also, more often than not, a recombination event results in a violation of the prevailing principle in an SPC structure, namely that an SPC pair is not found both in an independency as well as a dependency configuration. In the case shown in FIG. 5, the relationship between the two new SPCs and SPC-1 is one of apparent dependency (this is because SPC-1 recombined with SPC-0 which is devoid of SPCs) and an irregularity is only observed when considering the relation between SPC-1x and SPC-1y. This conflict in the relationship is indicated by the dashed lines in the network structure of FIG. 5D. An SPC map of the region at the $C=1$ threshold is shown in FIG. 5C. While SPC-1 is interrupted on both sides, the other SPCs are continuous and the strength of association of sites that are not implicated in the recombination is unaffected. The significance of recombination in a particular region—reflected either by the number of distinctive recombination events and/or by the frequency in the population—can again be assessed by examination of the clustering at lower threshold level. FIG. 5E/F and FIG. 5G/H show the identified SPCs and corresponding network at $C \geq 0.9$ and $C \geq 0.8$, respectively. It can be seen that SPC-1x and SPC-1y unite one at the time with SPC-1 at stepwise decreased stringencies. The merger of SPCs at lower threshold levels and, consequently, the reduction of the number of SPCs is valuable in that it reduces the number of genetic markers that are eventually needed to capture the genetic diversity. This is especially important in the context of an association study because it allows the application of these markers in large cohorts at an affordable cost. The reduction in the variation that is examined must however be balanced against the potential loss in efficiency of the association study.

Figure 6A:
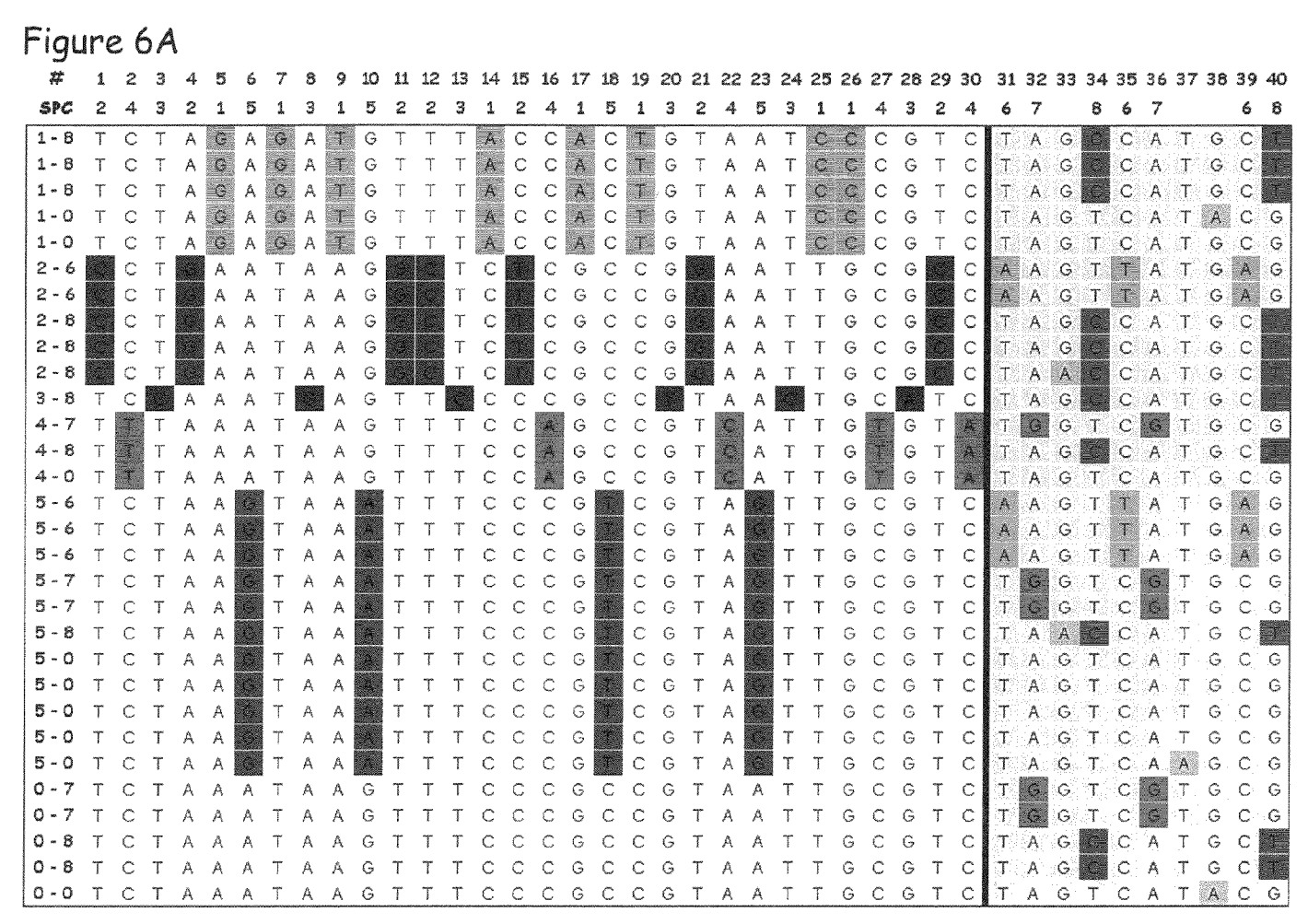
Figure 6B:
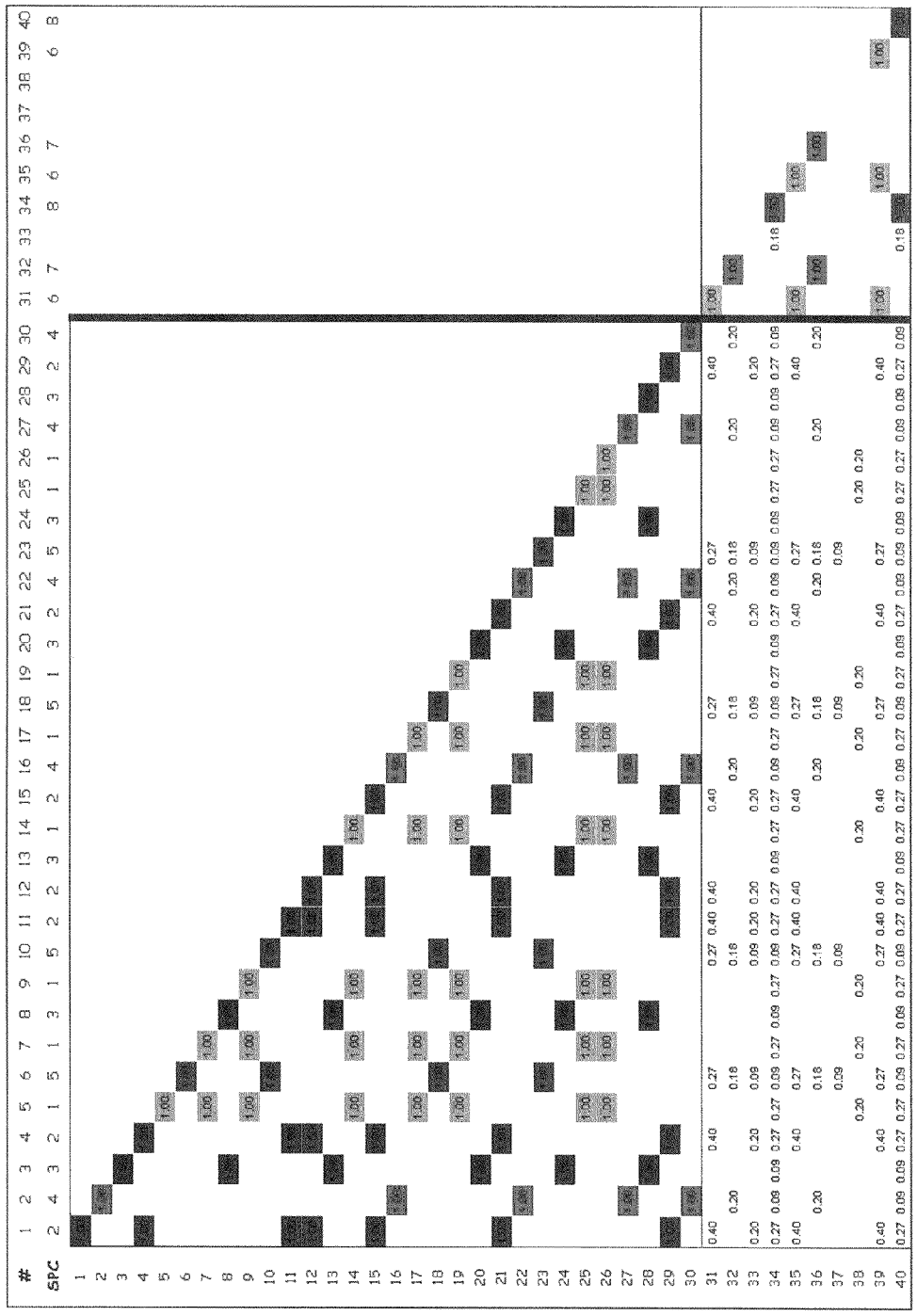
FIG. 6B shows the matrix of the pairwise C-values calculated from the data set of FIG. 6A. All positions for which C=1 are differentially highlighted and all positions for which C=0 are left blank. Note that in this case the matrix can be spit into two sub-matrices as indicated by the frames. Within each sub-matrix it can be seen that all SNPs belonging to the same SPC have pairwise values of C=1, while all SNPs belonging to the different SPCs have pairwise values of C=0. Note that the pairwise C-values between the SNPs of region 1 and region 2 are all <0.5 indicating that there is no clustering between the SPCs of the two regions.
Figures 6C, 6D:
FIG. 6C shows an SPC map of the locus in question. The SPCs found in the two distinct regions are shown separately (since they can occur in various combinations).
FIG. 6D shows that each region is characterized by a distinct SPC network.

In contrast to the case of a small number of recombination events, FIG. 6A/B shows that the association is low for all polymorphic site pairs that are spanning a hotspot of recombination. It can be seen in the matrix of FIG. 6B that these pairwise C-values are all <0.5 indicating that there is no clustering between the SNPs on both sides of the recombination hotspot. Recurrent recombination clearly demarcates the end of an LD-region. FIG. 6C shows an SPC map of the locus of interest. The SPCs found in the two distinct regions are shown separately to reflect the fact that they can occur in various combinations. Additionally, SPCs that belong to neighboring regions do not obey the hierarchical principle that is observed within non-recombinant regions, namely that the minor alleles of two SPCs cannot both be found on separate and the same haplotypes. In accordance with this, the SPC relationship can only be shown for each region separately (FIG. 6D).

An SPC map differs significantly from the haplotype map described by Daly and coworkers for the human genome [Daly et al., patent application US 2003/0170665 A1]. The haplotype map represents a 'block-like' partitioning of the human genome. The discrete haplotype blocks are segments of various sizes over which limited recombination is observed and which are bounded by sites of recombination. There is evidence to suggest that within each such haplotype block the genetic diversity is extremely limited, with an average of three to six common haplotypes that together comprise, on average, 90% of all chromosomes in the population sample.

In an SPC map, in contrast to the haplotype map of Daly, the map elements or SPCs in a region do not necessarily have the same boundaries. In many instances, one or more SPCs extend across the endpoints of other SPCs (even so when that endpoint is observed at a high frequency in the population) or encompass multiple other SPCs. The map elements are also defined differently: whereas haplotype blocks essentially correspond to non-recombinant regions, SPCs require the more strict condition of co-occurrence of the marker alleles (absolute LD). Additionally, non-clustering polymorphic sites were initially regarded as poor markers in the SPC concept whereas, in the haplotype block model, they were thought to be useful for inclusion in the panel of tag SNPs since they do contribute to haplotype diversity.

The inventors found regions where no SPC structure as described herein is present in the genetic variation data or where the SPC structure exhibits flagrant departures from an orderly network hierarchy. Such aberrations do not invalidate the present discovery and its applicability/utility. It should be noted that a data set might fail to reveal the intrinsic structure of the region under study when, for example, the SNP data are insufficiently dense and/or contain too many experimental errors. Additionally, persons skilled in the art will appreciate that the failure to identify an inherent (coherent) structure may not be readily explainable and may merely reflect the complex history of a locus. It will also be recognized that the number of polymorphisms that an SPC has to incorporate in order for it to be considered a genuine SPC very much depends on the data set at hand, more particularly on factors such as the SNP density, the number of samples in which the SPC is observed, the organism under study, and the data quality (see below).

To assess the statistical significance of SPCs detected at a given threshold, simulations can be run on a surrogate genetic variation table wherein the allele calls at the various polymorphic sites are randomized (without affecting the allele frequencies). In particular data sets even the smallest clusters, consisting of only two polymorphisms, are to be taken into consideration. A related issue is the relevance of SPCs that are observed only once in the sample under study. Indeed, sequence variations that are unique for one individual will, by definition, display clustering. The observation may, however, be reliable especially when (i) numerous polymorphisms are involved, and/or (ii) the event can be rationalized. For example, singleton SPCs were encountered more frequently in African individuals than in European samples which is in accordance with the notion that Africans carry a wider variety of haplotypes than Europeans [Gabriel et al., Science 296: 2225-2229, 2002].

The Rooting of SPC Networks

The SPC networks showing the hierarchical relationships between the SPCs represent unrooted phylogenetic trees. As a general rule, it is assumed in the representation of the SPC networks that the haplotype comprising the major allele at each SNP position corresponds to the root sequence. To obtain a bona fide phylogenetic tree, a comparison must be made with an outgroup species (i.e., a species that is closely related, and in the same phylogenetic lineage as the species being examined but is not the same as that species). For example, in the case of human, the most obvious outgroup species comparison is with the chimpanzee sequence. Although the present version of the chimpanzee genome sequence still comprises a number of gaps, it is possible to align some selected human regions (that display a clear SPC network) with the chimpanzee genome and to score the chimpanzee alleles at the majority (~95%) of the SNP positions. From these analyses it is shown that most of the major alleles of the SNPs in humans were identical to that of the chimpanzee. Additionally, in most cases where a different allele was found in the chimpanzee, that allele corresponded to the minor SNP allele and, importantly, essentially all these SNPs belonged to only one single independent SPC that derives from the SPC-0 sequence.

The comparison with the chimpanzee sequence is illustrated in FIG. 30 for one particular human genomic region. This ~112 kb region corresponds to part of the ENCODE block ENm014 and comprises 237 SNPs between positions 126,499,999 and 126,612,618 of chromosome 7. The 237 SNPs were genotyped in 30 trios, i.e. mother, father, and child. The SPC structure in this region is detailed in FIG. 30. In total 207 of the 237 SNPs were clustered into 14 SPCs, which define 12 different SPC-haplotypes. Deconvolution of the 90 diplotypes revealed that 89 of these could unambiguously be deconvoluted into the 12 SPC-haplotypes, and that 1 was a recombinant haplotype. The 119 SPC-haplotypes computed from the 30 trios are shown in FIG. 30. It can be seen that these 119 SPC-haplotypes can actually be grouped into 5 primary haplotypes, some of which diverged further into sub-haplotypes. Comparison with the chimpanzee sequence showed that the minor allele of 46 SNPs was actually ancestral and that, interestingly, 44 of these SNPs belonged to one single SPC (e.g. SPC-1; see FIG. 30). Note also that for 12 out of the 237 SNP positions it was not possible to identify the matching base in the chimpanzee sequence—at these positions, it was assumed the chimpanzee sequence to correspond to the human major allele.

The finding that (part of the minor alleles of) one SPC is ancestral has only minor implications in that the bona fide phylogenetic tree is very similar to the SPC network (refer to FIG. 30). The SPC that contains two types of SNPs, depending on whether their major or minor allele is ancestral, splits into two SPCs; these SPCs are denoted with the suffix M (major allele is ancestral) and m (minor allele is ancestral) in FIG. 30. SPC-1, which comprises 75 SNPs, can thus be split into SPC-1m (44 SNPs) and SPC-1M (31 SNPs). Note also that the two sets of SNPs, belonging to SPC-1M and SPC-1m, are clearly interlaced. In contrast to the unrooted network where all SPCs denote groupings of minor alleles, the rooted tree contains the ancestral SNP alleles (alleles shared between human and chimpanzee) at the root and incorporates an extra SPC that is formed by the major alleles of the SNPs whose minor allele are found in the ancestral sequence. In conclusion, the comparison with the chimpanzee sequence demonstrates that the SPC networks provide a good approximation of the true phylogeny, i.e. the relationships between the SPCs are only slightly affected by the rooting. More importantly, the rooted and unrooted trees exhibit the same overall topology and validate the notion that SPCs are to be viewed as 'evolutionary units'. It would indeed appear that the present day haplotypes can be explained as having evolved from the ancestral sequence in a punctuated mode, where each evolutionary step is defined by a specific group or cluster of mutations (e.g. an SPC). In principle, any SPC (or part of the SNPs of that SPC) in the unrooted network can be ancestral without violating the phylogenetic relationship between SPCs on condition that the SPCs that are higher up in the hierarchy are also ancestral.

The Selection of ctSNPs—Methodical Genetic Characterization of a Locus

The SPC map provides a rational and superior basis for the selection of informative SNPs that are of value in the discovery of associations with certain phenotypes. First, it represents a coherent method to reduce the number of variants that need to be assayed without the loss of information. Given the extent of linkage between the polymorphisms of an SPC, a single representative SNP, referred to as a ctSNP, can be chosen to test for association while all other polymorphisms of the SPC can be considered redundant. In addition to this basic notion, it is anticipated that the difference between the polymorphisms that do cluster and those that do not, will be highly relevant. The inventors identified cases where SPCs are shared between related species and, therefore, predate the speciation event (refer to Example 4). This observation substantiates the idea that the SPCs are 'very old' and indicates that these structures represent ancestral groupings of variations that have been subjected to extensive natural selection and have been retained throughout history because they effect or are linked to a particular phenotype. Thus, SPCs may be viewed as most significant to test as units for association to phenotype. In contrast, the polymorphisms that fail to cluster, even at relatively low stringency, are in all likelihood more recent mutations, in case they are found in conjunction with only one SPC, and may represent recurrent mutations in case the polymorphisms are in partial association with more than one SPC. Whatever the molecular origin of these non-clustering polymorphisms, it was initially thought that the non-clustering polymorphisms had little or no value, but it has been determined herein that even the non-clustering polymorphisms are useful in the methods discussed herein. It is therefore contemplated that the present clustering approach represents a novel diagnostic method for the genetic diagnosis of biologically (medically or agriculturally) relevant genetic variation. More specifically, it is projected that the method of the present invention will be very useful for selecting DNA markers that have superior diagnostic value.

Figures 4G, 4H, 4I:
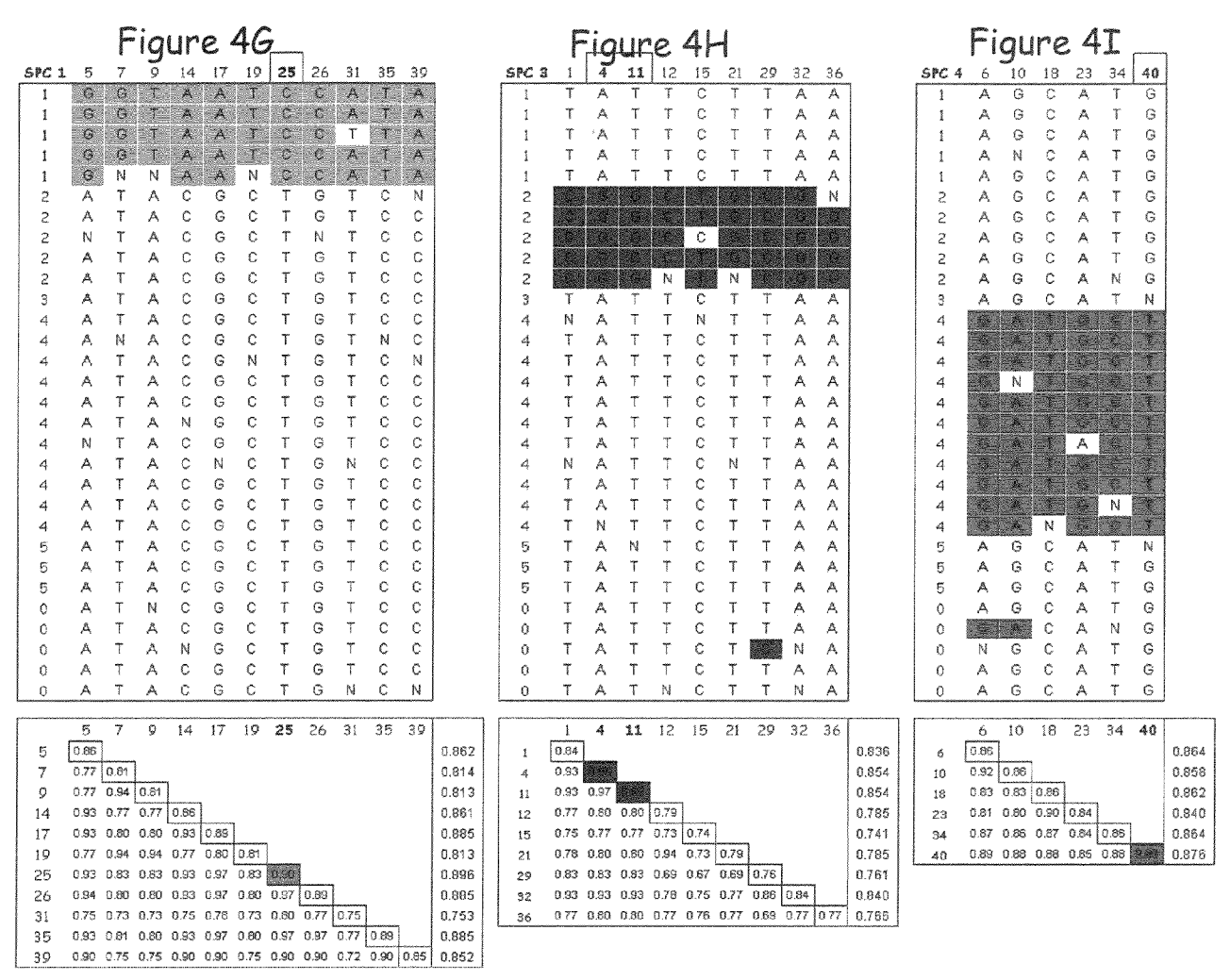

Although an SPC may contain polymorphisms other than SNPs (see Example 1), the polymorphism that is specified as a tag for the cluster will preferably be an SNP. This type of marker is readily assayed using one of several available procedures [Kwok P. Y., Annu. Rev. Genomics Hum. Genet. 2: 235-258, 2001; see also hereinafter]. The SNPs that belong to a particular SPC are not (all) equally useful as tag for that SPC. The possible concept that any one SNP that is in association with all other polymorphic sites of the SPC above a chosen threshold level qualifies as ctSNP is to a large extent arbitrary. Instead, an objective ranking is proposed that reflects how well the various SNPs represent the SPC they belong to. This can be achieved using one of several possible criteria—according to a preferred method the average strength of association of each SNP with all other polymorphisms of the cluster is used as the decisive criterion. The strength of association was computed as $C=P_{ab}/P_a$, where the allele and haplotype frequencies were determined following the most strict (i.e. statistical; refer to the section 'SPC-algorithm') handling of missing data points. This calculation method penalizes any missing data point as a deviation from perfect linkage. The selection of ctSNPs according to this measure is illustrated for three different SPCs in FIG. 4G/H/I. The data set used in FIG. 4 contains both missing as well as erroneous data points and the intended clusters can only for the largest part be exposed at the $C \geq 0.75$ threshold (FIG. 4C). FIGS. 4G, 4H, and 4I show two tables for SPC-1, SPC-2 and SPC-4, respectively. The first summary table lists the allele calls at each polymorphic site categorized in the respective SPCs. The second table shows the matrix of pairwise C-values within each cluster. As indicated above, these values were calculated differently as compared to those shown in FIG. 4D. The average C-value for each polymorphism is shown along the diagonal SNP as well as in the right margin. The most preferred ctSNP (or ctSNPs in case of an equal result) is that SNP with the highest average strength of association with the other polymorphisms of the cluster. In general, several SNPs with only marginal differences in the average strength of association with the other SPC polymorphisms may be used interchangeably as ctSNP. This offers the opportunity to select an SNP that is readily assayed on the platform of choice. Persons of ordinary skill in the art will appreciate that alternative ways can be conceived to rank SNPs and to select tag SNPs that best represent a cluster. It will also be understood that the validity of the choice of ctSNPs depends on the quality of the data. SNPs are justifiably rejected as ctSNP when the relative weak association with the other polymorphisms is genuine, i.e. is attributable to biological phenomena such as recurrent mutation or gene conversion. However, SNPs may also be declined inappropriately on the basis of poor assay results; it is obvious that the latter SNPs are in reality good candidate tag SNPs which may be selected by using superior data obtained, for instance, by means of an alternative assay protocol/platform.

Figure 3B:
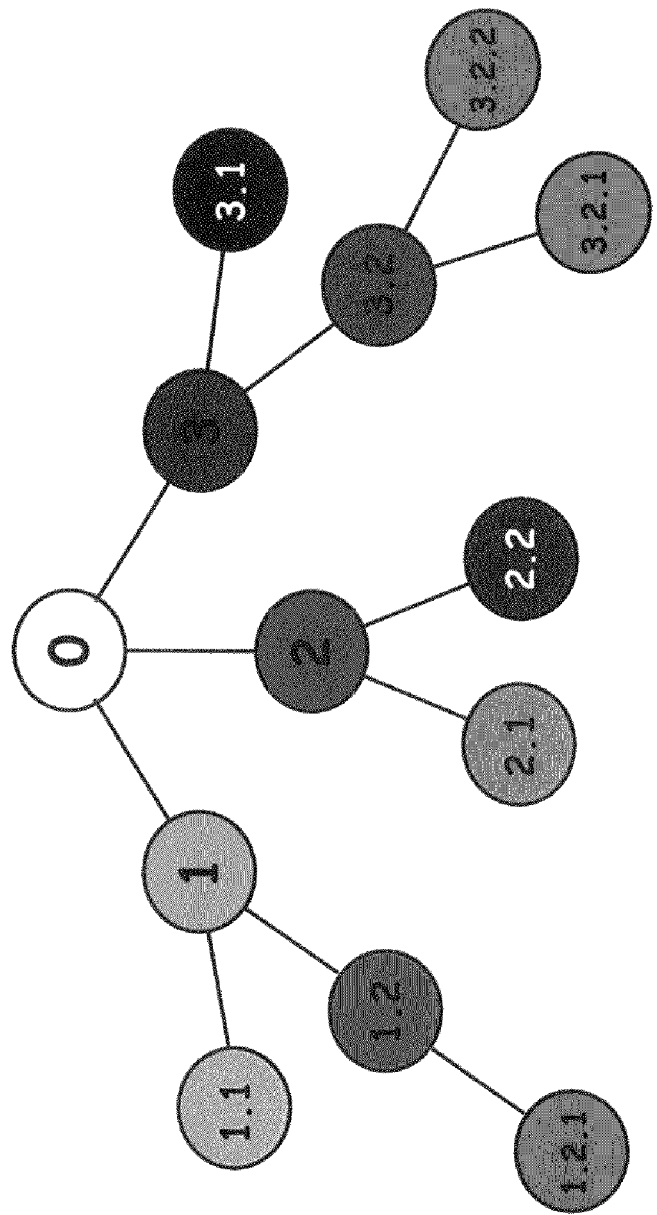
FIG. 3 illustrates a complex SPC structure with both independent and dependent relationships between a total of 12 SPCs. An idealized imaginary genetic variation data set, essentially devoid of confounding data, was used. Different colors are used to indicate the various SPCs.
FIG. 3A corresponds to the output of the algorithm and shows the genetic variation table (in which each column represents a polymorphic site and each row represents a sample) onto which the SPCs are depicted. The first two rows in FIG. 3A indicate respectively the SNPs and the SPCs to which the SNPs belong. The original table is sorted such that individuals that share the same SPCs are grouped. For the sake of simplicity, non-clustering polymorphisms were left out. The network representation in FIG. 3B shows the hierarchical relationships between the SPCs.

The SPC structure of a locus provides a logical framework that is of use in the design of experiments to genetically characterize that locus as well as to rationalize the experimental results. Association between an SPC (or the ctSNP that represents the SPC) and a particular phenotype reveals itself by an increase in the frequency of the rare allele in a population that is characterized by the phenotype as compared to a control population. The relationships between SPCs also imply a certain correlation in the allele frequencies measured for the various SPCs. For instance, in the case of independent SPCs (FIG. 1A), an association of the phenotype with one specific SPC will be accompanied by a decrease in the rare allele frequencies of (all) other SPCs. In contrast, associations with SPCs in a dependency relationship do coincide: a causal relation with one particular SPC necessarily implies linkage with the lower-level dependent SPCs as well as linkage (albeit less pronounced) with the SPCs that are higher up in the hierarchical tree. A clade-specific SPC that is high up in hierarchy is shared by a number of different haplotypes and can, in principle, be used to reveal an association with any of these different haplotypes. This formalism—which may fail in case of synergy or antagonism between the alleles of the various SPCs—can help to assess the reliability of allele frequency measurements at a particular locus. In addition, the SPC network leads to an insightful choice of ctSNPs in that it presents an objective way to reduce the number of SNPs for use in genome wide association studies with a minimum loss in information. First, SNPs can be chosen that correspond to the primary level of divergence, e.g. SNPs that tag the SPCs labeled 1, 2, and 3 in FIG. 3B. A more thorough study would involve the use of a larger number of SNPs, for example those that tag the subsequent layer of dependent SPCs (e.g. SPCs 1.1, 1.2, 2.1, 2.2, 3.1 and 3.2 in FIG. 3B). Such a more thorough study can be conducted either because the first search for association failed (the efficiency of an association study will indeed be related to the SPC level at which the study is performed) or to follow up on certain candidate SNPs that did show linkage; in the latter case a certain part of the network is analyzed in greater depth thereby exploring tag SNPs that correspond to all the subtle subdivisions in the structure. It is also important to realize that it is often not necessary to tag each individual SPC in order to comprehensively characterize a locus. Indeed, certain clade-specific SPCs are redundant over the dependent SPCs in case the clade-specific SPC always co-occur with lower-level dependent SPCs. In this event, the clade-specific SPC corresponds to a node in the SPC network that does not match with an actual sequences/haplotype in the sample under study. This is illustrated in FIG. 3B where the SPC-1 does not require tagging since it always coincides with either dependent SPC-1.1 or SPC-1.2 while, similarly, the detection of SPC-3.2.1 and SPC-3.2.2 render the identification of SPC-3.2 excessive.

A systematic genetic characterization is particularly useful for loci with a complex SPC map. Analyses according to the methods of the present invention have revealed that certain loci are characterized by a highly branched SPC structure with many levels of dependency (refer to FIGS. 3A and 3B). This has, for example, been observed in the 'SeattleSNPs' genetic variation data [UW-FHCRC Variation Discovery Resource; http://pga.gs.washington.edu/; see also Example 7]. It is to be anticipated that, in general, the recognition of such a highly divergent structure will require a fairly exhaustive search for the genetic variation by sequence determination of sizeable regions on a sufficient number of individuals, i.e. the variation data must be sufficiently dense and contain common as well as rare polymorphisms. Rare SPCs will only progressively emerge as the population is being examined to a greater depth. For instance, while the data of the International HapMap Project, at the current level of SNP density [e.g. ~274,500 SNPs as of Jan. 7, 2003; http://www.hapmap.org; Dennis C., Nature 425: 758-759 (2003)], exhibit already some SPC structure, at least in the most SNP dense parts (refer to Example 9), it should not be expected to reveal this structure to its full depth.

The SPC structure and its translation into a methodical genetic characterization can be applied to genome wide scans and in addition, it also is applicable to other studies, such as in vitro diagnosis. One can envisage that the stepwise genotyping may in certain cases be advantageous in terms of cost. The diagnostically important human MHC locus constitutes but one possible example. Indeed, the following Examples show an investigation of the MHC genotype data generated by Jeffreys and coworkers [Jeffreys et al., Nature Genet. 29: 217-222 (2001)] and show that at least certain regions are characterized by a highly branched SPC network-(refer to Example 8).

SPCs Can be Identified on Diploid Genotype Data

In another embodiment, the method of the present invention is directed to the identification of SPCs and ctSNPs using diploid genotype data. Sequence polymorphism clusters may indeed be detected by applying the present algorithm directly to diploid genotypes in place of a haplotype data set. This is less important for most economically important plant and animal species where essentially homozygous inbred lines are readily available. However, the ability to use genotype rather than haplotype data for the detection of SPCs represents an important advantage in the case of humans. It avoids the need to determine the haplotypes, which is hard to accomplish experimentally and error prone when based on computational approaches alone.

The identification of SPCs on the basis of diploid genotype data is illustrated in FIGS. 7 and 8. The first example is based on essentially the same data set used in FIG. 1, i.e. a simple case of a number of independent SPCs. The second example relates to genotype data exhibiting a more complex SPC structure. To identify SPCs in diploid genotype data, the input genetic variation table (FIGS. 7A and 8A), which contains the genotype calls at all the polymorphic sites for a multitude of individuals, is duplicated such that each sample is represented twice. This duplicate table is further modified in that all heterozygous scores are replaced by the minor allele in one copy and by the major allele in the second copy. The resultant artificial haplotypes are herein named minor metatypes, in case the heterozygous calls are replaced by the minor allele, and major metatypes when the heterozygous calls in the diploid genotypes were substituted for the major allele. The duplicated and reformatted genetic variation table is referred to as the metatype table. It is noted that two essential features are perfectly retained in the metatype format, namely the frequencies of the alleles and their co-occurrence or linkage. Indeed, the ratios of the heterozygous and homozygous alleles (i.e. 0.5:1) are correctly maintained by separating diploid genotypes in two metatypes. The linkages between the co-occurring sites are retained by the simultaneous replacement of all heterozygous genotypes on a single diploid genotype by either the minor alleles or the major alleles in respectively the minor and major metatypes.

Figure 7A:
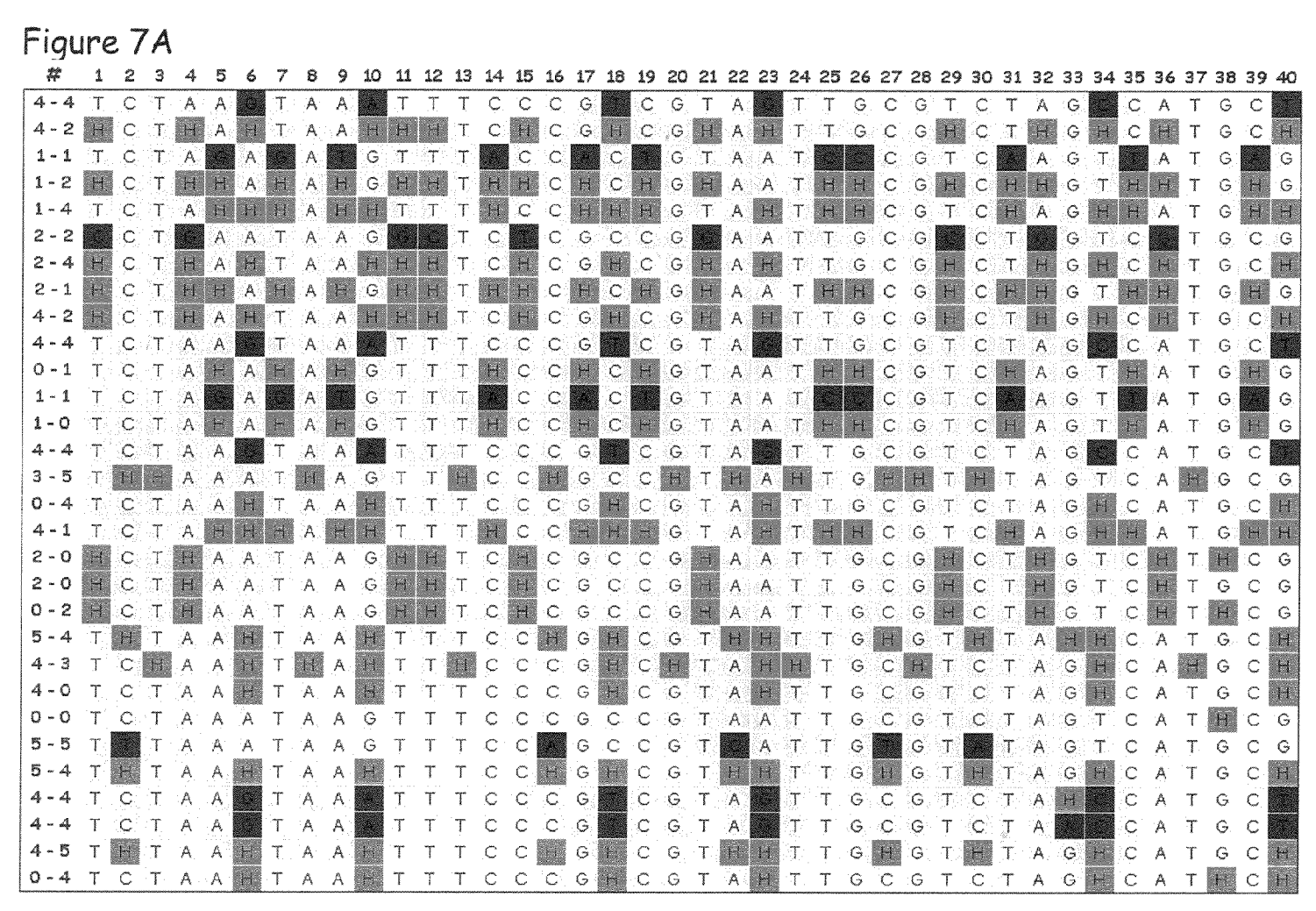
Figure 7B:
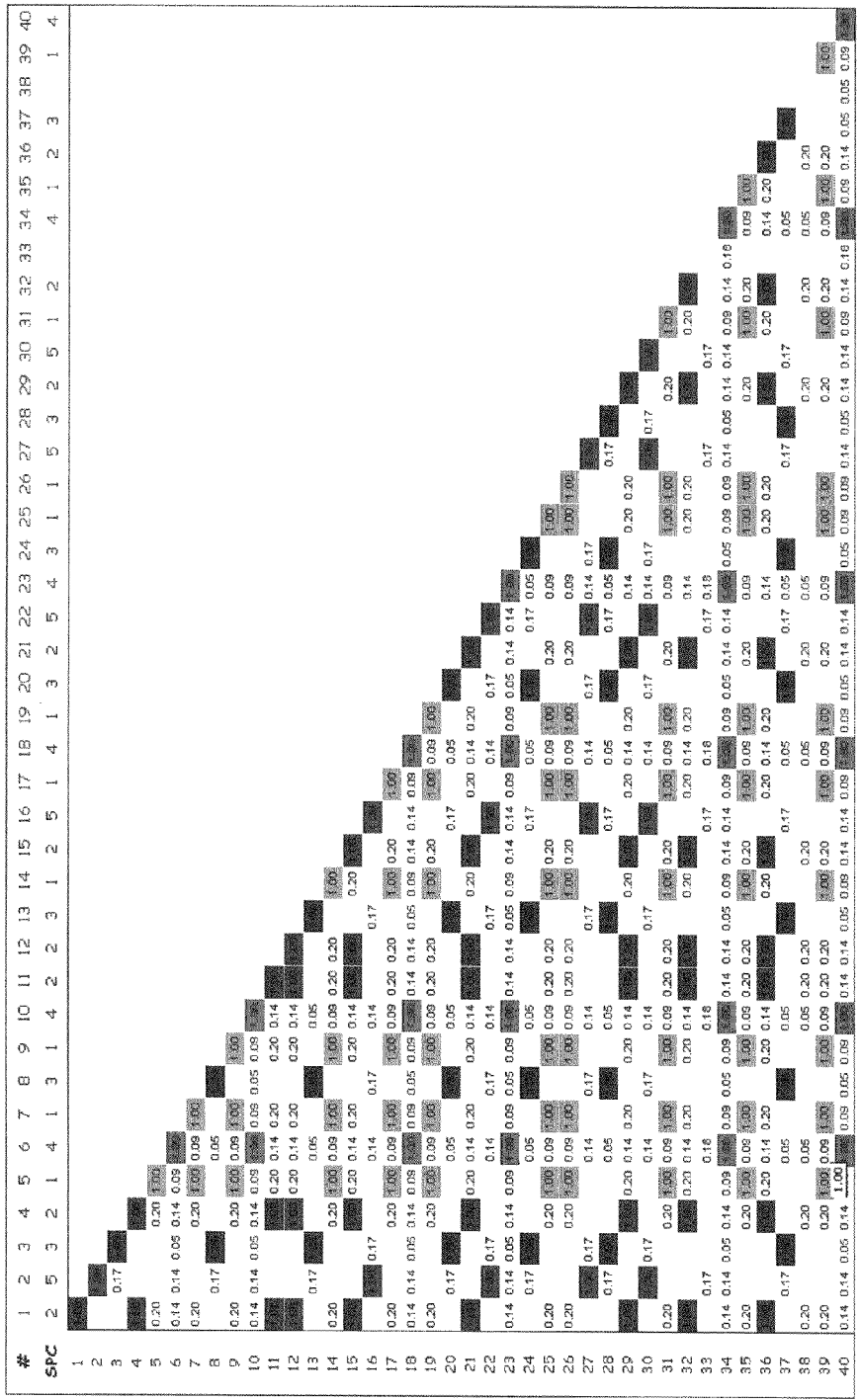
Figure 7C:
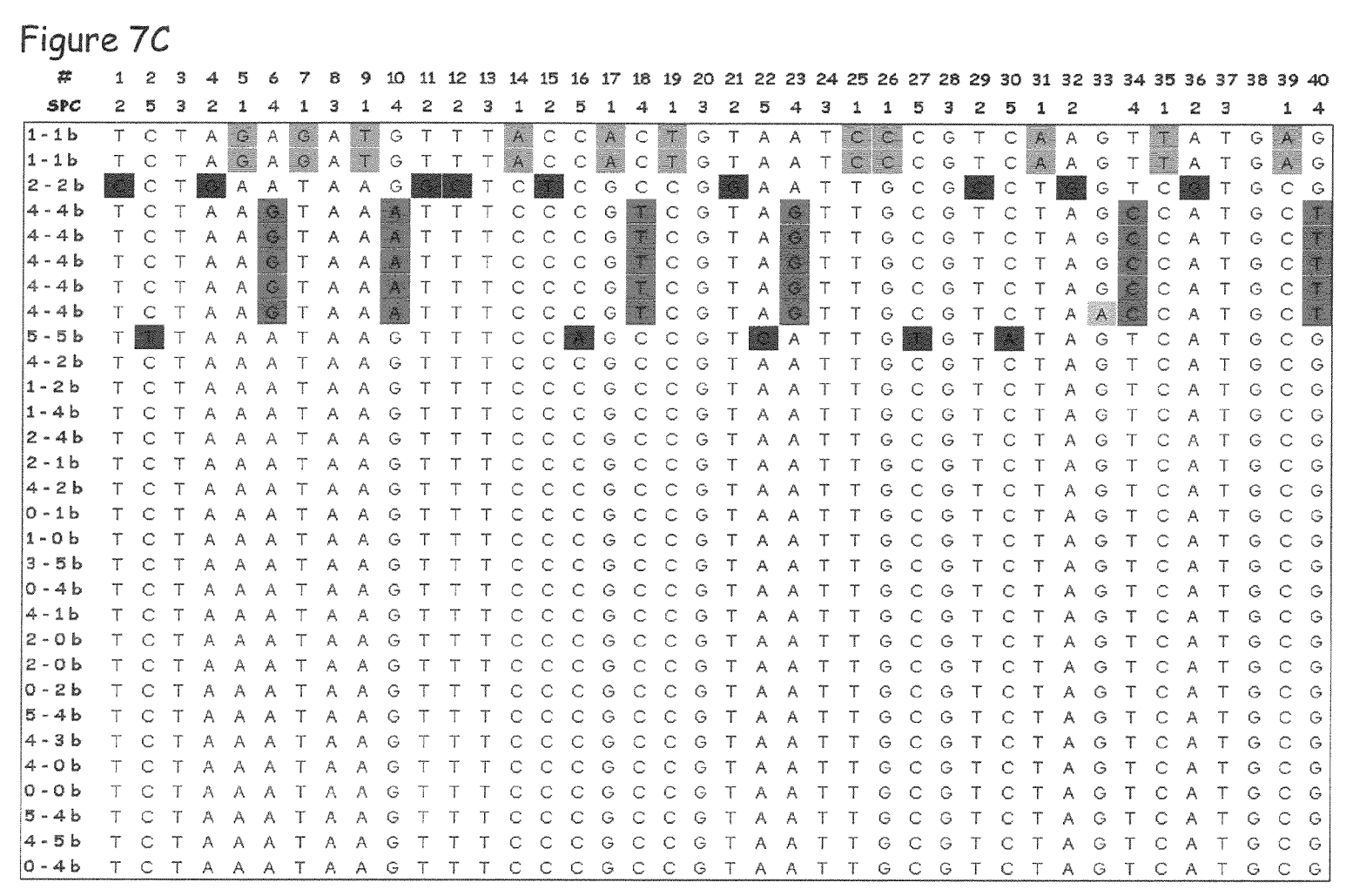
Figure 7D:
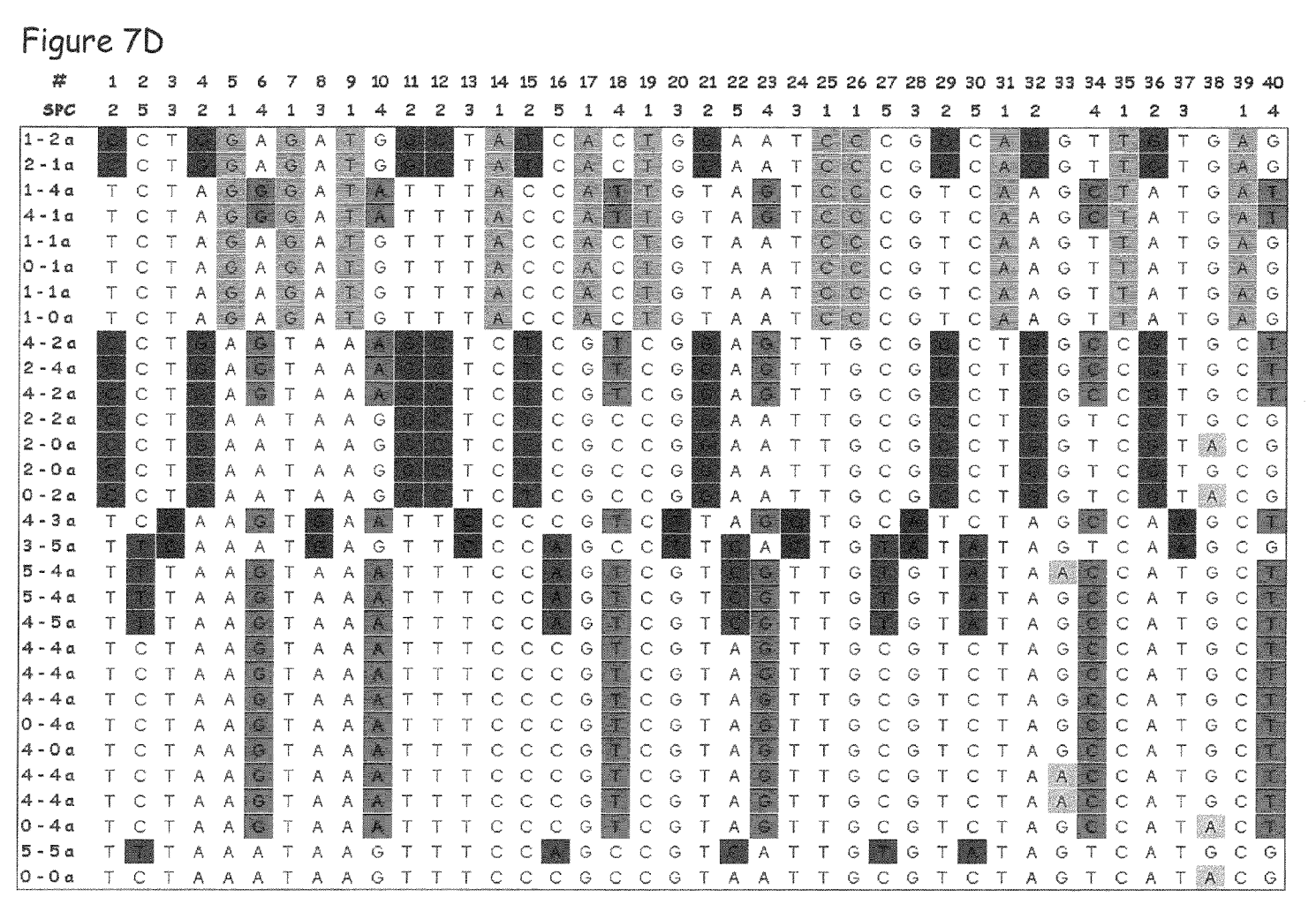
Figures 7E, 7F:
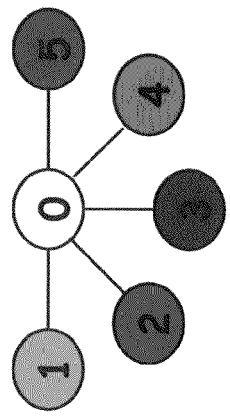
Figure 8A:
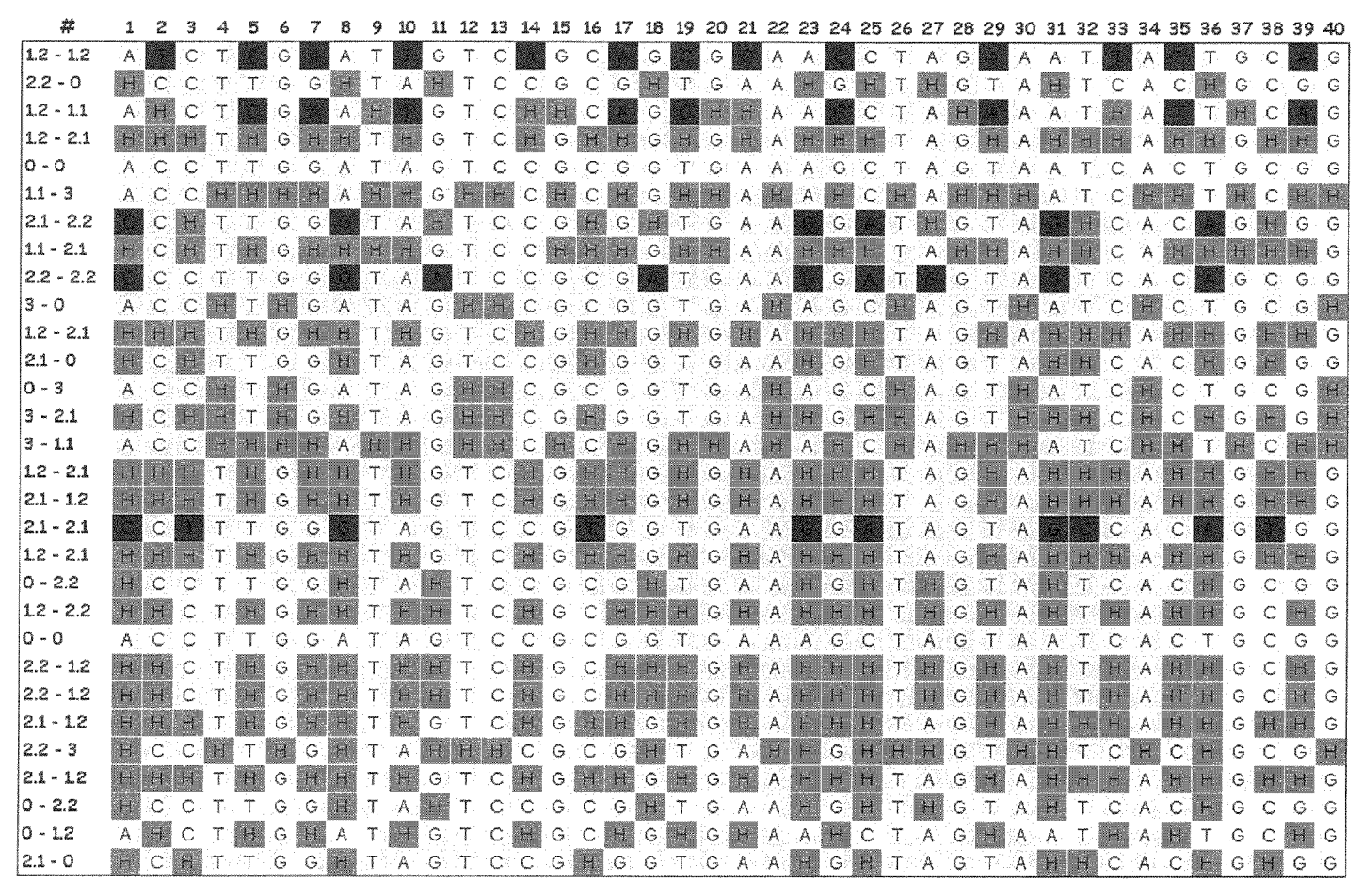
Figure 8B:
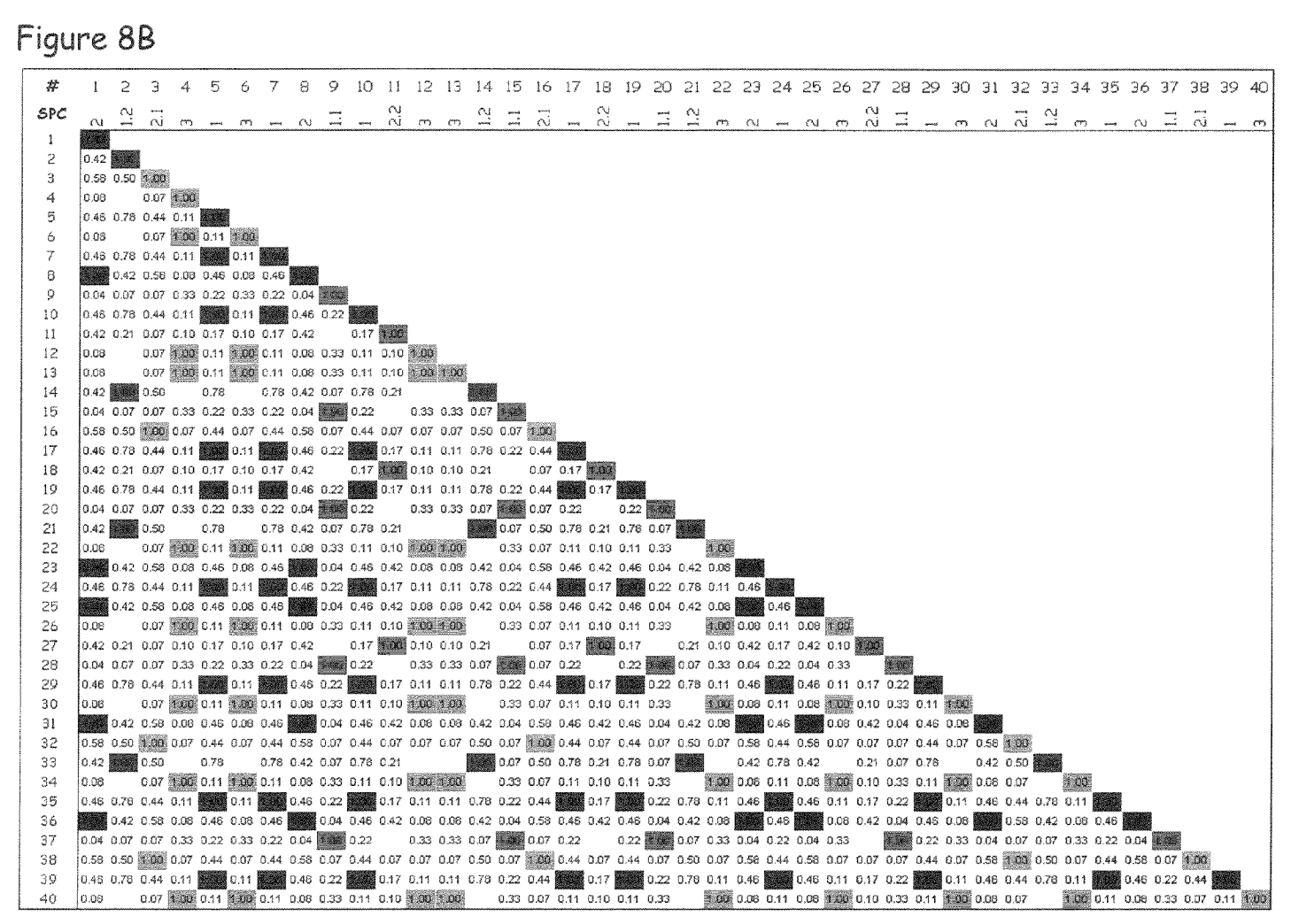
Figure 8C:
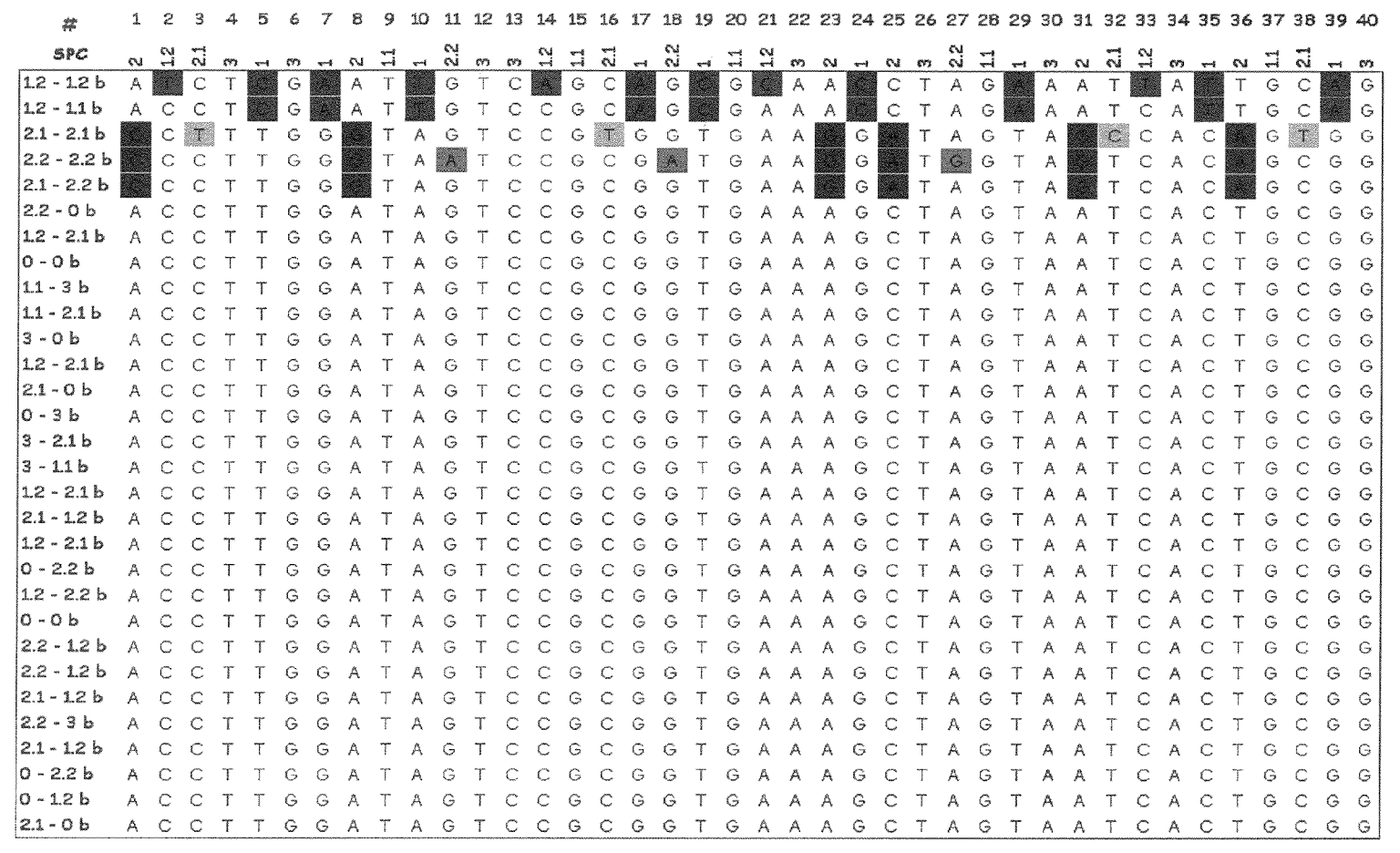
Figure 8D:
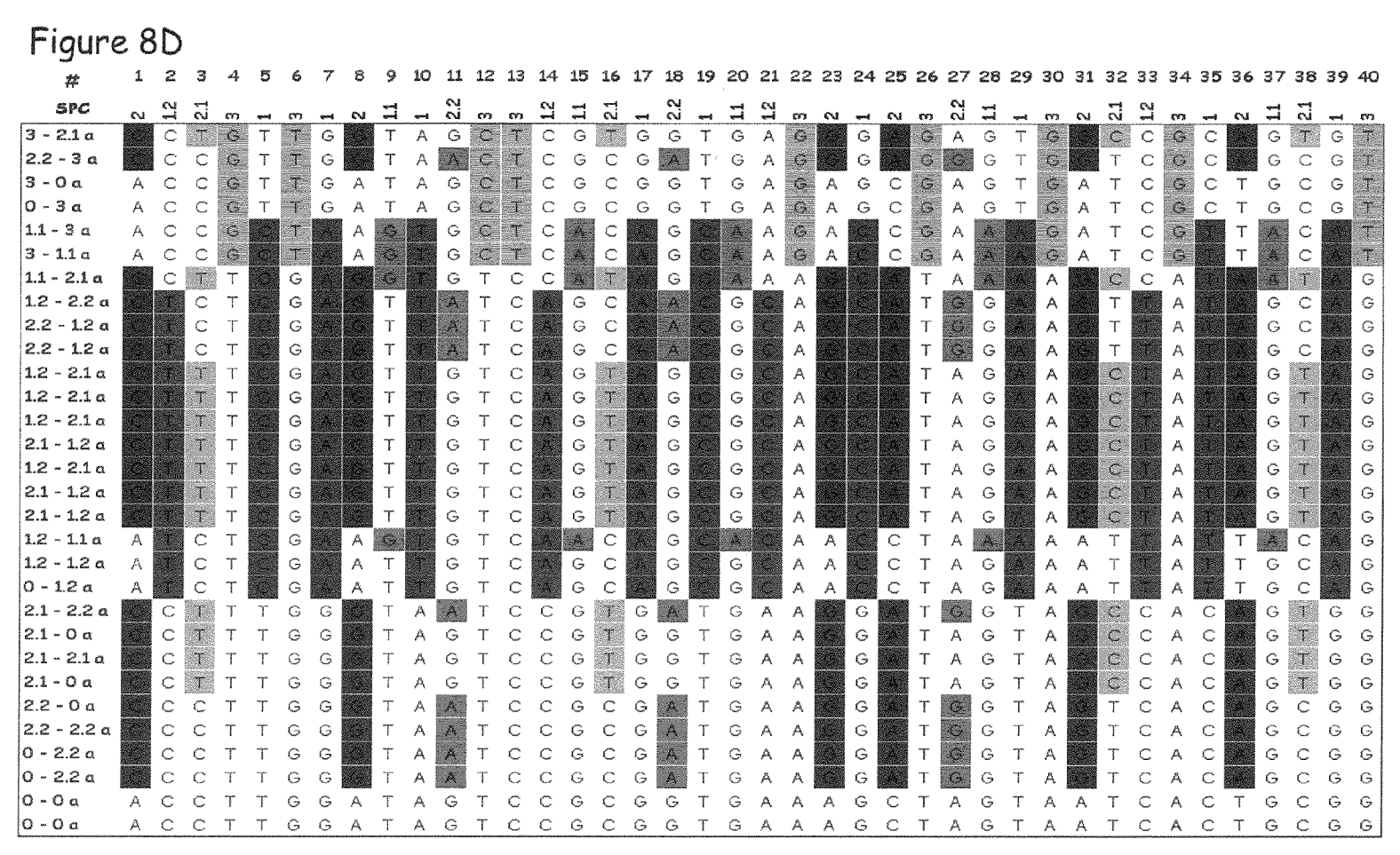
Figures 8E, 8F:
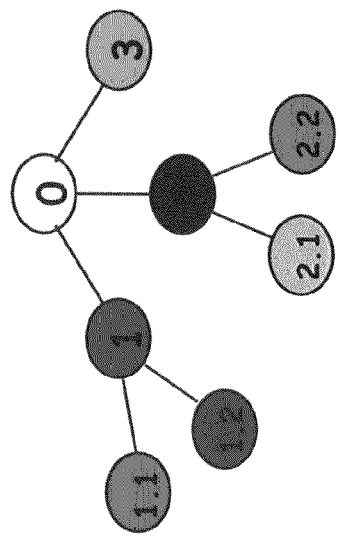

FIGS. 7B/C/D and 8B/C/D show the SPCs revealed by the analysis of the diploid genotypes. In both experiments, the diploid genotypes were generated by the random association of haplotypes with a known SPC structure (FIGS. 7E and 8E). A comparison indicates that the SPCs identified on the basis of diploid genotypes are identical to those found on the starting haplotypes. Thus, the analysis of the diploid genotype data would ultimately lead to the selection of the same set of ctSNPs as an analysis of the elementary haplotypes. The illustrations of FIGS. 7C/D and 8C/D however demonstrate one notable difference with bona fide haploid genotypes, namely that independent SPCs can coincide on certain metatypes (compare FIG. 1A with FIG. 7C/D) and that consequently there is an apparent loss of the orderly structure. The skilled person will realize that this is expected, given that diploid genotypes are the sum of two haplotypes and that the metatype table was generated by the arbitrary replacement of the heterozygous positions by either the minor or the major allele. The identification of SPCs starting from an authentic human diploid genotype data set is demonstrated in the Examples section.

The methods of the present invention differ in several aspects from the method developed by Carlson and coworkers to identify maximally informative tag SNPs [Carlson et al., Am. J. Hum. Genet. 74: 106-120, 2004]. Initially, the present invention teaches a method to recognize sets of clustered polymorphisms in diploid genotype data. Thus, the selection of ctSNPs can be performed without the prior need to infer haplotypes from these diploid genotype data (see Example 7). In contrast, Carlson and coworkers base their calculation of the LD-measure $r^2$ on inferred haplotype frequencies. The experimental determination of haplotypes from unrelated diploid (human) individuals is very demanding while the computational probabilistic approaches have limitations in accuracy. The present method avoids the possible errors in the computationally deduced haplotypes.

Secondly, the structure of genetic variation is, in the present invention, fully exposed on the basis of an examination of the association of marker alleles at different stringencies. In contrast, Carlson and coworkers consider bins of associated markers on the basis of a fixed statistic. It is amply demonstrated herein that any given threshold is data set dependent, and that association of markers at such a threshold provide an incomplete and unrefined picture of the genetic variation. This has practical consequences concerning the number, the comprehensiveness, and the information content of the selected tag SNPs. For example, certain SNPs that do not exceed the chosen threshold of association with any other SNP may unjustly be placed in singleton bins, which ultimately increase the number of tag SNPs that are required to probe the genetic variation in a region.

Thirdly, Carlson and coworkers designate SNPs that are above the threshold of association with all other SNPs of the bin as tag SNPs for that bin; the tag SNPs are considered equivalent and anyone SNP can be selected for assay. A preferred method of the present invention entails the ranking of SNPs according to their suitability as tag SNPs (ctSNP) for the SPC.

Fourthly, in contrast with the one bin/one tagSNP concept of Carlson, it is amply demonstrated herein how the insight in the SPC structure, as represented by the network, allows the further reduction in the number of tag SNPs with little or no loss in information. For example, the detection of clusters that always co-occur with dependent SPCs are redundant over these dependent SPCs. Alternatively, an unrefined analysis may be performed by selecting tags for the clade-specific SPCs only.

SPCs Can be Identified on the Basis of the Genotype of Sample Pools

In another embodiment, the method of the present invention is directed to the identification of SPCs and ctSNPs using genotype data obtained on pooled DNA samples. Similar to single samples, this genotyping of sample pools involves the simple scoring of the presence/absence of the allelic forms and does not require the quantification of the allele (frequency) in the pool. This application calls for a sensitive genotyping method where allele frequencies of 10% (corresponding to a pool of five diploid individuals), 5% (i.e. pool of ten diploid individuals) or even lower can be detected. Several such methods are known in the art that permit the unambiguous and reliable calling of an allele that is present as a lesser species [Ross et al., BioTechniques 29: 620-629, 2000; Hoogendoom et al., Hum. Genet. 107: 488-493, 2000; Sasaki et al., Am. J. Hum. Genet. 68: 214-218, 2001; Curran et al., Mol. Biotechnol. 22: 253-262, 2002; Blazej et al., Genome Res. 13: 287-93, 2003; Lavebratt et al., Hum Mutat. 23: 92-97, 2004]. The ability to compute SPCs and SPC maps from genotype data determined on sample pools represents a major advantage in that it substantially reduces the cost of genotyping (e.g. by a factor of 5 to 10 or more). The SPC technology may therefore have a major impact on the mapping of genetic variation in human as well as other species. A pooling strategy is not compatible with the aforementioned haplotype block method, which relies on the genotyping of individuals followed by the deconvolution of the unphased diploid genotypes into the component haplotypes.

The SNPs that are currently being mapped in the HapMap project represent the most common SNPs with high (>10%) population frequencies. In the HapMap project, the definition of haplotypes and haplotype blocks is based on the genotype of individual DNA samples. However, for SNPs with lower population frequencies, e.g. in the 1% to 10% range, the number of individual samples that needs to be analyzed in order to observe the minor allele and to correctly infer the haplotype structure increases considerably. This renders the inclusion of such low frequency SNPs in the HapMap prohibitively expensive. As noted above, the unique feature of the SPC technology is that SPC maps can be deduced from the genotype of pooled DNA samples. Depending on the allele frequencies, and the SNP genotyping method used, it may be possible to analyze pools of 5, 10 or more samples. In this way major cost savings can be achieved. This will become important when building the next generation human genetic variation map, in which SNPs with lower population frequencies (1% to 10%) will be mapped.

The identification of SPCs on the basis of the genotype of sample pools is essentially identical to the methodology used for derivation of the SPCs from diploid genotype data. The input genetic variation table consists of the genotype calls (homozygosity for one of the alleles or heterozygosity) at all the polymorphic sites for a multitude of pools instead of a multitude of individuals. This input genetic variation table is converted to a metatype table in the same way as is done for diploid genotypes. A "metatype" is used to refer to a pseudo-haplotype derived from a diploid genotype. Briefly, the genetic variation table is duplicated such that the genotype of each sample-pool is represented twice. The heterozygous calls are subsequently replaced by the minor allele in one copy and the major allele in the second copy. The resultant artificial haplotypes are herein named minor metatypes, in case the heterozygous calls are replaced by the minor allele, and major metatypes when the heterozygous calls were substituted for the major allele. It is noted that the essential feature of allele co-occurrence or linkage is perfectly retained in the metatype format.

Persons skilled in the art will readily realize that there is a relation between pool-size on the one hand and the frequency of the SPCs that can be distinguished on the other hand. Indeed, in the case of large pools and/or high-frequency SPCs, each individual pool will contain the minor alleles of all the frequent SPCs, which therefore can no longer be differentiated and will appear as one single SPC. The relation between pool-size and the ability to derive the correct SPC structure is illustrated in FIG. 31. For this in silico simulation study two imaginary genetic variation tables consisting of 200 samples/haplotypes were assembled. For the first table, the genotypes at the various polymorphic sites were chosen such that a total of nine independent SPCs with a frequency of 1%, 2%, 3%, 4%, 5%, 10%, 15%, 20% and 25% are present. In the second table, the nine SPCs with the same frequencies are in a dependency relationship. Starting from these reference data sets with known SPC structure, genetic variation tables were derived that list the genotypes of sample-pools. The pooling strategy consisted of the random combination of haplotypes as follows: 100 pools of 2 haplotypes, 50 pools of 4 haplotypes, 20 pools of 10 haplotypes, or 10 pools of 20 haplotypes. Each sampling was repeated 100 times. Finally, these genotype tables were converted to metatype tables and processed with the SPC algorithm. FIG. 31 is a plot of the success rate (%; number of times the SPC was detected in 100 simulation runs) with which the various SPCs are discerned given certain pool sizes. FIGS. 31A and 31B refer to the independent and dependent SPCs respectively. Results essentially identical to those shown in FIG. 31 were obtained in an additional series of simulation experiments where 100 diploid genotypes were first generated through the random pairwise combination of the 200 haplotypes and then assembled 50 pools of 2 diploid genotypes, 20 pools of 5 diploid genotypes, or 10 pools of 10 diploid genotypes (data not shown). The results clearly demonstrate that it is possible to unambiguously identify the lower frequency SPCs on the basis of the genotype of sample pools. A pooling strategy would thus ultimately lead to the selection of the same cluster tag polymorphisms for these SPCs as an analysis of the elementary haplotypes. The skilled person will-realize that the analysis of sample pools—similar to the analysis of diploid genotypes—results in an apparent loss of the orderly SPC structure in that independent SPCs can coincide on certain metatypes and that the reconstruction of the SPC network becomes gradually more difficult as the size of the pools increases.

FIGS. 31A and 31B demonstrate that the success rate of correct SPC identification diminishes as the SPC frequency and/or pool size increase. SPCs with a minor allele frequency of between 25 and 50% and pool sizes of greater than 20 were not included in the analysis; it seems clear however that in these cases the SPCs will be even more difficult to discern. While it should be realized that the precise success rate of SPC identification may depend on the context (i.e. what other SPCs are present), it would appear from the above-discussed simulation experiments that, in general, SPCs with a minor allele frequency of between 1% and 10% can be identified with satisfactory success using a pool-size of 10. Taken together, the results demonstrate that a practicable and cost-effective approach to construct an SPC map would consist of the genotyping of a collection of individual samples, permitting the identification of the most frequent SPCs, combined with the analysis of a set of pools to allow the recognition of the lower frequency SPCs. The identification of SPCs using a pooling strategy on authentic human diploid genotype data is demonstrated in the Examples section.

The pooling strategy can be applied with genotyping methods that characterize the sequence variations, but also it can be applied with experimental approaches where the output reflects the genetic variation that is present in the interrogated nucleic acid without actually determining the full sequence or characterizing the variable positions. These approaches can be directed at either polymorphism discovery or the scoring of previously identified polymorphic sites. An example of such an approach is the hybridization-based detection of polymorphisms described hereinafter (refer to the section "SPC analysis on various types of genetic variation data"). Experimental signals, rather than the exact underlying sequences, are equally well suited for the identification of SPCs and ctSNPs using the SPC algorithm. Similar to the case where the polymorphisms are identified, a distinction can be made between relevant (i.e. clustering) and spurious (i.e. non-clustering) signals. An important advantage of these methods is that dedicated assays for certain polymorphisms are not developed until after their utility as SPC tags is demonstrated.

The identification of the SPCs in a genomic region suffices to proceed with the selection of cluster tag polymorphisms as the most informative markers. While not imperative, it is in sometimes useful to ascertain the relationship of the SPCs and to deduce the SPC network. The establishment of the SPC relation is less straightforward when based on the unphased diploid genotype data (refer to the section 'SPCs can be identified on diploid genotype data') and becomes even more complicated when based on the genotype of sample pools. When SPCs are identified by means of a pooling strategy, their relationship can best be ascertained by selecting one or more tag polymorphisms (ctSNPs) per SPC and typing these tags in all the individual samples. The resultant genotypes can be used to establish whether the SPCs are in a dependent or an independent relation according to the prevailing principle that independent SPCs are found separately while a dependent SPC coincides with one or more other SPCs. Again, this is less straightforward in case the individual samples are of a diploid nature because then the genotypes are the sum of two haplotypes which makes that independent SPCs can happen together (see also 'SPCs can be identified on diploid genotype data'). Nonetheless, when the data set consists of a sufficient number of observations/genotypes, it will, in general, be possible to decide whether a tag always coincides with one or more other tags (i.e. the SPC is in a dependency relation) or is at least sometimes found on its own (independent relation).

Use of the SPC Structure to Infer Haplotypes

Also encompassed by the present invention is a method to unambiguously establish the phase of the mutations starting from diploid genotype data without the need for supplementary experimental haplotype resolution. The in silico inference of haplotypes from diploid genotype data is illustrated by means of the aforementioned FIGS. 7 and 8. The exemplary genotype data, assembled from known haplotypes, serve the purpose of teaching the rationale used in the deconvolution of the genotypes. As discussed above, the SPCs were already established directly from the genotype data (see FIGS. 7C/D and 8C/D).

The example of FIG. 7 comprises a total of 8 haplotypes (FIG. 7E), 5 of which correspond to independent SPCs 1 to 5, a sixth haplotype that contains no SPC (SPC-0 in FIG. 7E/F), and two additional ones, related to SPC-4 and SPC-0, that result from the presence of non-clustering SNPs. As a consequence of the independence of the SPCs, i.e. their occurrence on separate haplotypes, it follows that the major metatypes will contain not more than one type of SPC, whereas the minor metatypes will comprise no SPC (in case of SPC-0 homozygosity), one SPC (in case SPC-0 is one of the haplotypes) or two SPCs at most. This can be clearly seen in FIG. 7C/D. The major metatypes contain the SPCs 1, 2, 4 and 5, and the minor metatypes exhibit various combinations of the different SPCs (FIG. 7C/D). Note that the existence of SPC-3 can only be inferred from the minor metatypes. From these Figures it would—in the absence of knowledge about the underlying haplotypes—be straightforward to ascertain the independence of the SPCs and to deduce the SPC network shown in FIG. 7F. That being established, the rules for the deconvolution of the underlying haplotypes are simple. (1) If the minor metatypes contain only one SPC, then this genotype is deconvoluted into one haplotype containing the SPC and one haplotype that contain no SPC (SPC-0). (2) If the minor metatypes contain two SPCs, then this genotype is deconvoluted into one haplotype containing the first and a second haplotype containing the second SPC. SNPs that are not part of an SPC may be phased as well. In the present example, this is the case for both SNP-33 and SNP-38. The simplest interpretation, which can explain all genotypes with the fewest haplotypes, is that SNP-33 is in partial association with SPC-4 only. Similarly, SNP-38 is associated with SPC-0 since it found in minor metatypes containing either only SPC-0 or one single SPC. Alternative genotype data sets, assembled through random combination of the same haplotypes, did not always permit the unambiguous phasing of all non-clustering alleles. The skilled person will realize that this limitation is inherent to the data at hand and not a shortcoming of the deconvolution method per se.

The example of FIG. 8 aims to describe the deconvolution of more complex SPC structures, which are more likely to be encountered in practical reality. The example comprises a total of 7 SPCs, of which 3 are unrelated/independent and 4 are dependent on them. These 7 SPCs occur on 5 different haplotypes; an additional sixth haplotype contains no SPCs (FIG. 8E/F). In this case, contrary to the previous example, the resultant minor metatypes may comprise more than two SPCs, thus requiring the prior establishment of the hierarchical relationships between the SPCs before the simple rules outlined above can be applied. By definition an SPC is dependent on another SPC if the SPC is always co-occurring with that other SPC. Such co-occurrences can be deduced from inspection of both the major metatypes and the minor metatypes. While a co-occurrence in the major metatypes unambiguously establishes that the SPCs are dependent, the dependency of an SPC may not be unequivocally ascertained on the basis of the minor metatypes because of co-occurrence with multiple SPCs that are in an independent relation to one another. The likelihood to unambiguously determine the hierarchy increases with the number of observations. For this reason, the SPC structure is analyzed separately, first in the major and then in the minor metatypes.

Inspection of the SPCs observed in the major metatypes of FIG. 8C shows that SPC 1.2 co-occurs with SPC-1 and that SPCs 2.1 and 2.2 co-occur coincide with SPC-2, and thus unambiguously establishes these dependencies. Inspection of the SPCs observed in the minor metatypes of FIG. 8D shows that SPCs 1.1 and 1.2 always coincide with SPC-1 and that SPCs 2.1 and 2.2 always coincide with SPC-2. The latter observations confirm the dependencies of SPCs 1.2, 2.1 and 2.2 deduced from the major metatypes, and in addition establishes the dependency of SPC 1.1. In this case, the dependency of SPC 1.1 is unambiguous because the minor metatypes show all possible combinations of SPC 1.1 with the other independent SPCs 2 and 3. Inspection of the SPCs observed in FIG. 8C/D shows yet another rule that is useful for interpreting and confirming dependency relationships: when two SPCs that depend from the same SPC co-occur in minor metatypes, then the corresponding major metatypes will exhibit the SPC from which the two SPCs are dependent.

The above analysis demonstrates that even in the absence of knowledge about the underlying haplotypes, it is straightforward to establish the relationships between the SPCs and to deduce the SPC network shown in FIG. 8F from the data in FIG. 8C/D. Once the dependencies are resolved, the deconvolution can be performed by applying the rules outlined above on the independent SPCs (which in turn dictate the deconvolution of the appended dependent SPCs). As pointed out above, the number of observations at hand may in certain cases not suffice to unambiguously define the SPC hierarchy. For example, in one particular replicate simulation using another randomly generated genotype data set, SPC-1.1 was always found together with both SPCs 1 and 2 making it impossible to unambiguously infer the dependency of SPC1.1. It will be realized that this is not a shortcoming of the present deconvolution method but rather a limitation that is inherent to the data. The skilled person will also appreciate that the present method can also be applied when the underlying SPC structure is more complex than those shown in FIGS. 7F and 8F and displays, for example, several more levels of dependency. It should be noted that the identification of SPCs starting from unphased diploid genotypes should not be performed at too low a stringency so as to prevent the coalescence of dependent SPCs, which would impair the correct deconvolution. Compared to other state-of-the-art computational methods for haplotype inference, the present method is accurate and scalable to large numbers of polymorphisms.

SPC Analysis on Various Types of Genetic Variation Data

The novel clustering approach of the present invention can be applied to any type of sequence or genetic variation data. In cases as documented here, it can be applied to sequence variations identified in DNA sequences of a specific locus derived from different individuals of either the same species or even different (related) species. Alternatively, the method can be applied to a set of closely linked SNPs scored in a number of individuals using state of the art genotyping methods. In a generic sense the method can be used on any data set of genetic variants from a particular locus, like for instance on experimentally observed variations that reflect but do not allow definition of the genetic differences in an interrogated target nucleic acid. Various experimental approaches are available for differential nucleic acid analysis and to interrogate the sequence of a target nucleic acid without actually determining the full sequence of that target or, in particular, the sequence at the variable positions. For example, hybridization of a test and a reference DNA sample to an array containing thousands of unique oligonucleotides (termed features) may reveal statistical differences in the hybridization intensity of particular features—such differential intensity signals need not be assigned to specific underlying sequence differences and can be used as such with the method of the present invention. Similar to the case where the exact sequences at the polymorphic sites are known [supra], the present method allows discrimination between hybridization differences that are relevant—i.e. the clustered differences— and those that are spurious—i.e. the differences that do not cluster. The feasibility of the hybridization approach has been documented: Winzeler et al., Science 281: 1194-1197, 1998; Winzeler et al., Genetics 163: 79-89, 2003; Borewitz et al., Genome Res. 13: 513-523, 2003. Arrays containing 25-mer oligonucleotides that were primarily designed for expression analysis have been used to detect allelic variation (termed Single Feature Polymorphism or SFP) via direct hybridization of total genomic DNA. SFPs could be discovered in yeast as well as in the more complex 120-Mb *Arabidopsis* genome. The main advantage of the method is that it uses far less features than the Variation Detection Arrays [VDAs; Halushka et al., Nat. Genet. 22: 239-247, 1999; Patil et al., Science 294: 1719-1723, 2001]. VDAs tile every basepair along the chromosome and therefore require a vast number of features (eight for each basepair), making the approach more expensive. Array hybridization is both a polymorphism discovery tool as well as a method for the routine genotyping. There is no need to fully characterize the SFPs and to convert them to dedicated assays using different array designs on the same platform or using entirely different genotyping methodologies.

The preferred embodiment of DNA hybridization thus constitutes a novel method for genetic analysis in which the majority of the polymorphisms in a given DNA segment are recorded in a single assay, and are subsequently analyzed using the present novel clustering approach so as to genetically diagnose the individual using the pattern of clustered hybridization differences (refer to Example 11). In this respect, the DNA hybridization technology constitutes a genetic marker technology highly suited for determining the genetic state of a locus. The advantages of the above described hybridization approach for the identification of the SPC structure in defined regions of a genome are as follows. First, the method does not require the systematic discovery of the genetic variation that is present in a locus by full sequence determination using either conventional Sanger based methods or the above-mentioned VDAs ('sequence-by-hybridization). The hybridization patterns provide a sufficiently detailed record of the sequence variation present and application of the present novel clustering approach will reveal a clustering in the hybridization signals similar to that observed when analyzing the sequence variations directly. The skilled person will understand that the successful translation of the hybridization results to an SPC map requires that a sufficiently large number of features be used per locus. Secondly, the hybridization reaction itself can be used for the routine determination of the allelic state at various polymorphism clusters in a single assay, where the conventional approach would require the design and validation of separate assays for several ctSNPs per locus. The fact of being able to record the greater part of sequence variations present offers a unique approach for genotyping, which will in certain applications be of the uttermost importance.

Methods of Using SPC Maps

The methods of the present invention are particularly useful in two distinct fields of application, namely for genetic analysis and diagnosis in a wide range of areas from human genetics to marker assisted breeding in agriculture and livestock and for the genetic identity determination of almost any type of organism.

The method of the present invention whereby the SPC structure of a locus is examined provides a logical framework for the design of superior genetic markers, ctSNPs. One important field of application of ctSNPs will be genome wide association studies in a variety of organisms. In human for instance, the use of ctSNPs will be to identify genetic components responsible for predispositions, health risk factors or drug response traits. In crop and live stock improvement the use of ctSNPs will be to identify genetic factors involved in quantitative traits that determine agricultural performance such as yield and quality. It is contemplated that ctSNPs may either lead to the identification of such genetic factors either indirectly through their linkage to the causative mutations in a nearby gene or directly through their association with causative mutations that belong the same SPC. In this respect its is important to stress the major scientific finding that derives from the results obtained with method of the present invention, namely that a substantial fraction of the genetic variation found in nature is structured in SPC modules that in certain cases comprise a large number of different mutations. The mere existence of such SPC modules suggests that these have not arisen by chance alone, but rather represent clusters of mutations that have been selected in the course of evolution and hence represent allelic variants of genes that confer(ed) some kind of selective advantage to the species.

It is therefore contemplated that SPCs are likely modules of genetic variation associated with traits, and complex traits in particular, and this for the simple reason that these are determined not by single mutations but rather by clusters of mutations. This is apparently the case in one of the first quantitative traits recently characterized, the so called heterochronic mutations, namely mutations that affect the timing of gene expression [Cong et al., Proc. Natl. Acad. Sci. USA 99: 13606-13611, 2002].

The method of the present invention whereby the SPC structure of genomic regions is examined provides a logical framework for genetic identity determination. The SPC map of an individual will represent the ultimate description of the genetic identity of that individual, and this for any organism, from bacteria to humans. Consequently once the SPC map has been determined for an organism, this logical framework allows the design of an exhaustive panel of ctSNPs that can be used to determine or diagnose the genetic identity of individuals. While the utility of this application in human in vitro diagnostics is particularly contemplated, numerous other applications of this technology also are envisioned. For instance, in the in vitro diagnosis of "identity preserved foods", through the identification of the genetic material used in the production. Another application involves the identification of bacterial strains, in particular pathogenic strains.

Simply by way of example, in human in vitro diagnostics, it is contemplated that phenotypic traits which can be indicative of a particular SPC include symptoms of, or susceptibility to, diseases of which one or more components is or may be genetic, such as autoimmune diseases, inflammation, cancer, diseases of the nervous system, and infection by pathogenic microorganisms. Some examples of autoimmune diseases include rheumatoid arthritis, multiple sclerosis, diabetes (insulin-dependent and non-dependent), systemic lupus erythematosus and Graves disease. Some examples of cancers include cancers of the bladder, brain, breast, colon, esophagus, kidney, leukemia, liver, lung, oral cavity, ovary, pancreas, prostate, skin, stomach and uterus. Phenotypic traits also include characteristics such as longevity, appearance (e.g., baldness, color, obesity), strength, speed, endurance, fertility, and susceptibility or receptivity to particular drugs or therapeutic treatments. Many human disease phenotypes can be simulated in animal models. Examples of such models include inflammation (see e.g., Ma, Circulation 88:649-658 (1993)); multiple sclerosis (Yednock et al., Nature 356:63-66 (1992)); Alzheimer's disease (Games, Nature 373:523 (1995); Hsiao et al., Science 250:1587-1590 (1990)); cancer (see Donehower, Nature 356:215 (1992); Clark, Nature 359: 328 (1992); Jacks, Nature 359:295 (1992); and Lee, Nature 359:288 (1992)); cystic fibrosis (Snouwaert, Science 257: 1083 (1992)); Gaucher's Disease (Tybulewicz, Nature 357: 407 (1992)); hypercholesterolemia (Piedrahita, PNAS 89:4471 (1992)); neurofibromatosis (Brannan, Genes & Dev. 7:1019 (1994); Thalaemia & Shehee, PNAS 90:3177 (1993)); Wilm's Tumor (Kreidberg, Cell 74:679 (1993)); DiGeorge's Syndrome. (Chisaka, Nature 350:473 (1994)); infantile pyloric stenosis (Huang, Cell 75:1273 (1993)); inflammatory bowel disease (Mombaerts, Cell 75:275 (1993)).

Phenotypes and traits which can be indicative of a particular SPC also include agricultural and livestock performance traits, such as, among others, yield, product (e.g meat) quality, and stress tolerance The present invention therefore defines a powerful framework for genetic studies. Traditionally, association studies between a phenotype and a gene have involved testing individual SNPs in and around one or more candidate genes of interest. This approach is unsystematic and has no clear endpoint. More recently, a more comprehensive approach has been pioneered which is based on the selection of a sufficiently dense subset of SNPs that define the common allelic variation in so-called haplotype blocks. The present invention reveals the more basic and fundamental structure in genetic variation. The SPC maps described herein can explain the general observation that LD is extremely variable within and among loci and populations and provide the basis for the most rational and systematic genetic analysis of an entire genome, a sub-genomic locus or a gene. A subset of SNPs sufficient to uniquely distinguish each SPC (a ctSNP as described herein above) can then be selected and associations with each SPC can be definitively determined by determining the presence of such a ctSNP. In this manner, the skilled artisan could perform an exhaustive test of whether certain population variation in a gene is associated with a particular trait, e.g., disease state.

Finally, the approach provides a precise framework for creating a comprehensive SPC map of any genome for any given population, human, animal or plant. By testing a sufficiently large collection of SNPs, it should be possibly to define all of the underlying SPCs. Once these SPCs are identified, one or more unique SNPs associated with each SPC can be selected to provide an optimal reference set of SNPs for examination in any subsequent genotyping study. SPCs are therefore particularly valuable because they provide a simple method for selecting a subset of SNPs capturing the full information required for population association to find phenotype/trait-associated alleles, e.g., common disease-susceptibility associated alleles. Once the SPC structure is defined, it is sufficient to genotype a single ctSNP unique for a given SPC to describe the entire SPC. Thus, SPCs across an entire genome or sub-genomic region can be exhaustively tested with a particular set of ctSNPs.

Particular methods of selecting, detecting, amplifying, genotyping and data checking samples for use in the methods of the invention are described in the Examples of this application. It should be recognized, however, that any suitable methods known to those of skill in the art can be utilized. The following methods are further examples of methods that can be so utilized.

Non-clustering Polymorphisms

More often than not, a fraction of the polymorphisms present in a genomic region do not exhibit the tendency to cluster. As explained hereinabove, this may to a certain extent be attributed to the quality of the experimental data, more specifically missing or erroneous genotypes, and to the choice of the threshold. It is therefore contemplated in the present invention that the identification of SPCs in a data set involves the use of multiple threshold levels. However, detailed analyses of particular data sets show that some SNPs will not cluster at even the lowest threshold values and are truly standing apart.

While initially it was thought that non-clustering polymorphisms (see for example discussion above) had little diagnostic value, surprisingly, it was found that in some cases (depending on for example the quality of the data set) the majority of the non-clustering polymorphisms can be unambiguously fitted into the SPC network constructed for the region under study. This implies that the non-clustering polymorphisms behave as if they were 'single-element-SPCs'. Similar to SPCs, a 'single-element-SPC' is not found in conjunction with (dependent relationship) as well as separated from another SPC (independent relationship). The observation that many of the non-clustering polymorphisms conform to the network/phylogenetic tree was recurrently made in the case of human genomic regions that are essentially free of recombination events. This is exemplified in FIG. 32, which shows the SPC network of a particular region of the human genome, more specifically the ~44 kb segment of the ENCODE block ENm014 that comprises 94 SNPs and that runs from position 126,135,436 (rs#6950713) to 126,178,670 (Broad|BI192322) on chromosome 7. ENCODE regions are characterized by a high SNP density (e.g. about one SNP per 500 nucleotides) and thus provide the best view on the ultimate structure of genetic variation in the human genome. In addition to a regular network that only includes the SPCs, FIG. 32 shows a second network representation that incorporates the non-clustering SNPs. Note also that both networks were rooted through comparison with the chimpanzee outspecies sequence (see hereinabove) and thus represent bona fide phylogenetic trees. It can be seen in FIG. 32 that 80 out of the 94 SNPs were clustered into 8 SPCs, representing 3 independent SPCs and 5 dependent SPCs. These 8 SPCs define 6 different SPC-haplotypes. Of the 14 SNPs that failed to cluster, 10 had an occurrence frequency of >1%. These 10 SNPs could be fitted unambiguously into the SPC network as shown in FIG. 32. In a similar vein the remaining non-clustering SNPs could also be fitted into the network but were omitted because of their low frequency (<1%).

One important aspect illustrated in FIG. 32 is that most of the non-clustering SNPs (9 out of 10) define the exterior branches of the phylogenetic tree and occur at low frequency (a few % t), indicating that they represent recent mutations. The minor alleles of these polymorphisms are found in conjunction with only one type of SPC (but do not occur in all samples), and create minor variants/subdivisions of the evolved SPC-haplotypes. The finding that the non-clustering polymorphisms are mostly of recent origin corroborates the notion that such markers are of inferior value (at least when searching for associations with principal phenotypes or traits that were selected and maintained throughout history).

Another important aspect illustrated in FIG. 32 is that a fraction of the non-clustering polymorphisms is higher up in the phylogenetic tree and appears to have arisen prior to the emergence of certain SPCs (1 out of the 10 non-clustering SNPs shown in FIG. 32). This category of 'single-element-SPCs', in contrast to the recent/low frequency non-clustering SNPs, may be included in the analysis of genetic association because these represent old genetic variants that have been maintained through balanced selection, and hence may be considered for selection as marker (outlined in the section "The selection of ctSNPs—Methodical genetic characterization of a locus"). Also, in genomic regions that are essentially devoid of recombination, it is frequently observed that SPCs and non-clustering polymorphisms that are higher up in the phylogenetic tree appear to have undergone recombination prior to the emergence of the dependent SPCs. This observation is consistent with the proposed genealogy because older mutations are more likely to have undergone recombination that more recent mutations. The consequence of such ancient recombination events is that while the local networks around the ancient or ancestral SPCs and non-clustering polymorphisms are consistent, longer range networks may exhibit more complex patterns of SPC dependencies, in which more recently evolved SPCs simultaneously depend from more than one older SPC or non-clustering polymorphism. In certain cases, it appears that the emergence of the dependent SPCs correlates with one or more ancient recombination events between the older SPCs or non-clustering polymorphisms. These observations lend further support to the notion that the old SPCs or non-clustering polymorphisms may be functionally important, and should be included in the analysis of genetic association.

In addition to the non-clustering polymorphisms that conform the orderly network structure, part of the non-clustering polymorphisms (the percentage is variable and depends on, for example, the genomic region under study) cannot be fitted unambiguously into the phylogenetic tree. In certain cases the underlying reasons are obvious. For instance, SNPs located in regions where recurrent recombination is observed often cannot be fitted into the networks on either side of the recombination site, and these obviously represent SNPs that whose linkage has been scrambled by the recombination events. For some others it seems clear that they may represent recurrent mutations. Examples of this type are the single or multiple base deletions in homopolymer tracts, which are known to be highly mutable (refer also to Example 1). In other cases, the observation may simply be caused by genotyping errors.

Additional instances where the majority of the non-clustering polymorphisms can be unambiguously fitted into an SPC network/phylogenetic tree are given in Example 13.

In conclusion, it would appear that the SPC concept—which identifies discrete sets of coinciding polymorphisms as evolutionary units—can be extended to include some or all of the non-clustering SNPs. This comprehension has some important implications.

First, the non-clustering polymorphisms that comply with the network system can be included in the deconvolution of the unphased diploid genotype data. As set forth hereinabove (see section "Use of the SPC structure to infer haplotypes"), the SPC network structure represents a tool to guide the deconvolution process. Inclusion of some or all of the non-clustering polymorphisms will ultimately result in the derivation of not just the basic SPC-haplotypes but in a more refined and comprehensive set of haplotypes that comprises both the older polymorphisms that are shared between the different SPC haplotypes as well as some of the minor variants/subdivisions of the evolved SPC-haplotypes.

Second, the extended network including some or all of the non-clustering SNPs provides the ultimate description of the structure of the comprehensive set of haplotypes found, and thus provides guidance for selecting a minimal set of tag SNPs for genetic association analysis. As set forth hereinabove (see section "The selection of ctSNPs—Methodical genetic characterization of a locus"), the SPC map provides a rational basis for the selection of informative SNPs. One approach for selecting a minimal set of tag SNPs comprises selecting one tag SNP for each SPC or non-clustering polymorphism that is unique to each haplotype in the comprehensive set. The information provided by the network specifies precisely which SPCs or non-clustering polymorphisms are unique to each haplotype, and which are shared between the different haplotypes. The latter information thus defines exactly which are the combinations of tag SNPs that represent these shared SPCs or non-clustering polymorphisms. As a consequence, this minimal set of tags will test the possible association of a trait or phenotype with each and all SNPs that are present in the set of haplotypes. Simply put, if an association is found with only one of the tag SNPs, that result can be interpreted to mean that particular SPC or non-clustering polymorphism is associated, while a simultaneous association with a number of tag SNPs can be interpreted to mean that the SPC or non-clustering polymorphism that is shared between the tagged haplotypes is associated. Persons skilled in the art will realize that the ability to test the possible association of a trait or phenotype with each and all SNPs present in the set of haplotypes is a unique and extremely valuable attribute of the method of the present invention, and that such is not provided for by the haplotype block methods. Indeed, the haplotype block methods typically generate simple listings of the different haplotypes found in a particular region and select n-1 tag SNPs (where n-equals the number of different haplotypes) to differentiate the different haplotypes. Without the knowledge of the underlying structure of these haplotypes obtained using the method of the present invention, it is impossible to interpret whether simultaneous associations observed with two or more tag SNPs are meaningful. If indeed older mutation(s) that are shared by different haplotypes are involved in a trait, such associations will not readily be detected when using tag SNPs identified with the haplotype block methods.

Third, the identification of deviant or erroneous genotypes on the basis of inconsistencies in the SPC map of the region being considered can be also be performed at non-clustering sites (as illustrated in Example 13). As set forth hereinabove (see section "EXAMPLE 9 SPC map of HapMap SNPs of human chromosome 22"), the present invention also encompasses a method to identify possible erroneous data points in a genetic variation data set through the comparison of the actual genotypes of an individual sample with the network structure. Unexpected genotypes at non-clustering sites are readily identified when the genotype at those sites in one or more of the individual DNA samples prevents the unambiguous placement of the polymorphism in the network structure. Such unexpected genotypes may be selected for experimental verification in a repeat analysis, and preferably the SNP should not be included in the computation of the haplotypes. A direct comparison of the haplotypes computed with the method of the present invention and with the state of the art haplotype block methods (Haploview, http://www.broad.mit-.edu/mpg/haploview/index.php) reveals that a fraction of the haplotypes computed with the latter method are artifacts produced by such erroneous genotypes. Persons skilled in the art will realize that each genotyping error will result in an additional haplotype and that consequently data sets with very low error rates, such as the HapMap genotypes, will yield a sizable fraction of erroneous haplotypes. Furthermore, since the haplotype block method selects one tag SNP for each haplotype, a fraction of the tag SNPs selected will correspond to SNPs that have yielded genotyping errors. With the method of the present invention such genotyping errors are readily identified, and hence fewer and more accurate haplotypes are obtained which consequently yield fewer and more reliable tag SNPS.

Diagnosis of Non-clustering Disease Mutations

The present invention uncovers that SPCs represent discrete steps in evolution and are, for that reason, to be viewed as units that are useful to test for association with particular phenotypes or traits. It is however projected that certain causal mutations may not be part of an SPC, i.e. are non-clustering. This may for example be the case with so-called null-mutations and with the wide array of mutations in the genes that were found to be associated with uncommon genetic disease (e.g. CFTR, BRCA, etc). In general, the rare mutations that underlie the human genetic disorders are relatively young [Rannala B. & Bertorelle G., Human Mut. 18: 87-100, 2001]. It may be anticipated that many of these mutations will unambiguously fit into the SPC network of the disease locus—as illustrated in the network representation shown in FIG. 32, the mutations will be found in partial association with only one SPC and generate minor haplotype variants.

In the future, much effort will be directed towards the diagnosis of these disease-related genetic variations at the nucleotide level. The diagnosis is however severely impeded by the growing number of such disease-related mutations. This necessitates the design and use of a multiplex assays series so as to reduce the effort and cost. The orderly SPC structure of the disease locus provides for an alternative strategy for diagnosis. The approach would entail the exhaustive characterization of the genetic variation followed by the construction of the SPC network, which would reveal the genetic contexts in which the various disease mutations have arisen. While the details of the protocol would depend on the characteristics of the network structure at hand, one can envisage that, in general, the diagnosis can be facilitated by first testing an appropriate set of SPCs and then to limit the subsequent examination to that subset of disease mutations that is known to occur in combination with the SPCs that are actually present in the query sample. The number of SPCs that are selected for the initial test depends on the network structure but should, as a rule, establish sufficient resolution so that the number of disease mutations that needs to be surveyed in (a) secondary assay(s) is considerably reduced and outweighs the effort of the primary test.

Methods of Identifying SNPs

The present inventors have demonstrated the feasibility and desirability of building a map of a genome (region) in which the SPCs are defined. This SPC map contains sets of co-occurring alleles, e.g., cosegregating polymorphisms. Within an SPC map there may be one or more SPCs and each SPC may be further identified by a polymorphism that is characteristic of that particular SPC. Using such SPC maps, sequence variation can be captured by a relatively small number of SNPs. Of course, a comprehensive description of the SPC map in a human, animal or plant population can require a high density of polymorphic markers. Across the genome of the human as well as some other (model) species a rapidly growing number of polymorphisms is available and these data may be used to produce the SPC maps described herein. However, in certain circumstances, it may be desirable to identify new SNPs and/or to genotype previously known SNPs in additional samples of the same or a different population. This can be readily achieved using methods known in the art.

A. Sample Population

Polymorphism information can be obtained from any sample population to produce a map of the invention. "Information" as used herein in reference to sample populations is intended to encompass data regarding frequency and location of polymorphisms and other data such as background and phenotypic (e.g. health) information useful in genotype studies and the methods and maps of the invention described herein. In some cases it can be desirable to utilize a diverse (multiethnic) population sample. Such a sample can include a total random sample in which no data regarding (ethnic) origin is known. Alternatively, such a sample can include samples from two or more groups with differing (ethnic) origins. Such diverse (multiethnic) samples can also include samples from three, four, five, six or more groups. In other cases it can be desirable to utilize a homogeneous (monoethnic) sample in which all members of the population have the same (ethnic) origin. Ethnicity refers to the human case and can be, for example, European, Asian, African or any other ethnic classification or any subset or combination thereof. In the case of plant or animal genetic studies, the populations can consist of breeding germplasm, specific races, varieties, lines, accessions, landraces, introgression lines, wild species or any subset or combination thereof. The population samples can be of any size including 5, 10, 15, 20, 25, 30, 35, 40, 50, 75, 100, 125, 150 or more individuals.

Information for producing a map of the invention can also be obtained from multiple sample populations. Such information can be used concurrently or sequentially. For example, studies can be performed using homogeneous (monoethnic) population samples. The results of these studies can then be utilized with the results of a study on a diverse (multiethnic) sample. Alternatively, the results from the homogeneous (monoethnic) sample can be combined to form a diverse (multiethnic) study.

B. Sample Preparation

Polymorphisms can be detected from a target nucleic acid from an individual being analyzed. For assay of human genomic DNA, virtually any biological sample may be used. For example, convenient tissue samples include whole blood, semen, saliva, tears, urine, fecal material, sweat, buccal, skin and hair have readily been used to assay for genomic DNA. In the case of plants, any part (e.g. leaves, roots, seedlings) can be used for genomic DNA preparation. For assay of cDNA or mRNA, the sample must be obtained from an organ or tissue in which the target nucleic acid is expressed.

Many of the methods described below require amplification of DNA from target samples. Amplification techniques are well described in the literature. For example, PCR is a generally preferred method for amplifying a target nucleic acid, See generally PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19:4967 (1991); Eckert et al., PCR Methods and Applications 1, 17 (1991); PCR (eds. McPherson et al., IRL Press, Oxford); and U.S. Pat. No. 4,683,202 (each of which is incorporated by reference for all purposes).

Other suitable amplification methods include the ligase chain reaction (LCR) (see Wu and Wallace, Genomics 4:560 (1989); Landegren et al., Science 241:1077 (1988)), transcription amplification (Kwoh et al., Proc. Natl. Acad. Sci. USA 86:1173 (1989)), and self-sustained sequence replication (Guatelli et al., Proc. Nat. Acad. Sci. USA 87:1874 (1990)) and nucleic acid based sequence amplification (NASBA). The latter two amplification methods involve isothermal reactions based on transcription, which produce both single stranded RNA (ssRNA) and double stranded DNA (dsDNA) as the amplification products in a ratio of about 30 or 100 to 1, respectively.

C. Detection of SNPs in Target DNA

There are two distinct types of analysis depending whether or not a polymorphism in question has already been characterized. The first type of analysis is sometimes referred to as de novo characterization and makes use of a differential nucleic acid analysis. This analysis compares target sequences in different individuals to identify points of variation, i.e., polymorphic sites. By analyzing a group of individuals representing the greatest variety characteristic patterns of alleles can be identified, and the frequencies of such alleles in the population determined. Additional allelic frequencies can be determined for subpopulations characterized by criteria such as geography, race, or gender. The second type of analysis is determining which form(s) of a characterized polymorphism are present in individuals under test. There are a variety of suitable procedures for sequence-based genotyping, which are discussed in turn.

Allele-Specific Probes and Primers. The design and use of allele-specific probes for analyzing SNPs is described by e.g., Saiki et al., Nature 324:163-166 (1986); Dattagupta, EP 235, 726, Saiki, WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably be selected such that a hybridizing probe hybridizes to only one of the alleles. Some probes are designed to hybridize to a segment of target DNA such that the polymorphic site aligns with a central position (e.g., in a 15 mer at the 7 position; in a 16 mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

In allele-specific polymerase chain reaction (PCR) analysis, the allele-specific primer hybridizes to a site on target DNA overlapping a SNP and only primes amplification of an allelic form to which the primer exhibits perfect complementarity. See Gibbs, Nucleic Acids Res. 17: 2427-2448 (1989). This primer is used in conjunction with a second primer which hybridizes at a distal site. Amplification proceeds from the two primers leading to a detectable product signifying the particular allelic form is present. A control is usually performed with a second pair of primers, one of which shows a single base mismatch at the polymorphic site and the other of which exhibits perfect complementarily to a distal site. The single-base mismatch prevents amplification and no detectable product is formed. The method works best when the mismatch is included in the 3'-most position of the oligonucleotide aligned with the polymorphism because this position is most destabilizing to elongation from the primer.

Tiling Arrays. The SNPs can also be identified by hybridization to nucleic acid arrays (DNA chip analysis). Subarrays that are optimized for detection of variant forms of precharacterized polymorphisms can also be utilized. Such a subarray contains probes designed to be complementary to a second reference sequence, which is an allelic variant of the first reference sequence. The inclusion of a second group (or further groups) can be particular useful for analyzing short subsequences of the primary reference sequence in which multiple mutations are expected to occur within a short distance commensurate with the length of the probes (i.e., two or more mutations within 9 to 21 bases). Methods and compositions for making such subarrays are well known to those of skill in the art, see e.g., U.S. Pat. No. 6,368,799, which describes methods of detecting gene polymorphisms and monitoring allelic expression employing a probe array.

Direct Sequencing. The direct analysis of a sequence of any samples for use with the present invention can be accomplished using either the dideoxy-chain termination method or the Maxam-Gilbert method (see Sambrook et al., Molecular Cloning, A Laboratory Manual (2nd Ed., CSHP, New York 1989); Zyskind et al., Recombinant DNA Laboratory Manual, (Acad. Press, 1988)).

Sequencing by Hybridization. A well-recognized alternative to using direct-sequencing is the use of sequencing by hybridization (SBH), a method by which the sequence of a target nucleic acid is reconstructed from a collection of probes to which the target nucleic acid sequence hybridizes. Methods and compositions for sequencing by hybridization are described, e.g., in U.S. Pat. No. 6,689,563; U.S. Pat. No. 6,670,133; U.S. Pat. No. 6,451,996; U.S. Pat. No. 6,399,364; U.S. Pat. No. 6,284,460, U.S. Pat. No. 6,007,987; U.S. Pat. No. 5,552,270. Each of these documents are incorporated herein by reference as providing a teach of the methods and compositions for making and using SBH chips for SBH analyses.

Denaturing Gradient Gel Electrophoresis. Amplification products generated using the polymerase chain reaction can be analyzed by the use of denaturing gradient gel electrophoresis. Different alleles can be identified based on the different sequence-dependent melting properties and electrophoretic migration. Erlich, ed., PCR Technology, Principles and Applications for DNA Amplification, (W. H. Freeman and Co, New York, 1992), Chapter 7.

Single-Strand Conformation Polymorphism Analysis. Alleles of target sequences can be differentiated using single-strand conformation polymorphism analysis, which identifies base differences by alteration in electrophoretic migration of single stranded PCR products, as described in Orita et al., Proc. Natl. Acad. Sci. USA 86, 2766-2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence difference between alleles of target sequences.

Allele-specific Primer Extension—Minisequencing. A primer is specifically annealed upstream of the SNP site of interest, which may then be extended by the addition of an appropriate nucleotide triphosphate mixture, before detection of the allele-specific extension products on a suitable detection system. If dideoxynucleotide triphosphates labelled with different dyes are used, single base extension (SBE) products can be analyze by electrophoresis using a fluorescent sequencer, either gel or capillary based. Conventional detection methods, such as an immunochemical assay, can also be used to detect the SBE products. Alternatively, Matrix-assisted laser desorption ionisation time-of-flight mass spectrometry (MALDI-TOF-MS) can be used to separate the extension products as well as the primer to a high degree of precision by their respective molecular masses without the need for any labelled tags [Storm et al., Methods Mol. Biol. 212: 241-262, 2003]. In pyrosequencing [Nyrén et al., Anal. Biochem. 208: 171-175, 1993] complementary strand synthesis is performed in the absence of dideoxynucleotides. Each dNTP substrate is added individually and incorporation is monitored by the release of pyrophosphate which is converted to ATP fuelling a luciferase reaction. If the dNTP is not incorporated, it is degraded with no light emission. The sequence of events is followed and is specific to the sequence of the variant.

Allele-specific Oligonucleotide Ligation. For an oligonucleotide ligation assay (OLA), two primers are designed that are directly next to each other when hybridized to the complementary target DNA sequence in question. The two adjacent primers must be directly next to each other with no interval, or mismatch, for them to be covalently joined by ligation. This discriminates whether there is an SNP present. There are many different labelling and detection methods, including ELISA [Nickerson et al., Proc. Natl. Acad. Sci USA 87: 8923-8927, 1990], or electrophoresis and detection on a fluorescence sequencer.

Allele-specific Cleavage of a Flap-Probe. This assay, called Invader, uses a structure-specific 5' nuclease (or flap endonuclease) to cleave sequence-specific structures in each of two cascading reactions. The cleavage structure forms when two synthetic oligonucleotide probes hybridise to the target. The cleaved probes then participate in a second generic Invader reaction involving a dye-labelled fluorescence resonance energy transfer (FRET) probe. Cleavage of this FRET probe generates a signal, which can be readily analysed by fluorescence microtitre plate readers. The two cascading reactions amplify the signal significantly and permit identification of single base changes directly from genomic DNA without prior target amplification [Fors et al. Pharmacogenomics 1: 219-229, 2000].

Linkage Analyses

The genomic maps and the methods of the invention can be readily used in several ways. The mapping of discrete regions which contain sequence polymorphisms permits, for example, the identification of phenotypes associated with particular SPCs, the localization of the position of a locus associated with a particular phenotype (e.g. a disease) as well as the development of in vitro diagnostic assays for (disease) phenotypes.

For example, linkage studies can be performed for particular SPCs because such SPCs contain particular linked combinations of alleles at particular marker sites. A marker can be, for example, a RFLP, an STR, a VNTR or a single nucleotide as in the case of SNPs. The detection of a particular marker will be indicative of a particular SPC. If, through linkage analysis, it is determined that a particular ctSNP is associated with, for example, a particular disease phenotype, then the detection of the ctSNP in a sample derived from a patient will be indicative of an increased risk for the particular disease phenotype. Additionally, if a particular phenotype is known to be associated with a particular discrete SPC, then the locus can be sequenced and scanned for coding regions that code for products that potentially lead to the disease phenotype. In this manner, the position of a disease-susceptibility locus of a disease can be located.

Linkage analysis can be accomplished, for example, by taking samples from individuals from a particular population and determining which allelic variants the individuals have at the marker sites that tag discrete SPCs. Using algorithms known in the art, the occurrence of a particular allele can be compared to, for example, a particular phenotype in the population. If, for example, it is found that a high proportion of the population that has a particular disease phenotype also carries a particular allele at a particular polymorphic site—then one can conclude that the particular allele is linked to the particular phenotype in that population. Linkage analyses and algorithms for such analyses are well known to those of skill in the art and exemplary methods are described in greater detail in e.g., U.S. Pat. No. 6,479,238 (see especially section IV therein). Additionally, since the marker alleles embody discrete SPCs, the phenotype is also determined to be linked to a discrete SPC. Thus, by using genetic markers, e.g., ctSNPs, that tag discrete SPCs, linkage analysis can be performed that allows for the conclusion that a particular phenotype is linked to a particular SPC.

The foregoing aspects of the invention are further described by the Examples hereinafter.

EXAMPLE 1

Intraspecies SPC Map of the sh2 Locus of Maize

The present example provides proof of concept that the methods of the present invention can be used to generate an SPC map of a complete gene locus that has been sequenced in a number of individuals of a particular species. Many studies on the genetic diversity of specific genes have been conducted in a broad range of plant and animal species, and these sequences are publicly available from GenBank (http://www.ncbi.nlm.nih.gov). In most of these studies relatively short gene segments, less than 1000 bp, have been sequenced and only in a few studies have complete genes been sequenced. From the available complete or near complete gene sequences available in GenBank, the shrunken2 (sh2) locus from maize was chosen to exemplify the different aspects of the invention. The published shrunken2 locus sequences from 32 maize cultivars (Zea mays subsp. mays) comprise a region of 7050 bp containing the promoter and the coding region of the sh2 gene [Whitt et al., Proc. Natl. Acad. Sci. USA 99: 12959-12962, 2002].

The sequences for this analysis were retrieved from GenBank (http://www.ncbi.nlm.nih.gov) accession numbers AF544132-AF544163. The sequences were aligned using ClustalW [Thompson et al., Nucleic Acids Res. 22: 4673-4680, 1994] and the alignments around the indels were manually optimized. Using a perl script all the polymorphic sites in the aligned sequences were scored to generate a genetic variation table in which each column represents a polymorphic site and each row represents a sample. In the columns the corresponding alleles (bases) in each sample are represented, except for indels that are represented by two dots at respectively the start and the end position of the deletion. When more than two (minor) alleles were found at a polymorphic site, this polymorphic site was duplicated such that each column contained only one of the minor alleles, and replacing the other minor allele(s) by a blank. Note that the number of polymorphic sites in the genetic variation table is larger than the number of variable positions in the sequence because of the indels and multi-allelic sites.

Figure 9A:
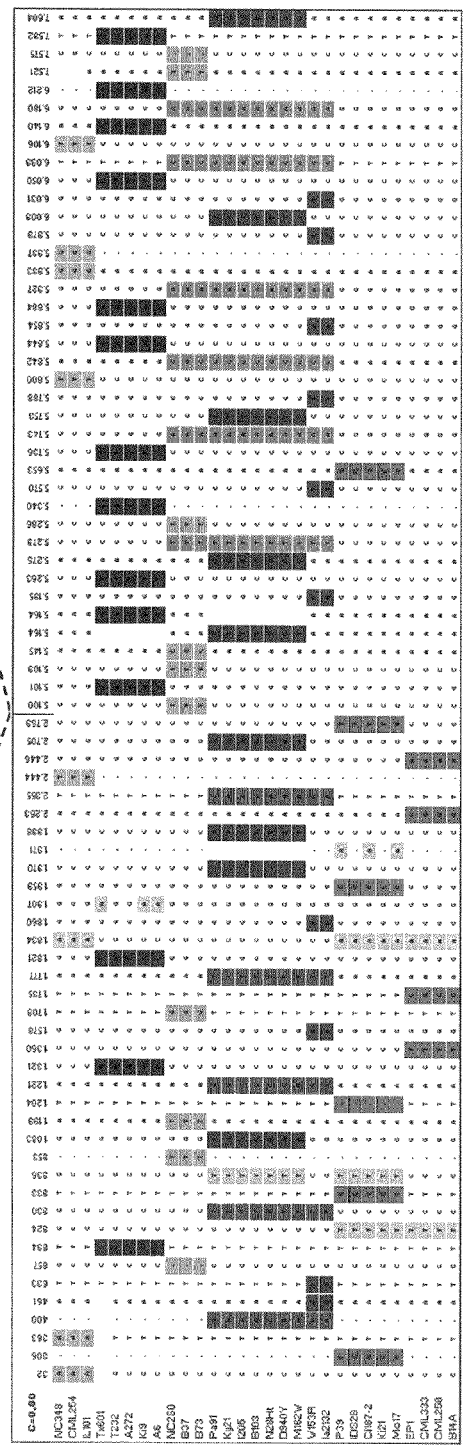
FIG. 9A corresponds to the output of the algorithm and shows the genetic variation table onto which the SPCs are depicted. The maize lines for each genotype are shown in the left most column. The position of each variation on the physical map of the 7 kb sh2 locus is indicated above the columns. The polymorphic sites in the middle segment of the locus are omitted to bring down the size of the table. The table is organized such that individuals that share the same SPCs are grouped. Polymorphic sites that do not cluster are for the most part omitted—the ones that are shown are colored in grey and are located at positions 924, 936, 1834, 1907 and 1971.

The genetic variation table of the sh2 gene comprises 212 polymorphic sites. To simplify the analysis and the representation of the results, the singletons, i.e. the polymorphic sites at which the minor allele occurs only once, three recombinant genotypes and the duplicate indel sites were excluded from the analysis. This reduced the number of polymorphic sites in the genetic variation table to 141. From this compacted genetic variation table the SPCs that comprise 3 or more polymorphic sites were computed with the SPC algorithm using the following thresholds: C=1, C≧0.90, C≧0.85, C≧0.80 and C≧0.75. At the threshold of C≧0.80 (shown in FIG. 9A) the algorithm clustered a total of 124 polymorphic sites (88%) of the sh2 locus into 9 different SPCs, most of which extended throughout the entire locus. The five largest SPCs comprise between 10 and 39 polymorphisms (note that not all polymorphisms are displayed in FIG. 9A). The sh2 locus thus yields a continuous SPC map, as is shown in FIG. 9A. The figure shows the SPCs in 29 of the 32 non-recombinant individuals. The uninterrupted SPC map of the 7 kb sh2 locus indicates that the locus has experienced few historical recombination events. This is further supported by the observation that only 3 of the 32 samples sequenced appear recombinant.

Figure 9B:
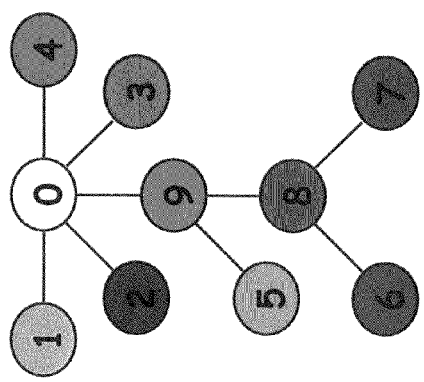
FIG. 9B shows the SPC network of the locus. The putative source sequence that is devoid of an SPC is referred to as SPC-0.

Apart from the identification of the overall SPC structure of the sh2 gene, the present example serves to illustrate a number of specific aspects of the present invention. First the example provides a clear illustration of the two types of relationships that can exist between SPCs, namely independence or dependence of the SPCs. It can be seen from FIG. 9B that the sh2 locus comprises 5 primary independent SPCs, each comprising a large number of different polymorphisms (SPCs 1, 2, 3, 4, and 9). In addition, several layers of dependency can be observed involving SPCs 9, 5, 8, 6, and 7. When taking also the SPCs comprising two polymorphisms and the SPCs comprising the singletons into account, several additional dependent SPCs are found (not shown). Consequently, the SPC-network of FIG. 9B is a simplified representation of the SPC structure of the sh2 locus. Furthermore, it can be anticipated that the actual SPC structure of the sh2 locus of maize may be even more complex, because the number of individuals that has been sequenced is relatively small, and hence may represent only a fraction of the full genetic diversity of the maize (Zea mays subsp. mays) germplasm.

A second important aspect concerns the mutations that do not cluster: only 17 of the 141 polymorphic sites could not be clustered at the threshold of C≧0.80. A sample of non-clustering polymorphic sites is shown in the left part of FIG. 9A. Analysis of these polymorphic sites revealed that these comprise three types. First, some polymorphic sites are associated with only one SPC but do not occur in all samples, and thus presumably represent more recent mutations. The second type comprises polymorphic sites that are found associated with more than one SPC. For some of these it seems clear that they represent recurrent mutations. Examples of this type are the single or multiple base deletions in homopolymer tracts, which are known to be highly mutable. The third type comprises polymorphic sites that are associated with two or three different SPCs. Some of these may represent ancestral mutations that are common to these SPCs. However, irrespective of the explanation for the lack of clustering, the non-clustering polymorphisms were initially thought to represent a subset of the polymorphic sites with an erratic association of poor diagnostic value. However, as demonstrated herein the non-clustering polymorphisms also for a useful aspect of the SPC networks of the present invention. Consequently, this analysis demonstrates that the methods of the present invention provide a selection of polymorphic sites exhibiting superior diagnostic value, thus providing proof of concept for one of the principal utilities of the method of the invention, namely the selection of genetic markers for analyzing genetic traits.

A third aspect of the present example concerns the thresholds for calculating the SPCs. As outlined above the SPC analysis was performed on a subset of samples comprising the 29 non-recombinant samples. At a threshold of C=1, 121 of the 141 polymorphic sites were clustered. Lowering the threshold to C≧0.80 added 3 additional polymorphic sites to the SPCs. These were three SNP that had one aberrant data point. In this case the use of lower thresholds had marginal effects. The reasons for this are several; For one, the sequences were obviously of high quality, and the frequency of erroneous allele calls was low. Second, by excluding the recombinants prior to clustering, the analysis was biased.

A fourth aspect emerging from our analysis is that the SPCs of the sh2 locus comprise both indels and SNPs, supporting that the method of clustering captures all mutational events. In addition, analysis of multi-allelic polymorphic sites shows that some of these represent independent mutations of the same position that are linked to different SPCs. The latter is illustrated by the polymorphism at position 5154 in FIG. 9A.

A fifth aspect concerns the design of cluster tag SNPs. Since most SPCs are defined by large numbers of markers that are in absolute linkage, the choice of tag SNPs in this case is straightforward. The only remark is that one should avoid using any of the 3 markers that are not in perfect linkage. The SPC network shown in FIG. 9B has considerable practical utility for the selection of genetic markers for genetic analysis of the sh2 locus. While there is a total of 9 SPCs, it is clear that a genotyping study can, depending on the desired level of resolution, address a subset of these SPCs. For instance, a genotyping, could be limited to the ctSNPs that tag the 5 primary independent SPCs (i.e. SPCs 1, 2, 3, 4, and 9). Even for an exhaustive analysis of the locus only a subset of the SPCs would have to be addressed, more specifically SPCs 1, 2, 3, 4, 5, 6, and 7 because the clade-specific SPCs 8 and 9 are redundant over the dependent SPCs.

EXAMPLE 2

Intraspecies SPC Map of the sh1 Locus of Maize

The present example provides proof of concept that the methods of the present invention can be used to generate an SPC map of a complete gene in which extensive recombination has occurred. This example presents an analysis of the polymorphic sites in the shrunken1 (sh1) locus from maize to exemplify further aspects of the invention. The published shrunken1 locus sequences from 32 maize cultivars (*Zea mays* subsp. *mays*) comprise a region of 6590 bp containing the promoter and the coding region of the sh2 gene [Whitt et al., Proc. Natl. Acad. Sci. USA 99: 12959-12962, 2002].

The sequences for this analysis were retrieved from GenBank (http://www.ncbi.nlm.nih.gov) accession numbers AF544100-AF544131. The sequences were aligned to generate a genetic variation table as described in detail in Example 1. The genetic variation table of the sh1 gene comprises 418 polymorphic sites. Because of this very large number of polymorphic sites, the singletons were excluded from the analysis. This reduced the number of polymorphic sites to 282. From this compacted genetic variation table the SPCs that comprise 3 or more polymorphic sites were computed with the SPC algorithm using the following thresholds: C=1, C≧0.90, C≧0.85, C≧0.80 and C≧0.60. At the threshold of C≧0.80 (see FIG. 10) the algorithm clustered 145 polymorphic sites (51%) of the sh1 locus into 26 SPCs. This result is quite different from that obtained with the sh2 locus in Example 1, and illustrates that polymorphisms in this locus can exhibit a strikingly different structure.

Figure 10:
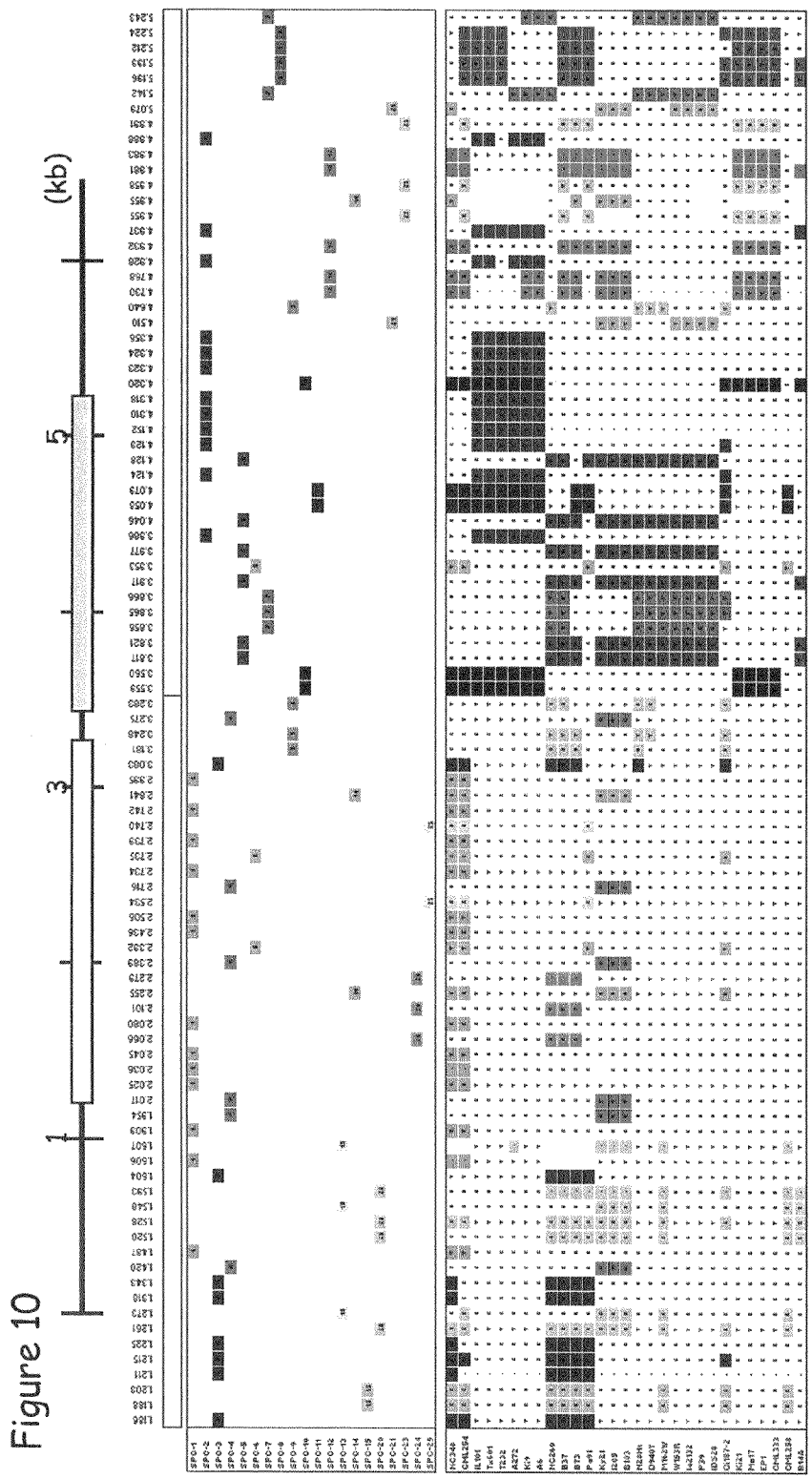
FIG. 10 shows the intraspecies SPC map of the sh1 locus of maize. Different highlights are used to indicate the various SPCs. The upper part of the figure is a schematic representation of the physical map of the 7 kb sh1 locus, in which the differentially highlighted rectangles indicate the map positions of the polymorphic sites that are listed in the genetic variation table. The middle panel corresponds to the output of the algorithm and lists the different SPCs in the locus. Each row represents the polymorphic sites that belong to a particular SPC. The lower panel corresponds to the output of the algorithm and shows the genetic variation table onto which the SPCs are depicted. The maize lines for each genotype are shown in the left most column. The table is organized such that individuals that share the same SPCs are grouped as much as possible. Polymorphic sites that do not cluster are not shown.

In contrast to the sh2 locus from Example 1, in which ~90% of the polymorphic sites were clustered, only ~50% of the sh1 polymorphic sites could be clustered. While the sh2 locus yielded a relatively small number of SPCs comprising many polymorphic sites, the sh1 locus yielded a much larger number of SPCs containing on average fewer polymorphic sites. Furthermore, as can be seen from FIG. 10, most of the SPCs identified were located in two segments (positions 1186 to 3283 and 3559 to 5243) comprising about half of the locus, and a third very short (120 bp) highly polymorphic segment (positions 6315 to 6436; not shown). The sh1 locus thus yields a discontinuous SPC structure, which is represented in FIG. 10. It is evident that the observed SPC structure must be the result of recurrent recombination (or recombination hotspots), in the regions between the segments exhibiting a clear SPC structure. These recombination events not only generated the two distinct segments but also scrambled the polymorphic sites within the intervening regions such that none of these polymorphisms cluster, and this even at thresholds of C≧0.60. Finally it can be seen from FIG. 10 that recombination has occurred within the two segments exhibiting a clear SPC structure. This is particularly evident in the right segment where most SPCs are short The two contrasting Examples 1 and 2 illustrate that the methods of the present invention can be used to generate informative SPC maps of gene loci, irrespective of the recombination history of the locus. The structure of the resulting SPC maps is determined primarily by the recombination frequency in the region of interest. Extensive recombination within a locus will result in a fragmented SPC structure with short range SPCs containing fewer polymorphic sites, while in the absence historical recombination, the locus will yield a highly continuous SCP map with SPCs comprising large numbers of polymorphic sites and extending over longer distances. Irrespective of the SPC structure of the locus, the methods of the present invention have clear practical utility. In both cases the methods of the present invention provide a selection of polymorphic sites exhibiting superior diagnostic value, thus providing proof of concept for one of the principal utilities of the method of the invention, namely the selection of genetic markers for analyzing genetic traits. While in the sh2 case a mere 7 ctSNPs will suffice to capture the majority of the genetic variation within the locus without loss of information, the ctSNPs selected for genotyping the sh1 locus will cover only a fraction of the genetic variation within the locus. Persons skilled in the art will understand that this is an intrinsic limitation and not one related to the method of the present invention.

EXAMPLE 3

Intraspecies SPC Map of the Y1 Locus of Maize

The present example provides proof of concept that the method of the present invention can be used to generate an SPC map of a locus in which several historical recombination events have occurred. This example presents an analysis of the polymorphisms in the Y1 phytoene synthase locus of maize to exemplify further aspects of the invention. The Y1 phytoene synthase gene, which is involved in endosperm color, was sequenced in 75 maize inbred lines [Palaisa et al., The Plant cell 15: 1795-1806, 2003], comprising 41 orange/yellow endosperm lines and 32 white endosperm lines.

The sequences for this analysis were retrieved from GenBank (http://www.ncbi.nlm.nih.gov) accession numbers AY296260-AY296483 and AY300233-AY300529. The sequences comprise 7 different segments from a region of 6000 bp containing the promoter and the coding region of the Y1 phytoene synthase gene. The individual sequences were aligned to generate 7 genetic variation tables as described in detail in Example 1, which were subsequently combined into a single genetic variation table. The combined genetic variation table of the Y1 phytoene synthase gene comprises 191 polymorphic sites. The SPCs that comprise 3 or more polymorphic sites were computed with the SPC algorithm using various thresholds. The algorithm clustered 85, 95 and 113 polymorphisms at a threshold value of C=1, C≧0.95 and C≧0.80, respectively.

Figures 11A, 11B:
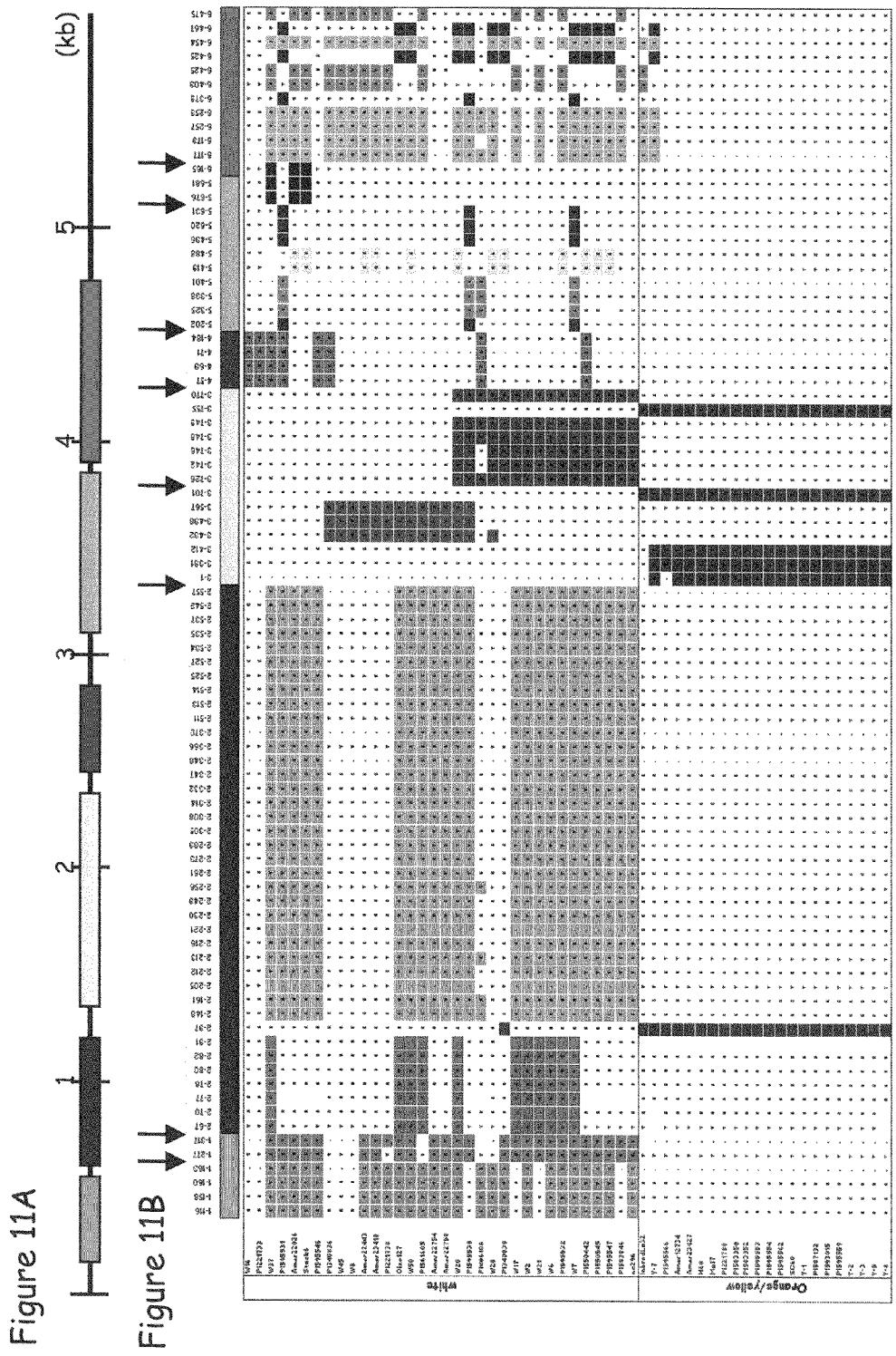
FIG. 11A is a schematic representation of the physical map of the 6 kb Y1 locus, in which the differentially highlighted rectangles indicate the map positions of the polymorphic sites that are listed in the genetic variation table of FIG. 11B.
FIG. 11B corresponds to the output of the algorithm and shows the genetic variation table onto which the SPCs are depicted. The maize lines for each genotype are shown in the left most column. The upper panel of FIG. 11B shows the SPCs in the white endosperm lines. The lower panel of FIG. 11B shows the SPCs in the orange/yellow endosperm lines. The table is organized such that individuals that share the same SPCs are grouped as much as possible. The arrows indicate the positions of some putative historical recombination events. Polymorphic sites that do not cluster are not shown.

The Y1 SPC map presented in FIG. 11B shows the SPCs obtained at the threshold value of C≧0.95, with in the upper half of the panel the white endosperm lines and in the lower half of the panel the orange/yellow endosperm lines. While the orange/yellow lines all share the same continuous SPC (SPC-1), the white lines exhibit a number of different SPCs, exhibiting a discontinuous pattern of SPCs. This pattern is consistent with a relatively small number of recombination events that occurred at the positions between the different SPCs, indicated by the arrows in FIG. 11B.The present example also illustrates one important aspect of the present invention, namely that SPCs may be highly correlated with phenotypes. Indeed the finding that all orange/yellow endosperm lines share the same SPC indicates that the polymorphisms that make up that SPC are either tightly linked to or are responsible for the orange/yellow phenotype.

The present example also illustrates another important aspect of the present invention, namely the importance of using different thresholds to identify SPCs. At the threshold of complete linkage, the SPCs include only those polymorphisms that are present in non-recombinant individuals, since the polymorphisms that are affected by (rare) recombination events will not exhibit complete linkage. In the present example, the only mutations within the single SPC present in the orange/yellow lines that are perfectly correlated with the phenotype are the polymorphisms at positions 3-701 and 3-755, which are the only ones present in InbredLo32 (see FIG. 11B), which moreover is a complex recombinant. This illustrates that while SPCs may be well correlated with phenotypes, not all polymorphisms in the SPC have necessarily the same diagnostic value.

EXAMPLE 4

Interspecies SPC Map of the Globulin 1 Locus of Maize

The present example provides proof of concept that the methods of the present invention can be used to generate an interspecies SPC map of a gene locus that has been sequenced in individuals from different closely related species. This example presents an analysis of the polymorphic sites in the globulin 1 (glb1) locus of maize to exemplify further aspects of the invention. Evidence is presented that the SPCs detected by the method of the present invention may have arisen before the split of the related species and can therefore be considered ancient.

The globulin 1 gene sequences analyzed in the present example have been generated in phylogenetic studies on the origins of domesticated maize [Hilton and Gaut, Genetics 150: 863-872,1998; Tenaillon et al., Proc. Natl. Acad. Sci. USA 98: 9161-9166, 2001; Tiffin and Gaut, Genetics 158: 401-412, 2001] and comprise a region of 1200 bp containing part of the coding region of the glb1 gene from 70 different accessions of maize inbred lines and landraces (*Zea mays* subsp. *mays*), the progenitor of cultivated maize (teosinte or *Zea mays* ssp. *parviglumis*), and the closely related species *Zea perennis, Zea diploperennis* and *Zea luxurians*.

Figure 12A:
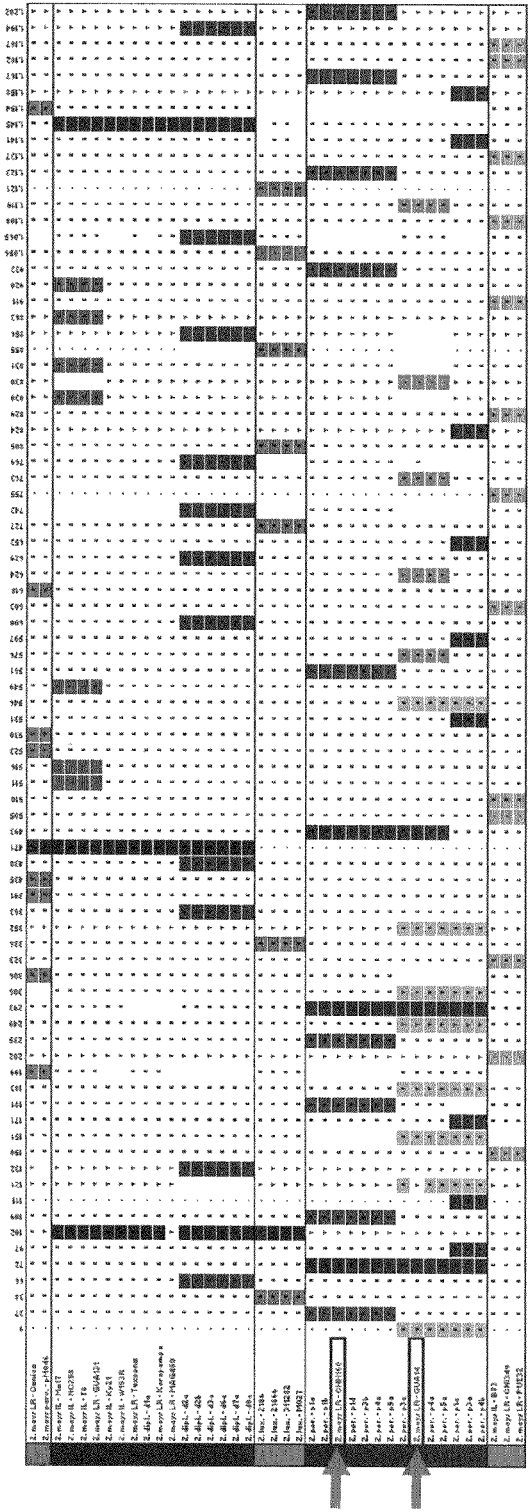
FIG. 12 shows the interspecies SPC map of the globulin 1 locus of maize. Different colors are used to indicate the various SPCs. The representation in FIG. 12A corresponds to the output of the algorithm and shows the genetic variation table onto which the SPCs are depicted. Non-clustering polymorphisms and some SPCs that cannot be placed in the network structure were omitted. The abbreviated species and accession numbers for each genotype are shown in the second column. The table is organized such that individuals that share the same independent SPC are grouped as indicated by the differentially highlighted left most column. The arrows indicate the *Zea mays* accessions that share SPCs with *Zea perennis*.
FIG. 12B shows the SPC network and the *Zea* species. The atypical branching of SPCs 1 and 3 symbolizes that both these SPCs share one polymorphism with SPC-2. The putative source sequence that is devoid of an SPC is referred to as SPC-0.
Figure 12B:
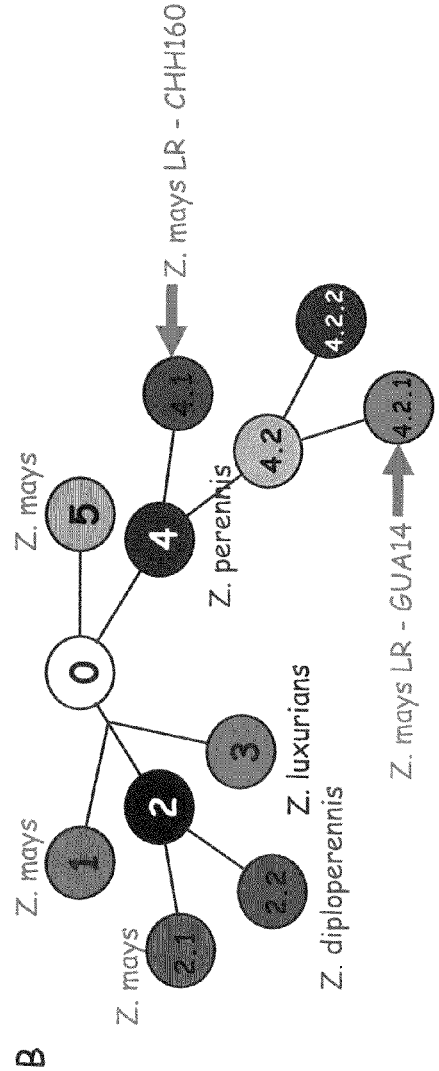

The sequences for this analysis were retrieved from GenBank (http://www.ncbi.nlm.nih.gov) accession numbers AF064212-AF064235, AF377671-AF377694 and AF329790-AF329813. The sequences were aligned to generate a genetic variation table as described in detail in Example 1. The genetic variation table of the glb1 gene comprises 317 polymorphic sites of which 66 were singletons. Because the primary interest of this analysis was to examine the polymorphic sites that were shared between the samples, the singletons were excluded from the analysis. The remaining 251 polymorphisms were clustered with the SPC algorithm using the following thresholds: C=1; C≧0.90, C≧0.85, C≧0.80 and C≧0.75. Inspection of the SPC map of the globulin 1 gene showed that in the majority of the samples the SPCs were uninterrupted throughout the gene. Analysis of the haplotypes revealed that 31 samples exhibited historical recombination and gene conversion events, and consequently these were excluded from the analysis. The clustering analysis was repeated on the samples exhibiting continuous SPC structures using the same thresholds. At the lowest threshold of C≧0.75 a total of 99 polymorphisms were clustered in a total of 14 SPCs with 3 or more polymorphisms per cluster. Of these, 3 were rejected that could not be represented in the network structure (see FIG. 12B). The SPC map of the globulin 1 gene, visually represented in FIG. 12A, shows that 5 primary SPCs can group all 39 sequences: SPC-1 and SPC-5 comprise different *Zea mays* accessions, SPC-2 comprises both *Zea mays* and *Zea diploperennis* accessions, SPC-3 comprises the *Zea luxurians* accessions and SPC-4 comprises the *Zea perennis* accessions, and can be further subdivided through the various dependent SPCs. Close inspection of FIGS. 12A and 12B shows that the SPCs are in general, but not always, specific for the different *Zea* species. In particular in the SPC-4 group two *Zea mays* accessions (landraces CHH160 and GUA14, denoted by the red arrows in FIG. 12A) were found to exhibit identical SPC maps to the *Zea perennis* accessions, respectively SPC-4.1 and SPC-4.2. 1. The fact that the shared SPCs comprise a large number of different polymorphisms, respectively 12 and 15, strongly suggests that these SPCs arose before the split of the species several hundred thousand years ago [Tiffin and Gaut, Genetics 158: 401-412, 2001], and were maintained independently in the two species.

It is anticipated that this type of analysis of SPC structures in sequences from related species will have various practical utilities. First, the identification of SPCs that are shared between species may serve as a useful criterion for identifying SPCs that could be functionally important. The rationale is that SPCs that have been retained in different species may represent alleles that one way or another confers selective advantage and hence may represent alleles with distinct functional properties. As most of the genomes of species of agricultural importance will become sequenced in the near future, it is anticipated that comparative sequencing of genes or even entire genomes of related species will become routine. In this future perspective, the methods of the present invention will provide a most valuable tool for targeting functionally important alleles of genes that are important for agricultural performance. Second, the comparative analysis of SPCs in loci from large numbers of different accessions of closely related species provides a logical framework for a rational approach for exploiting the genetic diversity in related species. It is projected that in the future the broadening of the genetic diversity of commercial germplasm in plant and animal breeding through interspecific crosses will become a major source of genetic innovation and improvement. This is now well documented in for example tomato. The problem however today is that we have no means for selecting appropriate accessions, nor do we have a valid means to evaluate or appreciate the genetic diversity present in accessions. The methods of the present invention provide a means to rationalize the structure of interspecies genetic diversity and to select the most appropriate accessions for interbreeding. For example, based on the SPC structures observed at a number of different loci, one can choose accessions that exhibit high frequencies of novel SPCs at various loci to broaden the basis of genetic variation available for genetic selection. Thus the method of the present invention provides a superior method of monitoring genetic diversity in wild accessions of the species and related species.

In conclusion, this example shows that the interspecific SPC maps of a locus can provide insights into the complex phylogenetic origins of genetic variation. When the same SPC is found in different species, then it is likely that the mutations that make up this SPC arose before the split of the species, whereas SPCs that are unique to one species presumably arose after the speciation event. It is noted that the extremely high variation found in the globulin 1 gene presumably results in a large number of recurrent mutations confounding the precise phylogeny.

EXAMPLE 5

SPC Map of the FRI Locus of *Arabidopsis thialiana*

The present example provides proof of concept that that the methods of the present invention can be used to construct SPC maps of entire genomic segments, covering large numbers of genes. Examples 1 through 3 illustrated that the analysis of gene loci with the methods of the present invention may yield different types of SPC maps depending upon the recombination history of the locus. This example presents an analysis of the polymorphic sites in the genomic region surrounding the FRI locus of *Arabidopsis thaliana* to provide proof of concept that SPC maps can also generated for genomic regions comprising many genes using polymorphism data sampled throughout a genomic region. One approach for assessing allelic diversity in genomic regions that is becoming widely used involves the sequencing of short segments (500 to 1000 bp, the length of a typical sequence run) from different places throughout the genomic region of interest. Several studies of this type have been published recently, and one of these was chosen in the present example.

The genomic sequences analyzed in the present example were generated in the study of a 450-kb genomic region surrounding the flowering time locus FRI [Hagenblad and Nordborg, Genetics. 161: 289-298, 2002] and comprises a set of 14 amplicons sequenced from 20 accessions of *Arabidopsis thaliana*.

The sequences for this analysis were retrieved from GenBank (http://www.ncbi.nlm.nih.gov) accession numbers AY092417-AY092756. The individual sequences were aligned to generate 14 genetic variation tables as described in detail in Example 1, which were subsequently combined into a single continuous genetic variation table. The genetic variation table of the FRI locus comprises 191 polymorphic sites. The SPCs that comprise 3 or more polymorphic sites were computed with the SPC algorithm using the following thresholds: $C=1$ and $C \geq 0.75$. The algorithm clustered respectively 85 and 94 polymorphisms at clustering thresholds of $C=1$ and $C \geq 0.75$.

Figures 13A, 13B:
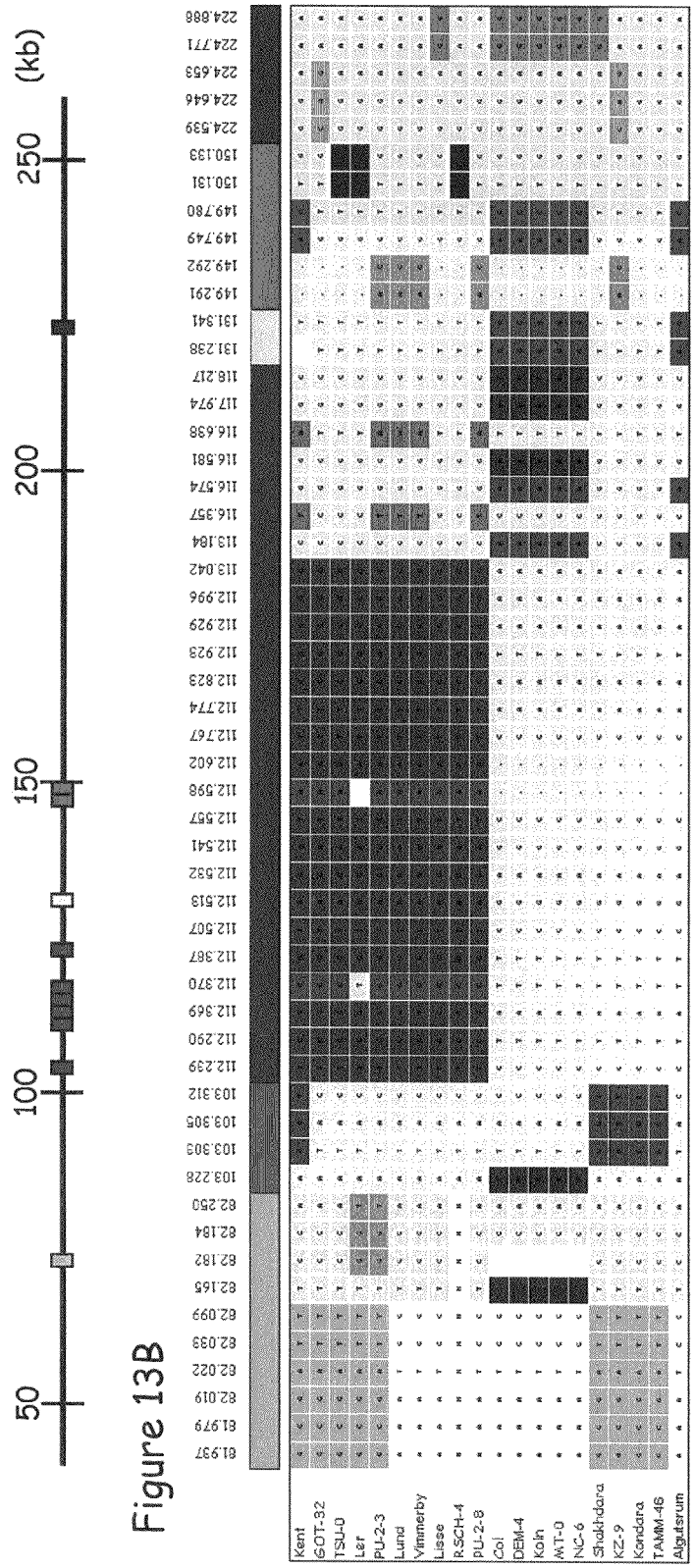
FIG. 13A is a schematic representation of the physical map of the 450 kb FRI locus, in which the differentially highlighted rectangles symbolize the sequenced regions and also indicate the map positions of the polymorphic sites that are listed in the genetic variation table of FIG. 13B.
FIG. 13B corresponds to the output of the algorithm and shows the genetic variation table onto which the SPCs are depicted. The *Arabidopsis* lines for each genotype are shown in the left most column. The table is organized such that individuals that share the same SPCs are grouped as much as possible.

FIG. 13A shows a physical map of the 450-kb region surrounding the flowering time locus FRI, and FIG. 13B shows the SPC map of the region obtained using the $C \geq 0.75$ threshold. For the sake of clarity, SPCs of singletons (40 out of 94 clustered polymorphisms) are not displayed. It can be seen that several SPCs extend over a part of the region, while others are confined to short segments. This example illustrates that in larger genomic regions where the frequency of recombination is low, some of the SPCs can extend over long distances. This is one of the principal distinctions between the method of the present invention and the haplotype block method. The haplotype block method will divide genomic regions into blocks according to observed recombination events, using a certain threshold. The method of the present invention will detect recombination events in the SPCs that are affected, but these will not affect the other SPCs. The results presented in the present example demonstrate that the SPC method is superior in capturing the structure in the genetic variation.

EXAMPLE 6

SPC Maps of Surveys of Genetic Diversity in *Arabidopsis thaliana*

The present example provides proof of concept that that the methods of the present invention can be used to construct SPC maps of entire genomes from genome-wide genetic diversity data, and that from the SPC map ctSNP markers can be derived for genome-wide association studies. Several approaches for surveying genetic diversity on a genome-wide scale are currently being pioneered, involving sequencing short fragments of 500 to 1000 bp amplified from genomic DNA from a collection of individuals representative for the species. In one approach the amplicons are chosen at regular intervals (20 or 50 kb) along the genome, while other approaches rely on the systematic sequencing of regions of known genes. This example presents an analysis of the polymorphic sites identified in a set of amplified fragments from chromosome 1 of *Arabidopsis thaliana*.

The genomic sequences analyzed in the present example were generated in the NSF 2010 Project "A genomic survey of polymorphism and linkage disequilibrium in *Arabidopsis thaliana*" [Bergelson J., Kreitman M., and Nordborg M., http://walnut.usc.edu/2010/2010.html] and comprises 255 amplicons from chromosome 1 sequenced from 98 accessions of *Arabidopsis thaliana*.

The sequences for this analysis were downloaded from the website http://walnut.usc.edu/2010/2010.html. The individual sequences were aligned to generate one genetic variation table per amplicon as described in detail in Example 1. Singletons and polymorphic sites with more than 33% missing data were excluded from the analysis. The individual tables were concatenated into a single genetic variation table in the same order in which the amplicons occur on the chromosome. The resulting genetic variation table of chromosome 1 contains 3378 polymorphic sites. The genetic variation table was analyzed with the SPC algorithm using a sliding window of 120 polymorphic sites and an overlap of 20 SNPs between each consecutive block. The following parameter settings were used in this analysis. First, since the genetic variation table contains a substantial number of missing data points (6.5%) the allele and two-site haplotype frequencies were calculated by the ratio of the observed number of alleles/haplotypes over the total number of samples minus the number of missing data points. Second, all SPCs of three or more polymorphisms were identified using the following thresholds for C: C=1, C≧0.90 and C≧0.80.

Figure 14:
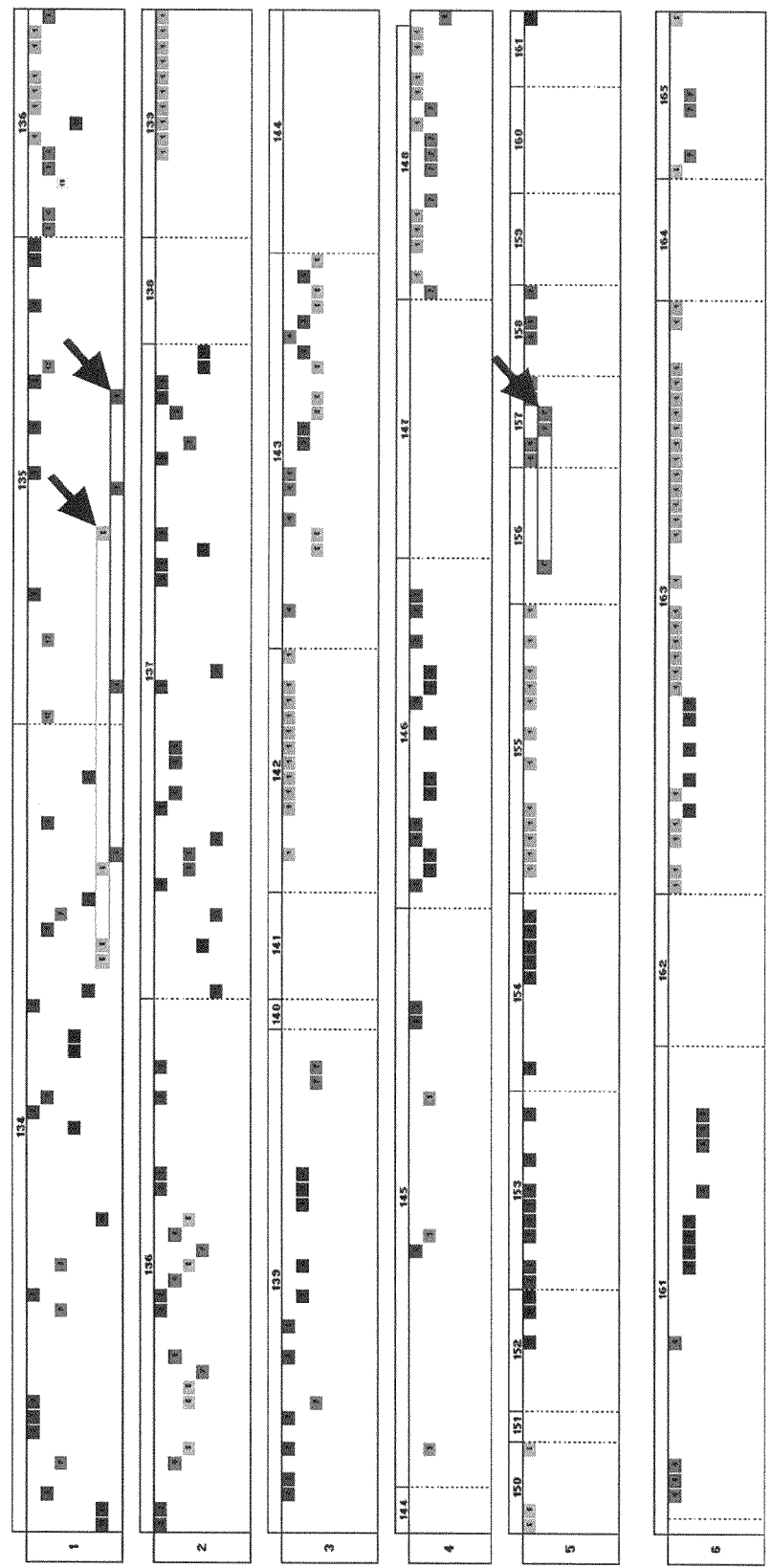
FIG. 14 shows the SPC maps of 31 amplicons from a 3.76 Mb segment of chromosome 1 of *Arabidopsis thaliana*. Different colors are used to indicate the various SPCs. The figure is composed of 6 panels, numbered 1 through 6, which represent 100 polymorphic sites each. The rectangles at the top of each panel represent the amplicons from which the polymorphic sites were analyzed. The amplicons are numbered from 134 through 165, corresponding respectively to positions 16,157,725 and 19,926,385 on chromosome 1. Note that the missing amplicon 149 has no polymorphic sites. The dotted lines that divide the panels mark the boundaries of the blocks of polymorphisms that belong to each amplicon. Each SPC is represented on a different row and marked by a different color. SPCs that span adjacent amplicons are outlined and marked by black arrows. The empty blocks represent the amplicons that have no SPCs. Note that amplicons may be represented in consecutive panels, and that corresponding SPCs may be represented on different rows and marked by a different color.

Analysis of the global results for chromosome 1 revealed that ~60% of the amplicons yielded one or more SPCs containing at least 3 polymorphisms at the threshold of C≧0.90. FIG. 14 shows the SPCs identified in 31 amplicons (from amplicon #134 to amplicon #165) from a 3.76 Mb segment of chromosome 1 (from position 16,157,725 to position 19,926,877). It can be seen that the amplicons that do not yield SPCs (10 of the amplicons of FIG. 14) generally have relatively few polymorphic sites, although occasionally amplicons are observed that have numerous polymorphisms that fail to cluster (e.g. amplicons 144 and 147). The amplicons yielding SPCs were broadly classified into 2 classes, each occurring with similar frequency. The class I amplicons reveal only one SPC (e.g. amplicons 142, 150, 152, 153, 154, 155 and 158). The class II amplicons reveal two or more overlapping SPCs (e.g. amplicons 136, 137, 139, 143, 145, 146, 148 and 163). The class I amplicons correspond to dimorphic loci, i.e. loci that have only two haplotypes (SPC-n and SPC-0), while the class II amplicons correspond to polymorphic loci, i.e. loci that have three or more haplotypes. While the polymorphic loci obviously reflect a greater genetic diversity, it can be seen from FIG. 14 that the number of SPCs observed in the class II amplicons is fairly small, mostly two or three and occasionally more. Finally it can be seen from FIG. 14 that nearly all the SPCs found are confined to a single amplicon, with three exceptions denoted by the black arrows. In each case it is a single polymorphic site in an adjacent amplicon that is included in the cluster. Since the average distance between the amplicons is in the order of 100 kilobases, the observation that the SPC structures are amplicon-specific indicates that the long range LD in *Arabidopsis* is less then 100 kilobases. It is therefore anticipated that a much higher density of sequences must be surveyed to construct an SPC map of this organism.

In conclusion, this example demonstrates that the SPC method is well suited to assess the genetic diversity at both the level of an entire genome. Moreover, the discovered SPC structures provide a logical framework for the development of useful sets of DNA markers for genetic analysis of a species. For each SPC only one representative ctSNP is chosen. This marker set will be universally applicable in the species.

This present method of analyzing genetic diversity has useful applications in plant and animal breeding, in that it provides both a means to develop useful genetic markers, as well as allowing breeders to select appropriate lines for introducing new genetic diversity in breeding programmes. Based on the SPCs found, one can develop SPC tags which can be used for both identifying genes involved in agronomical traits and for marker assisted breeding. The SPC maps are useful for identifying lines that carry novel SPCs that are not present in the breeding germplasm and that can provide novel genetic diversity.

EXAMPLE 7

SPC Map of the Human CYP4A11 Gene

The present example provides proof of concept that the methods of the present invention can be used on unphased diploid genotype data both to construct an SPC map of a gene and to select tag SNPs for genetic analysis. The present example will also provide proof of concept that the methods of the present invention can be used to infer haplotypes from the unphased diploid genotypes. This example presents an analysis of the polymorphic sites in the human CYP4A11 (cytochrome P450, family 4, subfamily A, polypeptide 11) gene to exemplify the different aspects of the invention. The genetic variation data analyzed in the present example was generated by the UW-FHCRC Variation Discovery Resource [SeattleSNPs; http://pga.gs.washington.edu/]. The UW-FHCRC Variation Discovery Resource (SeattleSNPs) is a collaboration between the University of Washington and the Fred Hutchinson Cancer Research Center and is one of the Programs for Genomic Applications (PGAs) funded by the National Heart, Lung, and Blood Institute (NHLBI). The goal of SeattleSNPs is to discover and model the associations between single nucleotide sequence differences in the genes and pathways that underlie inflammatory responses in humans.

The unphased diploid genotypes and the SNP allele data tables for this analysis were downloaded from the SeattleSNPs website (http://pga.gs.washington.edu/). The genetic variation data for the CYP4A11 gene comprise 103 polymorphic sites (SNPs and indels) that were identified by resequencing a segment of 13 kb in 24 African American and 23 European individuals. The diploid genotype data table lists the allele scores of the 103 polymorphic sites of the CYP4A11 gene in the 47 samples. The diploid genotype data table was first reformatted to the standard format for genetic variation tables as described in Example 1 using the following procedure. Homozygous diploid SNP genotypes were denoted by the symbols "A", "C", "G" or "T", while homozygous indel genotypes were denoted by a dot for the deletion allele or, alternatively, the first base of the insertion. The heterozygous diploid genotypes (polymorphic sites at which both alleles were scored) were denoted by the symbol "H". Thereafter a table of artificial haplotypes, termed metatypes, was derived from the genetic variation table using the following procedure. The table was first duplicated by adding a second copy of the sample rows. Thereafter the symbols "H" were replaced in each of the two copies respectively by the minor allele in the first copy and by the major allele in the second copy. The duplicated and reformatted genetic variation table is referred to as the metatype table. The diploid genotypes in which the symbols "H" were replaced by the minor allele are referred to as minor metatypes and the diploid genotypes in which the symbols "H" were replaced by the major allele are referred to as major metatypes. The sample names in the metatype table are denoted with the extension "−1" for the minor metatypes, and with the extension "−2" for the major metypes. It is noted that two essential features of the polymorphic sites are perfectly retained in the metatype format, namely the frequencies of the alleles and their co-occurrence or linkage. Indeed, each diploid genotype is disassembled in two metatypes, and each heterozygous genotype is correctly split into one minor and one major allele in the two metatypes. The linkages between the co-occurring polymorphic sites are retained by the simultaneous replacement of all heterozygous genotypes on a single diploid genotype by either the minor or the major alleles in respectively the minor and major metatypes.

The metatype table was analyzed with the SPC algorithm using the following parameter settings. First, since the metatype table contains a substantial number of missing data points, "N", (3.8%) the allele and two-site haplotype frequencies were calculated by the ratio of the observed number of alleles/haplotypes over the total number of samples minus the number of missing data points. Second, all SPCs of two or more polymorphisms were identified using the following thresholds for C: C=1, C$\geq$0.95 C$\geq$0.90, C$\geq$0.85 and C$\geq$0.80.

The SPC algorithm clustered the majority of the 103 polymorphic sites at the different thresholds: 69 (67%), 81 (79%) and 84 (82%) polymorphic sites at respectively C=1, C$\geq$0.90 and C$\geq$0.80. The polymorphisms were for most part clustered in similar SPCs at the different thresholds, with two exceptions. The polymorphisms of SPC-2 were clustered in two different SPCs at the threshold of C=1, which became merged into SPC-2 at the threshold of C$\geq$0.90. SPC-14 was found only at the threshold of C$\geq$0.80. In the section below the SPC map of the 81 polymorphic sites clustered at the threshold of C$\geq$0.90 is analyzed in detail, thus excluding SPC-14.

Figure 15A:
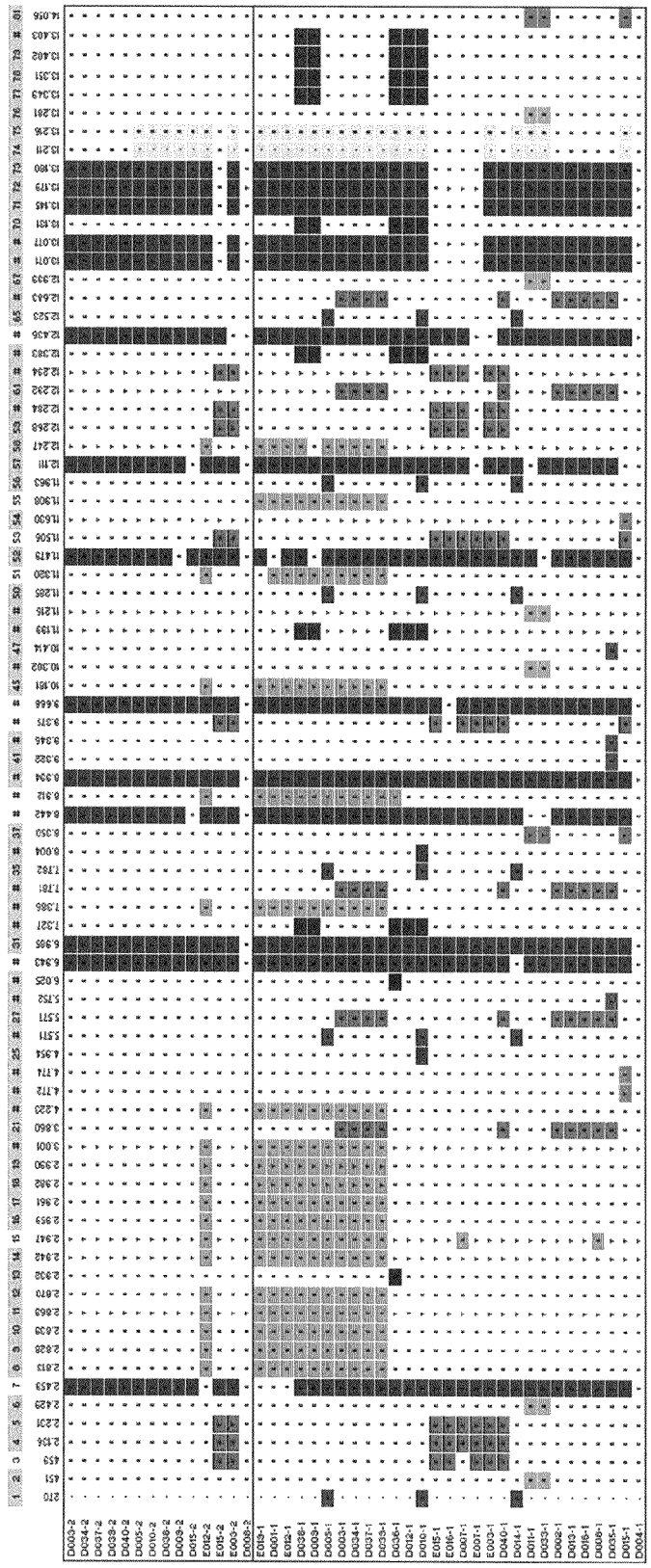
FIG. 15A corresponds to the output of the algorithm and shows the metatype table onto which the SPCs are depicted. The sample names for each metatype are shown in the left most column, and are denoted with the extension "−1" for the minor metatype and the extension "−2" for the major metatype. The position of each polymorphic site in the sequence of the CYP4A11 gene is indicated above the columns. Polymorphic sites that do not cluster are omitted. The table is organized such that metatypes that share the same SPCs are grouped. The upper panel shows the major metatypes and the lower panel the minor metatypes. Metatypes that have no SPCs are omitted except for one in each panel. In the upper row the polymorphic sites are numbered consecutively and the sites that were clustered at the threshold of C=1 are highlighted.

In FIG. 15A the 13 different SPCs clustered at the threshold of C$\geq$0.90, comprising 81 polymorphisms, are visualized onto the metatypes. In the upper half of FIG. 15A the SPCs found in the major metatypes (sample name followed by "-2") are shown, while the lower half of FIG. 15A shows the SPCs observed in the minor metatypes (sample name followed by "-1"). The 69 polymorphisms that were clustered at the threshold of C=1 are highlighted in the upper row of FIG. 15A. Only those metatypes that do contain one or more SPCs (comprising minor alleles) are listed. The metatypes that are devoid of an SPC (SPC-0) are omitted, except for one representative in each table half. The minor and major metatypes were sorted according to the SPCs present. A striking feature of FIG. 15A is that SPC-2 is present in all metatypes that are not SPC-0, either alone or in combination with other SPCs. This observation suggests that many (if not all) SPCs are dependent on SPC-2.

The relationships between the SPCs were inferred in a two step process: first, the SPC combinations observed in the major metatypes were examined; second, the SPCs observed in the minor metatypes were systematically compared to the SPCs observed in the corresponding major metatypes. This comparison between the major and minor metatypes is illustrated in FIG. 15B. Examination of the SPCs found in the major metatypes (upper panel of FIG. 15A) reveals that (1) SPC-13 is invariably found in combination with SPC-2, but not vice versa, while (2) SPC-1 and SPC-4 each appear on a fraction of the metatypes that contain both SPC-2 and SPC-13. It follows from these observations that SPC-1 and SPC-4 depend on SPC-13, which in turn depends on SPC-2.

For the comparison between the major and minor metatypes shown in FIG. 15B, the subgroup of representative metatypes was arranged into three separate classes. Class I, shown in the upper panel of FIG. 15B, represents those metatypes that exhibit identical SPCs in both the minor and the major metatype. Class II, shown in the middle panel of FIG. 15B, represents those metatypes that exhibit different SPCs in the minor and the major metatype. Class III, shown in the lower panel of FIG. 15B, represents those minor metatypes for which the major metatype exhibits SPC-0. The class I metatypes reveal two SPC combinations: 1-2-13 and 2-4-13, consistent with the dependency of SPC-1, SPC-4 and SPC-13 on SPC-2. Analysis of the class II metatypes reveals that the minor metatypes which exhibit pairwise combinations of the SPCs 1, 3, 4, 5 and 7 all have a major metatype that exhibits SPC-2 (and often also SPC-13). This pattern is consistent with a relationship in which each of these SPCs is independent from one another and dependent on SPC-2 (either with or without SPC-13 as an intermediate). For example, the minor metatype D009-1 has the SPCs 1, 2, 3 and 13 and its major metatype has the SPC-2/SPC-13 couple, showing that both SPC-1 and SPC-3 are dependent on SPC-13, and the higher ranked SPC-2. The same logic applies to D005, leading to the conclusion that SPC-1, SPC-3 and SPC-5 are all mutually independent and that each depends on, sequentially, SPC-13 and SPC-2. Inspection of the sample D039 and D040, in which case the major metatypes only contain SPC-2, point to a first-degree dependence of SPC-4 and SPC-7 on SPC-2. According to the foregoing reasoning SPC-4 is observed both in direct dependency on SPC-2 as well as through the intermediate SPC-13; this apparent conflict in the relationship can be attributed to a historic recombination event. D007 and E016 are the recombinant samples that cause the dual observation (see FIG. 15A). Further analysis along the same line suggests that the SPC-9 and SPC-12 are also dependent on SPC-13, but it cannot be firmly concluded from the single observation in sample D015 whether SPC-9 and SCP-12 are in an independent or a dependent relationship with respect to each other. Finally, SPC-11 is observed once in a minor metatype that has also SPC-3 and SPC-5 (sample D010), indicating that SPC-11 must be dependent on one of them. Apart from the supplementary inference that SPC-12 cannot depend on SPC-9, the analysis of the class III metatypes only serves to confirm the above dependencies. In general class III metatypes do not provide additional information because the major metatypes are not informative. Hence, the dependencies of SPCs 6, 8 and 10, which are observed in one sample only, cannot be established. For example, the minor metatype D036-1 has the SPCs 2, 3, 10 and 13 and its major metatype has SPC-0. Apart from knowing the dependency rank of SPC-2, SPC-3 and SPC-13, one cannot unambiguously assign SPC-10: SPC-10 could be dependent on SPC-3 but could also be dependent on SPC-0. In conclusion, the analysis of the metatypes shows that of the 13 SPCs identified in the CYP4A11 gene, the dependencies of 9 of them could be established through logic inference from the SPC patterns observed in the metatypes. FIG. 15C shows a visual representation of the network of hierarchical relationships established between the 9 SPCs in the CYP4A11 gene.

In conclusion the above analysis demonstrates that the methods of the present invention can be used to cluster the polymorphic sites into SPCs starting from unphased diploid genotypes. The SPCs patterns observed in the minor and major metatypes, allows the deduction of the hierarchical relationships between most of the SPCs found. The analysis demonstrates that the inferred relationships between SPC-1, SPC-2, SPC-3, SPC-4, SPC-5, SPC-7, SPC-12 and SPC-13 are firmly established since they are based on multiple and complementary observations, but that certain relationships remain speculative because of insufficient observations (e.g.

SPC-9). In the present study, we have assumed that SPC-9 is directly dependent from SPC-13 and we included SPC-9 in the further analysis. Together these 9 SPCs account for 67 of the 81 clustered polymorphic sites. It should be noted that the SPCs whose relationship cannot be firmly established all have a low occurrence frequency: SPC-6 (occurs twice and consists of 6 SNPs), SPC-8 (singleton, 4 SNPs), SPC-10 (singleton, two polymorphisms), SPC-11 (singleton, 2 SNPs), and SPC-9 (singleton, 3 SNPs). It is anticipated that the analysis of additional samples would enable the establishment of the relationships of these SPCs. Indeed, the skilled person will realize that the outcome of the above analysis is determined primarily by the number of informative observations, and that the remaining ambiguity is not related to inherent limitation of the method.

Figure 15D:
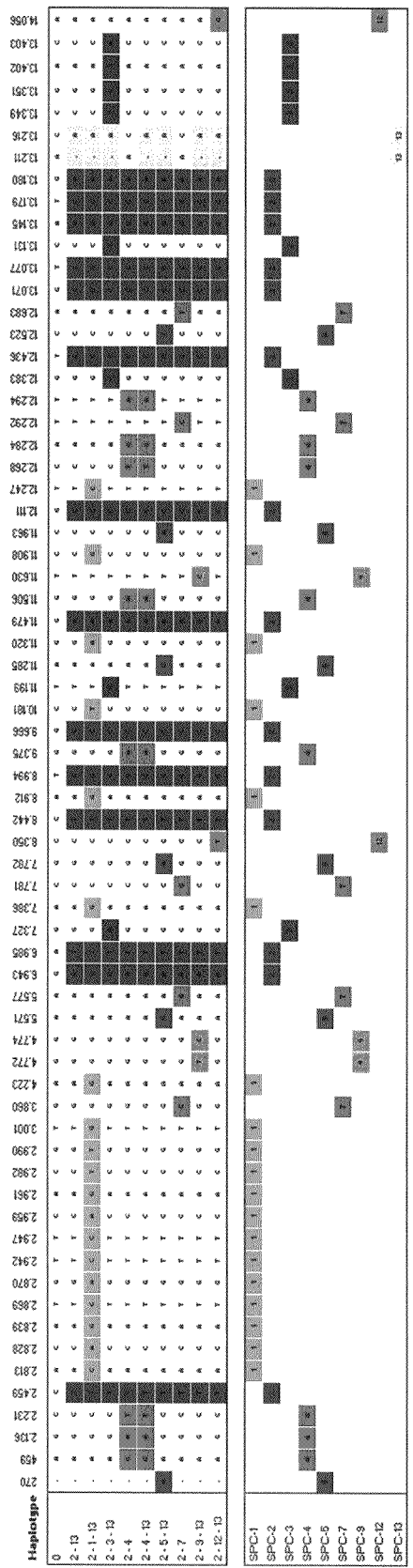
FIG. 15D shows the SPC map of the CYP4A11 gene. The upper panel shows the inferred SPC-haplotypes onto which the SPCs are depicted. The lower panel represents the SPCs such that each SPC is represented on a different row and marked by a different color.

Based on the established relationships between the 9 SPCs, the SPCs can now be mapped unambiguously. The SPC map presented in FIG. 15D shows in the upper panel the inferred haplotypes onto which the different SPC combinations observed in the metatypes are visualized, and the lower panel shows the 67 polymorphic sites that are clustered in each of the 9 SPCs. The 9 SPCs are organized in a total of only 10 inferred haplotypes designated by the SPC combinations present: 2-13, 2-1-13; 2-3-13; 2-4; 2-4-13; 2-5-13; 2-7; 2-9-13; 2-12-13 and 0 (the haplotype that has no SPC). It is noted that while all 10 inferred haplotypes were found in African American individuals only three of them were observed in European individuals (2-1-13; 2-4 and 2-4-13). This is in good agreement with earlier findings that Europeans carry only a subset of the haplotypes found in Africans.

The inferred haplotypes can now be used to deconvolute the diploid genotypes, as shown in the last two columns of FIG. 15B. The rationale for the deconvolution is that the minor metatypes represent combinations of two of the inferred haplotypes, and that the major metatypes represent those SPCs that are common between the two inferred haplotypes. The grouping of the metatypes into three classes (see FIG. 15B) is also useful for the deconvolution. The class I metatypes have identical SPC combinations in both minor and major metatype, and these SPC combinations are also found among the inferred haplotypes. Consequently the class I metatypes are simply deconvoluted into two identical haplotypes. For example, sample E012 which has the SPC combination 1-2-13 is deconvoluted into two 1-2-13 haplotypes. The class II metatypes display different SPC combinations in the minor and major metatypes. Each minor metatype must represent a combination of two inferred haplotypes other than "0", and which share the SPCs represented in the major metatype. For example, sample D009 which has in the minor metatype the SPC combination 1-2-3-13 and 2-13 in the major metatype is deconvoluted into the two haplotypes 1-2-13 and 2-3-13. The class III metatypes display SPC combinations in the minor metatypes and no SPCs in the major metatypes. Each minor metatype must thus represent a combination of two inferred haplotypes which share no SPCs. Since all the SPCs are dependent on SPC-2, one of the haplotypes must be "0". For example, sample E019 which has in the minor metatype the SPC combination 1-2-13 is deconvoluted into the two haplotypes 1-2-13 and 0.

In conclusion the above analysis demonstrates that the methods of the present invention can be used for correct inference of haplotypes from unphased diploid genotype data.

Finally it is demonstrated that the unphased diploid data that were used to compute the SPCs can also be used to select ctSNPs for genetic analysis, without the need for prior haplotype inference. The present invention provides a means to select those polymorphic sites that most closely match the SPC and are thus most suited to serve as ctSNPs. The method is based on a calculation of the average linkage value (AVL) of each polymorphism with all other polymorphisms of the SPC. As explained herein above, this calculation not only considers aberrant data (i.e. the minor alleles are not present in all samples carrying the SPC or are found in other samples) but also take missing genotypes into account to evaluate the suitability of SNPs. In the present example, the selection of ctSNPs is illustrated in FIGS. 15E, F and G for three SPCs, respectively SPC-1, SPC-2 and SPC-4. These Figures show the matrices of pairwise linkage values together with the metatypes of the polymorphic sites for each SPC. FIG. 15E shows the selection of ctSNPs for SPC-1. The two equivalent ctSNPs of choice, characterized by the largest ALV values, are SNP-33 and SNP-45. Both SNPs best represent the SPC because the minor alleles are found in all samples carrying the SPC and do not occur in other samples while, additionally, there are no missing data points. The next best tags also perfectly match with the SPC, but do have missing data in the remainder of the samples. FIG. 15F shows the selection of ctSNPs for SPC-2. Here again, the two SNPs that have the largest ALV values, SNP-31 and SNP-40 both perfectly match with the SPC without missing data points. All other SNPs have either missing data points or exhibit aberrant scores. FIG. 15G shows the selection of tag SNPs for SPC 4. Finally, it is noted that when there are no-aberrant or missing data points for the clustered polymorphic sites, i.e. when all polymorphic sites are clustered at the threshold of C=1, all sites are equivalent, and consequently each of them can serve as ctSNP.

EXAMPLE 8

SPC Map of a Class II Region of the Human MHC Locus

The present example provides further proof of concept that the methods of the present invention can be used on unphased diploid genotype data to construct SPC maps of complex genomic loci and to select ctSNPs for developing diagnostic markers for genetic analysis. The present example also provides proof of concept that the methods of the present invention can be used to analyze loci in the human genome exhibiting complex patterns of recombination. This example presents an analysis of polymorphic sites in the human major histocompatibility complex (MHC) locus. The MHC locus is known to exhibit complex patterns of genetic variation and is currently the focus of intensive genetic research because of its importance in many human diseases. The MHC locus is also one of the few loci in the human genome in which the existence of recombinational hotspots is well documented, and the present example comprises a 216-kb segment of the class II region of the MHC in which different recombinational hotspots have been mapped with great precision [Jeffreys et al., Nat. Genet. 29: 217-222, 2001].

The diploid genotypes and the SNP allele data for the "SNP genotypes from upstream of the HLA-DNA gene to the TAP2 gene in the Class II region of the MHC" [Jeffreys et al, Nat. Genet. 29: 217-222, 2001] were copied from the website http://www.le.ac.uk/genetics/ajj/HLA/Genotype.html. The data comprise 296 SNPs typed in a panel of 50 unrelated UK Caucasian semen donors using allele-specific oligonucleotide hybridisation of genomic PCR products. The diploid genotype table lists the allele scores of the 296 polymorphic sites of the class II region of the MHC in the 50 samples. This table was reformatted into a metatype table exactly as described in Example 7 with the following minor modifications: single base insertion/deletion genotypes (denoted as ±),were replaced by the symbol "A" or a dot, respectively, while the missing genotypes (denoted by "?" or ".") were converted into the symbol "N".

The metatype table was analyzed with the SPC algorithm using the same parameter settings as in Example 7, with the following thresholds for C: C=1, C≧0.95, C≧0.90, C≧0.85 and C≧0.80. At the C≧0.80 threshold, the SPC algorithm clustered 198 of the 296 polymorphisms into 40 different SPCs. The pattern of SPCs is shown in FIG. 16B and 16C. Note that, in order to reduce the size of the Figure, the analysis was performed on two separate sets of SNPs, more specifically the subgroup of SNPs with high frequency minor alleles (observed more than 8 times or >16%; FIG. 16B) and the SNPs characterized by low frequency minor alleles (≦16%; FIG. 16C). The SNPs in each subgroup cluster into 20 SPCs. FIG. 16B/C clearly shows that nearly all of the SPCs are confined to 7 different domains within the 216-kb segment; these domains are represented by the differently highlighted rectangles that refer to the physical map shown in FIG. 16A. Overall, each domain comprises a different set of SPCs and there are (almost) no SPCs that extend into adjacent domains. This is consistent with the presence of recombination hotspots between the domains that have disrupted the SPCs. Indeed, the domain boundaries predicted by the SPC map correspond very well with the positions of the recombination hotspots which were identified by Jeffreys and co-workers, and which are indicated by the red arrows in FIG. 16A. Further inspection of FIG. 16B/C shows that there are a few exceptional SPCs that are spanning multiple domains, most notably SPC-2 and SPC-7 that are indicated by heavy arrows in FIG. 16C. SPC-2 is found in domains 1, 3 and 6 and comprises singleton SNPs observed in one sample. The other SPC, SPC-7, occurs in domains 4 and 7 and is observed in eight individuals. These results illustrate an important difference between the SPC and the haplotype block concepts: irrespective of the incidence of recombination, the integrity of certain SPC is unaffected (i.e. the association of certain polymorphisms, belonging to different blocks, remains intact) resulting ultimately in the selection of a smaller set of tag SNPs. The present example provides a clear illustration that the SPC patterns in regions that have long history of recombination can readily be obtained from unphased diploid genotype data.

Once the domain structure of a genomic region under investigation is established, it is then possible to determine the hierarchical relationships between the SPCs in each domain. Once the SPC structure of a genomic region under investigation is established, it is then possible to determine the hierarchical relationships between the SPCs. This is illustrated for the SNPs of domain 4 in FIG. 16A. This domain comprises 67 SNPs between positions 35.095 and 89.298. In this analysis the subset of 57 SNPs with a minor allele frequency of 5% or more were selected. The metatype table for the 57 SNPs was reanalyzed with the SPC algorithm using the same parameter settings as above. In total 52 of the 57 SNPs were clustered in 9 SPCs. The relationships between the SPCs are shown in the network structure of FIG. 16E; they were inferred by comparing the SPCs found in the minor metatypes and their corresponding major metatypes as outlined in detail in Example 7. The analysis revealed that the SPCs are organized in 8 SPC-haplotypes (including the haplotype that is devoid of SPCs) as shown in the SPC map in FIG. 16D. In essence all of the metatypes were consistent with the deduced SPC-haplotypes or occasional recombinants between these. Tag SNPs (ctSNPs) that best represent the various clusters can obviously be selected in the absence of an SPC map and accompanying network structure. However, in cases where the network is multi-layered and shows many levels of dependency, as in the present example, it provides a rational basis to further reduce the number of tag SNPs. For instance, it is possible to restrict an analysis to tag SNPs that are specific for SPCs that are high up in the hierarchy (i.e. that are clade-specific).

It should be noted that in comparison with the SPC map of the CYP4A11 locus described in Example 7, the SPC map of the MHC locus is much more complex. This is consistent with the much higher genetic variability of the MHC locus. It can be anticipated that the SPC-haplotypes described in the present example represent only a fraction of those that may be uncovered in the human population. Indeed the data analyzed here were from a limited population sample of North Europeans. Hence the SPC mapping strategy provides a useful method to analyze the organizational patterns of SNPs and to design reliable tag SNPs for genetic resting.

EXAMPLE 9

SPC Map of HapMap SNPs of Human Chromosome 22

The present example provides further proof of concept that the methods of the present invention can be used on unphased diploid genotype data to construct SPC maps of the human genome and that the SPC maps are particularly useful for selecting ctSNPs as diagnostic markers for genome-wide genetic association studies. This example presents an analysis of the genetic variation data recently generated in the International human HapMap project (The International HapMap Consortium, Nature 426: 789-796, 2003) to exemplify the different aspects of the invention. The aim of the International HapMap Project is to determine the common patterns of DNA sequence variation in the human genome, by characterizing sequence variants, their frequencies, and correlations between them, in DNA samples from populations with ancestry from parts of Africa, Asia and Europe. The project will provide tools that will allow the indirect association approach to be applied readily to any functional candidate gene in the genome, to any region suggested by family-based linkage analysis, or ultimately to the whole genome for scans for disease risk factors.

The unphased diploid genotypes and the SNP allele data of public data release #3 for chromosome 22 was downloaded from the HapMap website http://www.hapmap.org/ (The International HapMap Consortium, Nature 426: 789-796, 2003). Chromosome 22 was chosen for this analysis because of the relatively high density of SNPs genotyped on this chromosome, averaging 1 SNP per ~5 kb. The unphased diploid genotypes list the SNP allele scores of the 5865 polymorphic sites of chromosome 22, genotyped in 30 father-mother-child CEPH trios and 5 duplicate samples (95 individuals in total). The chromosomal positions of each SNP are given in basepairs on reference sequence "ncbi_b34". A genetic variation table was derived from the unphased diploid genotypes by converting the homozygous genotypes denoted by two identical symbols (e.g. "AA") into single letter symbols (e.g. "A") and the heterozygous genotypes denoted by two different symbols (e.g. "AG") into the symbol "H". Missing genotypes are represented by the symbol "N". The genetic variation table of chromosome 22 was divided into consecutive blocks of 120 SNPs with an overlap of 20 SNPs between each consecutive block. Finally, a reformatting into consecutive tables of metatypes was performed as described in Example 7.

The metatype table was analyzed with the SPC algorithm with the same parameter settings as in Example 7. The present Example is directed at the analysis of a segment of 2.27 Mb comprising 700 SNPs, corresponding to an average of 1 SNP per 3.24 kb. The SPC algorithm clustered a substantial fraction of the SNPs at the different thresholds: respectively 48%, 66% and 74% at the thresholds of C=1, C≧0.90 and C≧0.80. As can be seen from the SPC map obtained at a clustering threshold of C≧0.90 shown in FIG. 17B, roughly half of the SNPs were clustered in domains exhibiting extensive and interspersed SPC patterns, while the other half of the SNPs yielded mostly short isolated SPCs comprising a few SNPs. In total 11 domains comprising 10 or more clustered SNPs were identified; the domains are drawn to scale on the physical map shown in FIG. 17A. These 11 domains represent 785 kb or ~35% of the 2.27 Mb segment. While most domains are between 25 kb and 50 kb, the 4 largest domains span 100 to 200 kb and comprise 45 to 65 SNPs. It is noted that the SPCs are separated by stretches of SNPs that do not cluster, not even at low thresholds.

These results from a small sample of the HapMap data demonstrate that the methods of the present invention are capable of capturing the SPC structure in the unphased diploid HapMap genotype data, and provide a robust approach for the identification of domains of extensive haplotype structure. It can be anticipated that a much more extensive SPC structure will be uncovered as the density of the SNPs genotyped in the project increases. At the same time, one can also expect that in certain regions of the genome the SPC structure will remain highly fragmented as a result of extensive recombination. These may correspond to the regions in which little or no SPC structure is observed in the present release. Based on the SPCs found in the HapMap data, the methods of the present invention may furthermore be used for the selection of tag SNPs (ctSNPs). Such ctSNPs can be selected both in the less structured regions and in the domains of extensive SPC structure. When genotypes for additional SNPs become available in the future, this list can simply be updated by adding tag SNPs for the novel SPCs that will be uncovered. It should be stressed that the tag SNPs that are identified on the basis of the current analysis will, in general, remain valid in the future.

Figure 17E:
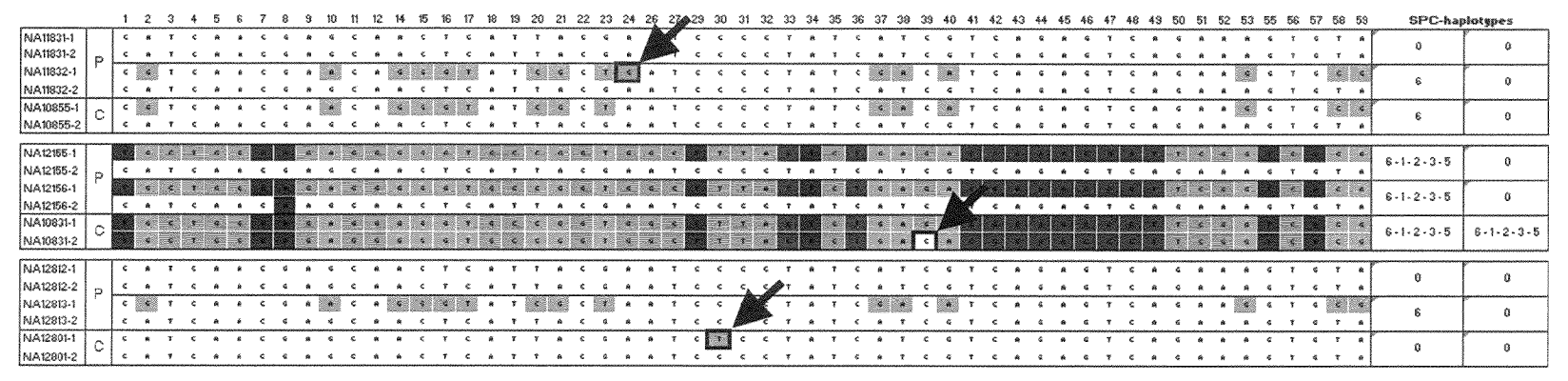

Domain 9 of FIG. 17B was analyzed in detail to exemplify one of the aspects of the present invention, more specifically the ability to identify potentially erroneous genotype data that one may want to verify experimentally. Domain 9 comprises 59 SNPs of which 58 are clustered in 6 SPCs at a threshold of C≧0.90. The relationships between 5 of the 6 SPCs, shown in the network structure of FIG. 17D, were inferred by comparing the SPCs found in the minor metatypes and their corresponding major metatypes as outlined in detail in Example 7. The sixth SPC comprises 3 singleton SNPs observed in one sample that was excluded from the analysis. The deconvolution analysis revealed that the SPCs are organized in 6 SPC-haplotypes (including the haplotype that is devoid of SPCs) as shown in the SPC map in FIG. 17C. Apart from the aberrant sample, all 89 metatypes were consistent with the 6 SPC-haplotypes or occasional recombinants between these. The SNP genotypes that were inconsistent with the SPC map were examined in detail. An inconsistency consists of either the absence of a SNP minor allele in metatypes that contain the SPC to which the SNP belongs, or, alternatively, the presence of a minor allele in a metatype that does not carry the SPC. In total 15 of the 5220 SNP genotypes (58 SNPs×30 trios) were observed that were inconsistent with the SPC structure (<0.3%). Of these, 6 genotypes could be classified as genotyping errors because of discrepancies between the genotype of the parents and that of the child. This is illustrated in FIG. 17E which represents the metatypes of 3 trios (parents and child) with their corresponding SPC-haplotypes. In the first trio (upper panel of FIG. 17E) the minor allele of SNP-24 (belonging to SPC-1) is genotyped in one of the parents, but not in the child. In the second trio (middle panel of FIG. 17E) the minor allele of SNP-39 (belonging to SPC-1) was not genotyped in the child, which inherited one copy of SPC-1 from each parent. In the third trio (lower panel of FIG. 17E) the minor allele of SNP-30 (belonging to SPC-1) was genotyped in the child, while SPC-1 is not present in either parent. In the last two cases the genotyping error is evident, while it is likely in the first case. This finding highlights another aspect of the present invention, namely the identification of potentially incorrect genotypes based on inconsistencies with the SPC structure.

EXAMPLE 10

SPC Map of 500 Kilobases on Chromosome 5q31

The present example provides an illustration of the differences between the SPC maps constructed with the methods of the present invention and the haplotype blocks obtained with the approach proposed by Daly et al. [Daly et al., Nat. Genet. 29: 229-232, 2001; Daly et al., patent application US 2003/0170665 A1]. The present example also provides an illustration of the differences between the tag SNPs (ctSNPs) selected with the methods of the present invention and the haplotype tag SNPs (htSNPs) selected with the haplotype block method. This example presents a reanalysis of the polymorphic sites in a 500 kb segment on chromosome 5q31, which had been used to establish the presence of haplotype blocks in the human genome [Daly et al., Nat. Genet. 29: 229-232, 2001]. The results of the analysis presented provides evidence that the ctSNPs selected with the methods of the present invention are superior diagnostic markers for genome wide genetic association studies, and genetic analysis in general.

The unphased diploid genotypes and the SNP allele data for the "High-resolution haplotype structure in the human genome" [Daly et al., Nat. Genet. 29: 229-232, 2001] were downloaded as "Download raw-data page" from the website http://www.broad.mit.edu/humgen/IBD5/haplodata.html.

The data of the 500 kb segment on chromosome 5q31 comprise 103 SNPs typed in a panel of 129 trios, amounting to 387 individuals. The raw-data page lists numerical symbols representing the alleles of the 103 polymorphic sites genotyped in the 387 samples. The numerical symbols were replaced by the symbols "A", "C", "G" and "T" for the homozygous genotypes and by the symbol "H" and "N" for respectively the heterozygous genotypes and the missing genotypes. The genetic variation table was reformatted into a metatype table as described in Example 7.

The metatype table was analyzed with the SPC algorithm using the following thresholds for C: C=1, C≧0.95, C≧0.90, C≧0.875, C≧0.85 and C≧0.825. The analysis of the present data set was encumbered by the large number of missing data points (i.e. 10.4%) combined with the relatively high incidence of recombination. The SPC pattern that was ultimately assembled gathers information about the clustering at different stringencies. Basically, the 15 SPCs that were identified at the C≧0.875 threshold were retained and SNPs that clustered at the lower thresholds were added (without allowing the SPCs themselves to coalesce). In total 87 of the 103 SNPs were clustered.

FIG. 18 shows that the SPC pattern of the 103 SNPs is discontinuous at both ends of the map (short alternating SPCs), while the central part comprises long overlapping SPCs. The haplotype block structure [Daly et al., Nat. Genet. 29: 229-232, 2001] is represented by the numbered grey rectangles in FIG. 18. Comparison of the SPC pattern with the 11 haplotype blocks shows that several SPCs are running across two or more blocks, illustrating that the SPC structure provides a more concise representation of the organization in the genetic variation. The principal difference between the two methods lays in the selection of tag SNP markers for genotyping. In the haplotype block method tag SNPs are derived from the haplotypes identified within the blocks as SNPs that are diagnostic for each haplotype, while the methods of the present invention define (at the most) one tag SNP for each SPC. Consequently, the SPCs that are spanning multiple adjacent blocks will be tagged more than once, actually as many times as the number of blocks the SPC is encompassing. In contrast to the SPC concept, the consideration of independent blocks, leads a redundancy in the selection of markers. In the present example only 15 SNPs would be required for tagging the SPCs while a comprehensive coverage of all block-specific haplotypes require up to 37 htSNPs assuming one htSNP for each major haplotype within each haplotype block [refer to FIG. 2 in Daly et al., Nat. Genet. 29: 229-232, 2001]. In addition, as documented in Example 7, the methods of the present invention provide a rational approach for selecting tag SNPs that yield the most reliable marker for each SPC. A further prime difference between the SPC and the haplotype block concept, that is of great practical utility, is that the SPC structure may be derived directly from unphased diploid genotype data whereas the inference of haplotypes is a prerequisite for the haplotype block method.

EXAMPLE 11

SPC Map of Single-feature Polymorphisms in Yeast

The present example provides proof of concept that the methods of the present invention can be used on genetic variation data other than defined sequence differences, and that the SPC maps thus obtained are particularly useful for examining genome-wide patterns of genetic variation. The present example provides this proof of concept for single-feature polymorphisms (SFPs) obtained using high-density oligonucleotide arrays and demonstrates that the methods of the present invention can be used to design diagnostic microarrays that address selected tag SFPs derived from the SPC maps. This example presents an analysis of the polymorphic sites in chromosome 1 of common laboratory strains of yeast identified using high-density oligonucleotide arrays [Winzeler et. al., Genetics. 163: 79-89, 2003]. In this study, the Affymetrix S98 oligonucleotide array (Affymetrix Inc, Santa Clara, Calif.) containing 285,156 different 25-mers from the yeast genomic sequence was used to discover 11,115 single-feature polymorphisms (SFPs) in 14 different yeast strains and to assess the genome-wide distribution of genetic variation in this yeast population. High-density oligonucleotide arrays using short 25-mer oligonucleotides are particularly useful for discovering polymorphisms because the strength of the hybridisation signal can be used to detect nucleotide changes. Polymorphisms, detected through differential hybridisation to one single oligonucleotide on an array (termed a feature) are referred to as "Single-Feature Polymorphisms" (SFPs). Thus, with oligonucleotide arrays carrying large numbers of probes of this length, a substantial proportion of the genomic sequence can be interrogated and the approximate position of allelic variation between two genomic sequences can be ascertained. Microarrays of this type thus provide a powerful platform for genetic variation discovery and for future diagnostic genotyping on a genome-wide scale.

The allelic variation data of intraspecies polymorphisms between laboratory strains of yeast [Winzeler et. al., Genetics. 163: 79-89, 2003] used in the present analysis were downloaded from the website http://www.scripps.edu/cb/winzeler/genetics_supplement/supplement.htm. The allelic variation data table comprises the presence/absence scores (1/0) of 11,115 SFPs in 14 different yeast strains, together with their position on each of the 16 yeast chromosomes. The allelic variation data table was converted into the standard format of the genetic variation table by substituting the numerical symbols 0 and 1 by the symbols "C" and "A" respectively. The SFPs were sorted by chromosome and the genetic variation table was partitioned into 16 tables comprising the SFPs of individual chromosomes. The genetic variation table of chromosome 1, analyzed in the present example, comprises 406 SFPs, of which 174 were singletons. To simplify the analysis and the representation of the results, the singletons were excluded from the analysis. The remaining 232 polymorphisms were clustered with the SPC algorithm using the following thresholds: C=1, C≧0.90 and C≧0.80. At the threshold of C=1 and C≧0.90 the algorithm clustered a total of 117 SFPs (50%) of chromosome 1 into 19 different SPCs comprising 3 or more SFPs. The representation of FIG. 19 shows the chromosomal distribution of the SFPs in the 12 largest clusters comprising 4 or more SFPs. It can be seen that some of these are confined to relatively short segments of a few kilobases to 30 kb (e.g. SPCs 1, 2, 4, 5 and 7), while others span a major part of the chromosome (e.g. SPC-3 and SPC-6). This analysis reveals patterns of SFP polymorphisms shared between yeast strains that consist of both locally clustered SFPs and chromosome-wide clusters, and signifies the onset of the construction of an SPC map of the yeast genome. A complete SPC map will entail the analysis of the yeast genome in greater depth, both in terms of the size of the strain collection and the density of polymorphisms.

The SPC map of chromosome 1 can be used to select informative tag SFPs that are diagnostic for each SPC identified and which can be used for genotyping yeast strains. A subset of 12 or 19 tag SFPs can be identified (depending on the minimum number of SFPs per cluster), representing a more than 20-fold reduction of the 406 initially observed SFPs. While the exact fold of reduction will depend on the extent of linkage of SFPs, the example demonstrates that the methods of the present invention provide a straightforward approach for selecting a subset of SFPs that have the highest diagnostic value. Dedicated arrays, comprising only those oligonucleotides that interrogate the tag SFPs can then be designed.

The present example illustrates that the methods of the present invention provide a rational framework for analyzing complex patterns of genetic variation generated on a genome-wide scale, obtained by microarray analysis. The example also demonstrates that the methods of the present invention permit the selection of tag SFPs that may be assembled on purposely designed microarrays that are useful for in vitro diagnostic tests or genetic analysis in general.

EXAMPLE 12

SPC Analysis of Nucleotide Sequence Typing Data in Bacteria

The present example provides proof of concept that the methods of the present invention can be used on genetic variation data obtained with multilocus sequence typing (MLST) of bacteria, and that the SPC maps thus obtained are particularly useful for determining the genetic identity of bacteria. Multilocus sequence typing (MLST) is rapidly becoming one of the standard techniques for the characterization of bacteria. In this technique neutral genetic variation from multiple genomic locations is indexed by analyzing stretches of nucleotide sequence of 500 bp from loci coding for house keeping genes. Sequence data are readily compared among laboratories and lend themselves to electronic storage and distribution. A World Wide Web site for the storage and exchange of data and protocols for MLST has-been established (http://mlst.zoo.ox.ac.uk). This example presents an analysis of some of the MLST data from a study of the gram-negative bacterium *Campylobacter jejuni* [Dingle et al., J. Clin. Microbiol. 39:14-23, 2001].

The aligned nucleotide sequences of the glutamine synthetase (glnA) gene from 108 *C. jejuni* strains used in the present analysis were downloaded from the website http://mlst.zoo.ox.ac.uk. The genetic variation table of the glnA gene comprises 107 polymorphic sites (excluding the singletons), which were clustered with the SPC algorithm using the following thresholds: $C=1$, $C \geq 0.95$, $C \geq 0.90$, $C \geq 0.85$ and $C \geq 0.80$. At the threshold of $C=1$ and $C \geq 0.90$ the algorithm clustered a total of respectively 52 and 67 polymorphic sites into SPCs comprising 3 or more polymorphic sites. The representation of FIG. 20 shows the SPC map obtained at a threshold of $C \geq 0.90$ in which the polymorphic sites are clustered into 4 SPCs. It can be seen that the majority of polymorphic sites exhibit a simple SPC structure in that they fall into three SPCs, two of which (SPC-2 and SPC-3) are dependent on SPC-1. The fourth SPC (SPC-4) contains sites at which a third allele occurs in one sample only. The simple SPC pattern demonstrates that a very large number (over one hundred) of polymorphisms can be reduced to a mere three cluster tag polymorphism to type the 108 strains at this locus. Moreover, the straightforward dependency relationships observed provide a clear genealogical picture of the evolution of the glnA locus.

The present example illustrates that the methods of the present invention provide a rational framework for analyzing complex patterns of genetic variation generated by multilocus sequence typing (MLST) of bacteria. The example also demonstrates that the methods of the present invention permit the selection of cluster tag SNPs that may be assembled on the basis of the observed SPCs at different loci, and which are useful for precise in vitro diagnostic of particular groups of bacteria in general.

EXAMPLE 13

Non-clustering Polymorphisms in the Surveys of Genetic Diversity in *Arabidopsis thaliana*

The present example illustrates that the majority of the non-clustering polymorphisms in a particular genomic region can be unambiguously placed in the SPC network deduced for that region. This is illustrated hereinabove for a particular human genomic region. The current example presents an analysis of the polymorphic sites identified in a set of amplified fragments from chromosome 1 of *Arabidopsis thaliana*.

Similar to Example 6, the genomic sequences analyzed here were generated in the NSF 2010 Project "A genomic survey of polymorphism and linkage disequilibrium in *Arabidopsis thaliana*" [Bergelson J., Kreitman M., and Nordborg M., http://walnut.usc.edu/2010/2010.html] and comprises, to date, 297 amplicons from chromosome 1 sequenced from 98 accessions of *Arabidopsis thaliana*. The sequences for this analysis were downloaded from the website http://walnut.usc.edu/2010/2010.html, and were aligned using ClustalW [Thompson et al., Nucleic Acids Res. 22: 4673-4680, 1994]. Using a perl script the aligned sequences were converted to a genetic variation table in which each row represents a sample and each column represents a polymorphic score. In addition to the common bi-allelic single nucleotide substitutions, indels as well as multi-allelic polymorphisms were observed, and were included in the analysis. Single nucleotide indels, analogous to bi-allelic single nucleotide substitutions, are easily represented in a single column of the genetic variation table. Tri-allelic SNPs are represented by two columns in the genetic variation table, where each entry lists the major allele in combination with one of the minor alleles while the third-allele-calls are replaced by blanks. Thus, the two mutational events that gave rise the tri-allelic marker are treated as separate polymorphisms. Blank spaces in the genetic variation table are ignored and frequencies of a particular allele (e.g. $P_a$) or two-site haplotype (e.g. $P_{ab}$) are calculated by simply dividing the observed number of the allele or two-site haplotype by the total number of samples. Indels involving two or more nucleotides are identified by two dots at the start and the end position of the deletion. As a result of these indels, there is a distinction between the number of polymorphic scores (i.e. columns) in the genetic variation table and the number of mutational events in the sequence.

The polymorphism frequency observed in the 297 amplicons from chromosome 1 ranges from 0 (no mutations found) to over 25% (number of polymorphic scores over number of bases). The 5 amplicons presented here were chosen among the most polymorphic amplicons, and are representative for the different patterns of genetic variation found in *Arabidopsis*. The table below summarizes the basic characteristics of these amplicons: chromosome position, length, total number of polymorphic scores, percent of polymorphic scores clustered and number of SPCs observed.

| amplicon | chromosome position[1] | length[2] | polymorphic scores total[3] | clustered[4] | number of SPCs[5] |
|---|---|---|---|---|---|
| A | 22,903,880 | 540 | 58 | 43 (74%) | 6 |
| B | 5,380,792 | 574 | 58 | 47 (81%) | 5 |
| C | 16,568,120 | 609 | 64 | 44 (69%) | 13 |
| D | 22,569,092 | 616 | 61 | 49 (80%) | 7 |
| E | 13,002,329 | 577 | 89 | 60 (69%) | 20 |

[1]Position of the first nucleotide on chromosome 1
[2]Total lengths of the aligned sequences including insertions
[3]Total number of polymorphic scores
[4]Total number of polymorphic scores that were clustered at the threshold of $C = 1$
[5]Total numbers of SPCs containing two or more polymorphic scores The results presented in the table and in FIG. 33 were obtained by computing the clustering of the polymorphic scores at the most stringent threshold ($C=1$). It can be seen that most of the polymorphic sites (69% to 81%) could be clustered in a discrete number of SPCs. The panels A to D of FIG. 33 show that nearly all of the polymorphic sites (236/241)—comprising all of the SPCs as well as most of the non-clustering polymorphisms—can unambiguously be fitted into highly branched networks. The genetic variation tables show that only part of the haplotypes is defined by (major) SPCs and that a significant number of the haplotypes is defined by non-clustering polymorphisms. This is presumably a reflection of the fact that only short (~600 nucleotides long) segments have been analyzed. Some of these non-clustering polymorphisms may very well be found to belong to SPCs in case more extended chromosomal regions would be sequenced. Certain other non-clustering polymorphisms define the exterior branches of the networks and occur at low frequency (1% to 2%), indicating that they represent recent mutations. The amplicons A to D are representative for the type of SPC and haplotype patterns most commonly observed in the entire data set. Clearly, amplicon E is rather divergent in that it comprises a large number of haplotypes defined by 17 independent SPCs. The network of amplicon E is essentially star shaped with few dependent SPCs.

The rare polymorphic sites (5/241) that do not fit the SPC network structures are also shown in FIG. 33. These represent sites whose scores are in conflict with the proposed phylogeny of genetic variants in the amplicons. Such conflicts can have a variety of causes: sequencing errors, recurrent mutations, historic recombination and gene conversion. Detailed analysis of the conflicting polymorphic scores suggests that three of these may represent sequencing errors (amplicons A, B and D), because in each case only one single or two genotype discrepancies are observed. The first conflicting site of amplicon C is presumably a recurrent mutation of an oligo-A run, while the second site is not readily explained.

In conclusion, the results of the analysis of genomic surveys of genetic variation demonstrate that the SPC technology provides a crisp approach for assessing haplotype diversity. With respect to the tag SNPs, it is worth mentioning that a broad coverage will not only require the selection of tags for the major SPCs, but also the inclusion of some of the non-clustering polymorphisms, more specifically those that define major haplotypes. As noted above, the present data sets cover very short genomic segments of less than 1 kb, and a non-clustering polymorphism may be the only polymorphism of a cluster that falls in the chosen amplicon. While a short amplicon may not reveal the full genetic diversity in a particular chromosomal region, it seems clear that the SPC analysis of the data at hand allows the identification of the most informative polymorphisms for genetic association analysis.

While this invention has been particularly shown and described with references to preferred embodiments thereof, it will be understood by those skilled in the art that various changes in form and details may be made therein without departing from the scope of the invention encompassed by the appended claims.

---

What is claimed is:

1. A computer-implemented method of producing a map of a genomic region of interest said map on a computer comprising one or more sequence polymorphism clusters (SPCs), wherein each SPC comprises a subset of polymorphisms from said genomic region wherein said polymorphisms of said subset co-segregates with each other polymorphism of said subset; and wherein said map further comprises non-co-segregating polymorphisms that are associated with the map, wherein said non-co-segregating polymorphisms are such that they do not co-segregate with any other polymorphism but do co-segregate with at least one SPO, said method comprising the steps of:

a. obtaining the nucleic acid sequence of said genomic region of interest from a plurality of subjects;
 b. identifying on a computer a plurality of polymorphisms in said nucleic acid sequences;
 c. identifying on a computer one or more SPCs, wherein each SPC comprises a subset of polymorphisms from said nucleic acid sequence wherein each of said polymorphisms of said subset co-segregates with each other polymorphism of said subset; and
 d. identifying on a computer non-co-segregating polymporphisms that do not co-segregate with any other polymorphism but do cosegregate with at least one SPC
 e. outputting from said computer the SPCs identified in step (c) and the non-co-segregating polymorphisms identified in step (d) into a user readable format that selects a genotype or genetic marker for a trait or phenotype.

2. The method of claim 1, wherein each said polymorphism of said subset co-segregates with each other polymorphism of said subset according to a percentage co-segregation of the minor alleles of said polymorphisms of between 75% and 100.

3. The method of claim 1, wherein the co-segregation of each said polymorphism of said subset with each other polymorphism of said subset is calculated according to a parameter selected from the group consisting of a pairwise C value, C* value, a r.sup.2 linkage disequilibrium value, a Δ linkage disequilibrium value, a δ linkage disequilibrium value, and a d linkage disequilibrium value.

4. The method of claim 1, wherein said parameter is a pairwise C value of from 0.75 to 1.

5. The method of claim 1, wherein said identifying one or more SPCs comprises identifying each polymorphism of said subset that co-segregates with each other polymorphism of said subset according to a percentage co-segregation of the minor alleles of said polymorphisms of between 75% and 100%.

6. The method of claim 1, wherein said identifying one or more SPCs comprises multiple rounds of co-segregation analysis.

7. The method of claim 1, wherein each successive round of co-segregation analysis is performed at a decreasing percentage co-segregation from 100% co-segregation to 75% co-segregation.

8. The method of claim 1, wherein the co-segregation of each said polymorphism of said subset with each other polymorphism of said subset is calculated according to a parameter selected from the group consisting of a pairwise C value, C* value, a $r^2$ linkage disequilibrium value, a Δ linkage disequilibrium value, a δ linkage disequilibrium value, and a d linkage disequilibrium value.

9. The method of claim 8, wherein said parameter is a pairwise C value of from 0.75 to 1.

10. An article comprising a machine-accessible medium having stored thereon instructions that, when executed by a machine, cause the machine to:
- obtain a nucleic acid sequence of a genomic region of interest from a plurality of subjects;
- identify a plurality of polymorphisms in said nucleic acid sequence;
- identify one or more SPCs, wherein each SPO comprises a subset of polymorphisms from said nucleic acid sequence wherein each said polymorphisms of said subset co-segregates with each other polymorphism of said subset;
- identify non-cosegregating polymorphisms that do not coincide with any other polymorphism but do coincide with at least one SPC, and
- output the identified SPCs and non-cosegregating polymorphisms into a user readable format that selects a genotype or genetic marker for a trait or phenotype.

* * * * *

UNITED STATES PATENT AND TRADEMARK OFFICE
CERTIFICATE OF CORRECTION

PATENT NO. : 7,593,818 B2
APPLICATION NO. : 11/077564
DATED : September 22, 2009
INVENTOR(S) : Zabeau et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 934 days.

Signed and Sealed this

Twenty-eighth Day of September, 2010

David J. Kappos
*Director of the United States Patent and Trademark Office*